(12) United States Patent
Palani et al.

(10) Patent No.: US 11,058,775 B2
(45) Date of Patent: Jul. 13, 2021

(54) INSULIN DIMER-INCRETIN CONJUGATES

(71) Applicant: Merck Sharp & Dohme Corp., Rahway, NJ (US)

(72) Inventors: Anandan Palani, Bridgewater, NJ (US); Zhiqiang Yang, Westfield, NJ (US); Lin Yan, East Brunswick, NJ (US); Songnian Lin, Holmdel, NJ (US); Pei Huo, Millburn, NJ (US); Ravi Nargund, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 31 days.

(21) Appl. No.: 16/092,155

(22) PCT Filed: Apr. 21, 2017

(86) PCT No.: PCT/US2017/028706
§ 371 (c)(1),
(2) Date: Oct. 8, 2018

(87) PCT Pub. No.: WO2017/189342
PCT Pub. Date: Nov. 2, 2017

(65) Prior Publication Data
US 2019/0192675 A1    Jun. 27, 2019

Related U.S. Application Data

(60) Provisional application No. 62/327,516, filed on Apr. 26, 2016.

(51) Int. Cl.
| | | |
|---|---|---|
| A61K 38/26 | (2006.01) | |
| A61K 38/28 | (2006.01) | |
| A61K 47/60 | (2017.01) | |
| A61K 47/62 | (2017.01) | |
| A61K 47/54 | (2017.01) | |

(52) U.S. Cl.
CPC .............. *A61K 47/62* (2017.08); *A61K 38/26* (2013.01); *A61K 38/28* (2013.01); *A61K 47/542* (2017.08); *A61K 47/545* (2017.08); *A61K 47/60* (2017.08)

(58) Field of Classification Search
None
See application file for complete search history.

(56) References Cited

U.S. PATENT DOCUMENTS

| | | | |
|---|---|---|---|
| 3,907,763 | A | 9/1975 | Brandenburg et al. |
| 5,304,473 | A | 4/1994 | Belagaje et al. |
| 6,630,348 | B1 | 10/2003 | Lee et al. |
| 6,908,897 | B2 | 6/2005 | Brandenburg et al. |
| 7,105,314 | B2 | 9/2006 | Kjeldsen |
| 2008/0057004 | A1 | 3/2008 | Bell et al. |
| 2009/0170750 | A1 | 7/2009 | Kjeldsen et al. |
| 2014/0221283 | A1* | 8/2014 | Dimarchi ............ A61P 25/28 514/5.3 |
| 2015/0274802 | A1 | 10/2015 | Dimarchi et al. |

FOREIGN PATENT DOCUMENTS

| | | | |
|---|---|---|---|
| WO | 9516708 A1 | 6/1995 | |
| WO | 9634882 A1 | 11/1996 | |
| WO | 2000050456 A2 | 8/2000 | |
| WO | 2005054291 A1 | 6/2005 | |
| WO | 2006097521 A1 | 9/2006 | |
| WO | 2007096332 A1 | 8/2007 | |
| WO | 2007104734 A1 | 9/2007 | |
| WO | 2007104736 A2 | 9/2007 | |
| WO | 2007104737 A1 | 9/2007 | |
| WO | 2007104738 A2 | 9/2007 | |
| WO | 2009099763 A1 | 8/2009 | |
| WO | 2009132129 A2 | 10/2009 | |
| WO | 2010080606 A1 | 7/2010 | |
| WO | 2010080609 A1 | 7/2010 | |
| WO | WO2011059895 A2 | 12/2011 | |
| WO | 2012098462 A1 | 7/2012 | |
| WO | WO2014052451 A2 | 4/2014 | |
| WO | WO2014141165 A1 | 9/2014 | |
| WO | WO2014158900 | * 10/2014 | ............. C07K 19/00 |
| WO | WO2016049190 A1 | 3/2016 | |
| WO | 2017205191 A1 | 11/2017 | |
| WO | WO2017189342 A1 | 11/2017 | |

OTHER PUBLICATIONS

US 5,691,198 A, 11/1997, Jin et al. (withdrawn)
Stephen Crotty et al., The New Insulins, Pediatric Emergency Care, 2007, 903-908, 23(12).
Achim Schuttler et al., Preparation and Properties of Covalently-Linked Insulin Dimers, Hoppe-Seyler's Z. Physiol. Chem., 1982, pp. 317-330, 363.
Brandt, Sara J., Synthesis and Characterization of Insulin Receptor Partial Agonists as a Route to improved Diabetes Therapy, PhD Dissertation, Indiana University, 2015, pp. 1-207, NA.
Deppe et al., Structure activity relationship of covalently dimerized insulin derivatives: correlation of partial agonist efficacy with cross linkage at lysine B29, Archives of Pharmacology, Springer, DE, 1994, pp. 213-217, 350.
Fuaad, Abdullah A. H. Ahmad, Peptide Conjugation via CuAAC "Click" Chemistry, Molecules, 2013, pp. 13148-13174, vol. 18.
John E. Gerich M.D., Novel Insulins: Expanding Options in Diabetes Management, The American Journal of Medicine, 2002, 308-316, vol. 113.
Knudsen et al., Agonism and Antagonism at the Insulin Receptor, PLos One, 2012, pp. 1-10, 7.
Kristensen et al., A single-chain insulin-like growth factor I/insulin hybrid binds with high affinity to the insulin receptor, Biochem. J., 1995, pp. 981-986, 305.
Tatnell et al., Evidence concerning the mechanism of insulin receptor interaction and the structure of teh insulin receptor from biological properties of covalently linked insulin dimers, Biochem. J., 1983, pp. 687-694, 216.

(Continued)

*Primary Examiner* — Julie Ha
*Assistant Examiner* — Kristina M Hellman
(74) *Attorney, Agent, or Firm* — Janet E. Fair; Catherine D. Fitch

(57) ABSTRACT

Insulin dimers conjugated to peptides having at least one incretin activity are disclosed.

22 Claims, 8 Drawing Sheets

Specification includes a Sequence Listing.

(56) References Cited

OTHER PUBLICATIONS

UniProtKB Accession No. P20394.2, RecName: Full=Exendin-3; AltName: Full=Glucagon-like 3; Flags: Precursor.

Weiland et al., Antagonistic Effects of a Covalently Dimerized Insulin Derivative on Insulin Receptors in 3T3-L1 Adipocytes, Proc. Natl. Acad. Sci. USA, 1990, pp. 1154-1158, 87.

Zaykov et al., Poster P212—Exploration of the Structural and Mechanistic Basis for Partial Agonism of Insulin Dimers, American Peptide Symposium—Poster, Orlando Florida, 2015, Poster, NA.

* cited by examiner

SEQUENCE LISTING

```
<160> NUMBER OF SEQ ID NOS: 141

<210> SEQ ID NO 1
<211> LENGTH: 29
<212> TYPE: PRT
<213> ORGANISM: Artificial Sequence
<220> FEATURE:
<223> OTHER INFORMATION: Glucagon-derived peptide

<400> SEQUENCE: 1

His Ser Gln Gly Thr Phe Thr Ser Asp Tyr Ser Lys Tyr Leu Asp Glu
1               5                   10                  15

Arg Ala Ala Gln Asp Phe Val Gln Trp Leu Leu Asp Thr
            20                  25

<210> SEQ ID NO 2
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugatedto lipid moiety and one of X20, X21, X24, X30,
      or X31 comprises the azide group or X20 is a Lysine residue
      conjugated lipid moiety and one of X21, X24, X30, or X31 comprises
      the azide group
<220> FEATURE:
<221> NAME/KEY: MISC_FEATURE
<222> LOCATION: (2)..(2)
<223> OTHER INFORMATION: Xaa is amionisobutyric acid (Aib), Gly,
      D-Serine (s), alpha-methyl Serine (?MS), or alpha-methyl D-Serine
      (alpha-Ms)
<220> FEATURE:
<221> NAME/KEY: MISC_FEATURE
<222> LOCATION: (3)..(3)
<223> OTHER INFORMATION: Xaa is Val, Glu or Asp
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
```

```
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      azide group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, ?MD, Azidonorleucine
      (Norleucine conjugated via its epsilon carbon to an azide group
      (Nle(?N3))), or Lysine conjugated via its epsilon amino group to a
      non-peptide linker comprising a terminal azide group
<220> FEATURE:
<221> NAME/KEY: MISC_FEATURE
<222> LOCATION: (22)..(22)
<223> OTHER INFORMATION: Xaa is Phe or alpha-MF
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated via its epsilon amino group to a non-peptide linker
      comprising a terminal azide group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW);
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Methionine, Leucine, Methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilonN3), or
      Xaa is absent
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amino group to a non-peptide
      linker comprising a terminal azide group, or Xaa is absent
```

```
<400> SEQUENCE: 2

His Xaa Xaa Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa Xaa
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with proviso that either X10 is a Lysine
      residue conjugated the lipid moiety and one of X20, X21, X24, X30,
      or X31 comprises the alkyne group or X20 is a Lysine residue
      conjugated to the lipid moiety and one of X21, X24, X30, or X31
      comprises the alkyne
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Val, Glu, or Asp
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu or alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      alkyne group or to a fatty acid or fatty diacid
```

```
<220> FEATURE:
<221> NAME/KEY: MISC_FEATURE
<222> LOCATION: (21)..(21)
<223> OTHER INFORMATION: Xaa is Aspartic acid, alpha-MD,
      Alkynylnorleucine (Norleucine conjugated via its epsilon carbon to
      an alkyne group (Nle(epsilon-alkyne))), or Lysine conjugated via
      its epsilon amino group to a non-peptide linker comprising a
      terminal alkyne
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF)
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated via its epsilon amino group to a non-peptide
      linker comprising a terminal alkyne group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Methionine, Leucine, methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent
<220> FEATURE:
<221> NAME/KEY: MISC_FEATURE
<222> LOCATION: (31)..(31)
<223> OTHER INFORMATION: Xaa is Glycine, ?Glu, Nle(epsilon-alkyne), or
      Lysine conjugated via its epsilon amino group to a non-peptide
      linker comprising a terminal alkyne group, or Xaa is absent

<400> SEQUENCE: 3

His Xaa Xaa Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa Xaa
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
```

```
<220> FEATURE:
<221> NAME/KEY: PEPTIDE
<222> LOCATION: (1)..(31)
<223> OTHER INFORMATION: with proviso that either X10 is a Lysine
      residue conjugated lipid moiety and one of X20, X21, X24, X30, or
      X31 comprises the azide group or X20 is a Lysine residue
      conjugated lipid moiety and one of X21, X24, X30, or X31 comprises
      the azide group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      azide group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD, Azidonorleucine
      (Norleucine conjugated via its epsilon carbon to an azide group
      (Nle(epsilon-N3))), or Lysine conjugated via its epsilon amino
      group to a non-peptide linker comprising a terminal azide group
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF)
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated via its epsilon amino group to a non-peptide linker
      comprising a terminal azide group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Methionine, Leucine, methionine
      sulfoxide, or L-methionine sulphone (2)
```

```
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, ?Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      X30 is absent
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amino group to a non-peptide
      linker comprising a terminal azide group, or X31 is absent

<400> SEQUENCE: 4

His Xaa Gln Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated lipid moiety and one of X20, X21, X24, X30, or
      X31 comprises the alkyne group or X20 is a Lysine residue
      conjugated lipid moiety and one of X21, X24, X30, or X31 comprises
      the alkyne group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
```

```
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      alkyne group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD,
      Alkynylnorleucine (Norleucine conjugated via its epsilon carbon to
      an alkyne group (Nle(epsilon-alkyne))), or Lysine conjugated via
      its epsilon amino group to a non-peptide linker comprising a
      terminal alkyne
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF)
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated via its epsilon amino group to a non-peptide
      linker comprising a terminal alkyne group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Methionine, Leucine, methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amino group to a non-peptide
      linker comprising a terminal alkyne group, or Xaa is absent

<400> SEQUENCE: 5

His Xaa Gln Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa
            20                  25                  30
```

```
<210> SEQ ID NO 6
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated lipid moiety and one of X20, X21, X24, X30, or
      X31 comprises the azide group or X20 is a Lysine residue
      conjugated lipid moiety and one of X21, X24, X30, or X31 comprises
      the azide group
<220> FEATURE:
<221> NAME/KEY: MISC_FEATURE
<222> LOCATION: (2)..(2)
<223> OTHER INFORMATION: Xaa is amionisobutyric acid (Aib), Gly,
      D-Serine (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Val, Glu, or Asp
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: X10 is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      azide group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD, Azidonorleucine
      (Norleucine conjugated via its epsilon carbon to an azide group
      (Nle(epsilon-N3))), or Lysine conjugated via its epsilon amino
      group to a non-peptide linker comprising a terminal azide group
```

```
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF),
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated via its epsilon amino group to a non-peptide linker
      comprising a terminal azide group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Met, Leucine, methionine sulfoxide, or
      L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amino group to a non-peptide
      linker comprising a terminal azide group, or Xaa is absent

<400> SEQUENCE: 6

Xaa Xaa Xaa Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa Xaa
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to lipid moiety and one of X20, X21, X24, X30,
      or X31 comprises the alkyne group or X20 is a Lysine residue
      conjugated to lipid moiety and one of X21, X24, X30, or X31
      comprises the alkyne
```

```
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Val, Glu, or Asp
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      alkyne group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD,
      Alkynylnorleucine (Norleucine conjugated via its epsilon carbon to
      an alkyne group (Nle(epsilon-alkyne))), or Lysine conjugated via
      its epsilon amino group to a non-peptide linker comprising a
      terminal alkyne
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF),
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated via its epsilon amino group to a non-peptide
      linker comprising a terminal alkyne group
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Methionine, Leucine, methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
```

```
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amino group to a non-peptide
      linker comprising a terminal alkyne group, or Xaa is absent and

<400> SEQUENCE: 7

Xaa Xaa Xaa Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa Xaa
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to lipid moiety and one of X20, X21, X24, X30,
      or X31 comprises the azide group or X20 is a Lysine residue
      conjugated to lipid moiety and one of X21, X24, X30, or X31
      comprises the azide group
<220> FEATURE:
<221> NAME/KEY: MISC_FEATURE
<222> LOCATION: (2)..(2)
<223> OTHER INFORMATION: Xaa is amionisobutyric acid (Aib), Gly,
      D-Serine (s), or alpha-methyl Serine (alpha-MS)
<220> FEATURE:
<221> NAME/KEY: MISC_FEATURE
<222> LOCATION: (10)..(10)
<223> OTHER INFORMATION: Xaa is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Glutamic acid, Asparagine, Serine,
      Alanine, or Aib
```

```
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      azide group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD, Azidonorleucine
      (Norleucine conjugated to an azide group (Nle(epsilonN3))), or
      Lysine conjugated via to a non-peptide linker comprising a
      terminal azide group
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF)
<220> FEATURE:
<221> NAME/KEY: MISC_FEATURE
<222> LOCATION: (24)..(24)
<223> OTHER INFORMATION: Xaa is Glutamine, Nle(epsilonN3), or Lysine
      conjugated via its epsilon amino group to a non-peptide linker
      comprising a terminal azide group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is methionine, Leucine, methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilonN3), or
      Xaa is absent and
<220> FEATURE:
<221> NAME/KEY: MISC_FEATURE
<222> LOCATION: (31)..(31)
<223> OTHER INFORMATION: XAA is Glycine, gamma-Glu, Nle(epsilonN3), or
      Lysine conjugated via its epsilon amino group to a non-peptide
      linker comprising a terminal azide group, or XAA is absent and

<400> SEQUENCE: 8

Xaa Xaa Gln Gly Thr Phe Thr Ser Xaa Xaa Ser Xaa Tyr Xaa Asp Xaa
1               5                   10                  15

Xaa Xaa Ala Xaa Xaa Xaa Val Xaa Xaa Xaa Xaa Xaa Xaa Xaa
            20                  25                  30
```

```
<210> SEQ ID NO 9
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to  lipid moiety and one of X20, X21, X24, X30,
      or X31 comprises the alkyne group or X20 is a Lysine residue
      conjugated to  lipid moiety and one of X21, X24, X30, or X31
      comprises the alkyne
<220> FEATURE:
<221> NAME/KEY: MISC_FEATURE
<222> LOCATION: (2)..(2)
<223> OTHER INFORMATION: X2 is aminoisobutyric acid (Aib), D-Serine (s),
      or alpha-methyl Serine (alpha-MS)
<220> FEATURE:
<221> NAME/KEY: MISC_FEATURE
<222> LOCATION: (9)..(9)
<223> OTHER INFORMATION: Xaa is Asp or alpha-methyl Aspartic acid
      (alpha-MD)
<220> FEATURE:
<221> NAME/KEY: MISC_FEATURE
<222> LOCATION: (10)..(10)
<223> OTHER INFORMATION: X10 is Tyr or Lys conjugated to a lipid moiety
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amino group to a non-peptide linker comprising a terminal
      alkyne group or to a fatty acid or fatty diacid
<220> FEATURE:
<221> NAME/KEY: MISC_FEATURE
<222> LOCATION: (21)..(21)
<223> OTHER INFORMATION: Xaa is Aspartic acid, alpha-MD,
      Alkynylnorleucine (Norleucine conjugated via its epsilon carbon to
      an alkyne group (Nle(epsilon-alkyne))), or Lysine conjugated via
      its epsilon amino group to a non-peptide linker comprising a
      terminal alkyne
<220> FEATURE:
<221> NAME/KEY: MISC_FEATURE
<222> LOCATION: (22)..(22)
<223> OTHER INFORMATION: Xaa is Phe or alpha-methyl Phenylalanine
      (alpha-MF)
```

```
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated via its epsilon amino group to a non-peptide
      linker comprising a terminal alkyne group
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is methionine, Leucine, methionine
      sulfoxide, or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amino group to a non-peptide
      linker comprising a terminal alkyne group, or Xaa is absent

<400> SEQUENCE: 9

Xaa Xaa Gln Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises azide or N3 group or X20 is a
      Lysine residue conjugated to PEG2PEG2-gamma-Glu-C18-OH or
<220> FEATURE:
<221> NAME/KEY: PEPTIDE
<222> LOCATION: (1)..(31)
<223> OTHER INFORMATION: the PEG2PEG2gamma-E-C20-OH and one of X21,
      X24, X30, or X31 comprises the azide or N3 group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
```

```
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5N3, PEG2PEG2-gamma-
      Glu-C16N3, PEG2PEG2-gamma-Glu-C18-OH, or PEG2PEG2gamma-E-C20-OH
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Azidonorleucine (Norleucine
      conjugated to an azide group (Nle(epsilon-N3))), or Lys conjugated
      via its epsilon amine group to PEG2-C5N3 , PEG2PEG2-C5N3, or
      PEG2PEG2-gamma-Glu-C16N3
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated to PEG2PEG2-gamma-Glu-C16N3
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      Xaa is absent and
```

```
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amine group to PEG2PEG2-gamma-
      Glu-C16N3 , PEG2-C5N3 or PEG2PEG2-C5N3, or Xaa is absent

<400> SEQUENCE: 10

His Xaa Gln Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the -alkyne or X20 is a Lysine
      residue conjugated to the PEG2PEG2-gamma-Glu-C18-OH or the
      PEG2PEG2gamma-E-C20-OH
<220> FEATURE:
<221> NAME/KEY: PEPTIDE
<222> LOCATION: (1)..(31)
<223> OTHER INFORMATION: and one of  X21, X24, X30, or X31 comprises the
      -alkyne
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: X20 is Glutamine or Lysine conjugated via its
      epsilon amine group to PEG2-C5N3, PEG2PEG2-C5-alkyne, PEG2PEG2-
      gamma-Glu-C16-alkyne, PEG2PEG2-gamma-Glu-C18-OH, or PEG2PEG2gamma-
      E-C20-OH
```

```
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Alkynylnorleucine (Norleucine
      conjugated via its epsilon carbon to an alkyne group (Nle(epsilon-
      alkyne))), or Lys conjugated v to PEG2-C5-alkyne, PEG2PEG2-C5-
      alkyne
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated to PEG2PEG2-gamma-Glu-C16-alkyne
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amine group to
      PEG2PEG2-gamma-Glu-C16-alkyne, PEG2-C5-alkyne,
      PEG2PEG2-C5-alkyne, or Xaa is absent

<400> SEQUENCE: 11

His Xaa Gln Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the azide or N3 group or X20 is a
      Lysine residue conjugated to the PEG2PEG2-gamma-Glu-C18-OH or
```

```
<220> FEATURE:
<221> NAME/KEY: PEPTIDE
<222> LOCATION: (1)..(31)
<223> OTHER INFORMATION: the PEG2PEG2gamma-E-C20-OH and one of X21,
      X24, X30, or X31 comprises the azide or N3 group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Glu or Asp
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5N3, PEG2PEG2-gamma-
      Glu-C16N3, PEG2PEG2-gamma-Glu-C18-OH, or PEG2PEG2gamma-E-C20-OH
<220> FEATURE:
<221> NAME/KEY: MISC_FEATURE
<222> LOCATION: (21)..(21)
<223> OTHER INFORMATION: X21 is Aspartic acid, alpha-methyl
      Phenylalanine (alpha-MF), alpha-MD, Azidophenylalanine (Norleucine
      conjugated via its epsilon carbon to an azide group (Nle(epsilon-
      N3))), or Lys conjugated v to PEG2-C5N3 , PEG2PEG2-C5N3, or
      PEG2PEG2-gamma-Glu-C16N3
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated to PEG2PEG2-gamma-Glu-C16N3
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
```

```
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      X30 is absent
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amine group to PEG2PEG2-gamma-
      Glu-C16N3 , PEG2-C5N3 or PEG2PEG2-C5N3, or Xaa is absent

<400> SEQUENCE: 12

His Xaa Xaa Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Pepetide
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the -alkyne or X20 is a Lysine
      residue conjugated to the PEG2PEG2-gamma-Glu-C18-OH or
<220> FEATURE:
<221> NAME/KEY: PEPTIDE
<222> LOCATION: (1)..(31)
<223> OTHER INFORMATION: the PEG2PEG2gamma-E-C20-OH and one of  X21,
      X24, X30, or X31 comprises the -alkyne
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Glu or Asp
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
```

```
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5-alkyne, PEG2PEG2-
      gamma-Glu-C16-alkyne, PEG2PEG2-gamma-Glu-C18-OH, or PEG2PEG2gamma-
      E-C20-OH
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Alkynylnorleucine (Norleucine
      conjugated to an alkyne group (Nle(epsilon-alkyne))), or Lys
      conjugated  to PEG2-C5-alkyne, PEG2PEG2-C5-alkyne, or
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated to PEG2PEG2-gamma-Glu-C16-alkyne
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amine group to
      PEG2PEG2-gamma-Glu-C16-alkyne, PEG2-C5-alkyne,
      PEG2PEG2-C5-alkyne, or Xaa is absent

<400> SEQUENCE: 13

His Xaa Xaa Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30
```

```
<210> SEQ ID NO 14
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the azide or N3 group or X20 is a
      Lysine residue conjugated to the PEG2PEG2-gamma-Glu-C18-OH or
<220> FEATURE:
<221> NAME/KEY: PEPTIDE
<222> LOCATION: (1)..(31)
<223> OTHER INFORMATION: the PEG2PEG2gamma-E-C20-OH and one of X21,
      X24, X30, or X31 comprises the azide or N3 group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Glu or Asp
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5N3, PEG2PEG2-gamma-
      Glu-C16N3, PEG2PEG2-gamma-Glu-C18-OH, or PEG2PEG2gamma-E-C20-OH
```

```
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Azidonorleucine (Norleucine
      conjugated via its epsilon carbon to an azide group (Nle(epsilon-
      N3))), or Lys conjugated to PEG2-C5N3 , PEG2PEG2-C5N3, or
      PEG2PEG2-gamma-Glu-C16N3
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated to PEG2PEG2-gamma-Glu-C16N3
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      Xaa is absent
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amine group to PEG2PEG2-gamma-
      Glu-C16N3 , PEG2-C5N3 or PEG2PEG2-C5N3, or Xaa is absent

<400> SEQUENCE: 14

Xaa Xaa Xaa Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: wherein the C-terminal amino acid optionally is
      amidated
<220> FEATURE:
<221> NAME/KEY: PEPTIDE
<222> LOCATION: (1)..(31)
<223> OTHER INFORMATION: C-terminal amino acid optionally is linked to a
      protecting group or amidated
```

-continued

```
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the -alkyne or X20 is a Lysine
      residue conjugated to the PEG2PEG2-gamma-Glu-C18-OH or
<220> FEATURE:
<221> NAME/KEY: PEPTIDE
<222> LOCATION: (1)..(31)
<223> OTHER INFORMATION: the PEG2PEG2gamma-E-C20-OH and one of  X21,
      X24, X30, or X31 comprises the -alkyne
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (3)..(3)
<223> OTHER INFORMATION: Xaa is Glu or Asp
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5-alkyne, PEG2PEG2-
      gamma-Glu-C16-alkyne, PEG2PEG2-gamma-Glu-C18-OH, or PEG2PEG2gamma-
      E-C20-OH
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Alkynylnorleucine (Norleucine
      conjugated  to an alkyne group (Nle(epsilon-alkyne))), or Lys
      conjugated to PEG2-C5-alkyne, PEG2PEG2-C5-alkyne, or PEG2PEG2-
      gamma-Glu-C16
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated to PEG2PEG2-gamma-Glu-C16-alkyne
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
```

```
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent and
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-alkyne),
      or Lysine conjugated via its epsilon amine group to
      PEG2PEG2-gamma-Glu-C16-alkyne, PEG2-C5-alkyne,
      PEG2PEG2-C5-alkyne, or Xaa is absent

<400> SEQUENCE: 15

Xaa Xaa Xaa Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the azide or N3 group or X20 is a
      Lysine residue conjugated to the PEG2PEG2-gamma-Glu-C18-OH or
<220> FEATURE:
<221> NAME/KEY: PEPTIDE
<222> LOCATION: (1)..(31)
<223> OTHER INFORMATION: the PEG2PEG2gamma-E-C20-OH and one of  X21,
      X24, X30, or X31 comprises the azide or N3 group
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
```

```
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
<220> FEATURE:
<221> NAME/KEY: MISC_FEATURE
<222> LOCATION: (20)..(20)
<223> OTHER INFORMATION: X20 is Glutamine or Lysine conjugated via its
      epsilon amine group to PEG2-C5N3, PEG2PEG2-C5N3, PEG2PEG2-gamma-
      Glu-C16N3, PEG2PEG2-gamma-Glu-C18-OH, or PEG2PEG2gamma-E-C20-OH
<220> FEATURE:
<221> NAME/KEY: MISC_FEATURE
<222> LOCATION: (21)..(21)
<223> OTHER INFORMATION: Xaa is Aspartic acid, alpha-methyl
      Phenylalanine (alpha-MF), alpha-MD, Azidonorleucine (Norleucine
      conjugated via its epsilon carbon to an azide group (Nle(epsilon-
      N3))), or Lys conjugated to PEG2-C5N3 , PEG2PEG2-C5N3, or
      PEG2PEG2-gamma-Glu-C16N3
<220> FEATURE:
<221> NAME/KEY: MISC_FEATURE
<222> LOCATION: (24)..(24)
<223> OTHER INFORMATION: Xaa is Glutamine, Nle(epsilon-N3), or Lysine
      conjugated to PEG2PEG2-gamma-Glu-C16N3
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-N3), or
      Xaa is absent
<220> FEATURE:
<221> NAME/KEY: MISC_FEATURE
<222> LOCATION: (31)..(31)
<223> OTHER INFORMATION: Xaa is Glycine, gamma-Glu, Nle(epsilon-N3), or
      Lysine conjugated via its epsilon amine group to PEG2PEG2-gamma-
      Glu-C16N3 , PEG2-C5N3 or PEG2PEG2-C5N3, or Xaa is absent
```

```
<400> SEQUENCE: 16

Xaa Xaa Gln Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa Xaa
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is Tyrosine, Phenylalanine, Tryptophan, or
      other amino acid with an aromatic group
<220> FEATURE:
<221> NAME/KEY: PEPTIDE
<222> LOCATION: (1)..(31)
<223> OTHER INFORMATION: C-terminal amino acid optionally is linked to a
      protecting group or amidated
<220> FEATURE:
<221> NAME/KEY: PEPTIDE
<222> LOCATION: (1)..(31)
<223> OTHER INFORMATION: with the proviso that either X10 is a Lysine
      residue conjugated to a gamma-Glu-gamma-Glu-C16 and one of X20,
      X21, X24, X30, or X31 comprises the -alkyne or X20 is a Lysine
      residue conjugated to the PEG2PEG2-gamma-Glu-C18-OH or
<220> FEATURE:
<221> NAME/KEY: PEPETIDE
<222> LOCATION: (1)..(31)
<223> OTHER INFORMATION: the PEG2PEG2gamma-E-C20-OH and one of  X21,
      X24, X30, or X31
<220> FEATURE:
<221> NAME/KEY: MISC_FEATURE
<222> LOCATION: (2)..(2)
<223> OTHER INFORMATION: Xaa is aminoisobutyric acid (Aib), D-Serine
      (s), or alpha-methyl Serine (alpha-MS)
<220> FEATURE:
<221> NAME/KEY: MISC_FEATURE
<222> LOCATION: (9)..(9)
<223> OTHER INFORMATION: Xaa is Serine or alpha-methyl Aspartic acid
      (alpha-MD)
<220> FEATURE:
<221> NAME/KEY: MISC_FEATURE
<222> LOCATION: (10)..(10)
<223> OTHER INFORMATION: Xaa is Tyr or Lys conjugated to gamma-Glu-
      gamma-Glu-C16
<220> FEATURE:
<221> NAME/KEY: MISC_FEATURE
<222> LOCATION: (12)..(12)
<223> OTHER INFORMATION: Xaa is Isoleucine, Lysine, Leucine, or Serine
<220> FEATURE:
<221> NAME/KEY: MISC_FEATURE
<222> LOCATION: (14)..(14)
<223> OTHER INFORMATION: Xaa is Leu of alpha-methyl Leucine (alpha-ML)
<220> FEATURE:
<221> NAME/KEY: MISC_FEATURE
<222> LOCATION: (16)..(16)
<223> OTHER INFORMATION: Xaa is Glutamic acid, Asparagine, Serine,
      Alanine, or Aib
<220> FEATURE:
<221> NAME/KEY: MISC_FEATURE
<222> LOCATION: (17)..(17)
<223> OTHER INFORMATION: Xaa is Arginine or Lysine
<220> FEATURE:
<221> NAME/KEY: MISC_FEATURE
<222> LOCATION: (18)..(18)
<223> OTHER INFORMATION: Xaa is Alanine or Arginine
```

```
<220> FEATURE:
<221> NAME/KEY: MISC_FEATURE
<222> LOCATION: (20)..(20)
<223> OTHER INFORMATION: Xaa is Glutamine or Lysine conjugated via its
      epsilon amine group to PEG2-C5N3, PEG2PEG2-C5-alkyne, PEG2PEG2-
      gamma-Glu-C16-alkyne, PEG2PEG2-gamma-Glu-C18-OH, or PEG2PEG2gamma-
      E-C20-OH
<220> FEATURE:
<221> NAME/KEY: MISC_FEATURE
<222> LOCATION: (21)..(21)
<223> OTHER INFORMATION: Xaa is Asp, alpha-methyl Phenylalanine (alpha-
      MF), alpha-MD, Alkynylnorleucine (Norleucine conjugated via its
      epsilon carbon to an alkyne group (Nle(epsilon-alkyne))), or Lys
      conjugated to PEG2-C5-alkyne, PEG2PEG2-C5-alkyne, or
<220> FEATURE:
<221> NAME/KEY: MISC_FEATURE
<222> LOCATION: (24)..(24)
<223> OTHER INFORMATION: Xaa is Glutamine, Nle(epsilon-alkyne), or
      Lysine conjugated to PEG2PEG2-gamma-Glu-C16-alkyne
<220> FEATURE:
<221> NAME/KEY: MISC_FEATURE
<222> LOCATION: (25)..(25)
<223> OTHER INFORMATION: Xaa is Tryptophan or alpha-methyl Tryptophan
      (alpha-MW)
<220> FEATURE:
<221> NAME/KEY: MISC_FEATURE
<222> LOCATION: (26)..(26)
<223> OTHER INFORMATION: Xaa is Leucine or alpha-ML
<220> FEATURE:
<221> NAME/KEY: MISC_FEATURE
<222> LOCATION: (27)..(27)
<223> OTHER INFORMATION: Xaa is Leucine or L-methionine sulphone (2)
<220> FEATURE:
<221> NAME/KEY: MISC_FEATURE
<222> LOCATION: (28)..(28)
<223> OTHER INFORMATION: Xaa is Aspartic acid, Alanine, Lysine,
      Asparagine, gamma-Glu, Glutamine, or alpha-MD
<220> FEATURE:
<221> NAME/KEY: MISC_FEATURE
<222> LOCATION: (29)..(29)
<223> OTHER INFORMATION: Xaa is Threonine or Glycine
<220> FEATURE:
<221> NAME/KEY: MISC_FEATURE
<222> LOCATION: (30)..(30)
<223> OTHER INFORMATION: Xaa is Arginine, Lysine, or Nle(epsilon-
      alkyne), or Xaa is absent
<220> FEATURE:
<221> NAME/KEY: MISC_FEATURE
<222> LOCATION: (31)..(31)
<223> OTHER INFORMATION: X31 is Glycine, gamma-Glu, Nle(epsilon-alkyne),
      or Lysine conjugated via its epsilon amine group to
      PEG2PEG2-gamma-Glu-C16-alkyne, PEG2-C5-alkyne,
      PEG2PEG2-C5-alkyne, or Xaa is absent

<400> SEQUENCE: 17

Xaa Xaa Gln Gly Thr Phe Thr Ser Xaa Xaa Ser Xaa Tyr Xaa Asp Xaa
1               5                   10                  15

Xaa Xaa Ala Xaa Xaa Phe Val Xaa Xaa Xaa Xaa Xaa Xaa Xaa
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(32)
<223> OTHER INFORMATION: with the proviso that only one of X10, X20,
      X21, or X28, or X29 is Nle(epsilon-N3) or Lysine conjugated via
      its epsilon amine group to PEG2PEG2-gamma-Glu-C16- N3, PEG2-C5-
      N3, PEG2PEG2-C5- N3
```

```
<220> FEATURE:
<221> NAME/KEY: PEPTIDE
<222> LOCATION: (1)..(32)
<223> OTHER INFORMATION: C-terminal amino acid optionally is linked to a
      protecting group or amidated
<220> FEATURE:
<221> NAME/KEY: MISC_FEATURE
<222> LOCATION: (10)..(10)
<223> OTHER INFORMATION: Xaa is Valine, Nle(epsilon-N3), or Lysine
      conjugated via its epsilon amine group to PEG2PEG2-gamma-Glu-C16-
      N3, PEG2-C5- N3, or PEG2PEG2-C5- N3
<220> FEATURE:
<221> NAME/KEY: MISC_FEATURE
<222> LOCATION: (20)..(20)
<223> OTHER INFORMATION: Xaa is Lysine, Nle(epsilon-N3), or Lysine
      conjugated via its epsilon amine group to PEG2PEG2-gamma-Glu-C16-
      N3, PEG2-C5- N3, or PEG2PEG2-C5- N3
<220> FEATURE:
<221> NAME/KEY: MISC_FEATURE
<222> LOCATION: (21)..(21)
<223> OTHER INFORMATION: Xaa is glutamic acid, Nle(epsilon-N3), or
      Lysine conjugated via its epsilon amine group to PEG2PEG2-gamma-
      Glu-C16- N3, PEG2-C5- N3, or PEG2PEG2-C5- N3
<220> FEATURE:
<221> NAME/KEY: MISC_FEATURE
<222> LOCATION: (28)..(28)
<223> OTHER INFORMATION: Xaa is Lysine, Nle(epsilon-N3), or Lysine
      conjugated via its epsilon amine group to PEG2PEG2-gamma-Glu-C16-
      N3, PEG2-C5- N3, or PEG2PEG2-C5- N3
<220> FEATURE:
<221> NAME/KEY: MISC_FEATURE
<222> LOCATION: (32)..(32)
<223> OTHER INFORMATION: Xaa Nle(epsilon-N3), or Lysine conjugated via
      its epsilon amine group to PEG2PEG2-gamma-Glu-C16- N3, PEG2-C5-
      N3, PEG2PEG2-C5- N3 or absent

<400> SEQUENCE: 18

His Gly Glu Gly Thr Phe Thr Ser Asp Xaa Ser Ser Tyr Leu Glu Glu
1               5                   10                  15

Gln Ala Ala Xaa Xaa Phe Ile Ala Trp Leu Val Xaa Gly Gly Gly Xaa
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(32)
<223> OTHER INFORMATION: with the proviso that only one of X10, X20,
      X21, or X28, or X29 is Nle(epsilon-N3) or Lysine conjugated via
      its epsilon amine group to PEG2PEG2-gamma-Glu-C16-alkyne, PEG2-C5-
      alkyne, PEG2PEG2-C5-alkyne
<220> FEATURE:
<221> NAME/KEY: PEPTIDE
<222> LOCATION: (1)..(32)
<223> OTHER INFORMATION: C-terminal amino acid optionally is linked to a
      protecting group or amidated
<220> FEATURE:
<221> NAME/KEY: MISC_FEATURE
<222> LOCATION: (10)..(10)
<223> OTHER INFORMATION: Xaa is Valine, Nle(epsilon-alkyne), or Lysine
      conjugated via its epsilon amine group to PEG2PEG2-gamma-Glu-C16-
      alkyne, PEG2-C5-alkyne, or PEG2-C5-alkyne
<220> FEATURE:
<221> NAME/KEY: MISC_FEATURE
<222> LOCATION: (20)..(20)
<223> OTHER INFORMATION: Xaa is Lysine, Nle(epsilon-N3), or Lysine
      conjugated via its epsilon amine group to PEG2PEG2-gamma-Glu-C16-
      alkyne, PEG2-C5-alkyne, or PEG2PEG2-C5-alkyne
```

```
<220> FEATURE:
<221> NAME/KEY: MISC_FEATURE
<222> LOCATION: (21)..(21)
<223> OTHER INFORMATION: Xaa is glutamic acid, Nle(epsilon-alkyne), or
      Lysine conjugated via its epsilon amine group to PEG2PEG2-gamma-
      Glu-C16-alkyne, PEG2-C5-alkyne, or PEG2PEG2-C5-alkyne
<220> FEATURE:
<221> NAME/KEY: MISC_FEATURE
<222> LOCATION: (28)..(28)
<223> OTHER INFORMATION: Xaa is Lysine, Nle(epsilon-alkyne), or Lysine
      conjugated via its epsilon amine group to PEG2PEG2-gamma-Glu-C16-
      alkyne, PEG2-C5-alkyne, or PEG2PEG2-C5-alkyne
<220> FEATURE:
<221> NAME/KEY: MISC_FEATURE
<222> LOCATION: (32)..(32)
<223> OTHER INFORMATION: Xaa Nle(epsilon-alkyne), or Lysine conjugated
      via its epsilon amine group to PEG2PEG2-gamma-Glu-C16-alkyne,
      PEG2-C5-alkyne, PEG2PEG2-C5-alkyne or absent

<400> SEQUENCE: 19

His Gly Glu Gly Thr Phe Thr Ser Asp Xaa Ser Ser Tyr Leu Glu Glu
1               5                   10                  15

Gln Ala Ala Xaa Xaa Phe Ile Ala Trp Leu Val Xaa Gly Gly Gly Xaa
            20                  25                  30

<210> SEQ ID NO 20
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is His, Phe, or Tyr
<220> FEATURE:
<221> NAME/KEY: PEPTIDE
<222> LOCATION: (1)..(29)
<223> OTHER INFORMATION: C-terminal amino acid optionally is linked to a
      protecting group or amidated
<220> FEATURE:
<221> NAME/KEY: PEPTIDE
<222> LOCATION: (1)..(29)
<223> OTHER INFORMATION: with provisio that peptide comprises only one
      Nle(eN3)
<220> FEATURE:
<221> NAME/KEY: PEPTIDE
<222> LOCATION: (1)..(29)
<223> OTHER INFORMATION: optionally the peptide includes a C-terminal
      extension selected from the group consisting of KK(PEG2PEG2)-C5N3,
      KQ-Nle(eN3), SEQ ID NO:21, RG-Nle(eN3), SEQ ID NO:22, SEQ ID
      NO:23, Nle(eN3), KSEQ ID NO:24), and SEQ ID NO:25 linked to the
      amino acid at 29
<220> FEATURE:
<221> NAME/KEY: PEPTIDE
<222> LOCATION: (1)..(29)
<220> FEATURE:
<221> NAME/KEY: MISC_FEATURE
<222> LOCATION: (2)..(2)
<223> OTHER INFORMATION: Xaa is amionisobutyric acid (Aib), Gly, Ala,
      Ser, D-Serine (s)
<220> FEATURE:
<221> NAME/KEY: MISC_FEATURE
<222> LOCATION: (3)..(3)
<223> OTHER INFORMATION: Xaa is Glu or Gln
<220> FEATURE:
<221> NAME/KEY: MISC_FEATURE
<222> LOCATION: (7)..(7)
<223> OTHER INFORMATION: Xaa is Tyr
<220> FEATURE:
<221> NAME/KEY: MISC_FEATURE
<222> LOCATION: (9)..(9)
<223> OTHER INFORMATION: Xaa is Asp or Lys
```

-continued

```
<220> FEATURE:
<221> NAME/KEY: MISC_FEATURE
<222> LOCATION: (10)..(10)
<223> OTHER INFORMATION: Xaa is Tyr, Val, Leu, or Lys
<220> FEATURE:
<221> NAME/KEY: MISC_FEATURE
<222> LOCATION: (11)..(11)
<223> OTHER INFORMATION: Xaa is Ser or Val
<220> FEATURE:
<221> NAME/KEY: MISC_FEATURE
<222> LOCATION: (12)..(12)
<223> OTHER INFORMATION: Xaa is Lysine, Iso, or Serine
<220> FEATURE:
<221> NAME/KEY: MISC_FEATURE
<222> LOCATION: (13)..(13)
<223> OTHER INFORMATION: Xaa is Gln, Ala, or Tyr
<220> FEATURE:
<221> NAME/KEY: MISC_FEATURE
<222> LOCATION: (14)..(14)
<223> OTHER INFORMATION: Xaa is Leu, Met, or met sulphone
<220> FEATURE:
<221> NAME/KEY: MISC_FEATURE
<222> LOCATION: (15)..(15)
<223> OTHER INFORMATION: Xaa is Glu or Asp
<220> FEATURE:
<221> NAME/KEY: MISC_FEATURE
<222> LOCATION: (16)..(16)
<223> OTHER INFORMATION: Xaa is Glu, Asn, Ser, Ala, or Aib
<220> FEATURE:
<221> NAME/KEY: MISC_FEATURE
<222> LOCATION: (17)..(17)
<223> OTHER INFORMATION: Xaa is Glu, Iso, Gln, or Arg
<220> FEATURE:
<221> NAME/KEY: MISC_FEATURE
<222> LOCATION: (18)..(18)
<223> OTHER INFORMATION: Xaa is Ala, His, or Arg
<220> FEATURE:
<221> NAME/KEY: MISC_FEATURE
<222> LOCATION: (19)..(19)
<223> OTHER INFORMATION: Xaa is Val, Gln, or Ala
<220> FEATURE:
<221> NAME/KEY: MISC_FEATURE
<222> LOCATION: (20)..(20)
<223> OTHER INFORMATION: Xaa is Arg, Lys, Gln, or Aib
<220> FEATURE:
<221> NAME/KEY: MISC_FEATURE
<222> LOCATION: (21)..(21)
<223> OTHER INFORMATION: Xaa is Leu, Glu, or Asp
<220> FEATURE:
<221> NAME/KEY: MISC_FEATURE
<222> LOCATION: (23)..(23)
<223> OTHER INFORMATION: Xaa is Iso or Val
<220> FEATURE:
<221> NAME/KEY: MISC_FEATURE
<222> LOCATION: (24)..(24)
<223> OTHER INFORMATION: Xaa is Glu, Ala, Gln, Nle(epsilon-N3), or
      Lysine conjugated via its epsilon amino group to aPEG2PEG2-gamma-
      Glu-C16N3
<220> FEATURE:
<221> NAME/KEY: MISC_FEATURE
<222> LOCATION: (27)..(27)
<223> OTHER INFORMATION: Xaa is Lys, Val, Met, Nle(epsilonN3), or Nle
<220> FEATURE:
<221> NAME/KEY: MISC_FEATURE
<222> LOCATION: (28)..(28)
<223> OTHER INFORMATION: Xaa is Asp, Arg, Lys, Ala, or Asn
<220> FEATURE:
<221> NAME/KEY: MISC_FEATURE
<222> LOCATION: (29)..(29)
<223> OTHER INFORMATION: Xaa is Gly, Tyr, Gln, or Gly

<400> SEQUENCE: 20

Xaa Xaa Xaa Gly Thr Phe Xaa Ser Xaa Xaa Ser Xaa Tyr Xaa Xaa Xaa
1               5                   10                  15

Xaa Xaa Xaa Xaa Xaa Phe Xaa Xaa Trp Leu Xaa Xaa Xaa
            20                  25
```

```
<210> SEQ ID NO 21
<211> LENGTH: 11
<212> TYPE: PRT
<213> ORGANISM: Artificial Sequence
<220> FEATURE:
<223> OTHER INFORMATION: C-terminal extension
<220> FEATURE:
<221> NAME/KEY: MISC_FEATURE
<222> LOCATION: (11)..(11)
<223> OTHER INFORMATION: Xaa is Nle(epsilon-N3)

<400> SEQUENCE: 21

Gly Pro Ser Ser Gly Ala Pro Pro Pro Ser Xaa
 1               5                  10

<210> SEQ ID NO 22
<211> LENGTH: 16
<212> TYPE: PRT
<213> ORGANISM: Artificial Sequence
<220> FEATURE:
<223> OTHER INFORMATION: C-terminal Extension
<220> FEATURE:
<221> NAME/KEY: MISC_FEATURE
<222> LOCATION: (16)..(16)
<223> OTHER INFORMATION: Xaa is Nle(epsilon-N3)

<400> SEQUENCE: 22

Gly Pro Ser Ser Gly Ala Pro Pro Ser Lys Lys Lys Lys Lys Lys Xaa
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: C-terminal extension
<220> FEATURE:
<221> NAME/KEY: MISC_FEATURE
<222> LOCATION: (16)..(16)
<223> OTHER INFORMATION: Xaa is Nle(epsilon-N3)

<400> SEQUENCE: 23

Gly Gly Gly Gly Gly Ser Gly Gly Ser Gly Gly Gly Ser Ala Xaa
 1               5                  10                  15

<210> SEQ ID NO 24
<211> LENGTH: 14
<212> TYPE: PRT
<213> ORGANISM: Artificial Sequence
<220> FEATURE:
<223> OTHER INFORMATION: C-terminal extension
<220> FEATURE:
<221> NAME/KEY: MISC_FEATURE
<222> LOCATION: (14)..(14)
<223> OTHER INFORMATION: Xaa is Nle(epsilon-N3)

<400> SEQUENCE: 24

Lys Gly Leu Leu Asn Asp Trp Lys His Asn Ile Thr Gln Xaa
 1               5                  10

<210> SEQ ID NO 25
<211> LENGTH: 9
<212> TYPE: PRT
<213> ORGANISM: Artificial Sequence
<220> FEATURE:
<223> OTHER INFORMATION: C-terminal extension
<220> FEATURE:
<221> NAME/KEY: MISC_FEATURE
<222> LOCATION: (9)..(9)
<223> OTHER INFORMATION: Xaa is Nle(epsilon-N3)
```

```
<400> SEQUENCE: 25

Lys Arg Asn Lys Asn Asn Ile Ala Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: C-terminal extension

<400> SEQUENCE: 26

Lys Arg Asn Lys Asn Asn Ile Ala
1               5

<210> SEQ ID NO 27
<211> LENGTH: 10
<212> TYPE: PRT
<213> ORGANISM: Artificial Sequence
<220> FEATURE:
<223> OTHER INFORMATION: C-terminal extension

<400> SEQUENCE: 27

Gly Pro Ser Ser Gly Ala Pro Pro Pro Ser
1               5                   10

<210> SEQ ID NO 28
<211> LENGTH: 15
<212> TYPE: PRT
<213> ORGANISM: Artificial Sequence
<220> FEATURE:
<223> OTHER INFORMATION: C-terminal extension

<400> SEQUENCE: 28

Gly Pro Ser Ser Gly Ala Pro Pro Ser Lys Lys Lys Lys Lys Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: C-terminal extension

<400> SEQUENCE: 29

Gly Gly Gly Gly Gly Ser Gly Gly Gly Ser Gly Gly Gly Ser Ala
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: C-terminal extension

<400> SEQUENCE: 30

Lys Gly Leu Leu Asn Asp Trp Lys His Asn Ile Thr Gln
1               5                   10

<210> SEQ ID NO 31
<211> LENGTH: 29
<212> TYPE: PRT
<213> ORGANISM: Artificial Sequence
<220> FEATURE:
<223> OTHER INFORMATION: Peptide
```

```
<220> FEATURE:
<221> NAME/KEY: MISC_FEATURE
<222> LOCATION: (1)..(1)
<223> OTHER INFORMATION: Xaa is His, Phe, or Tyr
<220> FEATURE:
<221> NAME/KEY: PEPTIDE
<222> LOCATION: (1)..(29)
<223> OTHER INFORMATION: wherein the C-terminal amino acid optionally
      linked to a protecting group or amidated
<220> FEATURE:
<221> NAME/KEY: PEPTIDE
<222> LOCATION: (1)..(29)
<223> OTHER INFORMATION: the peptide includes a C-terminal extension
      selected from the group consisting of KK(PEG2PEG2)-C5N3,
      KQ-Nle(eN3), SEQ ID NO:21, RG-Nle(eN3), SEQ ID NO:22, SEQ ID
      NO:23, Nle(eN3), KSEQ ID NO:24), and SEQ ID NO:25 linked to the
      amino acid at 29
<220> FEATURE:
<221> NAME/KEY: PEPTIDE
<222> LOCATION: (1)..(29)
<223> OTHER INFORMATION: with proviso peptide comprises only one
      Nle(eN3)
<220> FEATURE:
<221> NAME/KEY: MISC_FEATURE
<222> LOCATION: (2)..(2)
<223> OTHER INFORMATION: Xaa is amionisobutyric acid (Aib), Gly, Ala,
      Ser, D-Serine (s)
<220> FEATURE:
<221> NAME/KEY: MISC_FEATURE
<222> LOCATION: (3)..(3)
<223> OTHER INFORMATION: Xaa is Glu or Gln
<220> FEATURE:
<221> NAME/KEY: MISC_FEATURE
<222> LOCATION: (7)..(7)
<223> OTHER INFORMATION: Xaa is Tyr
<220> FEATURE:
<221> NAME/KEY: MISC_FEATURE
<222> LOCATION: (9)..(9)
<223> OTHER INFORMATION: Xaa is Asp or Lys
<220> FEATURE:
<221> NAME/KEY: MISC_FEATURE
<222> LOCATION: (10)..(10)
<223> OTHER INFORMATION: Xaa is Tyr, Val, Leu, or Lys
<220> FEATURE:
<221> NAME/KEY: MISC_FEATURE
<222> LOCATION: (11)..(11)
<223> OTHER INFORMATION: Xaa is Ser or Val
<220> FEATURE:
<221> NAME/KEY: MISC_FEATURE
<222> LOCATION: (12)..(12)
<223> OTHER INFORMATION: Xaa is Lysine, Iso, or Serine
<220> FEATURE:
<221> NAME/KEY: MISC_FEATURE
<222> LOCATION: (13)..(13)
<223> OTHER INFORMATION: Xaa is Gln, Ala, or Tyr
<220> FEATURE:
<221> NAME/KEY: MISC_FEATURE
<222> LOCATION: (14)..(14)
<223> OTHER INFORMATION: Xaa is Leu, Met, or met sulphone
<220> FEATURE:
<221> NAME/KEY: MISC_FEATURE
<222> LOCATION: (15)..(15)
<223> OTHER INFORMATION: Xaa is Glu or Asp
<220> FEATURE:
<221> NAME/KEY: MISC_FEATURE
<222> LOCATION: (16)..(16)
<223> OTHER INFORMATION: Xaa is Glu, Asn, Ser, Ala, or Aib
<220> FEATURE:
<221> NAME/KEY: MISC_FEATURE
<222> LOCATION: (17)..(17)
<223> OTHER INFORMATION: Xaa is Glu, Iso, Gln, or Arg
<220> FEATURE:
<221> NAME/KEY: MISC_FEATURE
<222> LOCATION: (18)..(18)
<223> OTHER INFORMATION: Xaa is Ala, His, or Arg
<220> FEATURE:
<221> NAME/KEY: MISC_FEATURE
<222> LOCATION: (19)..(19)
<223> OTHER INFORMATION: Xaa is Val, Gln, or Ala
```

```
<220> FEATURE:
<221> NAME/KEY: MISC_FEATURE
<222> LOCATION: (20)..(20)
<223> OTHER INFORMATION: Xaa is Arg, Lys, Gln, or Aib
<220> FEATURE:
<221> NAME/KEY: MISC_FEATURE
<222> LOCATION: (21)..(21)
<223> OTHER INFORMATION: Xaa is Leu, Glu, or Asp
<220> FEATURE:
<221> NAME/KEY: MISC_FEATURE
<222> LOCATION: (23)..(23)
<223> OTHER INFORMATION: Xaa is Iso or Val
<220> FEATURE:
<221> NAME/KEY: MISC_FEATURE
<222> LOCATION: (24)..(24)
<223> OTHER INFORMATION: Xaa is Glu, Ala, Gln, Nle(epsilon-N3), or
      Lysine conjugated via its epsilon amino group to aPEG2PEG2-gamma-
      Glu-C16N3
<220> FEATURE:
<221> NAME/KEY: MISC_FEATURE
<222> LOCATION: (27)..(27)
<223> OTHER INFORMATION: Xaa is Lys, Val, Met, Nle(epsilonN3), or Nle
<220> FEATURE:
<221> NAME/KEY: MISC_FEATURE
<222> LOCATION: (28)..(28)
<223> OTHER INFORMATION: Xaa is Asp, Arg, Lys, Ala, or Asn
<220> FEATURE:
<221> NAME/KEY: MISC_FEATURE
<222> LOCATION: (29)..(29)
<223> OTHER INFORMATION: Xaa is Gly, Tyr, Gln, or Gly

<400> SEQUENCE: 31

Xaa Xaa Xaa Gly Thr Phe Xaa Ser Xaa Xaa Ser Xaa Tyr Xaa Xaa Xaa
1               5                   10                  15

Xaa Xaa Xaa Xaa Xaa Phe Xaa Xaa Trp Leu Xaa Xaa Xaa
            20                  25

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
```

```
<220> FEATURE:
<221> NAME/KEY: MISC_FEATURE
<222> LOCATION: (21)..(21)
<223> OTHER INFORMATION: Xaa21 is Nle(epsilon-N3)

<400> SEQUENCE: 35

His Xaa Gln Gly Thr Phe Thr Ser Asp Lys Ser Lys Tyr Leu Asp Glu
1               5                   10                  15

Arg Ala Ala Gln Xaa Phe Val Gln Trp Leu Leu Asp Thr
            20                  25

<210> SEQ ID NO 36
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 36

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Gly Arg Gly
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone
```

<400> SEQUENCE: 37

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Xaa Lys Gly Arg Gly
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 38

His Xaa Gln Gly Thr Phe Thr Ser Asp Lys Ser Leu Tyr Leu Asp Xaa
1               5                   10                  15

Arg Ala Ala Gln Asp Phe Val Xaa Trp Leu Leu Asn Thr Lys Xaa
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

```
<400> SEQUENCE: 39

His Xaa Gln Gly Thr Phe Thr Ser Asp Lys Ser Leu Tyr Leu Asp Xaa
1               5                   10                  15

Arg Ala Ala Gln Asp Phe Val Gln Trp Leu Leu Asn Thr Xaa Xaa
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 40

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Thr Xaa Xaa
            20                  25                  30

<210> SEQ ID NO 41
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
```

<400> SEQUENCE: 41

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Leu Asp Thr
            20                  25

<210> SEQ ID NO 42
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 42

His Xaa Gln Gly Thr Phe Thr Ser Asp Lys Ser Ser Tyr Leu Asp Xaa
1               5                   10                  15

Arg Ala Ala Gln Asp Phe Val Gln Trp Leu Leu Asn Thr Xaa Xaa
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 43

His Xaa Gln Gly Thr Phe Thr Ser Asp Lys Ser Ser Tyr Leu Asp Xaa
1               5                   10                  15

Arg Ala Ala Gln Asp Phe Val Xaa Trp Leu Leu Asn Thr Lys Xaa
            20                  25                  30

<210> SEQ ID NO 44
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 44

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Xaa Asp Thr
            20                  25

<210> SEQ ID NO 45
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 45

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Xaa Thr
            20                  25

```
<210> SEQ ID NO 46
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 46

His Xaa Gln Gly Thr Phe Thr Ser Asp Lys Ser Lys Tyr Leu Asp Asn
1               5                   10                  15

Lys Arg Ala Gln Asp Phe Val Xaa Trp Leu Leu Gln Thr
            20                  25

<210> SEQ ID NO 47
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 47

His Xaa Gln Gly Thr Phe Thr Ser Asp Lys Ser Lys Tyr Leu Asp Ser
1               5                   10                  15

Arg Arg Ala His Asp Phe Val Xaa Trp Leu Leu Asn Thr
            20                  25

<210> SEQ ID NO 48
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
```

```
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to   PEG2-C5N3

<400> SEQUENCE: 48

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Leu Asp Thr
            20                  25

<210> SEQ ID NO 49
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to   PEG2PEG2-C5N3

<400> SEQUENCE: 49

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Leu Asp Thr
            20                  25

<210> SEQ ID NO 50
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (20)..(20)
<223> OTHER INFORMATION: Lys20 is conjugated to   PEG2-C5N3
```

<400> SEQUENCE: 50

His Xaa Gln Gly Thr Phe Thr Ser Asp Lys Ser Lys Tyr Leu Asp Glu
1               5                   10                  15

Arg Ala Ala Lys Asp Phe Val Gln Trp Leu Leu Asp Thr
            20                  25

<210> SEQ ID NO 51
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (20)..(20)
<223> OTHER INFORMATION: Lys20 is conjugated to PEG2PEG2-C5N3

<400> SEQUENCE: 51

His Xaa Gln Gly Thr Phe Thr Ser Asp Lys Ser Lys Tyr Leu Asp Glu
1               5                   10                  15

Arg Ala Ala Lys Asp Phe Val Gln Trp Leu Leu Asp Thr
            20                  25

<210> SEQ ID NO 52
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: Xaa31 is Nle(epsilon-N3)

<400> SEQUENCE: 52

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Leu Asp Thr Lys Xaa
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Peptide

```
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: Xaa31 is Nle(epsilon-N3)

<400> SEQUENCE: 53

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Xaa
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: K31 conjugated to  PEG2-C5N3

<400> SEQUENCE: 54

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Lys
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: Lys31 is conjugated to PEG2PEG2-C5N3

<400> SEQUENCE: 55

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Lys
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (31)..(31)
<223> OTHER INFORMATION: X31 is gamma-Glu

<400> SEQUENCE: 56

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Leu Asp Thr Lys Xaa
            20                  25                  30

<210> SEQ ID NO 57
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (21)..(21)
<223> OTHER INFORMATION: Xaa21 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 57

His Xaa Gln Gly Thr Phe Thr Ser Asp Lys Ser Lys Tyr Leu Asp Glu
1               5                   10                  15

Arg Ala Ala Gln Xaa Phe Val Gln Trp Leu Xaa Asp Thr
            20                  25

<210> SEQ ID NO 58
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (21)..(21)
<223> OTHER INFORMATION: Xaa21 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD

<400> SEQUENCE: 58

His Xaa Gln Gly Thr Phe Thr Ser Asp Lys Ser Lys Tyr Leu Asp Glu
1               5                   10                  15

Arg Ala Ala Gln Xaa Phe Val Gln Trp Leu Xaa Xaa Thr
            20                  25

<210> SEQ ID NO 59
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (21)..(21)
<223> OTHER INFORMATION: Xaa21 is Nle(epsilon-N3)
<220> FEATURE:
<221> NAME/KEY: MISC_FEATURE
<222> LOCATION: (24)..(24)
<223> OTHER INFORMATION: Lys24 is conjugated to  PEG2PEG2-gamma-Glu-
      C16N3

<400> SEQUENCE: 59

His Xaa Gln Gly Thr Phe Thr Ser Asp Tyr Ser Lys Tyr Leu Asp Glu
1               5                  10                  15

Arg Ala Ala Gln Asp Phe Val Lys Trp Leu Leu Asp Thr
            20                  25

<210> SEQ ID NO 60
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (20)..(20)
<223> OTHER INFORMATION: Lys20 is conjugated to  PEG2PEG2-gamma-Glu-
      C16N3

<400> SEQUENCE: 60

His Xaa Gln Gly Thr Phe Thr Ser Asp Tyr Ser Lys Tyr Leu Asp Glu
1               5                  10                  15

Arg Ala Ala Lys Asp Phe Val Gln Trp Leu Leu Asp Thr
            20                  25

<210> SEQ ID NO 61
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (21)..(21)
<223> OTHER INFORMATION: Lys21 is conjugated to  PEG2PEG2gamma-Glu-C16N3

<400> SEQUENCE: 61

His Xaa Gln Gly Thr Phe Thr Ser Asp Tyr Ser Lys Tyr Leu Asp Glu
1               5                  10                  15

Arg Ala Ala Gln Lys Phe Val Gln Trp Leu Leu Asp Thr
            20                  25
```

```
<210> SEQ ID NO 62
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: Lys31 is conjugated to  PEG2PEG2-gamma-Glu-
      C16N3

<400> SEQUENCE: 62

His Xaa Gln Gly Thr Phe Thr Ser Asp Tyr Ser Lys Tyr Leu Asp Xaa
1               5                   10                  15

Arg Ala Ala Gln Asp Phe Val Gln Trp Leu Leu Asp Thr Lys Lys
            20                  25                  30

<210> SEQ ID NO 63
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 is conjugated to  PEG2PEG2-gamma-Glu-
      C18OH
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 63

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 64
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
```

-continued

```
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (20)..(20)
<223> OTHER INFORMATION: Lys20 is cojugated to  PEG2PEG2-gamma-Glu-C18-
      OH
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 64

His Xaa Gln Gly Thr Phe Thr Ser Asp Tyr Ser Lys Tyr Leu Asp Ala
1               5                   10                  15

Arg Ala Ala Lys Asp Phe Val Xaa Trp Leu Xaa Asp Thr
            20                  25

<210> SEQ ID NO 65
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (20)..(20)
<223> OTHER INFORMATION: Lys20 is conjugated to  PEG2PEG2-gamma-Glu-C20-
      OH
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 65

His Xaa Gln Gly Thr Phe Thr Ser Asp Tyr Ser Lys Tyr Leu Asp Ala
1               5                   10                  15

Arg Ala Ala Lys Asp Phe Val Xaa Trp Leu Xaa Asp Thr
            20                  25

<210> SEQ ID NO 66
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
```

```
<220> FEATURE:
<221> NAME/KEY: MISC_FEATURE
<222> LOCATION: (9)..(9)
<223> OTHER INFORMATION: Xaa9 is alpha-MD
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 66

His Xaa Gln Gly Thr Phe Thr Ser Xaa Lys Ser Lys Tyr Leu Asp Glu
1               5                   10                  15

Arg Ala Ala Gln Asp Phe Val Xaa Trp Leu Xaa Asp Thr
            20                  25

<210> SEQ ID NO 67
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (14)..(14)
<223> OTHER INFORMATION: Xaa14 is alpha-ML
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 67

His Xaa Gln Gly Thr Phe Thr Ser Asp Lys Ser Lys Tyr Xaa Asp Glu
1               5                   10                  15

Arg Ala Ala Gln Asp Phe Val Xaa Trp Leu Xaa Asp Thr
            20                  25

<210> SEQ ID NO 68
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (21)..(21)
<223> OTHER INFORMATION: Xaa21 is alpha-MD
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 68

His Xaa Gln Gly Thr Phe Thr Ser Asp Lys Ser Lys Tyr Leu Asp Glu
1               5                   10                  15

Arg Ala Ala Gln Xaa Phe Val Xaa Trp Leu Xaa Asp Thr
            20                  25

<210> SEQ ID NO 69
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (9)..(9)
<223> OTHER INFORMATION: Xaa9 is alpha-MF
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 69

His Xaa Gln Gly Thr Phe Thr Ser Xaa Lys Ser Lys Tyr Leu Asp Glu
1               5                   10                  15

Arg Ala Ala Gln Asp Xaa Val Xaa Trp Leu Xaa Asp Thr
            20                  25

<210> SEQ ID NO 70
<211> LENGTH: 29
<212> TYPE: PRT
<213> ORGANISM: Artificial Sequence
<220> FEATURE:
<223> OTHER INFORMATION: Peptide
```

```
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (25)..(25)
<223> OTHER INFORMATION: Xaa25 is alpha-MW
<220> FEATURE:
<221> NAME/KEY: MISC_FEATURE
<222> LOCATION: (27)..(27)
<223> OTHER INFORMATION: Xaa27 is methione sulfone

<400> SEQUENCE: 70

His Xaa Gln Gly Thr Phe Thr Ser Asp Lys Ser Lys Tyr Leu Asp Glu
1               5                   10                  15

Arg Ala Ala Gln Asp Phe Val Xaa Xaa Leu Xaa Asp Thr
            20                  25

<210> SEQ ID NO 71
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (26)..(26)
<223> OTHER INFORMATION: Xaa26 is alpha-ML
<220> FEATURE:
<221> NAME/KEY: MISC_FEATURE
<222> LOCATION: (27)..(27)
<223> OTHER INFORMATION: Xaa27 is methione sulfone

<400> SEQUENCE: 71

His Xaa Gln Gly Thr Phe Thr Ser Asp Lys Ser Lys Tyr Leu Asp Glu
1               5                   10                  15

Arg Ala Ala Gln Asp Phe Val Xaa Trp Xaa Xaa Asp Thr
            20                  25

<210> SEQ ID NO 72
<211> LENGTH: 29
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD

<400> SEQUENCE: 72

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Xaa Xaa Thr
            20                  25

<210> SEQ ID NO 73
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is alpha-MS
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 73

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Leu Ala Thr Lys Xaa
            20                  25                  30
```

```
<210> SEQ ID NO 74
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is alpha-Ms
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 74

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Leu Ala Thr Lys Xaa
            20                  25                  30

<210> SEQ ID NO 75
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is alpha-MS
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 75

His Xaa Gln Gly Thr Phe Thr Ser Asp Lys Ser Lys Tyr Leu Asp Ala
1               5                   10                  15

Arg Ala Ala Gln Asp Phe Val Xaa Trp Leu Leu Asp Thr
            20                  25

<210> SEQ ID NO 76
<211> LENGTH: 29
<212> TYPE: PRT
<213> ORGANISM: Artificial Sequence
<220> FEATURE:
<223> OTHER INFORMATION: Peptide
```

```
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is alpha-Ms
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 76

His Xaa Gln Gly Thr Phe Thr Ser Asp Lys Ser Lys Tyr Leu Asp Ala
1               5                   10                  15

Arg Ala Ala Gln Asp Phe Val Xaa Trp Leu Leu Asp Thr
            20                  25

<210> SEQ ID NO 77
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is alpha-Ms
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 77

His Xaa Val Gly Thr Phe Thr Ser Asp Lys Ser Lys Tyr Leu Asp Xaa
1               5                   10                  15

Arg Ala Ala Gln Asp Phe Val Xaa Trp Leu Xaa Asp Thr
            20                  25

<210> SEQ ID NO 78
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone

<400> SEQUENCE: 78

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Xaa Asp Gly Arg Gly
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD

<400> SEQUENCE: 79

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Xaa Xaa Gly Arg Gly
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 80

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Xaa Xaa
            20                  25                  30

<210> SEQ ID NO 81
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 81

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Xaa Asp Thr Xaa Xaa
            20                  25                  30

<210> SEQ ID NO 82
<211> LENGTH: 31
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 82

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Xaa Xaa Thr Xaa Xaa
            20                  25                  30

<210> SEQ ID NO 83
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(28)
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD
```

```
<400> SEQUENCE: 83

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Xaa Xaa Thr
            20                  25

<210> SEQ ID NO 84
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 84

His Xaa Glu Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 85
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to  PEG2PEG2-C5N3
<220> FEATURE:
<221> NAME/KEY: MISC_FEATURE
<222> LOCATION: (27)..(27)
<223> OTHER INFORMATION: Xaa27 is methione sulfone

<400> SEQUENCE: 85

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Xaa Asp Thr
            20                  25
```

```
<210> SEQ ID NO 86
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to  PEG2PEG2-C5N3
<220> FEATURE:
<221> NAME/KEY: MISC_FEATURE
<222> LOCATION: (27)..(27)
<223> OTHER INFORMATION: Xaa27 is methione sulfone
<220> FEATURE:
<221> NAME/KEY: MISC_FEATURE
<222> LOCATION: (28)..(28)
<223> OTHER INFORMATION: Xaa28 is alpha-MD

<400> SEQUENCE: 86

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Xaa Xaa Thr
            20                  25

<210> SEQ ID NO 87
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to  PEG2-C10N3

<400> SEQUENCE: 87

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Leu Asp Thr
            20                  25

<210> SEQ ID NO 88
<211> LENGTH: 29
<212> TYPE: PRT
<213> ORGANISM: Artificial Sequence
<220> FEATURE:
<223> OTHER INFORMATION: Peptide
```

```
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to  PEG2-C16N3

<400> SEQUENCE: 88

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Leu Asp Thr
            20                  25

<210> SEQ ID NO 89
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Lys24 is conjugated to PEG2PEG2- C5N3
<220> FEATURE:
<221> NAME/KEY: MISC_FEATURE
<222> LOCATION: (27)..(27)
<223> OTHER INFORMATION: Xaa27 is methione sulfone

<400> SEQUENCE: 89

His Xaa Gln Gly Thr Phe Thr Ser Asp Lys Ser Lys Tyr Leu Asp Xaa
1               5                   10                  15

Arg Ala Ala Gln Asp Phe Val Lys Trp Leu Xaa Asp Thr
            20                  25

<210> SEQ ID NO 90
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
```

```
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Lys24 is conjugated to PEG2PEG2- C5N3
<220> FEATURE:
<221> NAME/KEY: MISC_FEATURE
<222> LOCATION: (27)..(27)
<223> OTHER INFORMATION: Xaa27 is methione sulfone

<400> SEQUENCE: 90

His Xaa Gln Gly Thr Phe Thr Ser Asp Lys Ser Lys Tyr Leu Asp Xaa
1               5                   10                  15

Arg Ala Ala Gln Asp Phe Val Lys Trp Leu Xaa Asp Thr
            20                  25

<210> SEQ ID NO 91
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (20)..(20)
<223> OTHER INFORMATION: Lys20 is conjugated to PEG2PEG2-gamma-Glu-C10N3

<400> SEQUENCE: 91

His Xaa Gln Gly Thr Phe Thr Ser Asp Lys Ser Lys Tyr Leu Asp Glu
1               5                   10                  15

Arg Ala Ala Lys Asp Phe Val Gln Trp Leu Leu Asp Thr
            20                  25

<210> SEQ ID NO 92
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
```

```
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (20)..(20)
<223> OTHER INFORMATION: Lys20 is conjugated to PEG2PEG2-gamma-Glu-C16N3

<400> SEQUENCE: 92

His Xaa Gln Gly Thr Phe Thr Ser Asp Lys Ser Lys Tyr Leu Asp Glu
1               5                   10                  15

Arg Ala Ala Lys Asp Phe Val Gln Trp Leu Leu Asp Thr
            20                  25

<210> SEQ ID NO 93
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 93

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Xaa
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
```

-continued

```
<220> FEATURE:
<221> NAME/KEY: MISC_FEATURE
<222> LOCATION: (30)..(30)
<223> OTHER INFORMATION: Xaa30 is Nle(epsilon-N3)
<220> FEATURE:
<221> NAME/KEY: MISC_FEATURE
<222> LOCATION: (31)..(31)
<223> OTHER INFORMATION: Xaa31 is  gamma-Glu

<400> SEQUENCE: 94

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr Lys Xaa
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (31)..(31)
<223> OTHER INFORMATION: Xaa31 is conjugated to  PEG2PEG2-C5N3

<400> SEQUENCE: 95

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Lys
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (31)..(31)
<223> OTHER INFORMATION: Xaa31 is conjugated to  PEG2PEG2-C5N3
```

<400> SEQUENCE: 96

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr Lys Lys
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 97

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Leu Asp Thr Lys Xaa
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Lys24 is conjugated to PEG2-C5N3
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 98

His Xaa Gln Gly Thr Phe Thr Ser Asp Lys Ser Lys Tyr Leu Asp Xaa
1               5                   10                  15

Arg Ala Ala Gln Asp Phe Val Lys Trp Leu Leu Asp Thr Lys Xaa
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Lys24 is conjugated to PEG2PEG2-C5N3
<220> FEATURE:
<221> NAME/KEY: MISC_FEATURE
<222> LOCATION: (31)..(31)
<223> OTHER INFORMATION: Xaa31 is gamma-Glu

<400> SEQUENCE: 99

His Xaa Gln Gly Thr Phe Thr Ser Asp Lys Ser Lys Tyr Leu Asp Xaa
1               5                   10                  15

Arg Ala Ala Gln Asp Phe Val Lys Trp Leu Leu Asp Thr Lys Xaa
            20                  25                  30

<210> SEQ ID NO 100
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (21)..(21)
<223> OTHER INFORMATION: Lys21 is conjugated to PEG2PEG2-gamma-GluC16N3

<400> SEQUENCE: 100

His Xaa Gln Gly Thr Phe Thr Ser Asp Lys Ser Lys Tyr Leu Asp Glu
1               5                   10                  15

Arg Ala Ala Gln Lys Phe Val Gln Trp Leu Leu Asp Thr
            20                  25

```
<210> SEQ ID NO 101
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys24 is conjugated to PEG2PEG2-gamma-glu-C16N3

<400> SEQUENCE: 101

His Xaa Gln Gly Thr Phe Thr Ser Asp Lys Ser Lys Tyr Leu Asp Glu
1               5                   10                  15

Arg Ala Ala Gln Asp Phe Val Lys Trp Leu Leu Asp Thr
            20                  25

<210> SEQ ID NO 102
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 102

His Xaa Gln Gly Thr Phe Thr Ser Asp Lys Ser Lys Tyr Leu Asp Xaa
1               5                   10                  15

Arg Ala Ala Gln Asp Phe Val Xaa Trp Leu Met Asn Thr Lys Gln
            20                  25                  30

<210> SEQ ID NO 103
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
```

```
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 103

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 104
<211> LENGTH: 31
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (20)..(20)
<223> OTHER INFORMATION: Xaa20 is Nle(epsilon-N3)

<400> SEQUENCE: 104

His Xaa Gln Gly Thr Phe Thr Ser Asp Lys Ser Lys Tyr Leu Asp Xaa
1               5                   10                  15

Arg Ala Ala Xaa Asp Phe Val Gln Trp Leu Met Asn Thr Lys Gln
            20                  25                  30

<210> SEQ ID NO 105
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (20)..(20)
<223> OTHER INFORMATION: Xaa20 is Nle(epsilon-N3)

<400> SEQUENCE: 105

His Xaa Gln Gly Thr Phe Thr Ser Asp Lys Ser Lys Tyr Leu Asp Glu
1               5                   10                  15

Arg Ala Ala Xaa Asp Phe Val Gln Trp Leu Leu Asp Thr
            20                  25

<210> SEQ ID NO 106
<211> LENGTH: 32
<212> TYPE: PRT
<213> ORGANISM: Artificial Sequence
```

```
<220> FEATURE:
<223> OTHER INFORMATION: Peptide
<220> FEATURE:
<221> NAME/KEY: PEPTIDE
<222> LOCATION: (1)..(32)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (16)..(16)
<223> OTHER INFORMATION: Xaa16 is aib
<220> FEATURE:
<221> NAME/KEY: MISC_FEATURE
<222> LOCATION: (32)..(32)
<223> OTHER INFORMATION: Xaa32 is Nle(epsilon-N3)

<400> SEQUENCE: 106

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asn Thr Lys Gln Xaa
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(30)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (30)..(30)
<223> OTHER INFORMATION: Xaa30 is Nle(epsilon-N3)

<400> SEQUENCE: 107

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr Xaa
            20                  25                  30

<210> SEQ ID NO 108
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Lys10 conjugated to  gamma-Glu-gamma-Glu-C16
```

```
<400> SEQUENCE: 108

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 109
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (10)..(10)
<223> OTHER INFORMATION: Lys10 conjugated to  gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilon-N3)

<400> SEQUENCE: 109

His Xaa Glu Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 110
<211> LENGTH: 40
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(40)
<223> OTHER INFORMATION: C terminal amide
<220> FEATURE:
<221> NAME/KEY: MISC_FEATURE
<222> LOCATION: (40)..(40)
<223> OTHER INFORMATION: Xaa40 is Nle(epsilonN3)

<400> SEQUENCE: 110

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 111
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (2)..(2)
<223> OTHER INFORMATION: Xaa2 is aib
```

```
<220> FEATURE:
<221> NAME/KEY: MISC_FEATURE
<222> LOCATION: (32)..(32)
<223> OTHER INFORMATION: Xaa32 is Nle(epsilonN3)

<400> SEQUENCE: 111

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Xaa
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (32)..(32)
<223> OTHER INFORMATION: Xaa32 is Nle(epsilonN3)

<400> SEQUENCE: 112

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly Xaa
            20                  25                  30

<210> SEQ ID NO 113
<211> LENGTH: 45
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(45)
<223> OTHER INFORMATION: C terminal amide
<220> FEATURE:
<221> NAME/KEY: MISC_FEATURE
<222> LOCATION: (45)..(45)
<223> OTHER INFORMATION: Xaa45 is Nle(epsilonN3)

<400> SEQUENCE: 113

His Gly Glu Gly Thr Phe Thr Ser Lys Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Xaa
            35                  40                  45

<210> SEQ ID NO 114
<211> LENGTH: 45
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(45)
<223> OTHER INFORMATION: C terminal amide
<220> FEATURE:
<221> NAME/KEY: MISC_FEATURE
<222> LOCATION: (45)..(45)
<223> OTHER INFORMATION: Xaa45 is Nle(epsilonN3)
```

<400> SEQUENCE: 114

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Ser Gly Gly Gly Ser Ala Xaa
        35                  40                  45

<210> SEQ ID NO 115
<211> LENGTH: 30
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa30 is Nle(epsilonN3)

<400> SEQUENCE: 115

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Xaa
            20                  25                  30

<210> SEQ ID NO 116
<211> LENGTH: 43
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (43)..(43)
<223> OTHER INFORMATION: Xaa43 is Nle(epsilonN3)

<400> SEQUENCE: 116

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Xaa
        35                  40

<210> SEQ ID NO 117
<211> LENGTH: 40
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(40)
<223> OTHER INFORMATION: C-terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (20)..(20)
<223> OTHER INFORMATION: Xaa20 is aib
<220> FEATURE:
<221> NAME/KEY: MISC_FEATURE
<222> LOCATION: (40)..(40)
<223> OTHER INFORMATION: Xaa44 is Nle(epsilonN3)

<400> SEQUENCE: 117

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Xaa
        35                  40

<210> SEQ ID NO 118
<211> LENGTH: 40
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(40)
<223> OTHER INFORMATION: c TERMINAL AMIDE
<220> FEATURE:
<221> NAME/KEY: MISC_FEATURE
<222> LOCATION: (2)..(2)
<223> OTHER INFORMATION: Xaa is aib
<220> FEATURE:
<221> NAME/KEY: MISC_FEATURE
<222> LOCATION: (40)..(40)
<223> OTHER INFORMATION: Xaa40 is Nle(epsilonN3)

<400> SEQUENCE: 118

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Xaa
        35                  40

<210> SEQ ID NO 119
<211> LENGTH: 38
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (38)..(38)
<223> OTHER INFORMATION: Xaa38 is Nle(epsilonN3)

<400> SEQUENCE: 119

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala Xaa
        35

<210> SEQ ID NO 120
<211> LENGTH: 37
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (27)..(27)
<223> OTHER INFORMATION: Xaa27 is Nle(epsilonN3)

```
<400> SEQUENCE: 120

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Lys Asn Asn Ile Ala
            35

<210> SEQ ID NO 121
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C terminal amide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (24)..(24)
<223> OTHER INFORMATION: Xaa24 is Nle(epsilonN3)

<400> SEQUENCE: 121

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 122
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C terminal amide
<220> FEATURE:
<221> NAME/KEY: MISC_FEATURE
<222> LOCATION: (2)..(2)
<223> OTHER INFORMATION: Xaa is D-Ser
<220> FEATURE:
<221> NAME/KEY: MISC_FEATURE
<222> LOCATION: (24)..(24)
<223> OTHER INFORMATION: Xaa24 is Nle(epsilonN3)

<400> SEQUENCE: 122

His Xaa Gln Gly Thr Phe Thr Ser Asp Lys Ser Lys Tyr Leu Asp Glu
1               5                   10                  15

Arg Ala Ala Gln Asp Phe Val Xaa Trp Leu Leu Asp Thr
            20                  25

<210> SEQ ID NO 123
<211> LENGTH: 32
<212> TYPE: PRT
<213> ORGANISM: Artificial Sequence
<220> FEATURE:
<223> OTHER INFORMATION: Peptide
```

```
<220> FEATURE:
<221> NAME/KEY: PEPTIDE
<222> LOCATION: (1)..(32)
<223> OTHER INFORMATION: C terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib

<400> SEQUENCE: 123

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Met Asn Thr Lys Gln Xaa
            20                  25                  30

<210> SEQ ID NO 124
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(29)
<223> OTHER INFORMATION: C terminal amide
<220> FEATURE:
<221> NAME/KEY: MISC_FEATURE
<222> LOCATION: (2)..(2)
<223> OTHER INFORMATION: Xaa2 is D-Ser
<220> FEATURE:
<221> NAME/KEY: MISC_FEATURE
<222> LOCATION: (24)..(24)
<223> OTHER INFORMATION: Lys24 conjugated to PEG2PEG2-gamma-Glu-C16N3

<400> SEQUENCE: 124

His Xaa Gln Gly Thr Phe Thr Ser Asp Tyr Ser Lys Tyr Leu Asp Glu
1               5                   10                  15

Arg Ala Ala Gln Asp Phe Val Lys Trp Leu Leu Asp Thr
            20                  25

<210> SEQ ID NO 125
<211> LENGTH: 32
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(31)
<223> OTHER INFORMATION: C terminal amide
<220> FEATURE:
<221> NAME/KEY: MISC_FEATURE
<222> LOCATION: (2)..(2)
<223> OTHER INFORMATION: Xaa2 is aib
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16
<220> FEATURE:
<221> NAME/KEY: MISC_FEATURE
<222> LOCATION: (16)..(16)
<223> OTHER INFORMATION: Xaa16 is aib
```

```
<220> FEATURE:
<221> NAME/KEY: MISC_FEATURE
<222> LOCATION: (31)..(31)
<223> OTHER INFORMATION: Lys31 conjugated to PEG2PEG2-C5N3
<220> FEATURE:
<221> NAME/KEY: misc_feature
<222> LOCATION: (32)..(32)
<223> OTHER INFORMATION: Xaa can be any naturally occurring amino acid

<400> SEQUENCE: 125

His Xaa Gln Gly Thr Phe Thr Ser Asp Lys Ser Lys Tyr Leu Asp Xaa
1               5                   10                  15

Arg Ala Ala Gln Asp Phe Val Gln Trp Leu Leu Asp Thr Lys Lys Xaa
            20                  25                  30

<210> SEQ ID NO 126
<211> LENGTH: 21
<212> TYPE: PRT
<213> ORGANISM: Homo sapiens

<400> SEQUENCE: 126

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 127
<211> LENGTH: 30
<212> TYPE: PRT
<213> ORGANISM: Homo sapiens

<400> SEQUENCE: 127

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Lispro B chain

<400> SEQUENCE: 128

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Aspart B chain

<400> SEQUENCE: 129

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

```
<210> SEQ ID NO 130
<211> LENGTH: 30
<212> TYPE: PRT
<213> ORGANISM: Artificial Sequence
<220> FEATURE:
<223> OTHER INFORMATION: Glulisine B chain

<400> SEQUENCE: 130

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 131
<211> LENGTH: 21
<212> TYPE: PRT
<213> ORGANISM: Artificial Sequence
<220> FEATURE:
<223> OTHER INFORMATION: Glargine A chain

<400> SEQUENCE: 131

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 132
<211> LENGTH: 32
<212> TYPE: PRT
<213> ORGANISM: Artificial Sequence
<220> FEATURE:
<223> OTHER INFORMATION: Glargine B chain

<400> SEQUENCE: 132

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 133
<211> LENGTH: 21
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<220> FEATURE:
<221> NAME/KEY: MISC_FEATURE
<222> LOCATION: (21)..(21)
<223> OTHER INFORMATION: Xaa is asparagine or glycine

<400> SEQUENCE: 133

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 134
<211> LENGTH: 21
<212> TYPE: PRT
<213> ORGANISM: Artificial Sequence
<220> FEATURE:
<223> OTHER INFORMATION: Peptide
```

```
<220> FEATURE:
<221> NAME/KEY: MISC_FEATURE
<222> LOCATION: (1)..(1)
<223> OTHER INFORMATION: Xaa is selected from the group consisting of
      histidine and threonine
<220> FEATURE:
<221> NAME/KEY: MISC_FEATURE
<222> LOCATION: (5)..(5)
<223> OTHER INFORMATION: Xaa is selected from the group consisting of
      alanine, glycine and serine;
<220> FEATURE:
<221> NAME/KEY: MISC_FEATURE
<222> LOCATION: (6)..(6)
<223> OTHER INFORMATION: Xaa is selected from the group consisting of
      histidine, aspartic acid, glutamic acid, homocysteic acid and
      cysteic acid

<400> SEQUENCE: 134

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 135
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa is selected from the group consisting of
      phenylalanine and desamino-phenylalanine.
<220> FEATURE:
<221> NAME/KEY: MISC_FEATURE
<222> LOCATION: (5)..(5)
<223> OTHER INFORMATION: Xaa is selected from the group consisting of
      histidine and threonine;
<220> FEATURE:
<221> NAME/KEY: MISC_FEATURE
<222> LOCATION: (9)..(9)
<223> OTHER INFORMATION: Xaa is selected from the group consisting of
      alanine, glycine and serine;
<220> FEATURE:
<221> NAME/KEY: MISC_FEATURE
<222> LOCATION: (10)..(10)
<223> OTHER INFORMATION: Xaa is selected from the group consisting of
      histidine, aspartic acid, glutamic acid, homocysteic acid and
      cysteic acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa is threonine, alanine, or a threonine-
      arginine-arginine tripeptide

<400> SEQUENCE: 135

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Xaa Xaa
            20                  25

<210> SEQ ID NO 136
<211> LENGTH: 22
<212> TYPE: PRT
<213> ORGANISM: Artificial Sequence
<220> FEATURE:
<223> OTHER INFORMATION: Peptide
```

```
<220> FEATURE:
<221> NAME/KEY: MISC_FEATURE
<222> LOCATION: (1)..(1)
<223> OTHER INFORMATION: Xaa1 is glycine (G) or lysine (K)
<220> FEATURE:
<221> NAME/KEY: MISC_FEATURE
<222> LOCATION: (3)..(3)
<223> OTHER INFORMATION: Xaa3 is valine (V), glycine (G), or lysine (K)
<220> FEATURE:
<221> NAME/KEY: MISC_FEATURE
<222> LOCATION: (5)..(5)
<223> OTHER INFORMATION: Xaa5 is valine (V), glycine (G), or lysine (K)
<220> FEATURE:
<221> NAME/KEY: MISC_FEATURE
<222> LOCATION: (8)..(8)
<223> OTHER INFORMATION: Xaa8 is threonine (T) or histidine (H)
<220> FEATURE:
<221> NAME/KEY: MISC_FEATURE
<222> LOCATION: (9)..(9)
<223> OTHER INFORMATION: Xaa9 is serine (S) or lysine (K)
<220> FEATURE:
<221> NAME/KEY: MISC_FEATURE
<222> LOCATION: (10)..(10)
<223> OTHER INFORMATION: Xaa10 is isoleucine (I) or lysine
<220> FEATURE:
<221> NAME/KEY: MISC_FEATURE
<222> LOCATION: (13)..(13)
<223> OTHER INFORMATION: Xaa13 is leucine (L) or lysine (K)
<220> FEATURE:
<221> NAME/KEY: MISC_FEATURE
<222> LOCATION: (14)..(14)
<223> OTHER INFORMATION: Xaa14 is tyrosine (Y) or lysine (K)
<220> FEATURE:
<221> NAME/KEY: MISC_FEATURE
<222> LOCATION: (15)..(15)
<223> OTHER INFORMATION: Xaa15 is glutamine (Q) or lysine (K)
<220> FEATURE:
<221> NAME/KEY: MISC_FEATURE
<222> LOCATION: (18)..(18)
<223> OTHER INFORMATION: Xaa18 is asparagine (N) or lysine (K)
<220> FEATURE:
<221> NAME/KEY: MISC_FEATURE
<222> LOCATION: (21)..(21)
<223> OTHER INFORMATION: Xaa21 is asparagine (N) or glycine (G)
<220> FEATURE:
<221> NAME/KEY: MISC_FEATURE
<222> LOCATION: (22)..(22)
<223> OTHER INFORMATION: Xaa22 is arginine (R), lysine (K) or absent

<400> SEQUENCE: 136

Xaa Ile Xaa Glu Xaa Cys Cys Xaa Xaa Xaa Cys Ser Xaa Xaa Xaa Leu
1               5                   10                  15

Glu Xaa Tyr Cys Xaa Xaa
            20

<210> SEQ ID NO 137
<211> LENGTH: 35
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa1 is phenylalanine (F) or lysine (K)
<220> FEATURE:
<221> NAME/KEY: MISC_FEATURE
<222> LOCATION: (3)..(3)
<223> OTHER INFORMATION: Xaa3 is asparagine (N) or lysine (K)
<220> FEATURE:
<221> NAME/KEY: MISC_FEATURE
<222> LOCATION: (4)..(4)
<223> OTHER INFORMATION: Xaa4 is glutamine (Q) or lysine (K)
```

```
<220> FEATURE:
<221> NAME/KEY: MISC_FEATURE
<222> LOCATION: (16)..(16)
<223> OTHER INFORMATION: Xaa16 is tyrosine (Y) or lysine (K)
<220> FEATURE:
<221> NAME/KEY: MISC_FEATURE
<222> LOCATION: (17)..(17)
<223> OTHER INFORMATION: Xaa17 is leucine (L) or lysine (K)
<220> FEATURE:
<221> NAME/KEY: MISC_FEATURE
<222> LOCATION: (25)..(25)
<223> OTHER INFORMATION: Xaa25 is phenylalanine (F) or lysine (K)
<220> FEATURE:
<221> NAME/KEY: MISC_FEATURE
<222> LOCATION: (28)..(28)
<223> OTHER INFORMATION: Xaa28 is proline (P) or lysine (K)
<220> FEATURE:
<221> NAME/KEY: MISC_FEATURE
<222> LOCATION: (29)..(29)
<223> OTHER INFORMATION: Xaa29 is lysine (K) or proline (P)
<220> FEATURE:
<221> NAME/KEY: MISC_FEATURE
<222> LOCATION: (30)..(30)
<223> OTHER INFORMATION: Xaa30 is threonine (T) or absent
<220> FEATURE:
<221> NAME/KEY: MISC_FEATURE
<222> LOCATION: (31)..(31)
<223> OTHER INFORMATION: Xaa31 is arginine (R) if Xaa30 is threonine
      (T), or absent
<220> FEATURE:
<221> NAME/KEY: MISC_FEATURE
<222> LOCATION: (32)..(32)
<223> OTHER INFORMATION: Xaa32 is proline (P) if Xaa31 is arginine (R),
      or absent
<220> FEATURE:
<221> NAME/KEY: MISC_FEATURE
<222> LOCATION: (33)..(33)
<223> OTHER INFORMATION: Xaa33 is arginine (R) if Xaa32 is proline (P),
      or absent
<220> FEATURE:
<221> NAME/KEY: MISC_FEATURE
<222> LOCATION: (34)..(34)
<223> OTHER INFORMATION: Xaa34 is proline (P) if Xaa33 is arginine (R),
      or absent
<220> FEATURE:
<221> NAME/KEY: MISC_FEATURE
<222> LOCATION: (35)..(35)
<223> OTHER INFORMATION: Xaa35 is arginine (R) if Xaa34 is proline (P),
      or absent

<400> SEQUENCE: 137

Xaa Val Xaa Xaa His Leu Cys Gly Ser His Leu Val Glu Ala Leu Xaa
1               5                   10                  15

Xaa Val Cys Gly Glu Arg Gly Phe Xaa Tyr Thr Xaa Xaa Xaa Xaa Xaa
            20                  25                  30

Xaa Xaa Xaa
        35

<210> SEQ ID NO 138
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa1 is phenylalanine (F) or lysine (K)
<220> FEATURE:
<221> NAME/KEY: MISC_FEATURE
<222> LOCATION: (3)..(3)
<223> OTHER INFORMATION: Xaa3 is asparagine (N) or lysine (K)
```

```
<220> FEATURE:
<221> NAME/KEY: MISC_FEATURE
<222> LOCATION: (4)..(4)
<223> OTHER INFORMATION: Xaa4 is glutamine (Q) or lysine (K)
<220> FEATURE:
<221> NAME/KEY: MISC_FEATURE
<222> LOCATION: (16)..(16)
<223> OTHER INFORMATION: Xaa16 is tyrosine (Y) or lysine (K)
<220> FEATURE:
<221> NAME/KEY: MISC_FEATURE
<222> LOCATION: (17)..(17)
<223> OTHER INFORMATION: Xaa17 is leucine (L) or lysine (K)
<220> FEATURE:
<221> NAME/KEY: MISC_FEATURE
<222> LOCATION: (25)..(25)
<223> OTHER INFORMATION: Xaa25 is phenylalanine (F) or lysine (K)
<220> FEATURE:
<221> NAME/KEY: MISC_FEATURE
<222> LOCATION: (28)..(28)
<223> OTHER INFORMATION: Xaa28 is proline (P) or lysine (K)
<220> FEATURE:
<221> NAME/KEY: MISC_FEATURE
<222> LOCATION: (29)..(29)
<223> OTHER INFORMATION: Xaa29 is lysine (K) or proline (P)

<400> SEQUENCE: 138

Xaa Val Xaa Xaa His Leu Cys Gly Ser His Leu Val Glu Ala Leu Xaa
1               5                   10                  15

Xaa Val Cys Gly Glu Arg Gly Phe Xaa Tyr Thr Xaa Xaa
            20                  25

<210> SEQ ID NO 139
<211> LENGTH: 35
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa1 is phenylalanine (F) or lysine (K)
<220> FEATURE:
<221> NAME/KEY: MISC_FEATURE
<222> LOCATION: (3)..(3)
<223> OTHER INFORMATION: Xaa3 is asparagine (N) or lysine (K)
<220> FEATURE:
<221> NAME/KEY: MISC_FEATURE
<222> LOCATION: (4)..(4)
<223> OTHER INFORMATION: Xaa4 is glutamine (Q) or lysine (K)
<220> FEATURE:
<221> NAME/KEY: MISC_FEATURE
<222> LOCATION: (16)..(16)
<223> OTHER INFORMATION: Xaa16 is tyrosine (Y) or lysine (K)
<220> FEATURE:
<221> NAME/KEY: MISC_FEATURE
<222> LOCATION: (17)..(17)
<223> OTHER INFORMATION: Xaa17 is leucine (L) or lysine (K)
<220> FEATURE:
<221> NAME/KEY: MISC_FEATURE
<222> LOCATION: (25)..(25)
<223> OTHER INFORMATION: Xaa25 is phenylalanine (F) or lysine (K)
<220> FEATURE:
<221> NAME/KEY: MISC_FEATURE
<222> LOCATION: (28)..(28)
<223> OTHER INFORMATION: Xaa28 is proline (P) or lysine (K)
<220> FEATURE:
<221> NAME/KEY: MISC_FEATURE
<222> LOCATION: (29)..(29)
<223> OTHER INFORMATION: Xaa29 is lysine (K) or proline (P)
```

<400> SEQUENCE: 139

Xaa Val Xaa Xaa His Leu Cys Gly Ser His Leu Val Glu Ala Leu Xaa
1               5                   10                  15

Xaa Val Cys Gly Glu Arg Gly Phe Xaa Tyr Thr Xaa Xaa Thr Arg Pro
            20                  25                  30

Arg Pro Arg
        35

<210> SEQ ID NO 140
<211> LENGTH: 33
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa1 is phenylalanine (F) or lysine (K)
<220> FEATURE:
<221> NAME/KEY: MISC_FEATURE
<222> LOCATION: (3)..(3)
<223> OTHER INFORMATION: Xaa3 is asparagine (N) or lysine (K)
<220> FEATURE:
<221> NAME/KEY: MISC_FEATURE
<222> LOCATION: (4)..(4)
<223> OTHER INFORMATION: Xaa4 is glutamine (Q) or lysine (K)
<220> FEATURE:
<221> NAME/KEY: MISC_FEATURE
<222> LOCATION: (16)..(16)
<223> OTHER INFORMATION: Xaa16 is tyrosine (Y) or lysine (K)
<220> FEATURE:
<221> NAME/KEY: MISC_FEATURE
<222> LOCATION: (17)..(17)
<223> OTHER INFORMATION: Xaa17 is leucine (L) or lysine (K)
<220> FEATURE:
<221> NAME/KEY: MISC_FEATURE
<222> LOCATION: (25)..(25)
<223> OTHER INFORMATION: Xaa25 is phenylalanine (F) or lysine (K)
<220> FEATURE:
<221> NAME/KEY: MISC_FEATURE
<222> LOCATION: (28)..(28)
<223> OTHER INFORMATION: Xaa28 is proline (P) or lysine (K)
<220> FEATURE:
<221> NAME/KEY: MISC_FEATURE
<222> LOCATION: (29)..(29)
<223> OTHER INFORMATION: Xaa29 is lysine (K) or proline (P)

<400> SEQUENCE: 140

Xaa Val Xaa Xaa His Leu Cys Gly Ser His Leu Val Glu Ala Leu Xaa
1               5                   10                  15

Xaa Val Cys Gly Glu Arg Gly Phe Xaa Tyr Thr Xaa Xaa Thr Arg Pro
            20                  25                  30

Arg

<210> SEQ ID NO 141
<211> LENGTH: 29
<212> TYPE: PRT
<213> ORGANISM: Artificial Sequence
<220> FEATURE:
<223> OTHER INFORMATION: Petide
<220> FEATURE:
<221> NAME/KEY: PEPTIDE
<222> LOCATION: (1)..(29)
<223> OTHER INFORMATION: C terminal amide
<220> FEATURE:
<221> NAME/KEY: MISC_FEATURE
<222> LOCATION: (2)..(2)
<223> OTHER INFORMATION: Xaa2 is D-Ser

```
<220> FEATURE:
<221> NAME/KEY: MISC_FEATURE
<222> LOCATION: (10)..(10)
<223> OTHER INFORMATION: Lys10 conjugated to gamma-Glu-gamma-Glu-C16

<400> SEQUENCE: 141

His Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Thr
            20                  25
```

INSULIN DIMER-INCRETIN CONJUGATES

CROSS-REFERENCE TO RELATED APPLICATIONS

This application is a U.S. National Phase application under 35 U.S.C. § 371 of PCT Application No. PCT/US2017/028706, filed Apr. 21, 2017, which published as WO2017/189342 A1 on Nov. 2, 2017, and claims priority under 35 U.S.C. § 365(b) from U.S. provisional patent application No. 62/327,516, filed Mar. 26, 2016.

REFERENCE TO SEQUENCE LISTING SUBMITTED ELECTRONICALLY

The sequence listing of the present application is submitted electronically via EFS-Web as an ASCII formatted sequence listing with a file name "24325USPCT-SEQLIST-02OCT2018.txt", creation date of Oct. 2, 2018, and a size of 144 Kb. This sequence listing submitted via EFS-Web is part of the specification and is herein incorporated by reference in its entirety.

BACKGROUND OF THE INVENTION

(1) Field of the Invention

The present invention relates to insulin dimers conjugated to peptides having at least one incretin activity.

(2) Description of Related Art

Insulin is an essential therapy for type 1 diabetes mellitus (T1DM) patients and many type 2 mellitus diabetics (T2DMs), prescribed to close to one third of U.S. patients among all anti-diabetic drug users in the past decade. The worldwide market for insulins was US$20.4 billion in 2013 and is growing at a faster rate than all other anti-diabetic agents combined. However, challenges of current insulin therapies, including narrow TI to hypoglycemia and body weight gain, limit their wider adoption and potential for patients to achieve ideal glycemic control.

In addition to prandial insulin secretion in response to meals, the pancreas releases insulin at a "basal" rate, governed largely by plasma glucose levels to maintain appropriate fasting glucose regulation. This is achieved mainly by controlling hepatic glucose release, through endogenous insulin's hepato-preferring action. Modern insulin analogs include rapid acting and basal insulins, as well as mixtures of these two. Rapid-acting insulin analogs (RAA) are developed to control post-prandial hyperglycemia while insulins with extended duration of action regulate basal glucose levels. Long-acting insulins are used by all T1DM (in combination with prandial injections) and the majority of T2DM patients start their insulin therapy from a basal product. Basal insulin consumption is growing rapidly as the worldwide diabetes population (particularly T2DM) soars.

Despite continuous development efforts over the past several decades, available long-acting insulins are still not optimized compared to physiological basal insulin. This is partially because major focus was on improving PK flatness of these analogs but not fixing the relative over-insulinization of peripheral tissues, which contributes to increased hypoglycemia risk. As a result, hypoglycemia remains a key medical risk with huge burden on patients and causes significant morbidity and mortality.

BRIEF SUMMARY OF THE INVENTION

The present invention provides compounds comprising two insulin molecules covalently linked to form an insulin dimer, which may activate the insulin receptor with regular insulin-like potency but with reduced maximum activity, and, which is conjugated to a peptide molecule having at least one incretin activity (insulin dimer conjugate). For example, the peptide may be a glucagon-like peptide 1 (GLP-1) peptide or a GLP-1 peptide analog, a glucagon (GCG)-related peptide, wherein the GCG-related peptide has agonist activity at the GLP-1 receptor, the GIP receptor, the GCG receptor, or combinations thereof. In particular embodiments, the GCG-related peptide has agonist activity at the GLP-1 and GCG receptors; or, the GLP-1 and GIP receptors; or, the GLP-1, GIP, and GCG receptors.

While insulin is the most effective therapy for controlling diabetes, its optimal benefit is limited due to its narrow therapeutic index (TI) between ideal glycemic control and hypoglycemic risk. Selected insulin dimers, which in particular embodiments, function as insulin receptor partial agonists (IRPA), offer unique tissue-specific actions and gradual dose-responsiveness in glucose lowering, resulting in basal insulin-like molecules with a lower hypoglycemia risk compared to existing insulin products. Conjugating the insulin dimer to a peptide displaying at least one incretin activity provides an insulin dimer conjugate having robust glycemic control without an increase in hypoglycemia.

The present invention provides an insulin dimer conjugate comprising an insulin dimer conjugated via a non-peptide linking moiety to a peptide having at least one incretin activity selected from glucagon-like 1 (GLP-1) activity, the glucagon (GCG) activity, and gastric inhibitory protein (GIP) activity, wherein the insulin dimer comprises a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides.

In a further aspect of the insulin dimer conjugate, the first and second insulin or insulin analog heterodimers are the same or the first and second insulin or insulin analog heterodimers are different.

In a further still aspect of the insulin dimer conjugate, the linking moiety covalently links the first insulin or insulin analog heterodimer and the second insulin or insulin analog heterodimer via the epsilon amino group of a lysine residue at or near the carboxy terminus of their respective B-chain polypeptides, e.g., the Lysine residues at position B29 of the respective B chain peptides.

In particular aspects of the insulin dimer conjugate, each A-chain polypeptide independently comprises the amino acid sequence $GX_2X_3EQCCX_8SICSLYQLX_{17}NX_{19}CX_{23}$ (SEQ ID NO:133) and each B-chain polypeptide independently comprises the amino acid sequence $X_{25}LCGX_{29}X_{30}LVEALYLVCGERGFX27YTX_{31}X_{32}$ (SEQ ID NO:134) or $X_{22}VNQX_{25}X_{26}CGX_{29}X_{30}LVEALYLVCGERGFX_{27}YTX_{31}X_{32}X_{33}X_{34}X_{35}$ (SEQ ID NO:135) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxy-phenylalanine, alanine, or 4-amino phenylalanine; $X_{23}$ is asparagine or glycine; $X_{22}$ is or phenylalanine and desamino-phenylalanine; $X_{25}$ is histidine or threonine; X26 is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In particular aspects of the insulin dimer conjugate, the first and second insulins or insulin analogs are independently native human insulin, insulin lispro, insulin aspart, desB30 insulin, or insulin glargine.

In particular aspects of the insulin dimer conjugate, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin dimer conjugate, the linking moiety is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect, the linking moiety is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

In particular embodiments, the insulin dimer comprises an alkyne and the peptide is a GLP-1 analog having the amino acid sequence (SEQ ID NO: 20)
$X_1X_2X_3GTFX_7SX_9X_{10}X_{11}X_{12}X_{13}X_{14}X_{15}X_{16}X_{17}X_{18}X_{19}X_{20}$ $X_{21}FX_{23}X_{24}WLX_{27}X_{28}X_{29}$ wherein $X_1$ is histidine (H), phenylalanine (F), or tyrosine (Y); $X_2$ is serine (S), D-serine (s), glycine (G), alanine (A), or α-aminoisobutyric acid (Aib or U); $X_3$ is glutamic acid (E) or glutamine (Q); $X_7$ is tyrosine (Y); $X_9$ is aspartic acid (D) or lysine (K); $X_{10}$ is lysine (K), valine (V), leucine (L), or Y; $X_{11}$ is S or valine (V); $X_{12}$ is K, isoleucine (I), or S; $X_{13}$ is Q, A, or Y; $X_{14}$ is methionine (M), methionine sulphone, or L; $X_{15}$ is E, or D; $X_{16}$ is K, Aib, E, G, or S; $X_{17}$ is E; I, Q, or arginine (R); $X_{18}$ is A, H, or R; $X_{19}$ is V, Q, or A; $X_{20}$ is R, K, Q, or Aib; $X_{21}$ is L, E, or D; $X_{23}$ is I or V; $X_{24}$ is E, A, Q, or Asparagine (N), $X_{27}$ is K, V, K, M, or norleucine (Nle); $X_{28}$ is D, R, K, A, or N; $X_{29}$ is G, Y, Q, or G; optionally, the peptide includes a C-terminal extension selected from the group consisting of KK, KQ, KRNKNNIA (SEQ ID NO:26), GPSSGAPPPS (SEQ ID NO:27), GPSSGAPPSKKKKKK (SEQ ID NO:28), GGGGGSGGGSGGGSA (SEQ ID NO:29, and KGLLNDWKHNITQ (SEQ ID NO:30) linked to the amino acid at position 29; and the peptide optionally includes a protecting group that, if present, is joined to the C-terminal carboxy group of the peptide.

In particular embodiments, the insulin dimer comprises an alkyne and the peptide is a GLP-1 analog having the amino acid sequence (SEQ ID NO: 31)
$X_1X_2X_3GTFX_7SX_9X_{10}X_{11}X_{12}X_{13}X_{14}X_{15}X_{16}X_{17}X_{18}X_{19}X_{20}$ $X_{21}FX_{23}X_{24}WLX_{27}X_{28}X_{29}$ wherein $X_1$ is histidine (H), phenylalanine (F), or tyrosine (Y); $X_2$ is serine (S), D-serine (s), glycine (G), alanine (A), or α-aminoisobutyric acid (Aib or U); $X_3$ is glutamic acid (E) or glutamine (Q); $X_7$ is tyrosine (Y); $X_9$ is aspartic acid (D) or lysine (K); $X_{10}$ is lysine (K), valine (V), leucine (L), or Y; $X_{11}$ is S or valine (V); $X_{12}$ is K, isoleucine (I), or S; $X_{13}$ is Q, A, or Y; $X_{14}$ is methionine (M), methionine sulphone, or L; $X_{15}$ is E, or D; $X_{16}$ is K, Aib, E, G, or S; $X_{17}$ is E; I, Q, or arginine (R); $X_{18}$ is A, H, or R; $X_{19}$ is V, Q, or A; $X_{20}$ is R, K, Q, or Aib; $X_{21}$ is L, E, or D; $X_{23}$ is I or V; $X_{24}$ is E, A, Q, Asparagine (N), Nle(εN$_3$), or K(PEG$_2$PEG$_2$γEC$_{16}$N$_3$) $X_{27}$ is K, V, K, M, Nle(εN$_3$), or norleucine (Nle); $X_{28}$ is D, R, K, A, or N; $X_{29}$ is G, Y, Q, or G; optionally, the peptide includes a C-terminal extension selected from the group consisting of KK(PEG$_2$PEG$_2$)-C$_5$N$_3$, KQ-Nle(εN$_3$), GPSSGAPPPS-Nle(εN$_3$) (SEQ ID NO:21), RG-Nle(εN$_3$), GPSSGAPPSKKKKKK-Nle(εN$_3$) (SEQ ID NO:22), GGGGGSGGGSGGGSA-Nle(εN$_3$) (SEQ ID NO:23), Nle(εN$_3$), KGLLNDWKHNITQ-Nle(εN$_3$) (SEQ ID NO:24), KRNKNNIA-Nle(εN$_3$) (SEQ ID NO:25), KRNKNNIA (SEQ ID NO:26), GPSSGAPPPS (SEQ ID NO:27), GPSSGAPPSKKKKKK (SEQ ID NO:28), GGGGGSGGGSGGGSA (SEQ ID NO:29, and KGLLNDWKHNITQ (SEQ ID NO:30) linked to the amino acid at position 29; and the peptide optionally includes a protecting group that, if present, is joined to the C-terminal carboxy group of the peptide, and further the proviso that the peptide comprises only one Nle(εN$_3$).

In particular embodiments of the insulin dimer conjugate, the peptide is a glucagon derived peptide that comprises the amino acid sequence (SEQ ID NO: 1)
HSQGTFTSDYSKYLDERAAQDFVQWLLDT which further includes at least the following modifications: (i) a substitution of the amino acid at position 2 with an amino acid that renders the peptide resistant to cleavage and inactivation by dipeptidyl peptidase IV; (ii) a lipid moiety covalently linked to the peptide at a lysine residue substituted for the tyrosine residue at position 10 or the glutamine at position 20 of the peptide; (iii) an azide group or an alkyne group conjugated to an amino acid at position 20, 21, 24, 30, or 31; (iv) 0, 1, 2, 3, 4, 5, 6, 7, 8, 9, or 10 additional amino acid substitutions or additions in addition to the substitution at position 2; and optionally, a protecting group that is joined to the C-terminal carboxy group and/or the N-terminal amino group. In embodiments in which the modified glucagon peptide has agonist activity at the GIP receptor, the Histidine at position 1 is substituted with Tyrosine, Phenylalanine, Tryptophan, or other amino acid with an aromatic group.

In particular embodiments of the insulin dimer conjugate, the peptide comprises a substitution of the Ser at position 2 with Val, Ile, Asp, Glu, Met, Trp, Asn, D-Ala, D-Ser, α-methyl-Ser, α-methyl-D-Ser or α-aminoisobutyric acid (aib or U). In particular embodiments, the Ser is substituted with D-Ser or aib. These substitutions at position 2 render the peptide resistant to DPP-4 and active at the GLP-1 receptor. Peptides with a substitution are co-agonists of the GCG and the GLP-1 receptors.

In particular embodiments of the insulin dimer conjugate, the Gln at position 3 is substituted with Glu or Asp. These substitutions increase the selectivity of the peptide for the GLP-1 receptor over the GCG receptor. Such peptides have little or no activity at the GCG receptor.

In particular embodiments of the insulin dimer conjugate, the peptide includes a substitution of the Glu at position 16 with aib, Asn, Ser, or Ala.

In particular embodiments of the insulin dimer conjugate, the His at position 1 is substituted with an amino acid with a large aromatic group, for example, Tyr, Phe, or Trp. When this substitution includes the substitution of the Ser at position 2 with aib or D-Ser, the substitution of the Lys at position 12 with Ile and substitution of the Glu at position 16 with aib, the peptide has agonist activity at the GCG, GLP-1 and GIP receptors. When the peptide further includes a substitution of the Gln at position 3 with Glu or Asp, the peptide has agonist activity at the GLP-1 and GIP receptors.

The present invention further provides pharmaceutical formulations comprising one or more of the insulin dimer conjugates disclosed herein and a pharmaceutically acceptable carrier.

The present invention further provides for the use of the insulin dimer conjugate disclosed herein in a treatment for a metabolic disease.

The present invention further provides for the use of an insulin dimer conjugate disclosed herein for the manufacture of a medicament for the treatment of a metabolic disease.

The present invention further provides a method for treating a metabolic disease, comprising administering to an individual in need an effective amount of insulin dimer conjugate disclosed herein to treat the metabolic disease. In particular embodiments, the metabolic disease is diabetes.

The present invention further provides an insulin dimer conjugate comprising the formula

A-LM-B wherein A is an insulin dimer comprising a first insulin or insulin analog heterodimer and a second insulin or insulin analog heterodimer each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a linking moiety joining the side chain of an amino acid at or near the carboxy terminus of the two respective B-chain polypeptides, for example the Lys residues at position 29 of the B-chains (B29); B is a peptide having at least one incretin activity (e.g., glucagon, GLP-1, or GIP) or a glucagon peptide modified to have agonist activity at the GLP1 receptor, agonist activity at the GIP receptor, agonist the GLP1 and GCG receptors, or agonist activity at the GLP-1 and GIP receptors, or agonist activity at the GLP-1, GIP, and GCG receptors; LM is a first linking moiety comprising a cyclic or acyclic bisamide, a heterocycle or a substituted heterocycle, a $C_1$-$C_{50}$ hydrocarbon chain or substituted hydrocarbon chain, a $PEG_n$ wherein n is 1-50, a $(PEG_2)_n$ wherein n is 1-50, a $(PEG_2)_n$-$(\gamma Glu)_p$-$C_n$ wherein each n is independently 1-50 and p is 1 or 2, a $(PEG_2)_n$-$C_n$ wherein each n is independently is 1-50, a $(PEG)_n(PEG)_n$ wherein each n is independently 1-50, a $PEG_n$-$(Lys$-$(\gamma Glu)_p$-$C_n)$-$C_n$ wherein each n is independently 1-50 and p is 1 or 2, or a $C_5$-$Lys(\gamma E$-$C_n)$-$PEG_n$ wherein each n is independently 1-50.

In particular embodiments of the insulin dimer conjugate, LM is selected from a straight or branched, saturated or unsaturated, optionally substituted $C_{1-30}$ hydrocarbon chain wherein one or more methylene units of Y are optionally and independently replaced by —O—, —S—, —N(R)—, —C(O)—, C(O)O—, OC(O)—, —N(R)C(O)—, —C(O)N(R)—, —S(O)—, —S(O)_2—, —N(R)SO_2—, SO_2N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In particular embodiments of the insulin dimer conjugate, the human insulin molecule or human insulin analog molecule may be a heterodimer comprising an A-chain peptide and a B-chain peptide connected by disulfide linkages characteristic of human insulin or a single-chain insulin molecule comprising the disulfide linkages characteristic of human insulin wherein the C-terminal amino acid of the B-chain is conjugated to the N-terminal amino acid of the A-chain peptide by a peptide or non-peptide linker.

In particular embodiments of the insulin dimer conjugate, the N-terminal amino acid of the A-chain peptide of the human insulin or human insulin analog molecule is conjugated via LM to an amino acid in the incretin peptide or modified glucagon peptide; or, the N-terminal amino acid of the B-chain peptide of the human insulin or human insulin analog molecule is conjugated via LM to an amino acid in the incretin peptide or modified glucagon peptide; or, the epsilon amino group of a Lysine in the human insulin or human insulin analog molecule is conjugated via LM to an amino acid in the incretin peptide or modified glucagon peptide.

In particular embodiments of the insulin dimer conjugate, the N-terminal amino acid of the A-chain peptide of the human insulin or human insulin analog molecule is conjugated via LM to a Lysine or Norleucine in the incretin peptide or modified glucagon peptide; or, the N-terminal amino acid of the B-chain peptide of the human insulin or human insulin analog molecule is conjugated via LM to a Lysine or Norleucine in the incretin peptide or modified glucagon peptide; or, the epsilon amino group of a Lysine in the human insulin or human insulin analog molecule is conjugated via LM to a Lysine or Norleucine in the incretin peptide or modified glucagon peptide.

In particular embodiments of the insulin dimer conjugate, LM comprises the formula

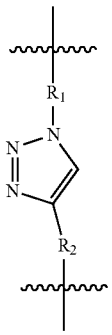

wherein $R_1$ and $R_2$ independently comprise a $C_1$-$C_{50}$ hydrocarbon chain or substituted hydrocarbon chain, a $PEG_n$ wherein n is 1-50, a $(PEG_2)_n$ wherein n is 1-50, a $(PEG_2)_n$-$(\gamma Glu)_p$-$C_n$ wherein each n is independently 1-50 and p is 1 or 2, a $(PEG_2)_n$-$C_n$ wherein each n is independently is 1-50, a $(PEG)_n(PEG)_n$ wherein each n is independently 1-50, a $PEG_n$-$(Lys$-$(\gamma Glu)_p$-$C_n)$-$C_n$ wherein each n is independently 1-50 and p is 1 or 2, and a $C_5$-$Lys(\gamma E$-$C_n)$-$PEG_n$ wherein each n is independently 1-50, and wherein the bond between the linking moiety and the insulin dimer and the incretin peptide are indicated by the wavy lines with the proviso that if the bond adjacent to $R_1$ is to the insulin dimer then the bond adjacent to $R_2$ is to the incretin peptide or that if the bond adjacent to $R_1$ is to the incretin peptide then the bond adjacent to $R_2$ is to the insulin dimer.

In particular embodiments of the insulin dimer conjugate having the formula A-LM-B, the insulin dimer A is represented by the formula $$D^1\text{-}L\text{-}D^2$$

wherein $D^1$ and $D^2$ are each independently an insulin or insulin analog polypeptide, wherein each insulin polypeptide is a heterodimer comprising an A-chain polypeptide and a B-chain polypeptide linked together through interchain disulfide bonds; L is a second linking moiety wherein one end of the second linker moiety is attached to an amino acid residue at or near the carboxyl group of $D^1$ and the other end of the second linker moiety is attached to an amino acid residue at or near the carboxyl end of $D^2$.

In a further aspect of the insulin dimer, $D^1$ and $D^2$ are the same or wherein $D^1$ and $D^2$ are different.

In a further aspect of the insulin dimer, the second linking moiety L covalently links $D^1$ and $D^2$ via the epsilon amino group of a lysine residue at or near the carboxy terminus of $D^1$ and $D^2$.

In particular aspects of the insulin dimer, the second linking moiety L may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In a further still aspect of the insulin dimer, the second linking moiety L is an acyl moiety, —C(O)RC(O)—, where R is alkyl chain, poly(ethylene glycol) (PEG) chain, amide-containing chain, triazole(s)-containing chain, cyclooctyne-containing moiety, a substituted acyl chain, or a polyethylene glycol (PEG) chain.

In a further aspect of the insulin dimer, the second linking moiety L is a C2-C20 acyl moiety.

In particular aspects, the second linking moiety L is an alkyldioyl, —C(O)(CH$_2$)$_n$C(O)—, wherein n=0-45, including but not limited to an oxalyl (C2) moiety, a succinyl (C4) moiety, an adipoyl (C6) moiety, a suberyol (C8) moiety, a decanedioyl (C10) moiety, a dodecanedioyl (C12) moiety, a tetradecanedioyl (C14) moiety, or a hexadecanedioyl (C16) moiety.

In particular aspects of the insulin dimer, each A-chain polypeptide independently comprises the amino acid sequence $GX_2X_3EQCCX_8SICSLYQLX_{17}NX_{19}CX_{23}$ (SEQ ID NO:133) and each B-chain polypeptide independently comprises the amino acid sequence $X_{25}LCGX_{29}X_{30}LVEALYLVCGERGFX27YTX_{31}X_{32}$ (SEQ ID NO:134) or $X_{22}VNQX_{25}X_{26}CGX_{29}X_{30}LVEALYLVCGERGFX_{27}YTX_{31}X_{32}X_{33}X_{34}X_{35}$ (SEQ ID NO:135) wherein $X_2$ is isoleucine or threonine; $X_3$ is valine, glycine, or leucine; $X_8$ is threonine or histidine; $X_{17}$ is glutamic acid or glutamine; $X_{19}$ is tyrosine, 4-methoxy-phenylalanine, alanine, or 4-amino phenylalanine; $X_{23}$ is asparagine or glycine; $X_{22}$ is or phenylalanine and desamino-phenylalanine; $X_{25}$ is histidine or threonine; X26 is leucine or glycine; $X_{27}$ is phenylalanine or aspartic acid; $X_{29}$ is alanine, glycine, or serine; $X_{30}$ is histidine, aspartic acid, glutamic acid, homocysteic acid, or cysteic acid; $X_{31}$ is aspartic acid, proline, or lysine; $X_{32}$ is lysine or proline; $X_{33}$ is threonine, alanine, or absent; $X_{34}$ is arginine or absent; and $X_{35}$ is arginine or absent; with the proviso at least one of $X_{31}$ or $X_{32}$ is lysine.

In a further aspect of the insulin dimer, $D^1$ and $D^2$ are independently native human insulin, insulin lispro, insulin aspart, desB30 insulin, or insulin glargine.

Further provided are compositions comprising any one of the aforementioned insulin receptor partial agonists or insulin dimer and a pharmaceutically acceptable carrier.

The present invention provides a method for treating diabetes comprising administering to an individual with diabetes a therapeutically effective amount of a composition comprising any one of the aforementioned insulin dimer conjugate. In particular aspects the diabetes is Type 1 diabetes, Type 2 diabetes, or gestational diabetes.

The present invention provides for the use of a composition for the treatment of diabetes comprising any one of the aforementioned insulin dimer conjugate. In particular aspects the diabetes is Type 1 diabetes, Type 2 diabetes, or gestational diabetes.

The present invention provides for the use of any one of the insulin dimer conjugate herein for the manufacture of a medicament for the treatment of diabetes. In particular aspects the diabetes is Type 1 diabetes, Type 2 diabetes, or gestational diabetes.

Definitions

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus. The term is a generic term that designates the 51 amino acid heterodimer comprising the A-chain peptide having the amino acid sequence shown in SEQ ID NO: 126 and the B-chain peptide having the amino acid sequence shown in SEQ ID NO: 127, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has less than 80% (or 70%) activity at the insulin receptor as does native insulin. These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Connecting peptide or C-peptide—as used herein, the term refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide, the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Amino acid substitution—as used herein refers to the replacement of one amino acid residue by a different amino acid residue.

Conservative amino acid substitution—as used herein, the term is defined herein as exchanges within one of the following five groups:
 I. Small aliphatic, nonpolar or slightly polar residues:
  Ala, Ser, Thr, Pro, Gly;
 II. Polar, negatively charged residues and their amides:
  Asp, Asn, Glu, Gln, cysteic acid and homocysteic acid;
 III. Polar, positively charged residues:
  His, Arg, Lys; Ornithine (Orn)
 IV. Large, aliphatic, nonpolar residues:
  Met, Leu, Ile, Val, Cys, Norleucine (Nle), homocysteine
 V. Large, aromatic residues:
  Phe, Tyr, Trp, acetyl phenylalanine Treat—As used herein, the term "treat" (or "treating", "treated", "treatment", etc.) refers to the administration of an IRPA of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition. For example, as used herein the term "treating diabetes" will refer in general to maintaining glucose blood levels near normal levels and may include increasing or decreasing blood glucose levels depending on a given situation.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents suitable for administration to or by an individual in need. The term also encompasses any of the agents approved by a regulatory agency of the US Federal government or listed in the US Pharmacopeia for use in animals, including humans.

Pharmaceutically acceptable salt—as used herein, the term refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium, zinc, and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." It is not always possible to determine the optimal effective amount prior to administration to or by an individual in need thereof. However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

DETAILED DESCRIPTION OF THE INVENTION

Figure 1:
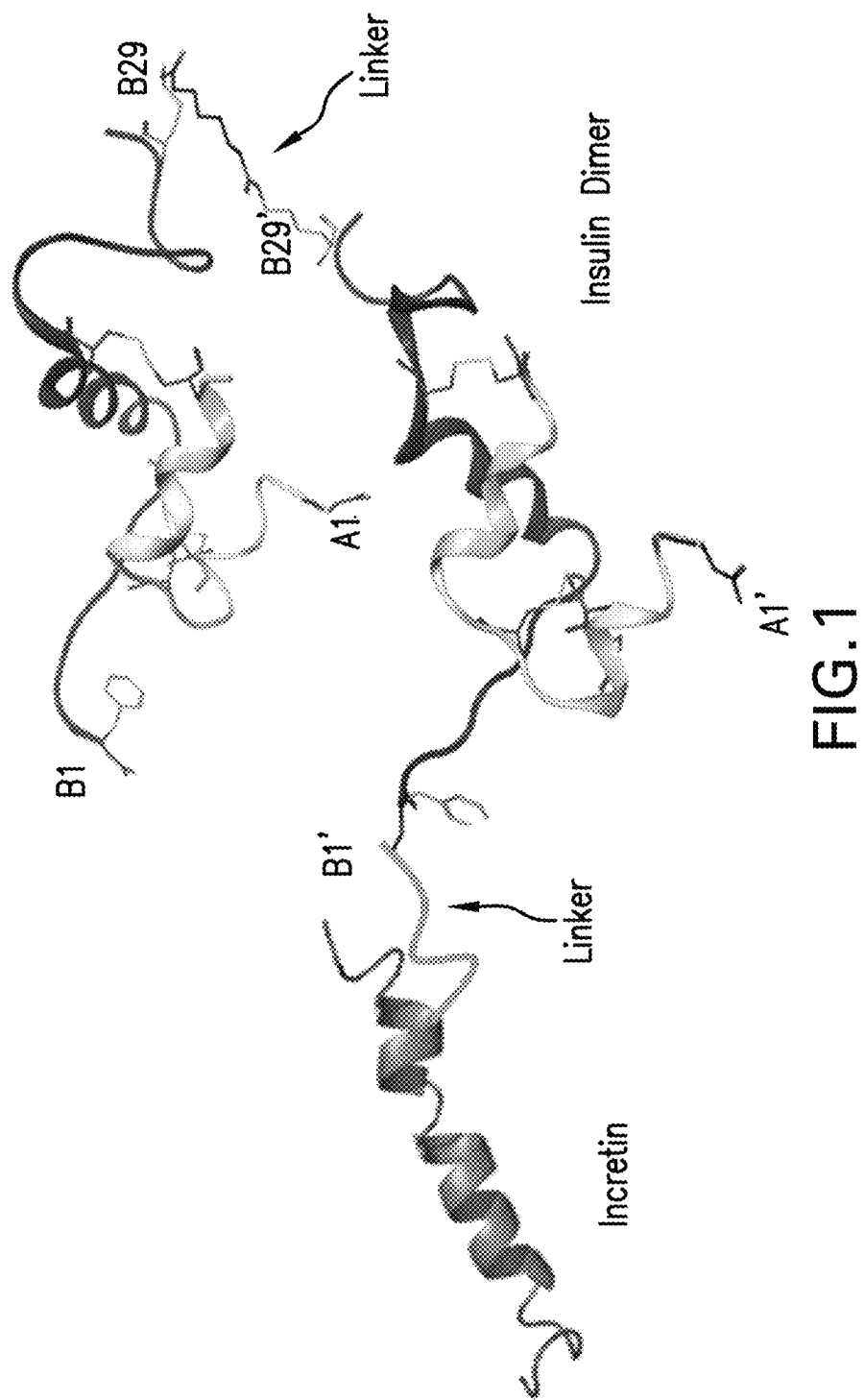
FIG. 1 shows a 3D schematic representation of an insulin dimer-incretin conjugate wherein a second linking moiety links the B1' amino acid of one of the insulin heterodimers comprising the insulin dimer to an amino acid in an incretin peptide. The insulin dimer is shown with a suberoyl linker (first linking moiety) linking the B29 Lysine of one heterodimer to the B29' Lysine of the other heterodimer.
Figure 2A:
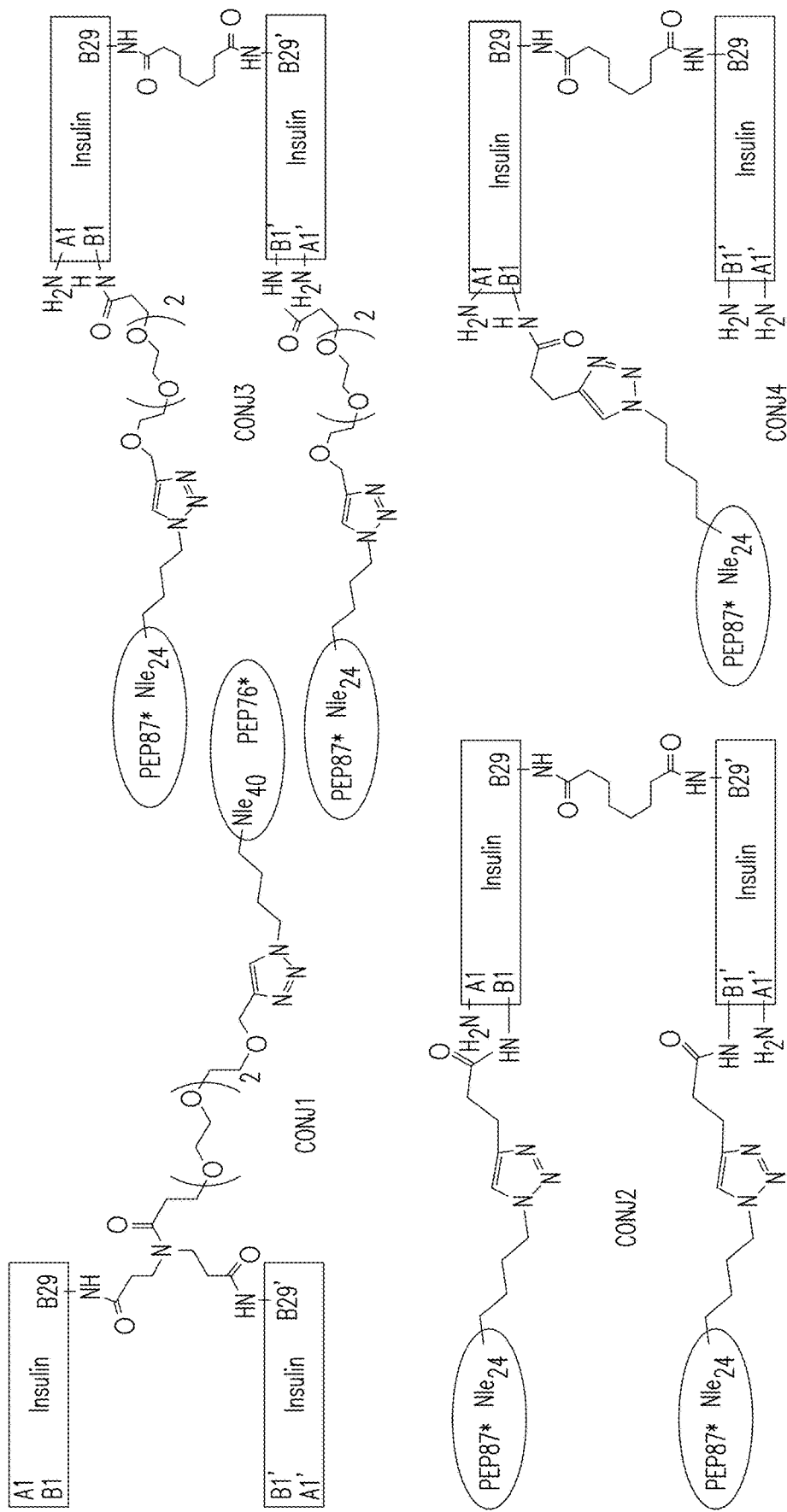
FIG. 2A, FIG. 2B, FIG. 2C, FIG. 2D, FIG. 2E, FIG. 2F, and FIG. 2G show various exemplary insulin dimer-incretin conjugates in which the Norleucine (Nle) amino acid of particular incretins is conjugated to an insulin dimer. The "*" indicates that the incretin has the amino acid sequence and structure of the indicated incretin but wherein the azide group of the linker has formed a 1,2-disubstituted 1,2,3-triazole with the alkyne group.
Figure 2B:
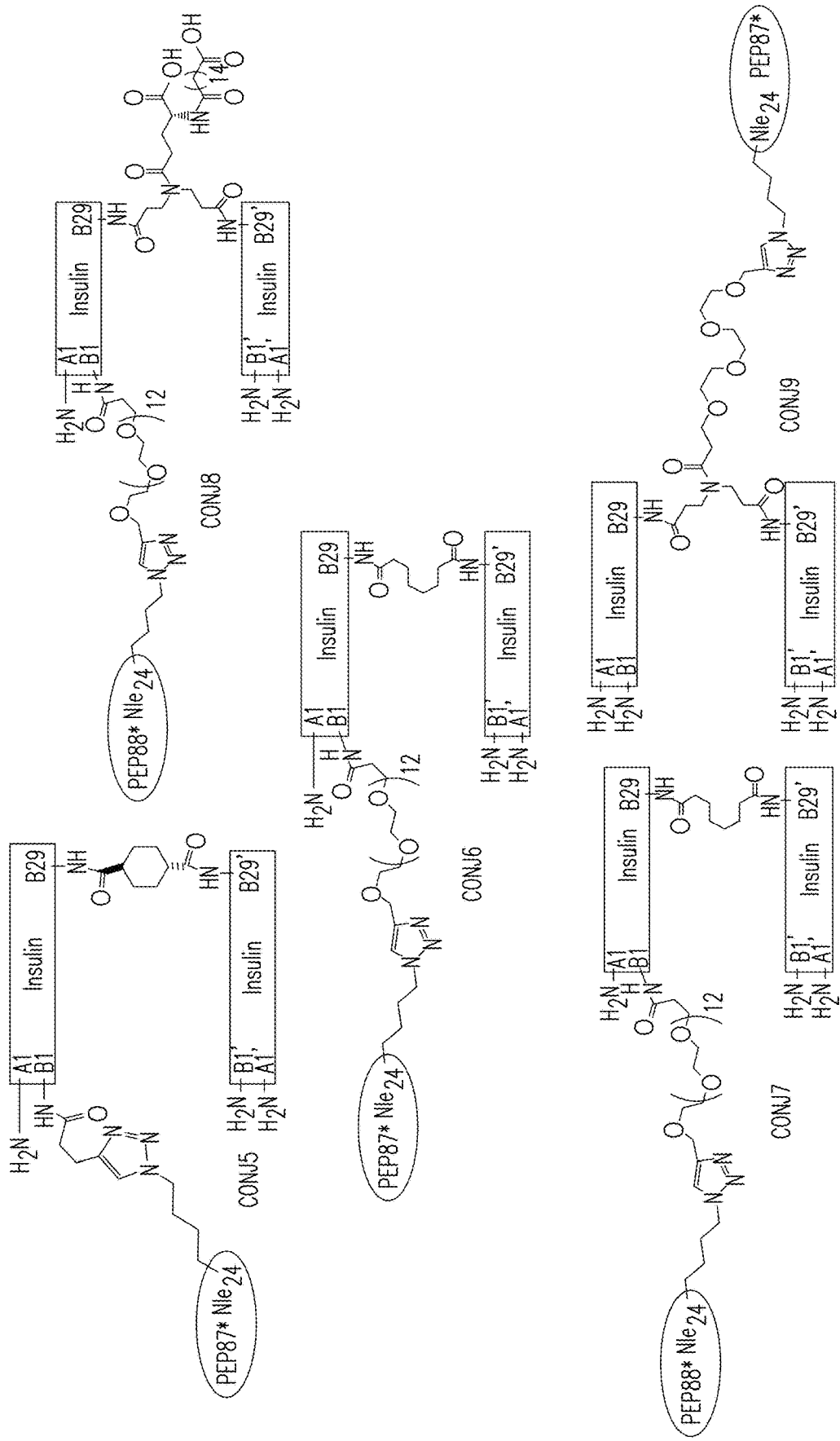
Figure 2C:
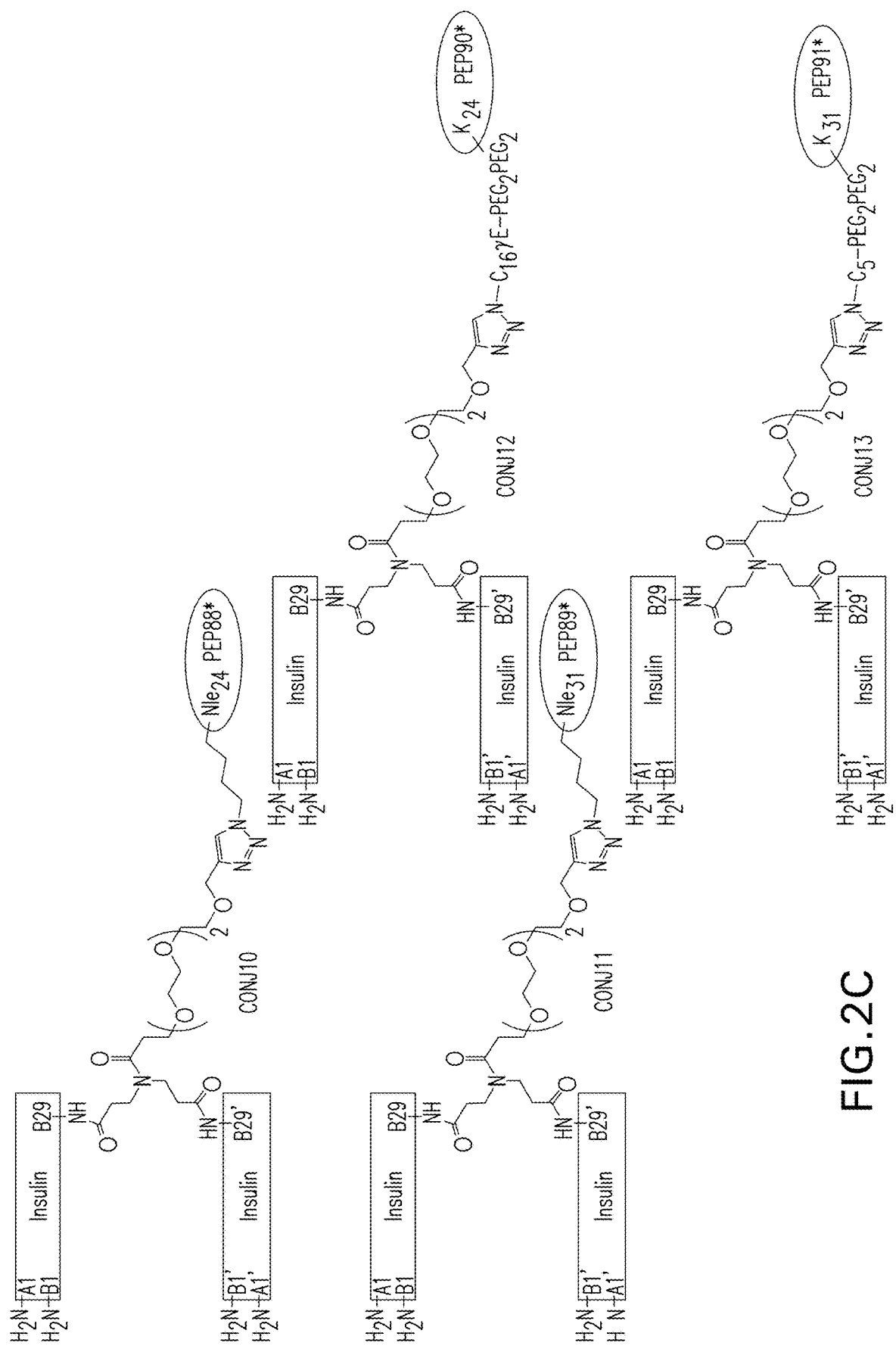
Figure 2D:
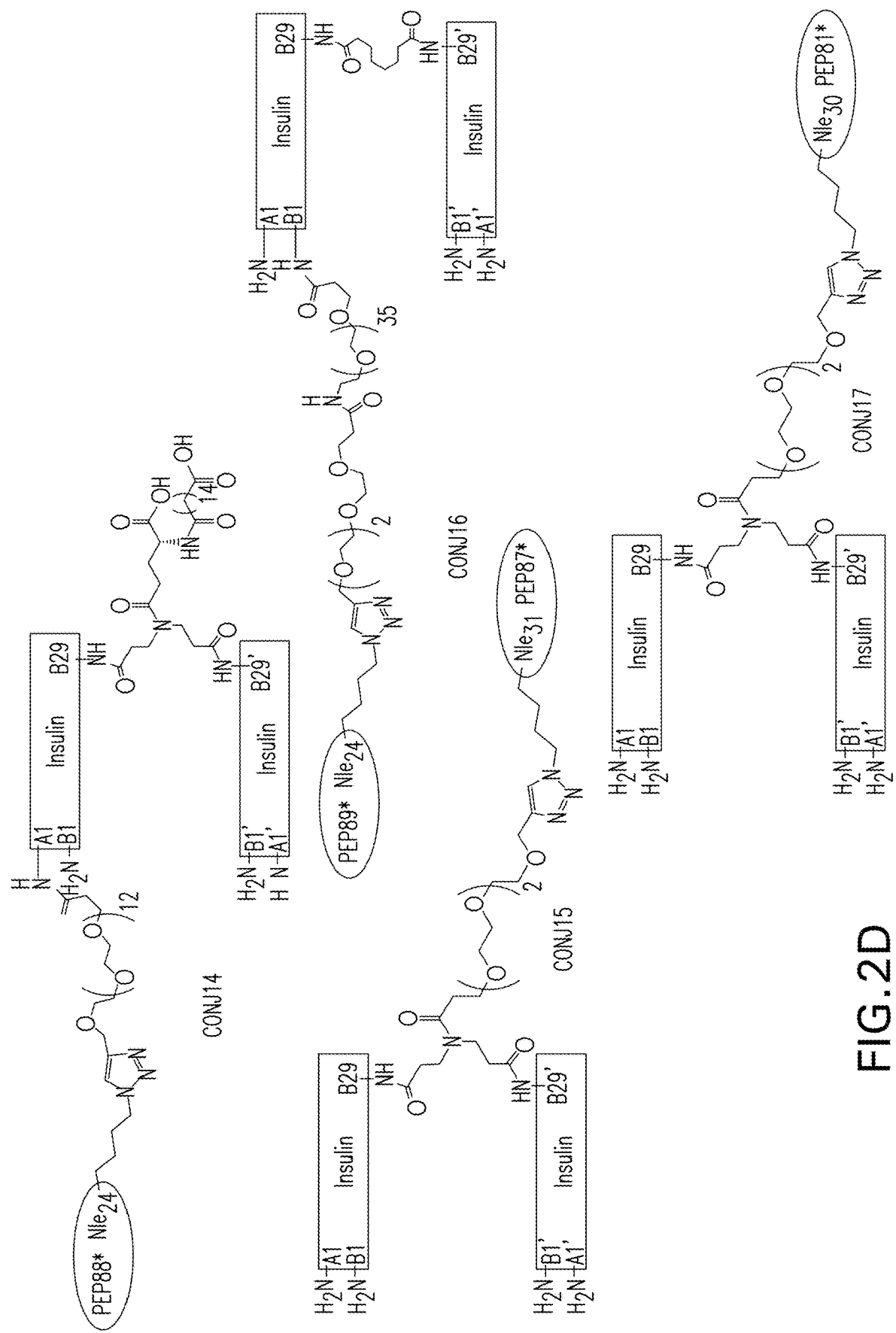
Figure 2E:
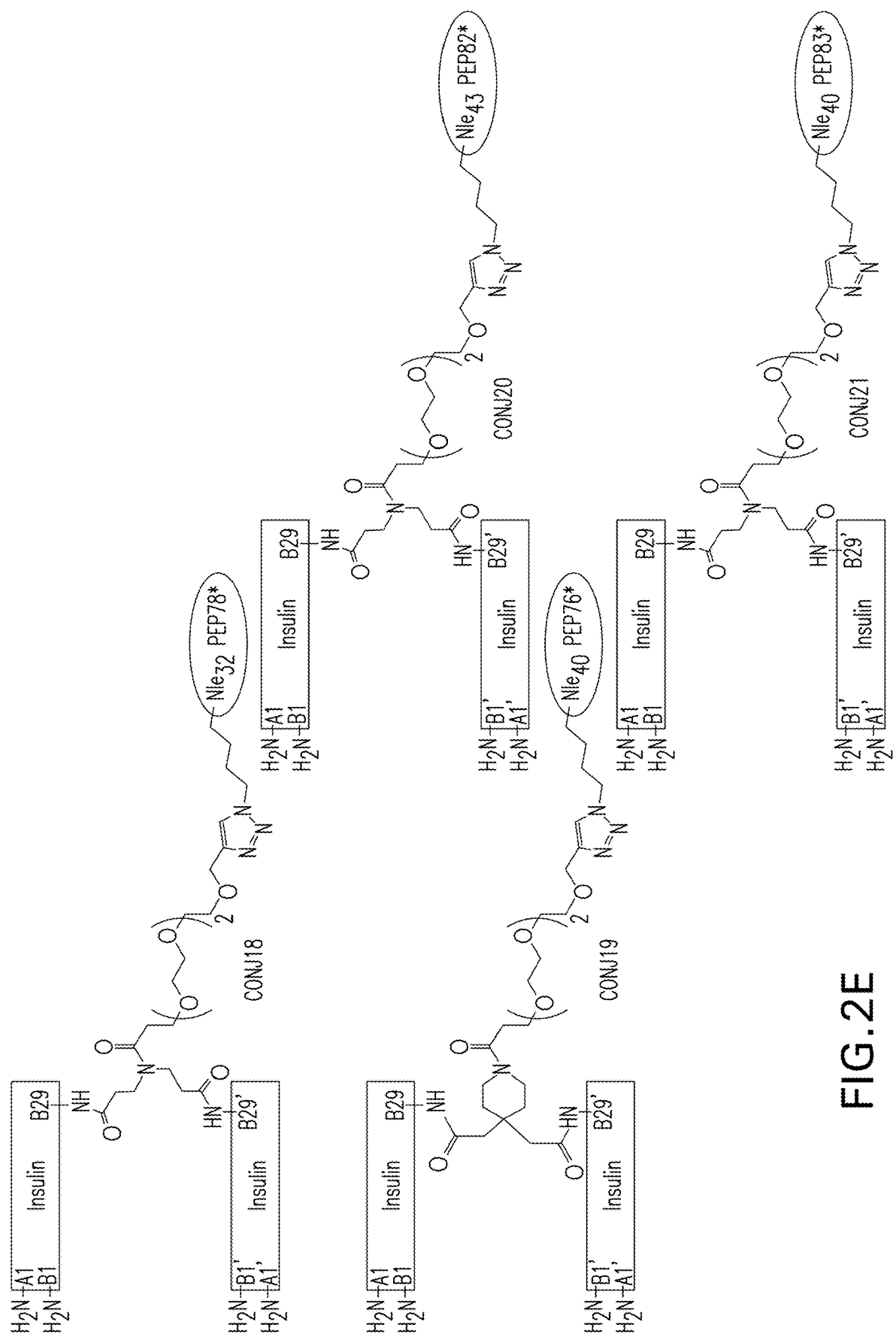
Figure 2F:
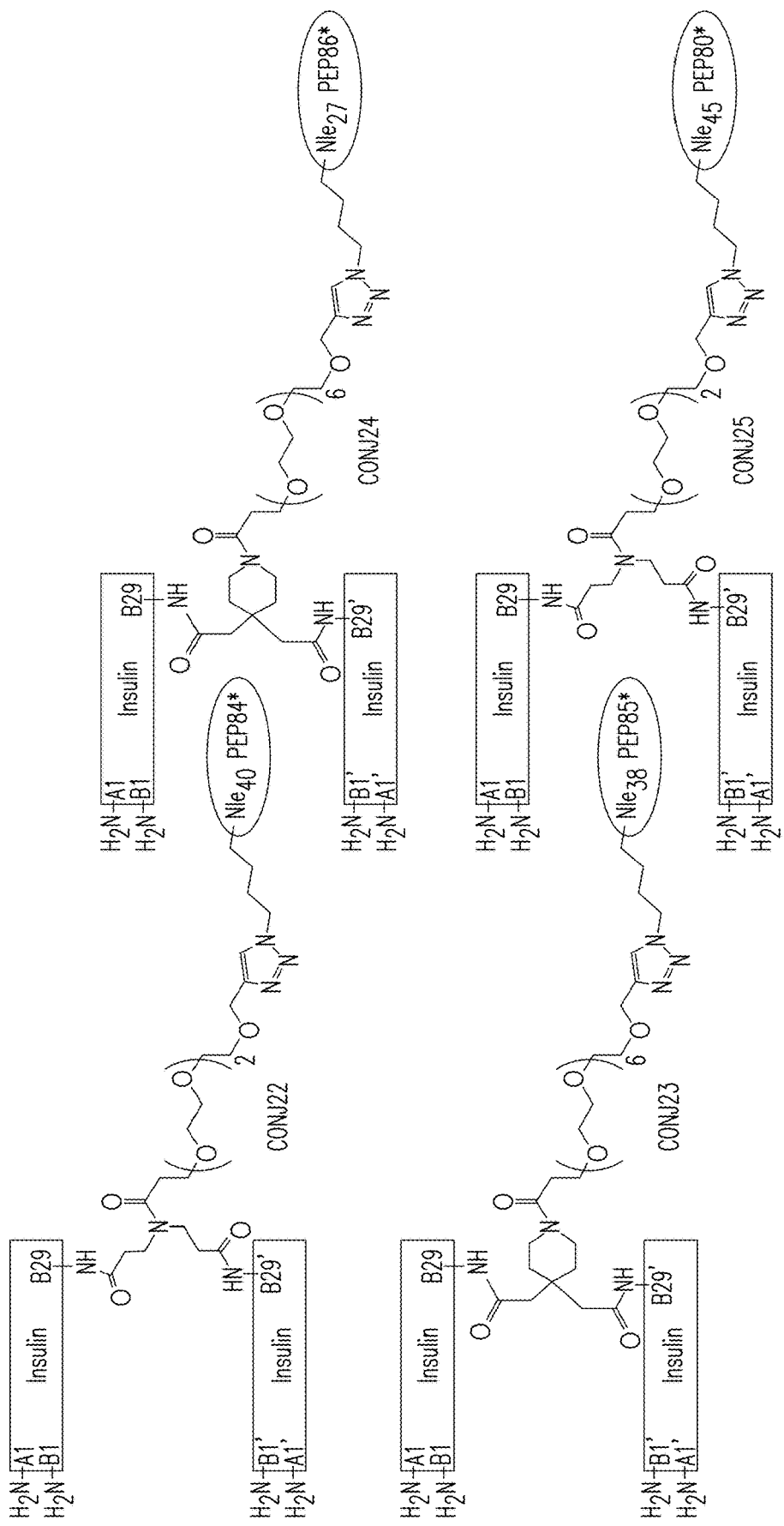
Figure 2G:
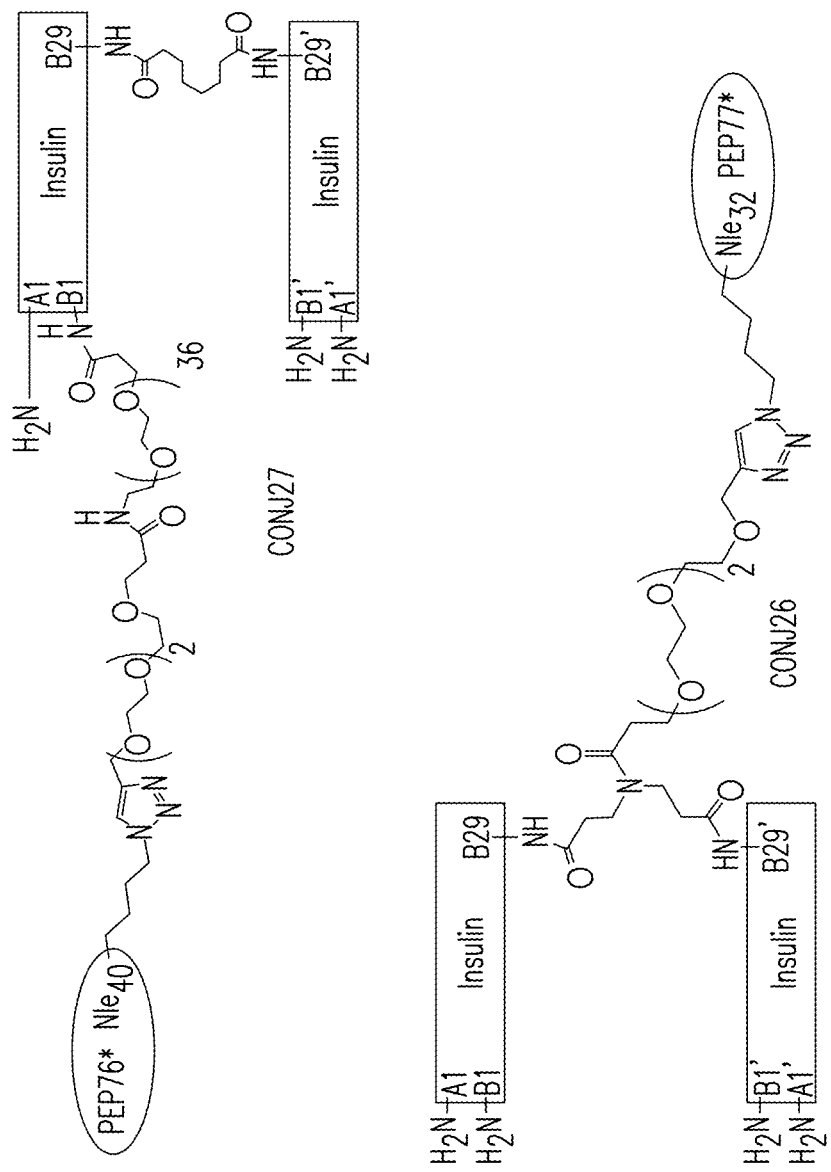

The present invention provides insulin dimer-incretin conjugates that are anticipated to impart a beneficial addition to insulin therapies for diabetes. For example, linking an incretin peptide having agonist activity at the GCG receptor to an insulin dimer molecule may enhance targeting of the conjugate to the liver since the GCG receptor is predominately located in the liver. Targeting the conjugate to the liver may be desirable since the liver is primarily involved in glucose production not glucose utilization. Thus, targeting the liver may provide a safer approach to shutting off glucose production than would occur when the insulin dimer contacts other tissues such as muscle or fat, where in addition to turning off glucose production it also stimulates glucose use leading to a higher risk of hypoglycemia. Also, there are GCG receptors present on the alpha cells of the pancreas. Delivering the conjugate to the alpha cells may suppress additional glucagon production or make the alpha cell more sensitive to hypoglycemia. It is also anticipated that the presence of GCG in the conjugates may serve as a buffer on the activity of the insulin dimer to provide a more baseline activity and thus avoid spikes in blood glucose levels. Furthermore, whereas insulin dimer may stimulate lipogenesis in fat cells and weight gain, GCG increases lipolysis and energy expenditure and effects a decrease in weight gain, which may be beneficial in countering the weight gain that may occur during insulin therapies.

Similarly, it is anticipated that conjugates of insulin dimers with other GCG-related peptides including the incretins GLP-1 and GIP and other related peptides having activity at the GLP-1 and/or GIP receptors may produce conjugates having beneficial properties. For example, GLP-1 receptor agonist-insulin conjugate may be targeted to the hypothalamus, to decrease appetite as well as reduce blood glucose. Alternatively or additionally, the GLP-1 receptor agonist-insulin dimer conjugate may be targeted to the beta cells to drive anabolic response (increase islet beta cells production of insulin).

In addition, the insulin dimers disclosed herein display partial agonist activity at the insulin receptor, which reduces the risk of hypoglycemia. The inventors of the instant invention have discovered that the level of insulin activity and partial agonist activity of the dimers is a function of the dimeric structure, the sequence of the insulin analog, the length of the dimerization linker, and the site of dimerization that connects the two insulin polypeptides. The inventors have discovered that the insulin dimers of the present invention have reduced risk of promoting hypoglycemia when administered in high doses than native insulin or other insulin analogs when administered at high doses.

Insulin dimers have been disclosed in Brandenburg et al. in U.S. Pat. No. 3,907,763 (1973); Tatnell et al., Biochem J. 216: 687-694 (1983); Shüttler and Brandenburg, Hoppe-Seyler's Z. Physiol. Chem, 363, 317-330, 1982; Weiland et al., Proc Natl. Acad. Sci. (USA) 87: 1154-1158 (1990); Deppe et al., Naunyn-Schmiedeberg's Arch Pharmacol (1994) 350:213-217; Brandenburg and Havenith in U.S. Pat. No. 6,908,897(B2) (2005); Knudsen et al., PLOS ONE 7: e51972 (2012); DiMarchi et al in WO2011/159895; DiMarchi et al. in WO 2014/052451; and Herrera et al., WO2014141165. More recently, insulin dimers have been described in Brant—*Synthesis and Characterization of Insulin Receptor Partial Agonists as a Route to Improved Diabetes Therapy*, Ph.D. Dissertation, Indiana University (April 2015) and Zaykov and DiMarchi, Poster P212—*Exploration of the structural and mechanistic basis for partial agonism of insulin dimers*, American Peptide Symposium, Orlando Fla. (Jun. 20-25 (2015).

The insulin dimer-incretin conjugates herein are also suitable for further structural enhancements that are envisioned to yield improved therapeutic index, through the use of prodrug chemistry; extended duration of action, by linkage of plasma proteins such as albumin, or other modifications, including pegylation and acylation; and enhanced physical stability, by glycosylation. The preparation of single chain insulin analogs using a C-peptide or peptide linker also provides a novel structural location for where many of these chemical modifications can be successfully deployed. The primary use of the conjugates disclosed herein would be in the treatment of insulin-dependent diabetes, including for example, T1DM, T2DM, and gestational diabetes.

As disclosed herein, the insulin dimers comprise two insulin heterodimer molecules covalently linked to each other via an amino acid at or near the C-terminus of the two insulin heterodimers (See FIG. 1). Each heterodimer comprises an A chain peptide and a B chain peptide covalently linked to each other via disulfide linkages between the cystine residues at positions 7 of the A and B chain peptides and between the cystine residue 20 of the A chain peptide and the cysteine residue at position 19 of the B chain peptide. In particular embodiments, the insulin dimer is a B29, B29' insulin dimer wherein the lysine at position B29 of the B chain peptide of a first heterodimer is covalently linked by a non-peptide linker (first linking moiety) to a lysine at position B29' of a second heterodimer to provide the B29, B29' insulin dimer. The insulin dimer is further conjugated via a non-peptide linker (second linking moiety) to a peptide having at least one incretin activity.

In particular embodiments the peptide is conjugated to the amino group of the N-terminal amino acid of the B-chain (B1 position) of at least insulin heterodimer comprising the insulin dimer. In particular embodiments the peptide is conjugated to the amino group of the N-terminal amino acid of the A-chain (A1 position) of at least insulin heterodimer comprising the insulin dimer. In particular embodiments the peptide is conjugated to the amino group of the N-terminal amino acid of the B-chain (B1 position) of both insulin heterodimers comprising the insulin dimer. In particular embodiments the peptide is conjugated to the amino group of the N-terminal amino acid of the A-chain (A1 position) of both insulin heterodimers comprising the insulin dimer. In particular embodiments the peptide is conjugated to the amino group of the N-terminal amino acid of the B-chain (B1 position) of the first insulin heterodimer comprising the insulin dimer and to the amino group of the N-terminal amino acid of the A-chain (A1 position) of the second heterodimer comprising the insulin dimer.

Insulin A and B Chains Comprising the Insulin Dimer

The insulin molecule comprising the insulin dimer disclosed herein encompasses all salt and non-salt forms of the insulin molecule. It will be appreciated that the salt form may be anionic or cationic depending on the insulin molecule. The term "insulin" or "an insulin molecule" is intended to encompass both wild-type insulin and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, Pediatr. Emerg. Care. 23:903-905, 2007 and Gerich, Am. J. Med. 113:308-16, 2002 and references cited therein). Modified forms of insulin (insulin analogs) may be chemically modified (e.g., by addition of a chemical moiety such as a PEG group or a fatty acyl chain as described below) and/or mutated (i.e., by addition, deletion or substitution of one or more amino acids).

In particular embodiments, an insulin molecule comprising the insulin dimer may be wild-type human recombinant insulin or may differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In particular embodiments, an insulin molecule of the present disclosure will differ from wild-type insulin by amino acid substitutions only. In particular embodiments, an insulin molecule of the present disclosure will differ from wild-type insulin by amino acid additions only. In particular embodiments, an insulin molecule of the present disclosure will differ from wild-type insulin by both amino acid substitutions and additions. In particular embodiments, an insulin molecule of the present disclosure will differ from a wild-type insulin by both amino acid substitutions and deletions.

In particular embodiments, amino acid substitutions may be made on the basis of similarity in polarity, charge, solubility, hydrophobicity, hydrophilicity, and/or the amphipathic nature of the residues involved. In particular embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In particular embodiments, the hydrophobic index of amino acids may be considered in choosing suitable mutations. The importance of the hydrophobic amino acid index in conferring interactive biological function on a peptide is generally understood in the art. Alternatively, the substitution of like amino acids can be made effectively on the basis of hydrophilicity. The importance of hydrophilicity in conferring interactive biological function of a peptide or peptide is generally understood in the art. The use of the hydrophobic index or hydrophilicity in designing peptides is further discussed in U.S. Pat. No. 5,691,198.

The wild-type sequence of recombinant human insulin (A-chain and B-chain) is shown in Table 1 below. In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin) (SEQ ID NO:128). This modification blocks the formation of insulin multimers. Insulin aspart (NOVOLOG®) is another rapid acting insulin mutant in which proline at position B28 has been substituted with aspartic acid ($Asp^{B28}$-human insulin) (SEQ ID NO:129). This mutant also prevents the formation of multimers. In some embodiments, mutation at positions B28 and/or B29 is accompanied by one or more mutations elsewhere in the insulin peptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin) (SEQ ID NO:130).

TABLE 1

| SEQ ID NO: | Description | Sequence |
|---|---|---|
| 126 | Human insulin A chain | GIVEQCCTSICSLYQLENYCN |
| 127 | Human insulin B chain | FVNQHLCGSHLVEALYLVCGERGFFYTPKT |
| 128 | Insulin lispro B chain | FVNQHLCGSHLVEALYLVCGERGFFYTKPT |

TABLE 1-continued

| SEQ ID NO: | Description | Sequence |
|---|---|---|
| 129 | Insulin aspart B chain | FVNQHLCGSHLVEALYLVCGERGFFYTDKT |
| 130 | Insulin glusiline B chain | FVKQHLCGSHLVEALYLVCGERGFFYTPET |
| 131 | Insulin glargine A chain | GIVEQCCTSICSLYQLENYCG |
| 132 | Insulin glargine B chain | FVNQHLCGSHLVEALYLVCGERGFFYTPKTRR |

In various embodiments, the insulin molecule comprising the insulin dimer may have an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin peptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine (SEQ ID NO:131), and two arginine residues have been added to the C-terminus of the B-peptide (SEQ ID NO:132). The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 and B32 are Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, the insulin molecule comprising the insulin dimer may be truncated. For example, in particular embodiments, a B-peptide sequence of an insulin peptide of the present disclosure is missing B1, B2, B3, B26, B27, B28, B29 and/or B30. In particular embodiments, combinations of residues are missing from the B-peptide sequence of an insulin peptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des(B30)-insulin glulisine, des (B30)-insulin glargine, etc.).

In some embodiments, the insulin molecule may comprise additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In particular embodiments, an insulin molecule does not include any additional amino acid residues at positions A0, A21, B0 or B31.

In particular embodiments, the insulin molecule comprising the insulin dimer may be mutated such that one or more amidated amino acids are replaced with acidic forms. For example, asparagine may be replaced with aspartic acid or glutamic acid. Likewise, glutamine may be replaced with aspartic acid or glutamic acid. In particular, $AsnA^{18}$, $AsnA^{21}$, or $AsnB^{3}$, or any combination of those residues, may be replaced by aspartic acid or glutamic acid. $GlnA^{15}$ or $GlnB^{4}$, or both, may be replaced by aspartic acid or glutamic acid. In particular embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$), replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In various embodiments, the insulin molecule comprising the insulin dimer may have a protracted profile of action. Thus, in particular embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type human insulin or may be acylated on lysine residue that has been introduced into the wild-type human insulin sequence. In particular embodiments, an insulin molecule may be acylated at position B1. In particular embodiments, an insulin molecule may be acylated at position B29. In particular embodiments, the fatty acid is selected from myristic acid ($C_{14}$), pentadecylic acid ($C_{15}$), palmitic acid ($C_{16}$), heptadecylic acid ($C_{17}$) and stearic acid ($C_{18}$). For example, insulin detemir (LEVEMIR®) is a long acting insulin mutant in which $Thr^{B30}$ has been deleted, and a $C_{14}$ fatty acid chain (myristic acid) has been attached to $Lys^{B29}$.

In some embodiments, the N-terminus of the A-peptide, the N-terminus of the B-peptide, or any other available amino group in an insulin molecule of the present disclosure is covalently linked to a fatty acid moiety of general formula:

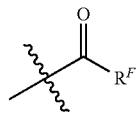

wherein $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In particular embodiments, the insulin molecule is conjugated to the moiety at the A1 position. In particular embodiments, the insulin molecule is conjugated to the moiety at the B1 position. In particular embodiments, position B3 of the insulin molecule is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In particular embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In various embodiments, the insulin molecule comprising the insulin dimer may have the three wild-type disulfide bridges (i.e., one between position 7 of the A-chain peptide and position 7 of the B-chain peptide, a second between position 20 of the A-chain peptide and position 19 of the B-chain peptide, and a third between positions 6 and 11 of the A-chain peptide). In particular embodiments, an insulin molecule is mutated such that the site of mutation is used as a conjugation point, and conjugation at the mutated site reduces binding to the insulin receptor (e.g., $Lys^{A3}$). In particular other embodiments, conjugation at an existing wild-type amino acid or terminus reduces binding to the insulin receptor (e.g., $Gly^{A}1$). In some embodiments, an insulin molecule is conjugated at position A4, A5, A8, A9, or B30. In particular embodiments, the conjugation at position A4, A5, A8, A9, or B30 takes place via a wild-type amino acid side chain (e.g., $Glu^{A4}$). In particular other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

In particular embodiments, the insulin molecule comprising the insulin dimer may have an A chain sequence comprising a sequence of GIVEQCCX$_1$SICSLYQLENYCX$_2$ (SEQ ID NO: 133); and a B chain sequence comprising a sequence of X$_3$LCGX$_4$X$_5$LVEALYLVCG ERGFF (SEQ ID NO: 134) or X$_8$VNQX$_3$LCGX$_4$X$_5$LVEALYLVCGE RGFFYTX$_6$X$_7$ (SEQ ID NO: 135) wherein X$_1$ is selected from the group consisting of threonine and histidine;

X$_2$ is asparagine or glycine;

X$_3$ is selected from the group consisting of histidine and threonine;

X$_4$ is selected from the group consisting of alanine, glycine and serine;

X$_5$ is selected from the group consisting of histidine, aspartic acid, glutamic acid, homocysteic acid and cysteic acid;

X$_6$ is aspartate-lysine dipeptide, a lysine-proline dipeptide, or a proline-lysine dipeptide;

X$_7$ is threonine, alanine, or a threonine-arginine-arginine tripeptide; and

X$_8$ is selected from the group consisting of phenylalanine and desamino-phenylalanine.

In particular embodiments, the A-chain may have the amino acid sequence set forth in SEQ ID NO:126 or SEQ ID NO:131 and the B-chain may have the amino acid sequence set forth in SEQ ID NO:127, SEQ ID NO:128, SEQ ID NO:129, or SEQ ID NO:130. In particular embodiments, the A-chain may have the amino acid sequence set forth in SEQ ID NO:131 and the B-chain may have the amino acid sequence set forth in SEQ ID NO:132. In particular embodiments, the insulin analog is a desB30 insulin analog, a des B29-B30 insulin analog, a des B28-B30 insulin analog, a des B27-B30 insulin analog or a des B26-B30 insulin analog.

In particular embodiments, at least one amino group of the insulin molecule is conjugated to a linker comprising a terminal azide group or alkyne group. The amino group may be at the A1 position or the B1 position. In particular embodiments, the lysine residue is at the B29 position of the B chain. In particular embodiments, the lysine residue is at the B28 position of the B chain, for example, insulin lispro has a lysine at the B28 position. In particular embodiments, the lysine residue is at the B3 position of the B chain, for example, insulin glulisine has a lysine at the B3 position. In particular embodiments, the epsilon amine of the lysine residue is converted to an azide group, which provides a norleucine with an epsilon azide group.

In particular embodiments, the insulin molecule comprising the insulin dimer has an A chain peptide sequence comprising a sequence of X$_1$I X$_2$E X$_3$CCX$_4$ X$_5$ X$_6$CS X$_7$ X$_8$ X$_9$LE X$_{10}$YC X$_{11}$X$_{12}$ (SEQ ID NO:136); and a B chain peptide sequence comprising a sequence of X$_{13}$VX$_{14}$X$_{15}$ HLCGSHLVEALX$_{16}$X$_{17}$VCGERGFX$_{18}$YTX$_{19}$X$_{20}$X$_{21}$X$_{22}$ X$_{23}$X$_{24}$X$_{25}$X$_{26}$ (SEQ ID NO:137) wherein X$_1$ is glycine (G) or lysine (K);

X$_2$ is valine (V), glycine (G), or lysine (K);

X$_3$ is glutamine (Q) or lysine (K);

X$_4$ is threonine (T) or histidine (H);

X$_5$ is serine (S) or lysine (K);

X$_6$ is isoleucine (I) or lysine;

X$_7$ is leucine (L) or lysine (K);

X$_8$ is tyrosine (Y) or lysine (K);

X$_9$ is glutamine (Q) or lysine (K);

X$_{10}$ is asparagine (N) or lysine (K);

X$_{11}$ is asparagine (N) or glycine (G);

X$_{12}$ is arginine (R), lysine (K) or absent;

X$_{13}$ is phenylalanine (F) or lysine (K);

X$_{14}$ is asparagine (N) or lysine (K);

X$_{15}$ is glutamine (Q) or lysine (K);

X$_{16}$ is tyrosine (Y) or lysine (K);

X$_{17}$ is leucine (L) or lysine (K);

X$_{18}$ is phenylalanine (F) or lysine (K);

X$_{19}$ is proline (P) or lysine (K);

X$_{20}$ is lysine (K) or proline (P);

X$_{21}$ is threonine (T) or absent;

X$_{22}$ is arginine (R) if X$_{21}$ is threonine (T), or absent;

X$_{23}$ is proline (P) if X$_{22}$ is arginine (R), or absent;

X$_{24}$ is arginine (R) if X$_{23}$ is proline (P), or absent;

X$_{25}$ is proline (P) if X$_{24}$ is arginine (R), or absent; and

X$_{26}$ is arginine (R) if X$_{25}$ is proline (P), or absent,

With the proviso that at least one of X$_1$, X$_2$, X$_3$, X$_5$, X$_6$, X$_7$, X$_8$, X$_9$, X$_{10}$, X$_{12}$, X$_{13}$, X$_{14}$, X$_{15}$, X$_{16}$, X$_{17}$, X$_{18}$, X$_{19}$, or X$_{20}$ is a lysine (K) wherein when X$_{20}$ is a lysine (K) then X$_{21}$ is absent or if X$_{21}$ is present then at least one of X$_1$, X$_2$, X$_3$, X$_4$, X$_5$, X$_6$, X$_7$, X$_8$, X$_9$, X$_{10}$, X$_{11}$, X$_{12}$, X$_{13}$, X$_{14}$, X$_{15}$, X$_{16}$, X$_{17}$ is lysine (K), or X$_4$ is histidine (H), or X$_{11}$ is glycine (G); or at least one of X$_{12}$ or X$_{22}$ is present. In particular aspects, if X$_1$, X$_2$, X$_3$, X$_5$, X$_6$, X$_7$, X$_8$, X$_9$, X$_{10}$, X$_{12}$, X$_{13}$, X$_{14}$, X$_{15}$, X$_{16}$, X$_{17}$, X$_{18}$, or X$_{19}$ is a lysine (K) then X$_{20}$ is not a lysine (K); and with the proviso that at least one Lysine (K) is conjugated to a linker having a terminal alkyne or azide group or the epsilon amine of at least one lysine residue is converted to an azide group, which provides a norleucine with an epsilon azide group.

In particular embodiments, the insulin molecule comprising the insulin dimer may be a desB30 human insulin analog, which may comprise an A chain peptide sequence comprising a sequence of $X_1I\,X_2E\,X_3CCX_4\,X_5\,X_6CS\,X_7\,X_8\,X_9LE\,X_{10}YC\,X_{11}X_{12}$ (SEQ ID NO:136); and a B chain peptide sequence comprising a sequence of $X_{13}VX_{14}X_{15}HLCGSHLVEALX_{16}X_{17}VCGERGFX_{18}YTX_{19}X_{20}$ (SEQ ID NO:138) wherein $X_1$ is glycine (G) or lysine (K);
$X_2$ is valine (V), glycine (G), or lysine (K);
$X_3$ is glutamine (Q) or lysine (K);
$X_4$ is threonine (T) or histidine (H);
$X_5$ is serine (S) or lysine (K);
$X_6$ is isoleucine (I) or lysine;
$X_7$ is leucine (L) or lysine (K);
$X_8$ is tyrosine (Y) or lysine (K);
$X_9$ is glutamine (Q) or lysine (K);
$X_{10}$ is asparagine (N) or lysine (K);
$X_{11}$ is asparagine (N) or glycine (G);
$X_{12}$ is arginine (R), lysine (K) or absent;
$X_{13}$ is phenylalanine (F) or lysine (K);
$X_{14}$ is asparagine (N) or lysine (K);
$X_{15}$ is glutamine (Q) or lysine (K);
$X_{16}$ is tyrosine (Y) or lysine (K);
$X_{17}$ is leucine (L) or lysine (K);
$X_{18}$ is phenylalanine (F) or lysine (K);
X19 is proline (P) or lysine (K);
$X_{20}$ is lysine (K) or proline (P);

With the proviso that at least one of $X_1$, $X_2$, $X_3$, $X_5$, $X_6$, $X_7$, $X_8$, $X_9$, $X_{10}$, $X_{12}$, $X_{13}$, $X_{14}$, $X_{15}$, $X_{16}$, $X_{17}$, $X_{18}$, $X_{19}$, or $X_{20}$ is a lysine (K); and with the proviso that at least one Lysine (K) is conjugated to a linker having a terminal alkyne or azide group or the epsilon amine of at least one lysine residue is converted to an azide group, which provides a norleucine with an epsilon azide group.

In particular embodiments, the insulin molecule comprising the insulin dimer may comprise an A chain peptide sequence comprising a sequence of $X_1I\,X_2E\,X_3CCX_4\,X_5\,X_6CS\,X_7\,X_8\,X_9LE\,X_{10}YC\,X_{11}X_{12}$ (SEQ ID NO:136); and a B chain peptide sequence comprising a sequence of $X_{13}VX_{14}X_{15}HLCGSHLVEALX_{16}X_{17}VCGERGFX_{18}YTX_{19X20}TRPRPR$ (SEQ ID NO:139) wherein $X_1$ is glycine (G) or lysine (K);
$X_2$ is valine (V), glycine (G), or lysine (K);
$X_3$ is glutamine (Q) or lysine (K);
$X_4$ is threonine (T) or histidine (H);
$X_5$ is serine (S) or lysine (K);
$X_6$ is isoleucine (I) or lysine;
$X_7$ is leucine (L) or lysine (K);
$X_8$ is tyrosine (Y) or lysine (K);
$X_9$ is glutamine (Q) or lysine (K);
$X_{10}$ is asparagine (N) or lysine (K);
$X_{11}$ is asparagine (N) or glycine (G);
$X_{12}$ is arginine (R), lysine (K) or absent;
$X_{13}$ is phenylalanine (F) or lysine (K);
$X_{14}$ is asparagine (N) or lysine (K);
$X_{15}$ is glutamine (Q) or lysine (K);
$X_{16}$ is tyrosine (Y) or lysine (K);
$X_{17}$ is leucine (L) or lysine (K);
$X_{18}$ is phenylalanine (F) or lysine (K);
$X_{19}$ is proline (P) or lysine (K);
$X_{20}$ is lysine (K) or proline (P);

With the proviso that at least one of $X_1$, $X_2$, $X_3$, $X_5$, $X_6$, $X_7$, $X_8$, $X_9$, $X_{10}$, $X_{12}$, $X_{13}$, $X_{14}$, $X_{15}$, $X_{16}$, $X_{17}$, $X_{18}$, $X_{19}$, or $X_{20}$ is a lysine (K); and with the proviso that at least one Lysine (K) is conjugated to a linker having a terminal alkyne or azide group or the epsilon amine of at least one lysine residue is converted to an azide group, which provides a norleucine with an epsilon azide group.

In particular embodiments, the insulin molecule comprising the conjugate may have an A chain peptide sequence comprising a sequence of $X_1I\,X_2E\,X_3CCX_4\,X_5\,X_6CS\,X_7\,X_8\,X_9LE\,X_{10}YC\,X_{11}X_{12}$ (SEQ ID NO: 136); and a B chain peptide sequence comprising a sequence of $X_{13}VX_{14}X_{15}HLCGSHLVEALX_{16}X_{17}VCGERGFX_{18}YTX_{19X20}TRPR$ (SEQ ID NO: 140) wherein $X_1$ is glycine (G) or lysine (K);
$X_2$ is valine (V), glycine (G), or lysine (K);
$X_3$ is glutamine (Q) or lysine (K);
$X_4$ is threonine (T) or histidine (H);
$X_5$ is serine (S) or lysine (K);
$X_6$ is isoleucine (I) or lysine;
$X_7$ is leucine (L) or lysine (K);
$X_8$ is tyrosine (Y) or lysine (K);
$X_9$ is glutamine (Q) or lysine (K);
$X_{10}$ is asparagine (N) or lysine (K);
$X_{11}$ is asparagine (N) or glycine (G);
$X_{12}$ is arginine (R), lysine (K) or absent;
$X_{13}$ is phenylalanine (F) or lysine (K);
$X_{14}$ is asparagine (N) or lysine (K);
$X_{15}$ is glutamine (Q) or lysine (K);
$X_{16}$ is tyrosine (Y) or lysine (K);
$X_{17}$ is leucine (L) or lysine (K);
$X_{18}$ is phenylalanine (F) or lysine (K);
$X_{19}$ is proline (P) or lysine (K);
$X_{20}$ is lysine (K) or proline (P);

With the proviso that at least one of $X_1$, $X_2$, $X_3$, $X_5$, $X_6$, $X_7$, $X_8$, $X_9$, $X_{10}$, $X_{12}$, $X_{13}$, $X_{14}$, $X_{15}$, $X_{16}$, $X_{17}$, $X_{18}$, $X_{19}$, or $X_{20}$ is a lysine (K); and with the proviso that at least one Lysine (K) is conjugated to a linker having a terminal alkyne or azide group or the epsilon amine of at least one lysine residue is converted to an azide group, which provides a norleucine with an epsilon azide group.

The following structure represents human insulin (e.g., recombinant human insulin (RHI)) or any insulin analog disclosed herein 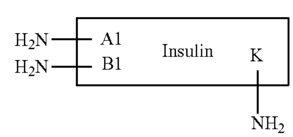 wherein the insulin is a heterodimer in which the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond and wherein A1 is the amino acid at position 1 of the A chain peptide, B1 is the amino acid at position 1 of the B chain peptide, and K is a lysine, which may be in any position in the insulin or insulin analog. In particular embodiments, the lysine is at position B29, B28, or B3. In particular embodiments, the lysine is at position B29 and is represented by the structure

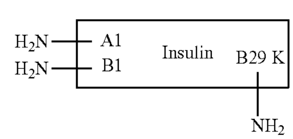

.

In particular embodiments, the lysine is at position B28 and is represented by the structure.

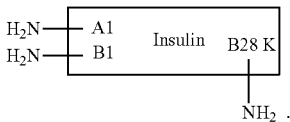

In particular embodiments, the lysine is at position B3 and is represented by the structure

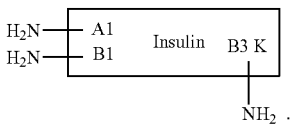

Unless otherwise indicated, the term "insulin" is used to indicate the insulin is a human insulin in which the A chain has amino acid sequence GIVEQCCTSICSLYQLENYCN (SEQ ID NO:126) and the B chain has amino acid sequence FVNQHLCGSHLVEALYLVCGERGFFYTPKT (SEQ ID NO:127).

The following structure represents a single-chain insulin analog (SCI) in which the C-terminal amino acid of the B chain is covalently linked the N-terminal amino acid of the A chain by a non-peptide linker or a peptide linker comprising three to 35 amino acids

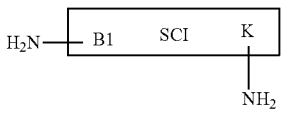

wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond and wherein B1 is the amino acid at position 1 of the B chain peptide and K is a lysine, which may be in any position in the insulin or insulin analog. In particular embodiments, the lysine is at position B29, B28, or B3. In particular embodiments, the lysine is at position B29 and is represented by the structure

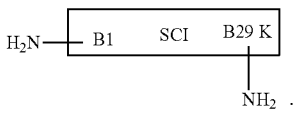

In particular embodiments, the lysine is at position B28 and is represented by the structure

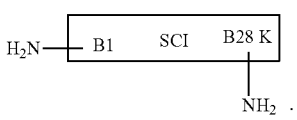

In particular embodiments, the lysine is at position B3 and is represented by the structure

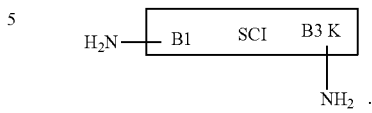

Unless otherwise indicated, the term "SCI" is used to indicate the single-chain insulin an A chain having an amino acid sequence GIVEQCCTSICSLYQLENYCN (SEQ ID NO:126) and a B chain having the amino acid sequence FVNQHLCGSHLVEALYLVCGERGFFYTPKT (SEQ ID NO:127).

Single-chain insulins and analogs thereof have been disclosed in U.S. Pat. No. 8,940,860, which is incorporated herein by reference in its entirety and U.S. Publications US 20150374795 and US 20150299285, which are incorporated herein by reference in their entirety.

Linking Moiety of the Insulin Dimer

The insulin dimers disclosed herein are formed between a first and second insulin polypeptide wherein each insulin polypeptide comprises an A chain and a B chain. The first and second insulin polypeptides may be two chain insulin analogs (i.e., wherein the A and B chains are linked only via inter-chain disulfide bonds between internal cysteine residues) wherein the first and second insulin polypeptides are linked to one another to form the dimer by a covalent bond, bifunctional linker, or using copper(I) catalyzed alkyne-azide cycloaddition (CuAAC) click chemistry or copper-free click chemistry to link linking moieties on the respective B chains. In accordance with one embodiment the first and second insulin polypeptides are linked to one another by a bifunctional linker joining the side chain of the B28 or B29 lysine of the B chain of the first insulin polypeptide to the side chain of the B28 or B29 amino acid of the B chain of the second insulin polypeptide.

In particular aspects of the insulin receptor partial agonists, the linking moiety may be an optionally substituted group selected from the group consisting of acyl, aliphatic, heteroaliphatic, aryl, heteroaryl, and heterocyclic. The linking moiety may be a bivalent, straight or branched, saturated or unsaturated, optionally substituted C1-C20 hydrocarbon chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety.

In one embodiment, the linking moiety comprises a PEG linker, a short linear polymer of about 2-25 ethylene glycol units or 2, 3, 4, 5, 6, 7, 8, 9, 10, 11, 12, 13, 14, 15, 16, or 25 ethylene glycol units and optionally one or more amino acids. In particular aspects of the insulin receptor partial agonists, the PEG linker comprises the structure (PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_{25}$. The PEG linker may be a bifunctional linker that may be covalently conjugated or linked to epsilon amino group of the position B29 or B28 lysine residues of the first and second insulin polypeptides. The structure of a bifunctional PEG linker conjugated to the epsilon amino group of the lysine groups at position B29 or B28 of the first and second insulin polypeptides may be represented by the following general formula

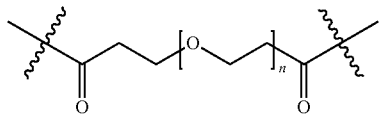

wherein n=1, 2, 3, 4, 5, 6, 7, 8, 9, 10, 11, 12, 13, 14, 15, 16, or 25 and the wavy line indicates the bond between the linker and the epsilon amino group. Methods for conjugating PEG to the epsilon amino group of lysine are well known in the art, see for example, Veronese, Biomaterials 22: 405-417 (2001).

In particular aspects of the insulin receptor partial agonists, PEG linking moiety conjugating the epsilon amino group of the lysine at position B29 or B28 of the first insulin polypeptide to the epsilon amino acid of the lysine at position B29 or B28 of the second insulin polypeptide is

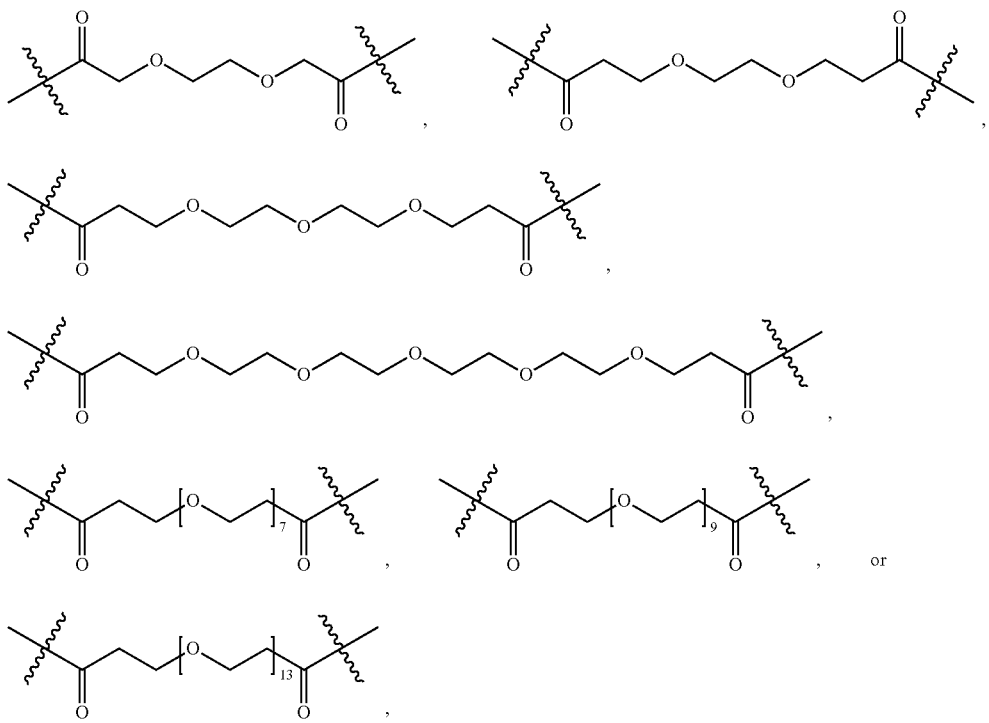

wherein the wavy lines indicate the bond between the linker and the epsilon amino group of the lysine at position B29 or B28 of the insulin polypeptides.

In another embodiment, the linking moiety comprises an acyl moiety comprising 4, 5, 6, 7, 8, 9, 10, 11, 12, 13, 14 15, or 16 carbons. In particular aspects of the insulin receptor partial agonists, the acyl moiety is a succinyl (4), adipoyl (C6), suberyol (C8), or hexadecanedioyl (C16) moiety. The acyl moiety may comprise a bifunctional linker that may be covalently conjugated or linked to epsilon amino group of the position B29 or B28 lysine residues of the first and second insulin polypeptides. The structure of a bifunctional acyl linker conjugated to the epsilon amino group of the lysine group at position B29 or B28 of the first and second insulin polypeptides may be represented by the following general formula

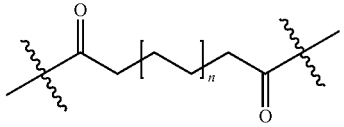

wherein n=0, 1, 2, 3, 4, 5, 6, 7, 8, 9, 10, 11, or 12 and the wavy lines indicate the bond between the linker and the epsilon amino group of the lysine at position B29 or B28 of the insulin polypeptides.

In particular aspects of the insulin receptor partial agonists, acyl linking moiety conjugating the epsilon amino group of the lysine at position B29 or B28 of the first insulin polypeptide to the epsilon amino acid of the lysine at position B29 or B28 of the second insulin polypeptide is

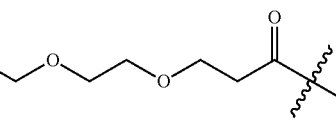

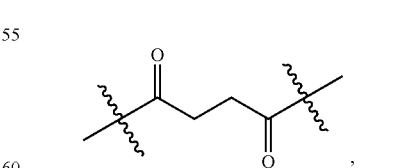

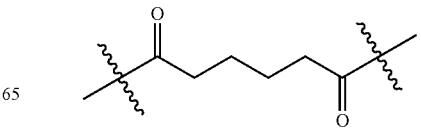

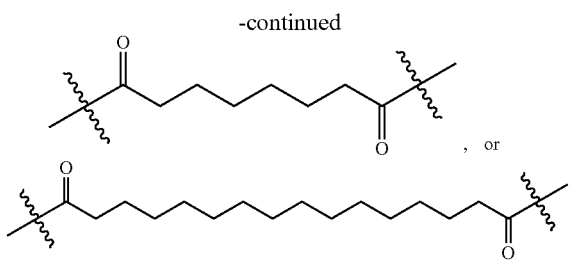

, or

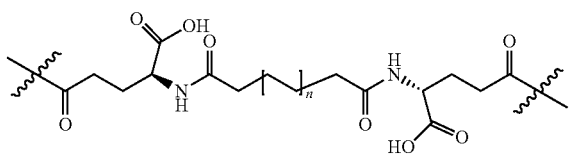

wherein the wavy lines indicate the bond between the linker and the epsilon amino group of the lysine at position B29 or B28 of the insulin polypeptides.

In particular aspects of the insulin receptor partial agonists, the bifunctional acyl linker may further include one or two amino acids at one or both termini of the acyl linker. For example, In particular aspects of the insulin receptor partial agonists, the amino acid at one or both termini of the linker is gamma glutamic acid (γE), which may be represented by the following general formula

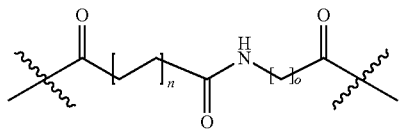

wherein n=0, 1, 2, 3, 4, 5, 6, 7, 8, 9, 10, 11, or 12 and the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides which may be represented by the following general formula

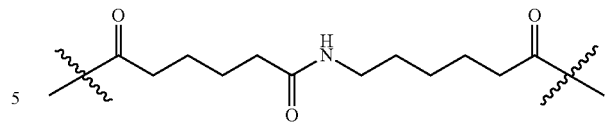

wherein n=1 or 2, o=1, 2, 3, 4, or 5, and the wavy lines indicate the bond between the linker and the epsilon amino group of the lysine at position B29 or B28 of the insulin polypeptides. In a particular embodiment, the linking moiety may have the structure wherein the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides which may be represented by the following general formula

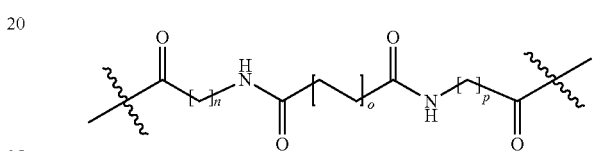

wherein n=1, 2, 3, 4, or 5, o=1 or 2, p=1, 2, 3, 4, or 5, and the wavy lines indicate the bond between the linker and the epsilon amino group of the lysine at position B29 or B28 of the insulin polypeptides. In a particular embodiment, the linking moiety may have the structure

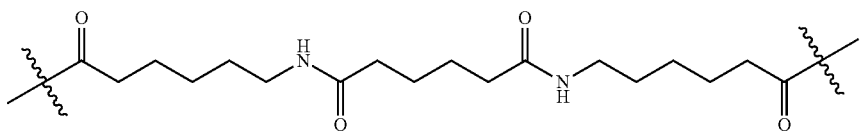 [SMILES: *C(=O)CCCCCNC(=O)CCCCC(=O)NCCCCCC(*)=O]

wherein the wavy lines indicate the bond between the linker and the epsilon amino group of the lysine at position B29 or B28 of the insulin polypeptides.

In another embodiment, the linking moiety comprises an amide-containing alkyl chain bifunctional linker that may be covalently conjugated or linked to epsilon amino group of the position B29 or B28 lysine residues of the first and second insulin polypeptides and which may be represented by the following general formula

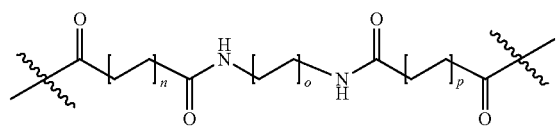

wherein n=1 or 2, o=1, 2, or 3, p=1 or 2, and the wavy lines indicate the bond between the linker and the epsilon amino group of the lysine at position B29 or B28 of the insulin polypeptides. In a particular embodiment, the linking moiety may have the structure

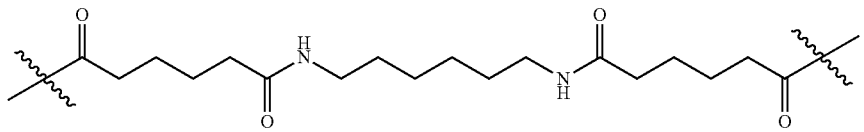 [SMILES: *C(=O)CCCCC(=O)NCCCCCCNC(=O)CCCCC(*)=O]

wherein the wavy lines indicate the bond between the linker and the epsilon amino group of the lysine at position B29 or B28 of the insulin polypeptides.

In particular embodiments, the linking moiety comprises a ring structure, which provides rigidity to the linking moiety. In particular embodiments, the ring structure comprises a benzyl group or a saturated or unsaturated alicyclic group having 3, 4, 5, 6, 7, or 8 carbons. In particular embodiments, the alicyclic group comprises a cyclopropyl, cyclobutyl, cyclopentyl, cyclohexyl, cyclopentyl, or cyclooctyl. In particular embodiments, the unsaturated alicyclic group (cycloalkane) comprises a cyclopropenyl, cyclobutenyl, cyclopentenyl, cyclohexenyl, cycloheptenyl, or cyclooctenyl group. In particular embodiments, the ring structure may further comprise one or more saturated or nonsaturated aliphatic side chains. In particular embodiments, the ring structure may further comprise one or more aliphatic side chains comprising one or more heteroatoms. In particular embodiments, the heteroatom is O, S, or N.

In particular embodiments, the ring structure comprises a heteroatom. In particular embodiments, the heteroatom may be O, S, or N. In particular embodiments, the ring structure comprises a benzyl group or a saturated or unsaturated alicyclic group having 3, 4, 5, 6, 7, or 8 carbons in which one or more carbons are substituted with a heteroatom selected from N, O, and S. Examples of ring structures that include a heteroatom include but are not limited to ethylene oxide, ethylenimime, trimethyloxide, furan, tetrhydrofuran, thiphene, pyrrolidine, pyran, piperidine, imidazole, thiazole, dioxane, morpholine, pyrimidine, triazole, thietane, 1,3-diazetine, 2,3-dihydroazete, 1,2-oxathiolane, isoxazole, oxazole, silole, oxepane, thiepine, 3, 4, 5, 6-tetrahydro-2H-azepine, 1,4-thiazepine, azocane, and thiocane.

In another embodiment, the linking moiety comprises a bifunctional linker that may be covalently conjugated or linked to epsilon amino group of the position B29 or B28 lysine residues of the first and second insulin polypeptides which may be represented by a benzene-1,1 diacyl having the following general formula

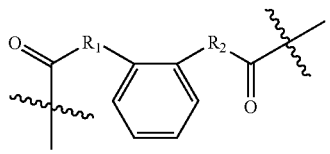

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,1 diacyl having the following general formula

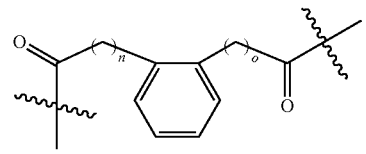

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

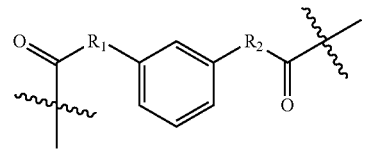

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG)$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

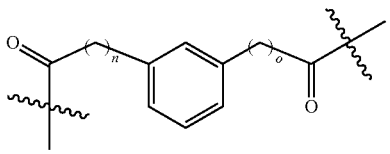

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,4 diacyl having the following general formula

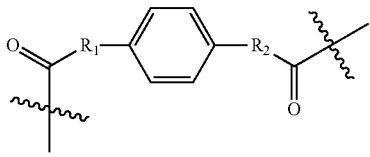

wherein $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,4 diacyl having the following general formula

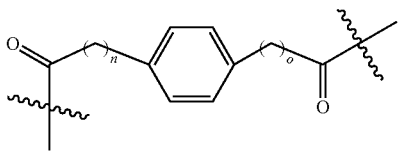

wherein n and o are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

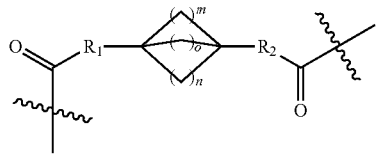

Wherein m, n, and o are each independently 1 or 2; $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

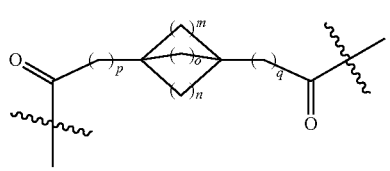

Wherein m, n, and o are each independently 1 or 2; wherein p and q are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

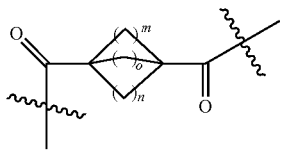

Wherein m, n, and o are each independently 1 or 2; wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclohexane-1,4 diacyl having the following general formula

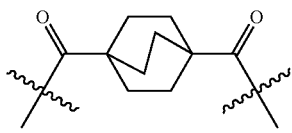

and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclohexane-1,4 diacyl having the following general formula

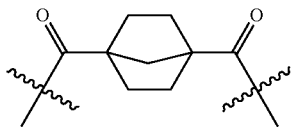

and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

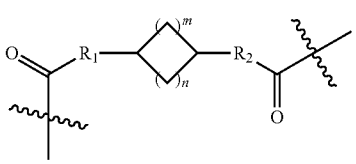

Wherein m and n are each independently 0, 1, or 2 with the proviso that both m and n are not 0; $R_1$ and $R_2$ may be same or different wherein $R_1$ and $R_2$ are independently a bond, a saturated or non-saturated C1-C20 or C1-C6 alkyl chain wherein one or more methylene units are optionally and independently replaced by —O—, —S—, —N(R)—, —C(O)—, C(O)O—, OC(O)—, —N(R)C(O)—, —C(O)N(R)—, —S(O)—, —S(O)$_2$—, —N(R)SO$_2$—, SO$_2$N(R)—, a heterocyclic group, an aryl group, or a heteroaryl group, wherein each occurrence of R is independently hydrogen, a suitable protecting group, an acyl moiety, arylalkyl moiety, aliphatic moiety, aryl moiety, heteroaryl moiety, or heteroaliphatic moiety, poly(ethylene glycol) (PEG) chain PEG$_2$, (PEG)$_3$, (PEG)$_4$, (PEG)$_5$, (PEG)$_6$, (PEG)$_7$, (PEG)$_8$, (PEG)$_9$, (PEG)$_{10}$, (PEG)$_{11}$, (PEG)$_{12}$, (PEG)$_{13}$, (PEG)$_{14}$, (PEG)$_{15}$, (PEG)$_{16}$, or (PEG)$_2$ and wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a benzene-1,3 diacyl having the following general formula

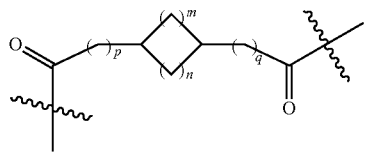

Wherein m and n are each independently 1 or 2; wherein p and q are independently 0, 1, 2, 3, 4, or 5 wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,1 diacyl having the following general formula

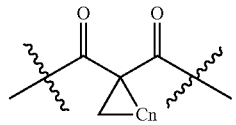

wherein n is 1, 2, 3, or 4 wherein the wavy lines indicate the bond between the linker and the epsilon amino group of the lysine at position B29 or B28 of the insulin polypeptides. In specific embodiments, the 1,1 diacyl may have a structure selected from

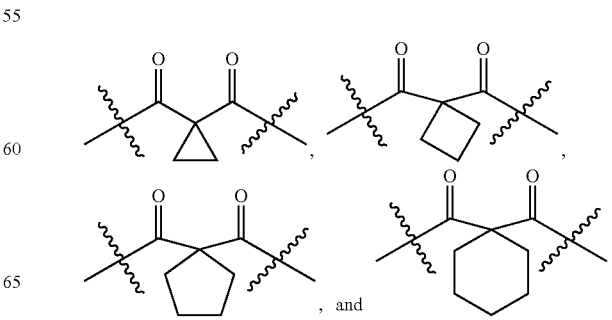

, and (1,1-diacyl-C3; 1,2-diacyl-C4; 1,1-diacyl-C5; and 1,1-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,2 diacyl having the following general formula

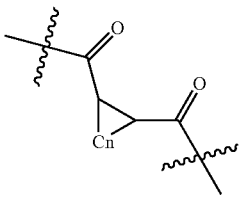

wherein n is 1, 2, 3, or 4 wherein the wavy lines indicate the bond between the linker and the epsilon amino group of the lysine at position B29 or B28 of the insulin polypeptides. In specific embodiments, the 1,2 diacyl may have a structure selected from

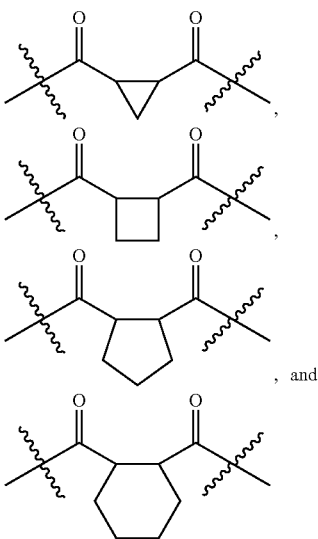

, and (1,2-diacyl-C3; 1,2-diacyl-C4; 1,2-diacyl-C5; and 1,2-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,3 diacyl having the following general formula

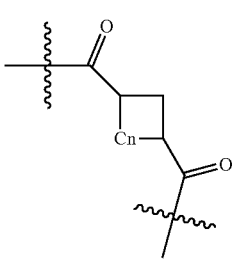

wherein n is 1, 2, or 3 wherein the wavy lines indicate the bond between the linker and the epsilon amino group of the lysine at position B29 or B28 of the insulin polypeptides. In specific embodiments, the 1,3 diacyl may have a structure selected from

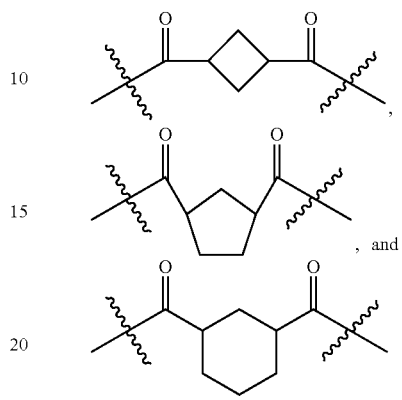

, and (1,3-diacyl-C4; 1,3-diacyl-C5; and 1,3-diacyl-C6, respectively) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a 1,4 diacyl having the following general formula

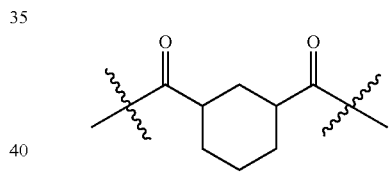

(1,4-diacyl-C6) wherein the wavy lines indicate the bond between the linker and the epsilon amino group of the lysine at position B29 or B28 of the insulin polypeptides.

In another embodiment, the linking moiety comprises a bifunctional linker that may be covalently conjugated or linked to epsilon amino group of the position B29 or B28 lysine residues of the first and second insulin polypeptides which may be represented by a cyclobutyl-1,3 diacyl having the following general formula

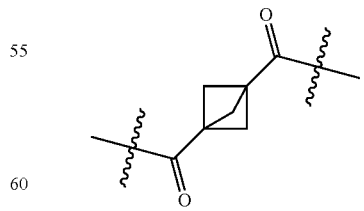

and wherein the wavy lines indicate the bond between the linker and the epsilon amino group of the lysine at position B29 or B28 of the insulin polypeptides.

In a further aspect of the present invention, the first and second insulin polypeptides may be conjugated together using copper-catalyzed Azide-Alkyne Huisgen Cycloaddition (CuAAc), in particular CuAAC click chemistry. In this aspect, the epsilon amino group of the B29 or B28 lysine of the first insulin polypeptide is conjugated to a linker moiety having a proximal end and a distal end wherein the proximal end of the linker moiety is conjugated to the epsilon amino group and the distal comprises an azide group. In this aspect, the epsilon amino group of the B29 or B28 lysine of the second insulin polypeptide is conjugated to a linker moiety having a proximal end and a distal end wherein the proximal end of the linker moiety is conjugated to the epsilon amino group and the distal comprises an alkyne group. In the presence of Cu2+ and a reducing agent, the azide and the alkyne groups will form a contiguous linking moiety comprising a triazole moiety. See U.S. Pat. No. 8,129,542, which is incorporated herein in its entirety, for a description of CuAAC click chemistry.

In particular aspects of the insulin receptor partial agonists, the first insulin polypeptide may have conjugated to the epsilon amino group of the B29 or B28 lysine a linker having the formula

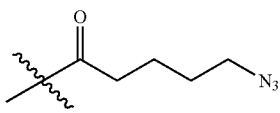 [SMILES: *C(=O)CCCCN=[N+]=[N-]]

and the second insulin polypeptide may have conjugated to the epsilon amino group of the B29 or B28 lysine a linker having the formula

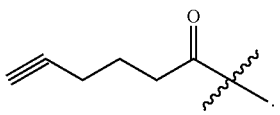 [SMILES: *C(=O)CCCC#C]

In the presence of Cu2+ and a reducing agent, the linkers combine to provide a linking moiety having the structure

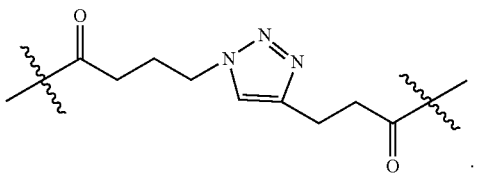 [SMILES: *C(=O)CCCn1cc(CCC(*)=O)nn1]

In particular aspects of the insulin receptor partial agonists, the first insulin polypeptide may have conjugated to the epsilon amino group of the B29 or B28 lysine a linker having the formula

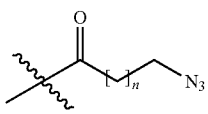

wherein n=1, 2, 3, 4, 5, 6, 7, 8, 9, or 10 and the second insulin polypeptide may have conjugated to the epsilon amino group of the B29 or B28 lysine a linker having the formula

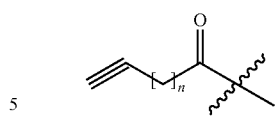

wherein n=1, 2, 3, 4, 5, 6, 7, 8, 9, or 10. In the presence of Cu2+ and a reducing agent, the linkers combine to provide a linking moiety having the structure

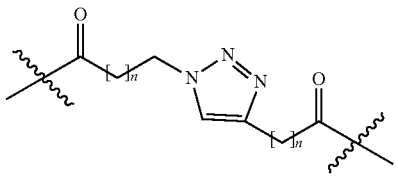

wherein each n independently is 1, 2, 3, 4, 5, 6, 7, 8, 9, or 10.

In a further aspect, both the first insulin polypeptide and the second insulin polypeptide may have conjugated to its respective epsilon amino group of the B29 or B28 lysine a linker having the formula

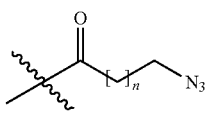

wherein each n is independently 1,2, 3, 4, 5, 6, 7, 8, 9, or 10. Conjugation of the linkers to form a linking moiety may be achieved by providing a molecule (intermediate or bridging linker) having a structure

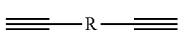

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG25.

In a further aspect, both the first insulin polypeptide and the second insulin polypeptide may have conjugated to its respective epsilon amino group of the B29 or B28 lysine a linker having the formula

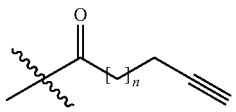

wherein each n is independently 1,2, 3, 4, 5, 6, 7, 8, 9, or 10. Conjugation of the linkers to form a linking moiety may be achieved by providing a molecule (intermediate or bridging linker) having a structure

wherein R is a covalent bond, a carbon atom, a phenyl, a heteroatom, or an optionally substituted group selected from the group consisting of acyl, aliphatic, heteroaliphatic, aryl, heteroaryl, and heterocyclic. In particular aspects R is a C2, C3, C4, C6, C7, C8, C9 or C10 acyl group or a PEG2, PEG3, PEG4, PEG5, PEG6, PEG7, PEG8, PEG9, PEG10, PEG11, PEG12, PEG13, or PEG 25.

In particular aspects, the first insulin polymer is conjugated at the epsilon amino group of the B29 or B28 lysine to an azide terminated linker as above and the second insulin polypeptide is conjugated at the epsilon amino group of the B29 or B28 lysine to a linker terminated with a cyclooctyne moiety and the linkers are conjugated to form a linker moiety using copper-free cycloaddition click chemistry. See for example, U.S. Pat. No. 7,807,619, which is incorporated herein in its entirety.

The following table shows exemplary linkers, which may be used to construct the dimers of the present invention. The dimers shown comprise 2,5-dioxopyrrolidin-1y groups for conjugating to the epsilon amino group of the B29 or B28 lysine residues of the two insulin heterodimers.

Table of Linkers
| | Linker | Name |
|---|---|---|
| 1 | 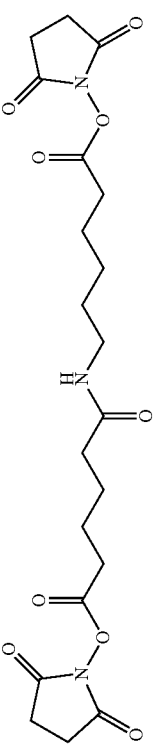 | C6 + Nc6 |
| 2 | 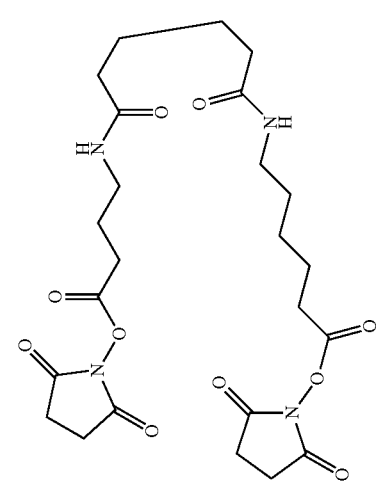 | C6N + C6 + NC6 |

-continued
Table of Linkers
| | Linker | Name |
|---|---|---|
| 3 | 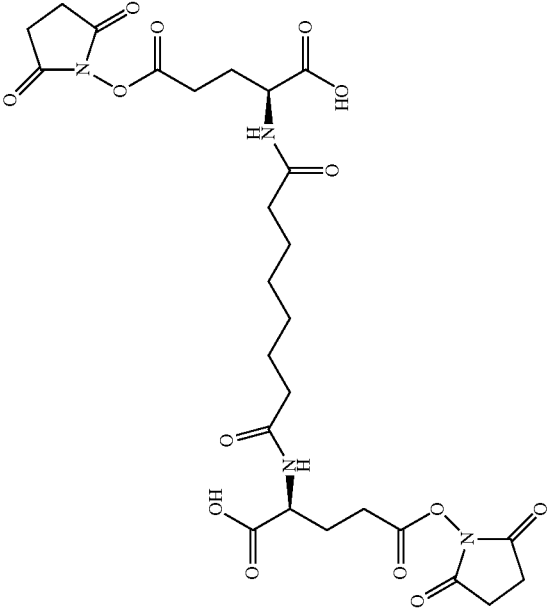 | γE-C8-γE |
| 4 | 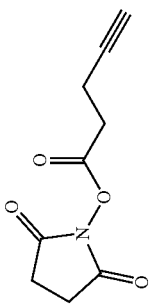 | Click-1 |
| 5 | 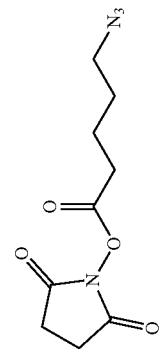 | Click-2 |

-continued
Table of Linkers
| | Linker | Name |
|---|---|---|
| 6 | 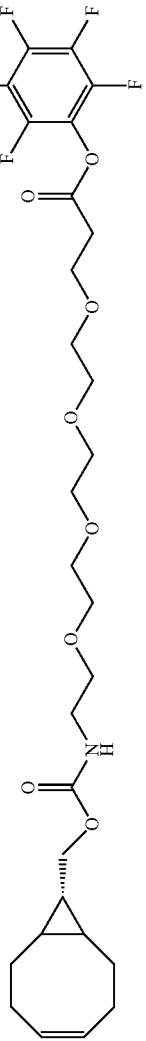 | Click-3 |
| 7 | 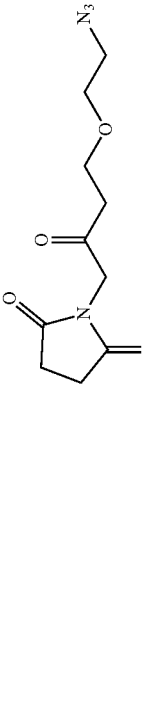 | Click-4 |
| 8 | 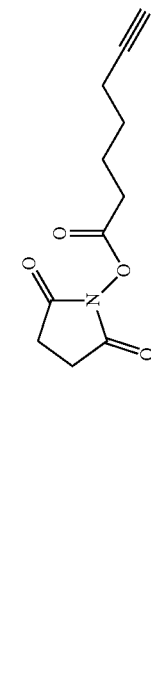 | Click-5 |
| 9 | 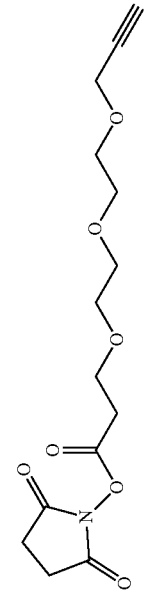 | Click-6 |
| 10 | 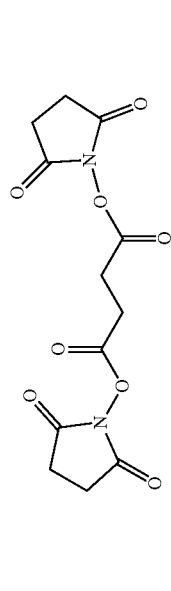 | C2 |

-continued

Table of Linkers

| | Linker | Name |
|---|---|---|
| 11 | (structure) | C4 |
| 12 | (structure) | C6 |
| 13 | (structure) | C8 |
| 14 | (structure) | C16 |

Table of Linkers -continued
| | Linker | Name |
|---|---|---|
| 15 | 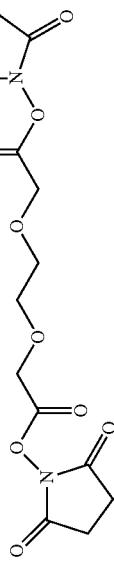 | PEG2 |
| 16 | 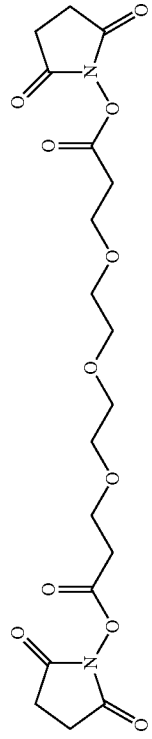 | PEG3 |
| 17 | 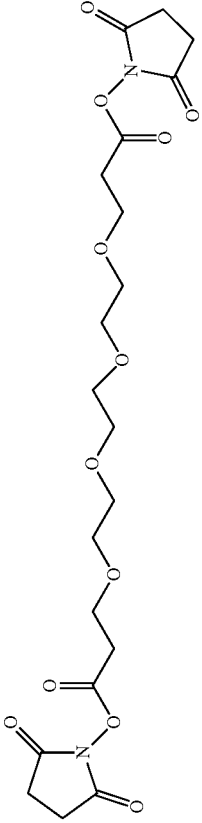 | PEG4 |
| 18 | 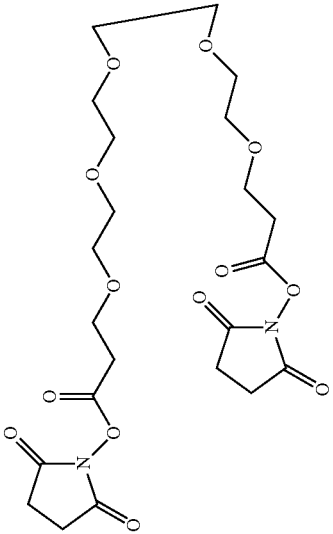 | PEG5 |

-continued
Table of Linkers
| | Linker | Name |
|---|---|---|
| 19 | 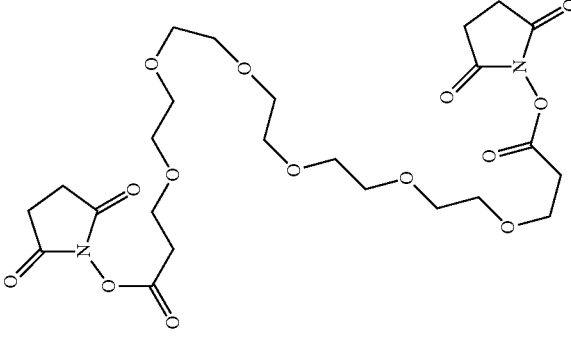 | PEG6 |

-continued

Table of Linkers

| | Linker | Name |
|---|---|---|
| 20 | (structure) | PEG7 |
| 21 | (structure) | PEG9 |

-continued
Table of Linkers
| | Linker | Name |
|---|---|---|
| 22 | 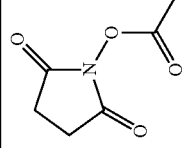 | PEG13 |

-continued
Table of Linkers
| | Linker | Name |
|---|---|---|
| 23 | 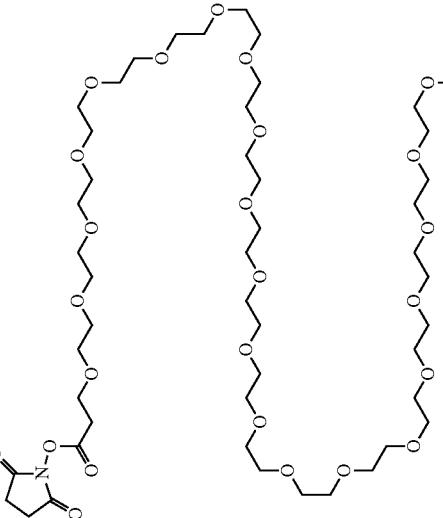 | PEG25 |
| 24 | 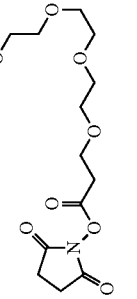 | C6-glycine |
| 25 | 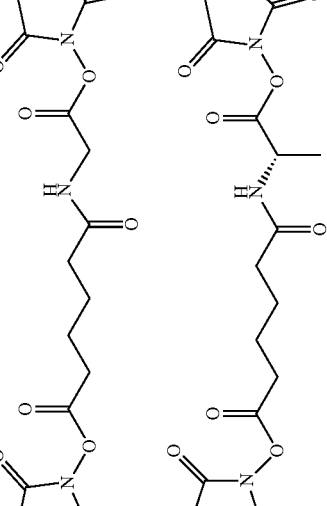 | C6-alanine |

| | Table of Linkers -continued | |
|---|---|---|
| | Linker | Name |
| 26 | 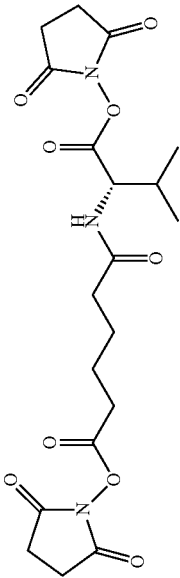 | C6-isoleucine |
| 27 | 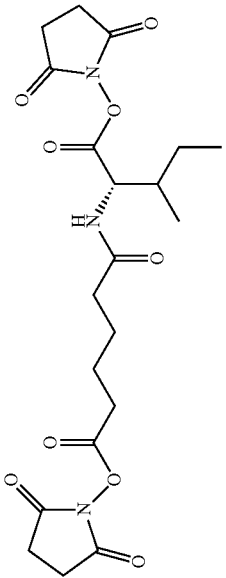 | C6-leucine |
| 28 | 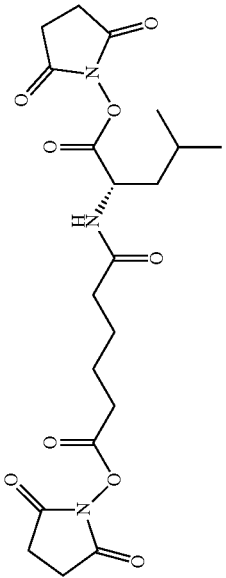 | C6-valine |
| 29 | 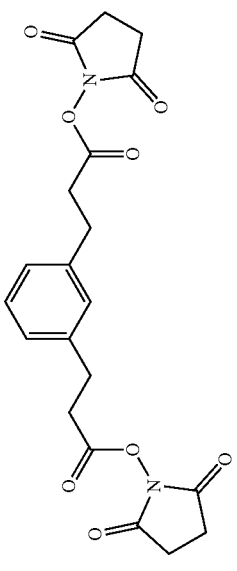 | Dipropyl phenol |

-continued

Table of Linkers

| | Linker | Name |
|---|---|---|
| 30 | | Trans-cyclohexane 1,4-diacid |
| 31 | | Cis-cyclohexane 1,4-diacid |
| 32 | | Tert-butyl-piperidine-tricarb |
| 33 | | C6N-chloro-1,3,5-Triazine-NC6 |

-continued
Table of Linkers
| | Linker | Name |
|---|---|---|
| 34 | 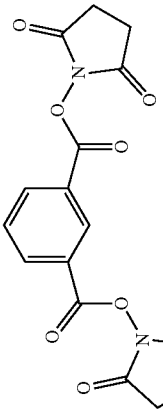 | Terephthalate |
| 35 | 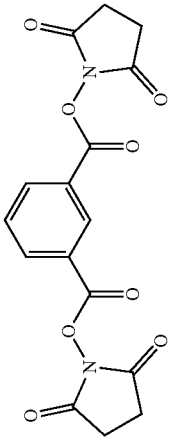 | isophthalate |
| 36 | 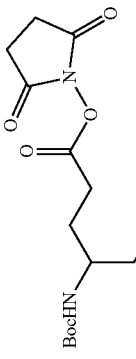 | Heptane-dioate |
| 37 | 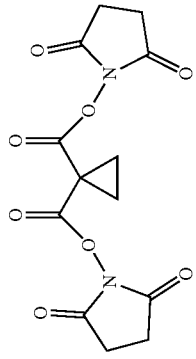 | 1,1-diacyl-C3 |

-continued

Table of Linkers

| | Linker | Name |
|---|---|---|
| 38 | (structure) | 1,1-diacyl-C4 |
| 39 | (structure) | 1,1-diacyl-C5 |
| 40 | (structure) n = 1, 2, 3, or 4 | 1,1-diacyl-C6 |
| 41 | (structure) | 1,2-diacyl-C3 |

-continued
Table of Linkers
| | Linker | Name |
|---|---|---|
| 42 | 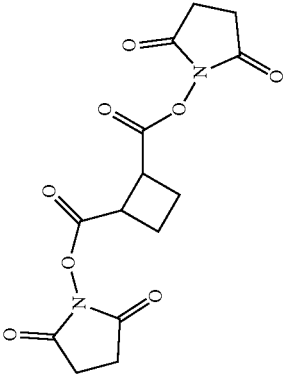 | 1,2-diacyl-C4 |
| 43 | 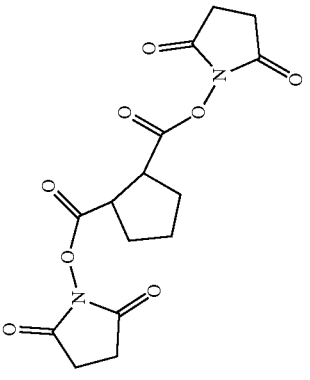 | 1,2-diacyl-C5 |
| 44 | 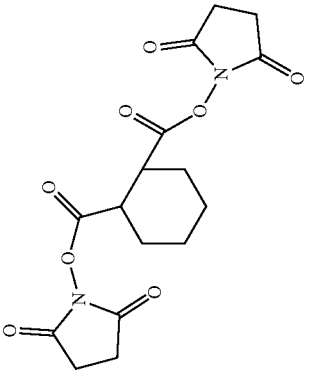 | 1,2-diacyl-C6 |

-continued

Table of Linkers

| | Linker | Name |
|---|---|---|
| 45 | | 1,3-diacyl-C4 |
| 46 | | 1,3-diacyl-C5 |
| 47 | | 1,3-diacyl-C6 |
| 48 | | 1,4-diacyl-cyclobutyl-C1 |

-continued

Table of Linkers

| | Linker | Name |
|---|---|---|
| 49 | | 1,4-cyclohexyl-C1 |
| 50 | | 1,4-cyclohexyl-C2 |
| 51 | | Tri-linker |

-continued
Table of Linkers
| | Linker | Name |
|---|---|---|
| 52 | 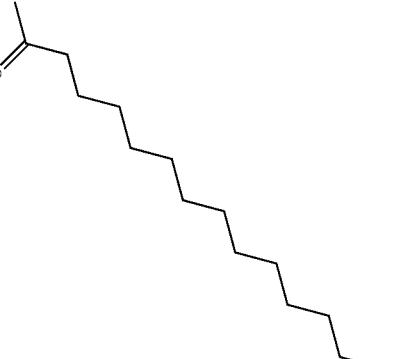 | Diacyl linker |
| 53 | 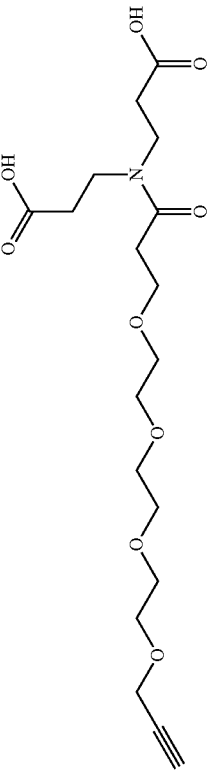 | Tri-linker |

-continued

Table of Linkers

| | Linker | Name |
|---|---|---|
| 54 | | Tri-linker |
| 55 | Exact Mass: 2297.22 | Tri-linker |

Conjugation of a bifunctional linker to the epsilon amino group of the lysine residue at position B29 or B28 of the B-chain polypeptide of two insulin or insulin analog molecules to form the insulin dimer linked by a linking moiety may be schematically shown as

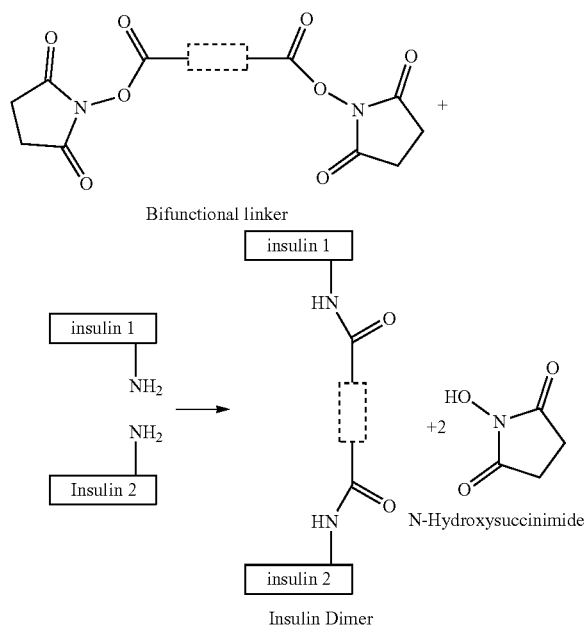

wherein the insulin 1 and insulin 2 molecules may be the same or different and the bifunctional linker and resulting and linking moiety following conjugation may have the structure of any linker and resulting linking moiety disclosed herein.

Incretin

The incretin comprising the insulin dimer-incretin conjugate may be any peptide having agonist activity at the glucagon-like 1 (GLP-1) receptor, the glucagon (GCG) receptor, the gastric inhibitory protein (GIP) receptor, or both the GLP-1 receptor and the GCG receptor or both the GLP-1 receptor and the GIP receptor. In particular embodiments, the incretin is a glucagon peptide modified to have agonist activity at the glucagon-like 1 (GLP-1) receptor, the glucagon (GCG) receptor, the gastric inhibitory protein (GIP) receptor, or both the GLP-1 receptor and the GCG receptor or both the GLP-1 receptor and the GIP receptor.

In particular embodiments, the peptide comprises a modified glucagon peptide comprising the amino acid sequence

HSQGTFTSDYSKYLDERAAQDFVQWLLDT (SEQ ID NO:1)

which further includes at least the following modifications: (i) a substitution of the amino acid at position 2 with an amino acid that renders the peptide resistant to cleavage and inactivation by dipeptidyl peptidase IV; (ii) a lipid moiety covalently linked to the peptide at a lysine residue substituted for the tyrosine residue at position 10 or the glutamine at position 20 of the peptide; (iii) an azide group or an alkyne group conjugated to an amino acid at position 20, 21, 24, 30, or 31; (iv) 0, 1, 2, 3, 4, 5, 6, 7, 8, 9, or 10 additional amino acid substitutions and/or additions in addition to the substitution at position 2; and optionally, a protecting group that is joined to the C-terminal carboxy group and/or the N-terminal amino group. In embodiments in which the modified glucagon peptide has agonist activity at the GIP receptor, the Histidine at position 1 is substituted Tyrosine, Phenylalanine, Tryptophan, or other amino acid with an aromatic group. In particular embodiments, the peptide further includes a lipid moiety covalently linked to the peptide at a lysine residue substituted for the tyrosine residue at position 10 or the glutamine at position 20 of the peptide.

In general, the peptide comprises a substitution of the Ser at position 2 with Val, Ile, Asp, Glu, Met, Trp, Asn, D-Ala, D-Ser, α-methyl-Ser, α-methyl-D-Ser or α-aminoisobutyric acid (aib or U). In particular embodiments, the Ser is substituted with D-Ser or aib. These substitutions at position 2 render the peptide resistant to DPP-4 and active at the GLP-1 receptor. Peptides with a substitution are co-agonists of the GCG and the GLP-1 receptors.

In particular embodiments, the Gln at position 3 is substituted with Glu or Asp. These substitutions increase the selectivity of the peptide for the GLP-1 receptor over the GCG receptor. Such peptides have little or no activity at the GCG receptor.

In particular embodiments, the peptide includes a substitution of the Glu at position 16 with aib, Asn, Ser, or Ala.

In particular embodiments the His at position 1 is substituted with an amino acid with a large aromatic group, for example, Tyr, Phe, or Trp. When this substitution includes the substitution of the Ser at position 2 with aib or D-Ser, the substitution of the Lys at position 12 with Ile and substitution of the Glu at position 16 with aib, the peptide has agonist activity at the GCG, GLP-1 and GIP receptors. When the peptide further includes a substitution of the Gln at position 3 with Glu or Asp, the peptide has agonist activity at the GLP-1 and GIP receptors.

In particular embodiments, the insulin dimer molecule comprises an alkyne group and the peptide agonist activity is selective for the GLP-1 receptor and comprises the structure (SEQ ID NO: 2)
$HX^2X^3GTFTSX^9X^{10}SX^{12}YX^{14}DX^{16}X^{17}X^{18}AX^{20}X^{21}X^{22}V$ $X^{24}X^{25}X^{26}X^{27}X^{28}X^{29}X^{30}X^{31}$ Wherein $X^2$ is amionisobutyric acid (Aib), Gly, D-Serine (s), alpha-methyl Serine (αMS), or alpha-methyl D-Serine (αMs);
$X^3$ is Val, Glu or Asp;
$X^9$ is Asp or alpha-methyl Aspartic acid (αMD);
$X^{10}$ is Tyr or Lys conjugated to a lipid moiety;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal azide group or to a fatty acid or fatty diacid;
$X^{21}$ is Aspartic acid, αMD, Azidonorleucine (Norleucine ($\varepsilon N_3$)), or Lysine conjugated via its epsilon amino group to a non-peptide linker comprising a terminal azide group;
$X^{22}$ is Phe or αMF;
$X^{24}$ is Glutamine, Nle($\varepsilon N_3$), or Lysine conjugated via its epsilon amino group to a non-peptide linker comprising a terminal azide group;
$X^{25}$ is Tryptophan or alpha-methyl Tryptophan (αMW);
$X^{26}$ is Leucine or αML;
$X^{27}$ is Methionine, Leucine, Methionine sulfoxide, or L-methionine sulphone (2);

$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(εN$_3$), or $X^{30}$ is absent; and
$X^{31}$ is Glycine, γGlu, Nle(εN$_3$), or Lysine conjugated via its epsilon amino group to a non-peptide linker comprising a terminal azide group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the azide group or $X^{20}$ is a Lysine residue conjugated via its epsilon amino acid to the lipid moiety and one of $X_{21}$, $X_{24}$, $X^{30}$, or $X^{31}$ comprises the azide group.

In particular embodiments, the insulin dimer molecule comprises an azide group and the peptide agonist activity is selective for the GLP-1 receptor and comprises the structure

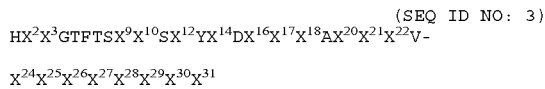

Wherein $X^2$ is aminoisobutyric acid (Aib), D-Serine (s), or alpha-methyl Serine (αMS);
$X^3$ is Val, Glu, or Asp;
$X^9$ is Asp or alpha-methyl Aspartic acid (αMD);
$X^{10}$ is Tyr or Lys conjugated to a lipid moiety;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal alkyne group or to a fatty acid or fatty diacid;
$X^{21}$ is Aspartic acid, αMD, Alkynylnorleucine (Norleucine conjugated via its epsilon carbon to an alkyne group (Nle (ε-alkyne))), or Lysine conjugated via its epsilon amino group to a non-peptide linker comprising a terminal alkyne group;
$X^{22}$ is Phe or alpha-methyl Phenylalanine (αMF);
$X^{24}$ is Glutamine, Nle(ε-alkyne), or Lysine conjugated via its epsilon amino group to a non-peptide linker comprising a terminal alkyne group;
$X^{25}$ is Tryptophan or alpha-methyl Tryptophan (αMW);
$X^{26}$ is Leucine or αML;
$X^{27}$ is Methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε-alkyne), or $X^{30}$ is absent; and
$X^{31}$ is Glycine, γGlu, Nle(ε-alkyne), or Lysine conjugated via its epsilon amino group to a non-peptide linker comprising a terminal alkyne group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the alkyne group or $X^{20}$ is a Lysine residue conjugated via its epsilon amino acid to the lipid moiety and one of $X^{21}$, $X^{24}$, $X^{30}$, or $X^{31}$ comprises the alkyne group.

In particular embodiments, the insulin dimer molecule comprises an alkyne group and the peptide has agonist activity at the GLP-1 and GCG receptors and comprises the structure (SEQ ID NO: 4)
HX$^2$QGTFTSX$^9$X$^{10}$SX$^{12}$YX$^{14}$DX$^{16}$X$^{17}$X$^{18}$AX$^{20}$X$^{21}$X$^{22}$V-X$^{24}$X$^{25}$X$^{26}$X$^{27}$X$^{28}$X$^{29}$X$^{30}$X$^{31}$ wherein $X^2$ is aminoisobutyric acid (Aib), D-Serine (s), or alpha-methyl Serine (αMS); $X^9$ is Asp or alpha-methyl Aspartic acid (αMD);
$X^{10}$ is Tyr or Lys conjugated to a lipid moiety;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal azide group or to a fatty acid or fatty diacid;
$X^{21}$ is Aspartic acid, αMD, Azidonorleucine (Norleucine conjugated via its epsilon carbon to an azide group (Nle (εN$_3$))), or Lysine conjugated via its epsilon amino group to a non-peptide linker comprising a terminal azide group;
$X^{22}$ is Phe or alpha-methyl Phenylalanine (αMF);
$X^{24}$ is Glutamine, Nle(εN$_3$), or Lysine conjugated via its epsilon amino group to a non-peptide linker comprising a terminal azide group;
$X^{25}$ is Tryptophan or alpha-methyl Tryptophan (αMW);
$X^{26}$ is Leucine or αML;
$X^{27}$ is Methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(εN$_3$), or $X^{30}$ is absent; and
$X^{31}$ is Glycine, γGlu, Nle(εN$_3$), or Lysine conjugated via its epsilon amino group to a non-peptide linker comprising a terminal azide group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the azide group or $X^{20}$ is a Lysine residue conjugated via its epsilon amino acid to the lipid moiety and one of $X^{21}$, $X^{24}$, $X^{30}$, or $X^{31}$ comprises the azide group.

In particular embodiments, the insulin dimer molecule comprises an azide group and the peptide has agonist activity at the GLP-1 and GCG receptors and comprises the structure

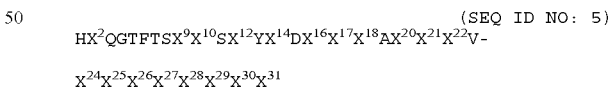

Wherein $X^2$ is aminoisobutyric acid (Aib), D-Serine (s), or alpha-methyl Serine (αMS);
$X^9$ is Asp or alpha-methyl Aspartic acid (αMD);
$X^{10}$ is Tyr or Lys conjugated to a lipid moiety;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal alkyne group or to a fatty acid or fatty diacid;
$X^{21}$ is Aspartic acid, αMD, Alkynylnorleucine (Norleucine conjugated via its epsilon carbon to an alkyne group (Nle (ε-alkyne))), or Lysine conjugated via its epsilon amino group to a non-peptide linker comprising a terminal alkyne group;
$X^{22}$ is Phe or alpha-methyl Phenylalanine (αMF);
$X^{24}$ is Glutamine, Nle(ε-alkyne), or Lysine conjugated via its epsilon amino group to a non-peptide linker comprising a terminal alkyne group;
$X^{25}$ is Tryptophan or alpha-methyl Tryptophan (αMW);
$X^{26}$ is Leucine or αML;
$X^{27}$ is Methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε-alkyne), or $X^{30}$ is absent; and
$X^{31}$ is Glycine, γGlu, Nle(ε-alkyne), or Lysine conjugated via its epsilon amino group to a non-peptide linker comprising a terminal alkyne group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the alkyne group or $X^{20}$ is a Lysine residue conjugated via its epsilon amino acid to the lipid moiety and one of $X^{21}$, $X^{24}$, $X^{30}$, or $X^{31}$ comprises the alkyne group.

In particular embodiments, the insulin dimer molecule comprises an alkyne group and the peptide has agonist activity predominantly at the GLP-1 receptor and GIP receptor and comprises the structure $$X^1X^2X^3GTFTSX^9X^{10}SX^{12}YX^{14}DX^{16}X^{17}X^{18}AX^{20}X^{21}X^{22}V\text{-}$$
$$X^{24}X^{25}X^{26}X^{27}X^{28}X^{29}X^{30}X^{31}$$
(SEQ ID NO: 6)

Wherein $X^1$ is Tyrosine, Phenylalanine, Tryptophan, or other amino acid with an aromatic group;
$X^2$ is amionisobutyric acid (Aib), Gly, D-Serine (s), or alpha-methyl Serine (αMS);
$X^3$ is Val, Glu, or Asp;
$X^9$ is Asp or alpha-methyl Aspartic acid (αMD);
$X^{10}$ is Tyr or Lys conjugated to a lipid moiety;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal azide group or to a fatty acid or fatty diacid;
$X^{21}$ is Aspartic acid, αMD, Azidonorleucine (Norleucine conjugated via its epsilon carbon to an azide group (Nle (εN₃))), or Lysine conjugated via its epsilon amino group to a non-peptide linker comprising a terminal azide group;
$X^{22}$ is Phe or alpha-methyl Phenylalanine (αMF),
$X^{24}$ is Glutamine, Nle(εN₃), or Lysine conjugated via its epsilon amino group to a non-peptide linker comprising a terminal azide group;
$X^{25}$ is Tryptophan or alpha-methyl Tryptophan (αMW);
$X^{26}$ is Leucine or αML;
$X^{27}$ is Met, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(εN₃), or $X^{30}$ is absent; and
$X^{31}$ is Glycine, γGlu, Nle(εN₃), or Lysine conjugated via its epsilon amino group to a non-peptide linker comprising a terminal azide group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the azide group or $X^{20}$ is a Lysine residue conjugated via its epsilon amino acid to the lipid moiety and one of $X^{21}$, $X^{24}$, $X^{30}$, or $X^{31}$ comprises the azide group.

In particular embodiments, the insulin dimer molecule comprises an azide group and the peptide has agonist activity at the GLP-1 receptor and GIP receptor and comprises the structure $$X^1X^2X^3GTFTSX^9X^{10}SX^{12}YX^{14}DX^{16}X^{17}X^{18}AX^{20}X^{21}X^{22}V\text{-}$$
$$X^{24}X^{25}X^{26}X^{27}X^{28}X^{29}X^{30}X^{31}$$
(SEQ ID NO: 7)

Wherein $X^1$ is Tyrosine, Phenylalanine, Tryptophan, or other amino acid with an aromatic group;
$X^2$ is aminoisobutyric acid (Aib), D-Serine (s), or alpha-methyl Serine (αMS);
$X^3$ is Val, Glu, or Asp;
$X^9$ is Asp or alpha-methyl Aspartic acid (αMD);
$X^{10}$ is Tyr or Lys conjugated to a lipid moiety;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal alkyne group or to a fatty acid or fatty diacid;
$X^{21}$ is Aspartic acid, αMD, Alkynylnorleucine (Norleucine conjugated via its epsilon carbon to an alkyne group (Nle (ε-alkyne))), or Lysine conjugated via its epsilon amino group to a non-peptide linker comprising a terminal alkyne group;
$X^{22}$ is Phe or alpha-methyl Phenylalanine (αMF),
$X^{24}$ is Glutamine, Nle(ε-alkyne), or Lysine conjugated via its epsilon amino group to a non-peptide linker comprising a terminal alkyne group;
$X^{25}$ is Tryptophan or alpha-methyl Tryptophan (αMW);
$X^{26}$ is Leucine or αML;
$X^{27}$ is Methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε-alkyne), or $X^{30}$ is absent; and
$X^{31}$ is Glycine, γGlu, Nle(ε-alkyne), or Lysine conjugated via its epsilon amino group to a non-peptide linker comprising a terminal alkyne group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the alkyne group or $X^{20}$ is a Lysine residue conjugated via its epsilon amino acid to the lipid moiety and one of $X^{21}$, $X^{24}$, $X^{30}$, or $X^{31}$ comprises the alkyne group.

In particular embodiments, the insulin dimer molecule comprises an alkyne group and the peptide has agonist activity at the GLP-1, GIP, and GCG receptors and comprises the structure (SEQ ID NO: 8)
X¹X²QGTFTSX⁹X¹⁰SX¹²YX¹⁴DX¹⁶X¹⁷X¹⁸AX²⁰X²¹X²²V-

X²⁴X²⁵X²⁶X²⁷X²⁸X²⁹X³⁰X³¹

Wherein $X^1$ is Tyrosine, Phenylalanine, Tryptophan, or other amino acid with an aromatic group;
$X^2$ is amionisobutyric acid (Aib), Gly, D-Serine (s), or alpha-methyl Serine (αMS);
$X^9$ is Asp or alpha-methyl Aspartic acid (αMD);
$X^{10}$ is Tyr or Lys conjugated to a lipid moiety;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal azide group or to a fatty acid or fatty diacid;
$X^{21}$ is Aspartic acid, αMD, Azidonorleucine (Norleucine conjugated via its epsilon carbon to an azide group (Nle (εN₃))), or Lysine conjugated via its epsilon amino group to a non-peptide linker comprising a terminal azide group;
$X^{22}$ is Phe or alpha-methyl Phenylalanine (αMF);
$X^{24}$ is Glutamine, Nle(εN₃), or Lysine conjugated via its epsilon amino group to a non-peptide linker comprising a terminal azide group;
$X^{25}$ is Tryptophan or alpha-methyl Tryptophan (αMW);
$X^{26}$ is Leucine or αML;
$X^{27}$ is methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(εN₃), or $X^{30}$ is absent; and
$X^{31}$ is Glycine, γGlu, Nle(εN₃), or Lysine conjugated via its epsilon amino group to a non-peptide linker comprising a terminal azide group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the azide group or $X^{20}$ is a Lysine residue conjugated via its epsilon amino acid to the lipid moiety and one of $X^{21}$, $X^{24}$, $X^{30}$, or $X^{31}$ comprises the azide group.

In particular embodiments, the insulin dimer molecule comprises an azide group and the peptide has agonist activity at the GLP-1, GIP, and GCG receptors and comprises the structure (SEQ ID NO: 9)
X¹X²QGTFTSX⁹X¹⁰SX¹²YX¹⁴DX¹⁶X¹⁷X¹⁸AX²⁰X²¹FV-

X²⁴X²⁵X²⁶X²⁷X²⁸X²⁹X³⁰X³¹

Wherein $X^1$ is Tyrosine, Phenylalanine, Tryptophan, or other amino acid with an aromatic group;
$X^2$ is aminoisobutyric acid (Aib), D-Serine (s), or alpha-methyl Serine (αMS);
$X^9$ is Asp or alpha-methyl Aspartic acid (αMD);
$X^{10}$ is Tyr or Lys conjugated to a lipid moiety;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amino group to a non-peptide linker comprising a terminal alkyne group or to a fatty acid or fatty diacid;
$X^{21}$ is Aspartic acid, αMD, Alkynylnorleucine (Norleucine conjugated via its epsilon carbon to an alkyne group (Nle (ε-alkyne))), or Lysine conjugated via its epsilon amino group to a non-peptide linker comprising a terminal alkyne group;
$X^{22}$ is Phe or alpha-methyl Phenylalanine (αMF);
$X^{24}$ is Glutamine, Nle(ε-alkyne), or Lysine conjugated via its epsilon amino group to a non-peptide linker comprising a terminal alkyne group;
$X^{25}$ is Tryptophan or alpha-methyl Tryptophan (αMW);
$X^{26}$ is Leucine or αML;
$X^{27}$ is methionine, Leucine, methionine sulfoxide, or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε-alkyne), or $X^{30}$ is absent; and
$X^{31}$ is Glycine, γGlu, Nle(ε-alkyne), or Lysine conjugated via its epsilon amino group to a non-peptide linker comprising a terminal alkyne group, or $X^{31}$ is absent; and
wherein the C-terminal amino acid optionally is amidated, and with the proviso that either $X^{10}$ is a Lysine residue conjugated via its epsilon amino acid to the lipid moiety and one of $X^{20}$, $X^{21}$, $X^{24}$, $X^{30}$, or $X^{31}$ comprises the alkyne group or $X^{20}$ is a Lysine residue conjugated via its epsilon amino acid to the lipid moiety and one of $X^{21}$, $X^{24}$, $X^{30}$, or $X^{31}$ comprises the alkyne group.

The lipid moiety may be a monocarboxylic acid comprising an aliphatic chain of 13 to 20 methylene groups (fatty acid) wherein one end of the molecule is the proximal end and the other end is the distal end and only one of the proximal end and the distal end has a carboxyl (COOH) group. The fatty acid may be represented by the structure $HO_2C(CH_2)_nCH_3$, wherein n is 11, 12, 13, 14, 15, 16, 17, or 18. The fatty acid may have one of the following structures

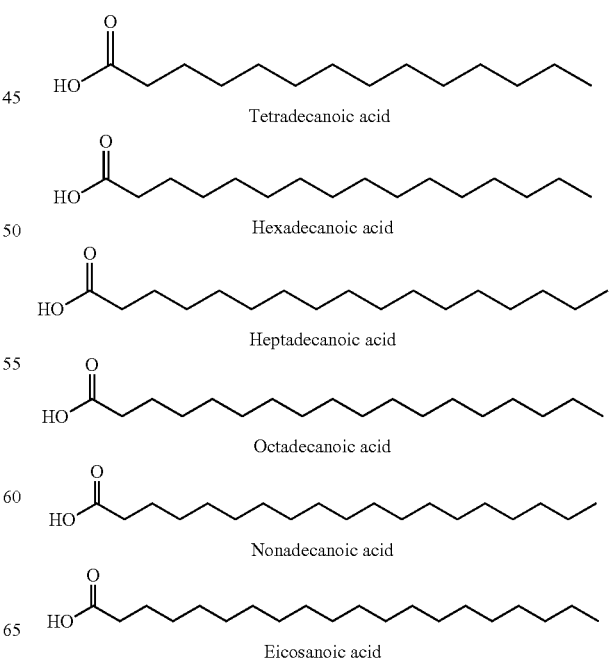

The lipid moiety may be an α,ω-dicarboxylic acid comprising an aliphatic chain of 13 to 20 methylene groups (fatty diacid) wherein one end of the molecule is the proximal end and the other end is the distal end and wherein the proximal end and the distal end both have a carboxyl (COOH) group. The fatty diacid may be represented by the structure $HO_2C(CH_2)_nCO_2H$, wherein n is 11, 12, 13, 14, 15, 16, 17, or 18. The fatty diacid may have one of the following structures

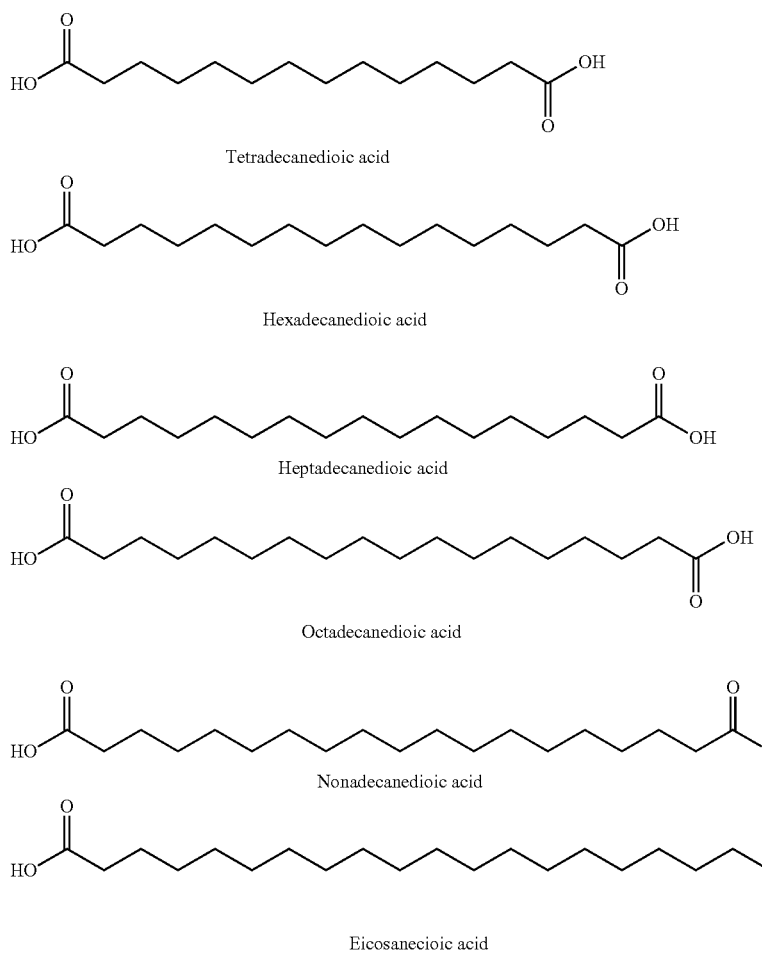

Tetradecanedioic acid

Hexadecanedioic acid

Heptadecanedioic acid

Octadecanedioic acid

Nonadecanedioic acid

Eicosanedioic acid

As a component of the peptide, the acid functionality at the proximal end of the fatty diacid is conjugated to the amino group of a linker in a C(O)—NH linkage and the acid functionality at the distal end of the fatty diacid is a free carboxyl group (COOH). The COOH group at the distal end helps confer a longer half-life to the peptide by its ability to non-covalently bind to serum albumin, a known carrier for fatty acids in serum. The COOH group enhances duration of action as it provides a better non-covalent interaction with serum albumin than peptides that have been acylated using a fatty acid, which bind serum albumin less efficiently and form a less stable non-covalent interaction with the serum albumin.

When the fatty acid or diacid is conjugated to a linking moiety or linker, it is subsequently referred to as a fatty acid component. The linker may be PEG$_2$ (8-amino-3,6-dioxaoctanoic acid) linked to Gamma-Glutamic acid (gamma-Glu, γGlu, or γE), which has the structure

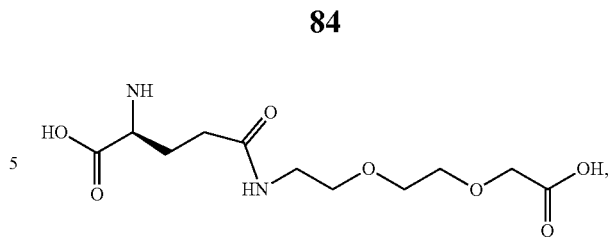

or the linker may be Gamma-Glutamic acid-gamma glutamic acid (gamma-Glu-gamma-Glu, or γGlu-γGlu, or γEγE), which has the structure

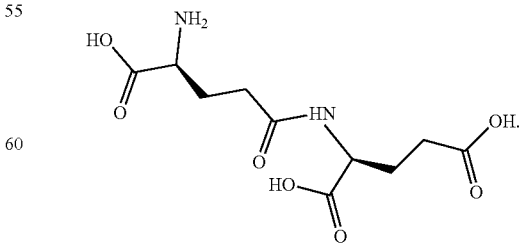

The structure of K(PEG$_2$PEG$_2$γE-fatty acid) wherein the linker is PEG$_2$PEG$_2$γE and the fatty acid component comprises C14, C16, C17, C18, C19, or C20 fatty acid is represented by

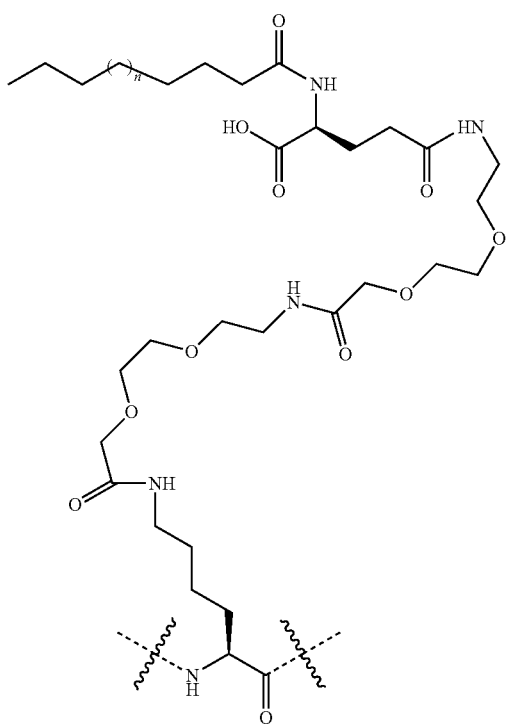

wherein n is 7, 9, 10, 11, 12, 13, or 14 respectively, and the wavy lines represent the bonds between adjacent amino acids in the peptide sequence.

The structure of K(PEG$_2$PEG$_2$γE-fatty acid) wherein the linker is PEG$_2$PEG$_2$γE and the fatty acid component comprises C14, C16, C17, C18, C19, or C20 fatty acid is represented by wherein n is 7, 9, 10, 11, 12, 13, or 14, respectively, and the wavy lines represent the bonds between adjacent amino acids in the peptide sequence.

The structure of K(PEG$_2$PEG$_2$γE-fatty acid) wherein the linker is PEG$_2$PEG$_2$γE and the fatty acid component comprises C14, C16, C17, C18, C19, or C20 fatty diacid is represented by

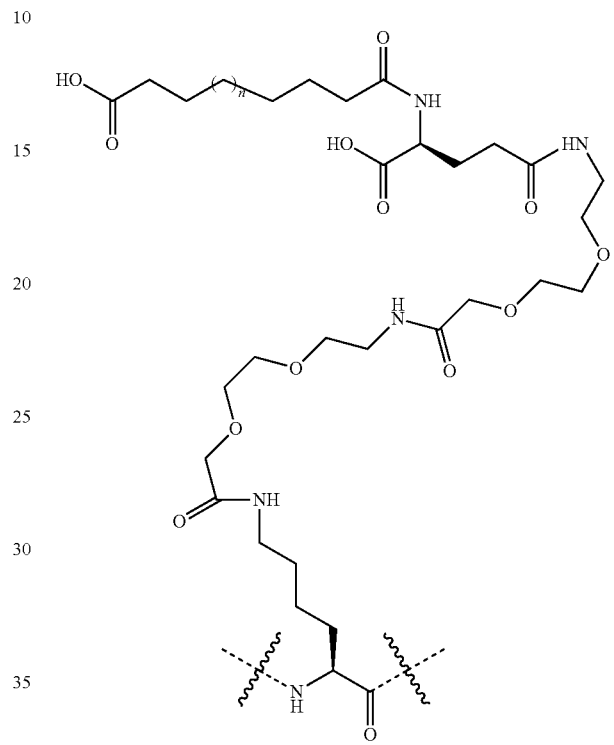

wherein n is 7, 9, 10, 11, 12, 13, or 14 respectively, and the wavy lines represent the bonds between adjacent amino acids in the peptide sequence.

The structure of K(γEγE-fatty acid) wherein the linker is γEγE and the fatty acid component comprises C14, C16, C17, C18, C19, or C20 fatty acid is represented by The structure of K(γEγE-fatty acid) wherein the linker is γEγE and the fatty acid component comprises C14, C16, C17, C18, C19, or C20 fatty diacid is represented by

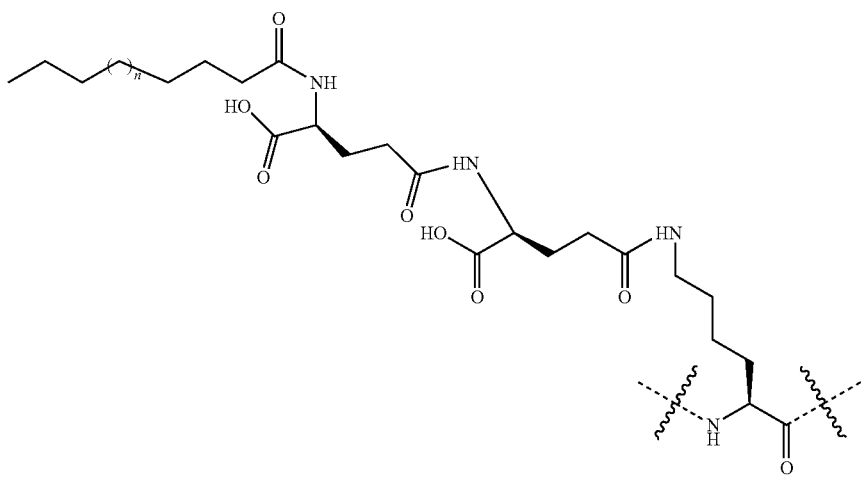

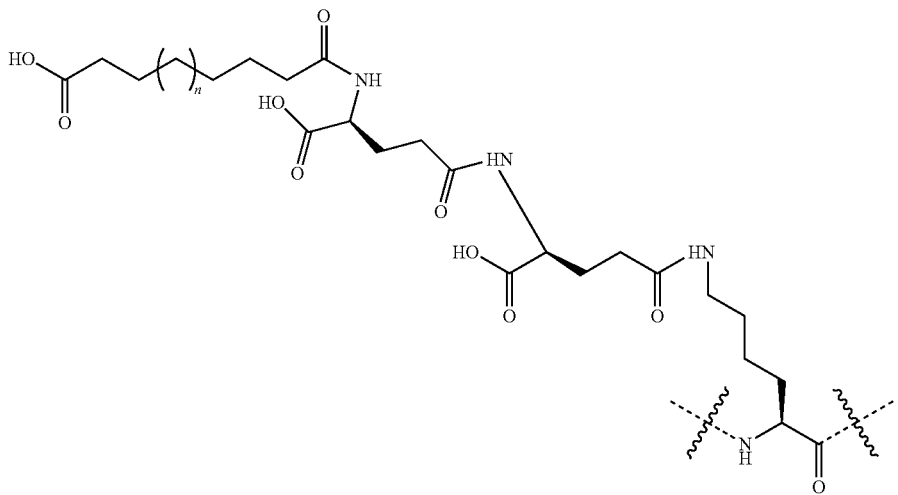

wherein n is 7, 9, 10, 11, 12, 13, or 14, respectively, and the wavy lines represent the bonds between adjacent amino acids in the peptide sequence.

In particular aspects, the peptide may comprise a lysine residue at the C-terminus that is conjugated to a γE residue to provide a KγE at position 30 in the peptide, which is represented by

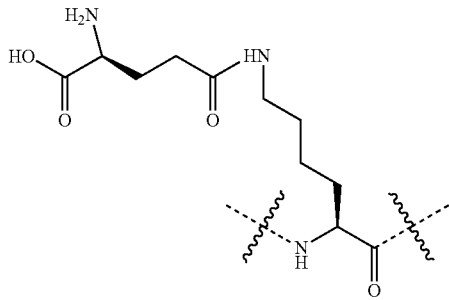

wherein the wavy lines represent the bonds between adjacent amino acids in the peptide sequence.

In a further embodiment, the insulin dimer molecule comprises an alkyne group and the peptide has agonist activity at the GLP-1 and GCG receptors and comprises the structure (SEQ ID NO: 10)
$HX^2QGTFTSX^9X^{10}SX^{12}YX^{14}DX^{16}X^{17}X^{18}AX^{20}X^{21}FV-$ $X^{24}X^{25}X^{26}X^{27}X^{28}X^{29}X^{30}X^{31}$ Wherein $X^2$ is aminoisobutyric acid (Aib), D-Serine (s), or alpha-methyl Serine (αMS);
$X^9$ is Serine or alpha-methyl Aspartic acid (αMD);
$X^{10}$ is Tyr or Lys conjugated to γGlu-γGlu-$C_{16}$;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amine group to $PEG_2$-$C_5N_3$, $PEG_2PEG_2$-$C_5N_3$, $PEG_2PEG_2$-γGlu-$C_{16}N_3$, $PEG_2PEG_2$-γGlu-$C_{18}$—OH, or $PEG_2PEG_2$γE-$C_{20}$—OH;

$X^{21}$ is Aspartic acid, alpha-methyl Phenylalanine (αMF), αMD, Azidonorleucine (Norleucine conjugated via its epsilon carbon to an azide group (Nle(εN$_3$))), or Lys conjugated via its epsilon
amine group to $PEG_2$-$C_5N_3$, $PEG_2PEG_2$-$C_5N_3$, or $PEG_2PEG_2$-γGlu-$C_{16}N_3$;
$X^{24}$ is Glutamine, Nle(εN$_3$), or Lysine conjugated to $PEG_2PEG_2$-γGlu-$C_{16}N_3$;
$X^{25}$ is Tryptophan or alpha-methyl Tryptophan (αMW);
$X^{26}$ is Leucine or αML;
$X^{27}$ is Leucine or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(εN$_3$), or $X^{30}$ is absent; and
$X^{31}$ is Glycine, γGlu, Nle(εN$_3$), or Lysine conjugated via its epsilon amine group to $PEG_2PEG_2$-γGlu-$C_{16}N_3$, $PEG_2$-$C_5N_3$ or $PEG_2PEG_2$-$C_5N_3$, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the azide or $N_3$ group or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the azide or $N_3$ group.

In a further embodiment, the insulin dimer molecule comprises an azide group and the peptide has agonist activity at the GLP-1 and GCG receptors and comprises the structure (SEQ ID NO: 11)
$HX^2QGTFTSX^9X^{10}SX^{12}YX^{14}DX^{16}X^{17}X^{18}AX^{20}X^{21}FV-$ $X^{24}X^{25}X^{26}X^{27}X^{28}X^{29}X^{30}X^{31}$ Wherein $X^2$ is aminoisobutyric acid (Aib), D-Serine (s), or alpha-methyl Serine (αMS);
$X^9$ is Serine or alpha-methyl Aspartic acid (αMD);
$X^{10}$ is Tyr or Lys conjugated to γGlu-γGlu-$C_{16}$;
$X^{12}$ is Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;

$X^{20}$ is Glutamine, Histidine, or Lysine conjugated via its epsilon amine group to $PEG_2$-$C_5N_3$, $PEG_2PEG_2$-$C_5$-alkyne, $PEG_2PEG_2$-γGlu-$C_{16}$-alkyne, $PEG_2PEG_2$-γGlu-$C_{18}$—OH, or $PEG_2PEG_2$γE-$C_{20}$—OH;

$X^{21}$ is Aspartic acid, alpha-methyl Phenylalanine (αMF), αMD, Alkynylnorleucine (Norleucine conjugated via its epsilon carbon to an alkyne group (Nle(ε-alkyne))), or Lys conjugated via its epsilon amine group to $PEG_2$-$C_5N_3$, $PEG_2PEG_2$-$C_5$-alkyne, or $PEG_2PEG_2$-γGlu-$C_{16}$-alkyne;

$X^{24}$ is Glutamine, Nle(ε-alkyne), or Lysine conjugated to $PEG_2PEG_2$-γGlu-$C_{16}$-alkyne;

$X^{25}$ is Tryptophan or alpha-methyl Tryptophan (αMW);

$X^{26}$ is Leucine or αML;

$X^{27}$ is Leucine or L-methionine sulphone (2);

$X^{28}$ is Aspartic acid, Alanine, Lysine, Asparagine, γGlu, Glutamine, or αMD;

$X^{29}$ is Threonine or Glycine;

$X^{30}$ is Arginine, Lysine, or Nle(ε-alkyne), or $X^{30}$ is absent; and $X^{31}$ is Glycine, γGlu, Nle(ε-alkyne), or Lysine conjugated via its epsilon amine group to $PEG_2PEG_2$-γGlu-$C_{16}$-alkyne, $PEG_2$-$C_5$-alkyne, $PEG_2PEG_2$-$C_5$-alkyne, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the -alkyne or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the -alkyne.

In a further embodiment, the insulin dimer molecule comprises an alkyne group and the peptide has agonist activity selective for the GLP-1 receptor and comprises the structure (SEQ ID NO: 12)
H$X^2X^3$GTFTS$X^9X^{10}$S$X^{12}$Y$X^{14}$D$X^{16}X^{17}X^{18}$A$X^{20}X^{21}$FV- $X^{24}X^{25}X^{26}X^{27}X^{28}X^{29}X^{30}X^{31}$ Wherein $X^2$ is aminoisobutyric acid (Aib), D-Serine (s), or alpha-methyl Serine (αMS);

$X^3$ is Glu or Asp;

$X^9$ is Serine or alpha-methyl Aspartic acid (αMD);

$X^{10}$ is Tyr or Lys conjugated to γGlu-γGlu-$C_{16}$;

$X^{12}$ is Lysine, Leucine, or Serine;

$X^{14}$ is Leu of alpha-methyl Leucine (αML);

$X^{16}$ is Glutamic acid, Asparagine, Serine, Alanine, or Aib;

$X^{17}$ is Arginine or Lysine;

$X^{18}$ is Alanine or Arginine;

$X^{20}$ is Glutamine, Histidine, or Lysine conjugated via its epsilon amine group to $PEG_2$-$C_5N_3$, $PEG_2PEG_2$-$C_5N_3$, $PEG_2PEG_2$-γGlu-$C_{16}N_3$, $PEG_2PEG_2$-γGlu-$C_{18}$—OH, or $PEG_2PEG_2$γE-$C_{20}$—OH;

$X^{21}$ is Aspartic acid, alpha-methyl Phenylalanine (αMF), αMD, Azidonorleucine (Norleucine conjugated via its epsilon carbon to an azide group (Nle(εN₃))), or Lys conjugated via its epsilon amine group to $PEG_2$-$C_5N_3$, $PEG_2PEG_2$-$C_5N_3$, or $PEG_2PEG_2$-γGlu-$C_{16}N_3$;

$X^{24}$ is Glutamine, Nle(εN₃), or Lysine conjugated to $PEG_2PEG_2$-γGlu-$C_{16}N_3$;

$X^{25}$ is Tryptophan or alpha-methyl Tryptophan (αMW);

$X^{26}$ is Leucine or αML;

$X^{27}$ is Leucine or L-methionine sulphone (2);

$X^{28}$ is Aspartic acid, Alanine, Lysine, Asparagine, γGlu, Glutamine, or αMD;

$X^{29}$ is Threonine or Glycine;

$X^{30}$ is Arginine, Lysine, or Nle(εN₃), or $X^{30}$ is absent; and $X^{31}$ is Glycine, γGlu, Nle(εN₃), or Lysine conjugated via its epsilon amine group to $PEG_2PEG_2$-γGlu-$C_{16}N_3$, $PEG_2$-$C_5N_3$ or $PEG_2PEG_2$-$C_5N_3$, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the azide or $N_3$ group or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the azide or $N_3$ group.

In a further embodiment, the insulin dimer molecule comprises an azide group and the peptide has agonist activity selective for the GLP-1 receptor and comprises the structure (SEQ ID NO: 13)
H$X^2X^3$GTFTS$X^9X^{10}$S$X^{12}$D$X^{14}$D$X^{16}X^{17}X^{18}$A$X^{20}X^{21}$FV- $X^{24}X^{25}X^{26}X^{27}X^{28}X^{29}X^{30}X^{31}$ Wherein $X^2$ is aminoisobutyric acid (Aib), D-Serine (s), or alpha-methyl Serine (αMS);

$X^3$ is Glu or Asp;

$X^9$ is Serine or alpha-methyl Aspartic acid (αMD);

$X^{10}$ is Tyr or Lys conjugated to γGlu-γGlu-$C_{16}$;

$X^{12}$ is Lysine, Leucine, or Serine;

$X^{14}$ is Leu of alpha-methyl Leucine (αML);

$X^{16}$ is Glutamic acid, Asparagine, Serine, Alanine, or Aib;

$X^{17}$ is Arginine or Lysine;

$X^{18}$ is Alanine or Arginine;

$X^{20}$ is Glutamine, Histidine, or Lysine conjugated via its epsilon amine group to $PEG_2$-$C_5N_3$, $PEG_2PEG_2$-$C_5$-alkyne, $PEG_2PEG_2$-γGlu-$C_{16}$-alkyne, $PEG_2PEG_2$-γGlu-$C_{18}$—OH, or $PEG_2PEG_2$γE-$C_{20}$—OH;

$X^{21}$ is Aspartic acid, alpha-methyl Phenylalanine (αMF), αMD, Alkynylnorleucine (Norleucine conjugated via its epsilon carbon to an alkyne group (Nle(ε-alkyne))), or Lys conjugated via its epsilon amine group to $PEG_2$-$C_5$-alkyne, $PEG_2PEG_2$-$C_5$-alkyne, or $PEG_2PEG_2$-γGlu-$C_{16}$-alkyne;

$X^{24}$ is Glutamine, Nle(ε-alkyne), or Lysine conjugated to $PEG_2PEG_2$-γGlu-$C_{16}$-alkyne;

$X^{25}$ is Tryptophan or alpha-methyl Tryptophan (αMW);

$X^{26}$ is Leucine or αML;

$X^{27}$ is Leucine or L-methionine sulphone (2);

$X^{28}$ is Aspartic acid, Alanine, Lysine, Asparagine, γGlu, Glutamine, or αMD;

$X^{29}$ is Threonine or Glycine;

$X^{30}$ is Arginine, Lysine, or Nle(ε-alkyne), or $X^{30}$ is absent; and $X^{31}$ is Glycine, γGlu, Nle(ε-alkyne), or Lysine conjugated via its epsilon amine group to $PEG_2PEG_2$-γGlu-$C_{16}$-alkyne, $PEG_2$-$C_5$-alkyne, $PEG_2PEG_2$-$C_5$-alkyne, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the -alkyne or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the -alkyne.

In a further embodiment, the insulin dimer molecule comprises an alkyne group and the peptide has agonist activity at the GLP-1 and GIP receptors and comprises the structure (SEQ ID NO: 14)
$X^1X^2X^3GTFTSX^9X^{10}SX^{12}YX^{14}DX^{16}X^{17}X^{18}AX^{20}X^{21}FV\text{-}$ $X^{24}X^{25}X^{26}X^{27}X^{28}X^{29}X^{30}X^{31}$ Wherein $X^1$ is Tyrosine, Phenylalanine, Tryptophan, or other amino acid with an aromatic group;
$X^2$ is aminoisobutyric acid (Aib), D-Serine (s), or alpha-methyl Serine (αMS);
$X^3$ is Glu or Asp;
$X^9$ is Serine or alpha-methyl Aspartic acid (αMD);
$X^{10}$ is Tyr or Lys conjugated to γGlu-γGlu-$C_{16}$;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amine group to $PEG_2$-$C_5N_3$, $PEG_2PEG_2$-$C_5N_3$, $PEG_2PEG_2$-γGlu-$C_{16}N_3$, $PEG_2PEG_2$-γGlu-$C_{18}$—OH, or $PEG_2PEG_2$γE-$C_{20}$—OH;
$X^{21}$ is Aspartic acid, alpha-methyl Phenylalanine (αMF), αMD, Azidonorleucine (Norleucine conjugated via its epsilon carbon to an azide group (Nle(ε$N_3$))), or Lys conjugated via its epsilon amine group to $PEG_2$-$C_5N_3$, $PEG_2PEG_2$-$C_5N_3$, or $PEG_2PEG_2$-γGlu-$C_{16}N_3$;
$X^{24}$ is Glutamine, Nle(ε$N_3$), or Lysine conjugated to $PEG_2PEG_2$-γGlu-$C_{16}N_3$;
$X^{25}$ is Tryptophan or alpha-methyl Tryptophan (αMW);
$X^{26}$ is Leucine or αML;
$X^{27}$ is Leucine or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε$N_3$), or $X^{30}$ is absent; and
$X^{31}$ is Glycine, γGlu, Nle(ε-alkyne), or Lysine conjugated via its epsilon amine group to $PEG_2PEG_2$-γGlu-$C_{16}N_3$, $PEG_2$-$C_5N_3$ or $PEG_2PEG_2$-$C_5N_3$, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the azide or $N_3$ group or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the azide or $N_3$ group.

In a further embodiment, the insulin dimer molecule comprises an azide group and the peptide has agonist activity at the GLP-1 and GIP receptors and comprises the structure (SEQ ID NO: 15)
$X^1X^2X^3GTFTSX^9X^{10}SX^{12}YX^{14}DX^{16}X^{17}X^{18}AX^{20}X^{21}FV\text{-}$ $X^{24}X^{25}X^{26}X^{27}X^{28}X^{29}X^{30}X^{31}$ Wherein $X^1$ is Tyrosine, Phenylalanine, Tryptophan, or other amino acid with an aromatic group;
$X^2$ is aminoisobutyric acid (Aib), D-Serine (s), or alpha-methyl Serine (αMS);
$X^3$ is Glu or Asp;
$X^9$ is Serine or alpha-methyl Aspartic acid (αMD);
$X^{10}$ is Tyr or Lys conjugated to γGlu-γGlu-$C_{16}$;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amine group to $PEG_2$-$C_5N_3$, $PEG_2PEG_2$-$C_5$-alkyne, $PEG_2PEG_2$-γGlu-$C_{16}$-alkyne, $PEG_2PEG_2$-γGlu-$C_{18}$—OH, or $PEG_2PEG_2$γE-$C_{20}$—OH;
$X^{21}$ is Aspartic acid, alpha-methyl Phenylalanine (αMF), αMD, Alkynylnorleucine (Norleucine conjugated via its epsilon carbon to an alkyne group (Nle(ε-alkyne))), or Lys conjugated via its epsilon amine group to $PEG_2$-$C_5$-alkyne, $PEG_2PEG_2$-$C_5$-alkyne, or $PEG_2PEG_2$-γGlu-$C_{16}$-alkyne;
$X^{24}$ is Glutamine, Nle(ε-alkyne), or Lysine conjugated to $PEG_2PEG_2$-γGlu-$C_{16}$-alkyne;
$X^{25}$ is Tryptophan or alpha-methyl Tryptophan (αMW);
$X^{26}$ is Leucine or αML;
$X^{27}$ is Leucine or L-methionine sulphone (2);
$X^{28}$ is Aspartic acid, Alanine, Lysine, Asparagine, γGlu, Glutamine, or αMD;
$X^{29}$ is Threonine or Glycine;
$X^{30}$ is Arginine, Lysine, or Nle(ε-alkyne), or $X^{30}$ is absent; and
$X^{31}$ is Glycine, γGlu, Nle(ε-alkyne), or Lysine conjugated via its epsilon amine group to $PEG_2PEG_2$-γGlu-$C_{16}$-alkyne, $PEG_2$-$C_5$-alkyne, $PEG_2PEG_2$-$C_5$-alkyne, or $X^{31}$ is absent; and wherein the C-terminal amino acid optionally is amidated, and with the proviso that either $X^{10}$ is a Lysine residue conjugated via its epsilon amino group to a γGlu-γGlu-$C_{16}$ and one of $X^{20}$, $X^{21}$, $X^{24}$, $X^{30}$, or $X^{31}$ comprises the -alkyne or $X^{20}$ is a Lysine residue conjugated via its epsilon amino group to the $PEG_2PEG_2$-γGlu-$C_{18}$—OH or the $PEG_2PEG_2$γE-$C_{20}$—OH and one of $X^{21}$, $X^{24}$, $X^{30}$, or $X^{31}$ comprises the -alkyne.

In a further embodiment, the insulin dimer molecule comprises an alkyne group and the peptide has agonist activity at the GLP-1, GIP, and GCG receptors and comprises the structure (SEQ ID NO: 16)
$X^1X^2QGTFTSX^9X^{10}SX^{12}YX^{14}DX^{16}X^{17}X^{18}AX^{20}X^{21}FV\text{-}$ $X^{24}X^{25}X^{26}X^{27}X^{28}X^{29}X^{30}X^{31}$ Wherein $X^1$ is Tyrosine, Phenylalanine, Tryptophan, or other amino acid with an aromatic group;
$X^2$ is aminoisobutyric acid (Aib), D-Serine (s), or alpha-methyl Serine (αMS);
$X^9$ is Serine or alpha-methyl Aspartic acid (αMD);
$X^{10}$ is Tyr or Lys conjugated to γGlu-γGlu-$C_{16}$;
$X^{12}$ is Isoleucine, Lysine, Leucine, or Serine;
$X^{14}$ is Leu of alpha-methyl Leucine (αML);
$X^{16}$ is Glutamic acid, Asparagine, Serine, Alanine, or Aib;
$X^{17}$ is Arginine or Lysine;
$X^{18}$ is Alanine or Arginine;
$X^{20}$ is Glutamine, Histidine, or Lysine conjugated via its epsilon amine group to $PEG_2$-$C_5N_3$, $PEG_2PEG_2$-$C_5N_3$, $PEG_2PEG_2$-γGlu-$C_{16}N_3$, $PEG_2PEG_2$-γGlu-$C_{18}$—OH, or $PEG_2PEG_2$γE-$C_{20}$—OH;
$X^{21}$ is Aspartic acid, alpha-methyl Phenylalanine (αMF), αMD, Azidonorleucine (Norleucine conjugated via its epsilon carbon to an azide group (Nle(ε$N_3$))), or Lys conjugated via its epsilon amine group to $PEG_2$-$C_5N_3$, $PEG_2PEG_2$-$C_5N_3$, or $PEG_2PEG_2$-γGlu-$C_{16}N_3$;
$X^{24}$ is Glutamine, Nle(ε$N_3$), or Lysine conjugated to $PEG_2PEG_2$-γGlu-$C_{16}N_3$;
$X^{25}$ is Tryptophan or alpha-methyl Tryptophan (αMW);
$X^{26}$ is Leucine or αML;
$X^{27}$ is Leucine or L-methionine sulphone (2);

$X^{28}$ is Aspartic acid, Alanine, Lysine, Asparagine, γGlu, Glutamine, or αMD;

$X^{29}$ is Threonine or Glycine;

$X^{30}$ is Arginine, Lysine, or Nle(εN$_3$), or $X^{30}$ is absent; and $X^{31}$ is Glycine, γGlu, Nle(εN$_3$), or Lysine conjugated via its epsilon amine group to PEG$_2$PEG$_2$-γGlu-C$_{16}$N$_3$, PEG$_2$-C$_5$N$_3$ or PEG$_2$PEG$_2$-C$_5$N$_3$, or $X^{31}$ is absent; and wherein the C-terminal amino acid optionally is amidated, and with the proviso that either $X^{10}$ is a Lysine residue conjugated via its epsilon amino group to a γGlu-γGlu-C$_{16}$ and one of $X^{20}$, $X^{21}$, $X^{24}$, $X^{30}$, or $X^{31}$ comprises the azide or N$_3$ group or $X^{20}$ is a Lysine residue conjugated via its epsilon amino group to the PEG$_2$PEG$_2$-γGlu-C$_{18}$—OH or the PEG$_2$PEG$_2$γE-C$_{20}$—OH and one of $X^{21}$, $X^{24}$, $X^{30}$, or $X^{31}$ comprises the azide or N$_3$ group.

In a further embodiment, the insulin dimer molecule comprises an azide group and the peptide has agonist activity at the GLP-1, GIP, and GCG receptors and comprises the structure $$X^1X^2QGTFTSX^9X^{10}SX^{12}YX^{14}DX^{16}X^{17}X^{18}AX^{20}X^{21}FV\text{-}X^{24}X^{25}X^{26}X^{27}X^{28}X^{29}X^{30}X^{31}$$
(SEQ ID NO: 17)

Wherein $X^1$ is Tyrosine, Phenylalanine, Tryptophan, or other amino acid with an aromatic group;

$X^2$ is aminoisobutyric acid (Aib), D-Serine (s), or alpha-methyl Serine (αMS);

$X^9$ is Serine or alpha-methyl Aspartic acid (αMD);

$X^{10}$ is Tyr or Lys conjugated to γGlu-γGlu-C$_{16}$;

$X^{12}$ is Isoleucine, Lysine, Leucine, or Serine;

$X^{14}$ is Leu of alpha-methyl Leucine (αML);

$X^{16}$ is Glutamic acid, Asparagine, Serine, Alanine, or Aib;

$X^{17}$ is Arginine or Lysine;

$X^{18}$ is Alanine or Arginine;

$X^{20}$ is Glutamine, Histidine, or Lysine conjugated via its epsilon amine group to PEG$_2$-C$_5$N$_3$, PEG$_2$PEG$_2$-C$_5$-alkyne, PEG$_2$PEG$_2$-γGlu-C$_{16}$-alkyne, PEG$_2$PEG$_2$-γGlu-C$_{18}$—OH, or PEG$_2$PEG$_2$γE-C$_{20}$—OH;

$X^{21}$ is Aspartic acid, alpha-methyl Phenylalanine (αMF), αMD, Alkynylnorleucine (Norleucine conjugated via its epsilon carbon to an alkyne group (Nle(ε-alkyne))), or Lys conjugated via its epsilon amine group to PEG$_2$-C$_5$-alkyne, PEG$_2$PEG$_2$-C$_5$-alkyne, or PEG$_2$PEG$_2$-γGlu-C$_{16}$-alkyne;

$X^{24}$ is Glutamine, Nle(ε-alkyne), or Lysine conjugated to PEG$_2$PEG$_2$-γGlu-C$_{16}$-alkyne;

$X^{25}$ is Tryptophan or alpha-methyl Tryptophan (αMW);

$X^{26}$ is Leucine or αML;

$X^{27}$ is Leucine or L-methionine sulphone (2);

$X^{28}$ is Aspartic acid, Alanine, Lysine, Asparagine, γGlu, Glutamine, or αMD;

$X^{29}$ is Threonine or Glycine;

$X^{30}$ is Arginine, Lysine, or Nle(ε-alkyne), or $X^{30}$ is absent; and $X^{31}$ is Glycine, γGlu, Nle(ε-alkyne), or Lysine conjugated via its epsilon amine group to PEG$_2$PEG$_2$-γGlu-C$_{16}$-alkyne, PEG$_2$-C$_5$-alkyne, PEG$_2$PEG$_2$-C$_5$-alkyne, or $X^{31}$ is absent; and wherein the C-terminal amino acid optionally is amidated, and with the proviso that either $X^{10}$ is a Lysine residue conjugated via its epsilon amino group to a γGlu-γGlu-C$_{16}$ and one of $X^{20}$, $X^{21}$, $X^{24}$, $X^{30}$, or $X^{31}$ comprises the -alkyne or $X^{20}$ is a Lysine residue conjugated via its epsilon amino group to the PEG$_2$PEG$_2$-γGlu-C$_{18}$—OH or the PEG$_2$PEG$_2$γE-C$_{20}$—OH and one of $X^{21}$, $X^{24}$, $X^{30}$, or $X^{31}$ comprises the -alkyne.

In particular embodiments, the insulin dimer comprises an alkyne and the peptide is a GLP-1 analog having the amino acid sequence $$HGEGTFTSDX^{10}SSYLEEQAAX^{20}X^{21}FIAWLVX^{28}GGGX^{29}$$
(SEQ ID NO: 18)

Wherein $X^{10}$ is Valine, Nle(ε-N$_3$), or Lysine conjugated via its epsilon amine group to PEG$_2$PEG$_2$-γGlu-C$_{16}$—N$_3$, PEG$_2$-C$_5$—N$_3$, or PEG$_2$PEG$_2$-C$_5$—N$_3$;

$X^{20}$ is Lysine, Nle(ε-N$_3$), or Lysine conjugated via its epsilon amine group to PEG$_2$PEG$_2$-γGlu-C$_{16}$—N$_3$, PEG$_2$-C$_5$—N$_3$, or PEG$_2$PEG$_2$-C$_5$—N$_3$;

$X^{21}$ is glutamic acid, Nle(ε-N$_3$), or Lysine conjugated via its epsilon amine group to PEG$_2$PEG$_2$-γGlu-C$_{16}$—N$_3$, PEG$_2$-C$_5$—N$_3$, or PEG$_2$PEG$_2$-C$_5$—N$_3$;

$X^{28}$ is Lysine, Nle(ε-N$_3$), or Lysine conjugated via its epsilon amine group to PEG$_2$PEG$_2$-γGlu-C$_{16}$—N$_3$, PEG$_2$-C$_5$—N$_3$, or PEG$_2$PEG$_2$-C$_5$—N$_3$;

$X^{29}$ Nle(ε-N$_3$), or Lysine conjugated via its epsilon amine group to PEG$_2$PEG$_2$-γGlu-C$_{16}$—N$_3$, PEG$_2$-C$_5$—N$_3$, PEG$_2$PEG$_2$-C$_5$—N$_3$ or absent;

with the proviso that only one of $X^{10}$, $X^{20}$, $X^{21}$, or $X^{28}$, or $X^{29}$ is Nle(ε-N$_3$) or Lysine conjugated via its epsilon amine group to PEG$_2$PEG$_2$-γGlu-C$_{16}$—N$_3$, PEG$_2$-C$_5$—N$_3$, PEG$_2$PEG$_2$-C$_5$—N$_3$.

The peptide may be a GLP-1 analog, for example a GLP(7-37) molecule and analogs thereof comprising 1, 2, 3, 4, 5, or 6 amino acid substitutions or deletions.

In particular embodiments, the insulin dimer comprises an azide and the peptide is a GLP-1 analog having the amino acid sequence $$HGEGTFTSDX^{10}SSYLEEQAAX^{20}X^{21}FIAWLVX^{28}GGGX^{29}$$
(SEQ ID NO: 19)

Wherein $X^{10}$ is Valine, Nle(ε-alkyne), or Lysine conjugated via its epsilon amine group to PEG$_2$PEG$_2$-γGlu-C$_{16}$-alkyne, PEG$_2$-C$_5$-alkyne, or PEG$_2$PEG$_2$-C$_5$-alkyne;

$X^{20}$ is Lysine, Nle(ε-N$_3$), or Lysine conjugated via its epsilon amine group to PEG$_2$PEG$_2$-γGlu-C$_{16}$-alkyne, PEG$_2$-C$_5$-alkyne, or PEG$_2$PEG$_2$-C$_5$-alkyne;

$X^{21}$ is glutamic acid, Nle(ε-alkyne), or Lysine conjugated via its epsilon amine group to PEG$_2$PEG$_2$-γGlu-C$_{16}$-alkyne, PEG$_2$-C$_5$-alkyne, or PEG$_2$PEG$_2$-C$_5$-alkyne;

$X^{28}$ is Lysine, Nle(ε-alkyne), or Lysine conjugated via its epsilon amine group to PEG$_2$PEG$_2$-γGlu-C$_{16}$-alkyne, PEG$_2$-C$_5$-alkyne, or PEG$_2$PEG$_2$-C$_5$-alkyne;

$X^{29}$ Nle(ε-alkyne), or Lysine conjugated via its epsilon amine group to PEG$_2$PEG$_2$-γGlu-C$_{16}$-alkyne, PEG$_2$-C$_5$-alkyne, PEG$_2$PEG$_2$-C$_5$-alkyne or absent;

with the proviso that only one of $X^{10}$, $X^{20}$, $X^{21}$, or $X^{28}$, or $X^{29}$ is Nle(ε-N$_3$) or Lysine conjugated via its epsilon amine group to PEG$_2$PEG$_2$-γGlu-C$_{16}$-alkyne, PEG$_2$-C$_5$-alkyne, PEG$_2$PEG$_2$-C$_5$-alkyne.

In particular embodiments, the insulin dimer comprises an alkyne and the peptide is a GLP-1 analog having the amino acid sequence $$X_1X_2X_3GTFX_7SX_9X_{10}X_{11}X_{12}X_{13}X_{14}X_{15}X_{16}X_{17}X_{18}X_{19}X_{20}X_{21}FX_{23}X_{24}WLX_{27}X_{28}X_{29}$$
(SEQ ID NO: 20)

wherein $X_1$ is histidine (H), phenylalanine (F), or tyrosine (Y);

$X_2$ is serine (S), D-serine (s), glycine (G), alanine (A), or α-aminoisobutyric acid (Aib or U);

$X_3$ is glutamic acid (E) or glutamine (Q);

$X_7$ is tyrosine (Y);
$X_9$ is aspartic acid (D) or lysine (K);
$X_{10}$ is lysine (K), valine (V), leucine (L), or Y;
$X_{11}$ is S or valine (V);
$X_{12}$ is K, isoleucine (I), or S;
$X_{13}$ is Q, A, or Y;
$X_{14}$ is methionine (M), methionine sulphone, or L;
$X_{15}$ is E, or D;
$X_{16}$ is K, Aib, E, G, or S;
$X_{17}$ is E; I, Q, or arginine (R);
$X_{18}$ is A, H, or R;
$X_{19}$ is V, Q, or A;
$X_{20}$ is R, K, Q, or Aib;
$X_{21}$ is L, E, or D;
$X_{23}$ is I or V;
$X_{24}$ is E, A, Q, Asparagine (N), Nle($\varepsilon N_3$), or K(PEG$_2$PEG$_2\gamma$EC$_{16}$N$_3$)
$X_{27}$ is K, V, K, M, Nle($\varepsilon N_3$), or norleucine (Nle);
$X_{28}$ is D, R, K, A, or N;
$X_{29}$ is G, Y, Q, or G;
optionally, the peptide includes a C-terminal extension selected from the group consisting of KK(PEG$_2$PEG$_2$)-C$_5$N$_3$, KQ-Nle($\varepsilon N_3$), GPSSGAPPPS-Nle($\varepsilon N_3$) (SEQ ID NO:21), RG-Nle($\varepsilon N_3$), GPSSGAPPSKKKKKK-Nle($\varepsilon N_3$) (SEQ ID NO:22), GGGGGSGGGSGGGSA-Nle($\varepsilon N_3$) (SEQ ID NO:23), Nle($\varepsilon N_3$), KGLLNDWKHNITQ-Nle($\varepsilon N_3$) (SEQ ID NO:24), KRNKNNIA-Nle($\varepsilon N_3$) (SEQ ID NO:25), KRNKNNIA (SEQ ID NO:26), GPSSGAPPPS (SEQ ID NO:27), GPSSGAPPSKKKKKK (SEQ ID NO:28), GGGGGSGGGSGGGSA (SEQ ID NO:29, and KGLLNDWKHNITQ (SEQ ID NO:30) linked to the amino acid at position 29; and the peptide optionally includes a protecting group that, if present, is joined to the C-terminal carboxy group of the peptide, and further the proviso that the peptide comprises only one Nle($\varepsilon N_3$).

In particular embodiments, the insulin dimer comprises and alkyne and the peptide is a GLP-1 analog having the amino acid sequence (SEQ ID NO: 31)
$X_1X_2X_3$GTF$X_7$S$X_9X_{10}X_{11}X_{12}X_{13}X_{14}X_{15}X_{16}X_{17}X_{18}X_{19}X_{20}$ $X_{21}$F$X_{23}X_{24}$WL$X_{27}X_{28}X_{29}$ wherein
$X_1$ is histidine (H), phenylalanine (F), or tyrosine (Y);
$X_2$ is serine (S), D-serine (s), glycine (G), alanine (A), or α-aminoisobutyric acid (Aib or U);
$X_3$ is glutamic acid (E) or glutamine (Q);
$X_7$ is tyrosine (Y);
$X_9$ is aspartic acid (D) or lysine (K);
$X_{10}$ is lysine (K), valine (V), leucine (L), or Y;
$X_{11}$ is S or valine (V);
$X_{12}$ is K, isoleucine (I), or S;
$X_{13}$ is Q, A, or Y;
$X_{14}$ is methionine (M), methionine sulphone, or L;
$X_{15}$ is E, or D;
$X_{16}$ is K, Aib, E, G, or S;
$X_{17}$ is E; I, Q, or arginine (R);
$X_{18}$ is A, H, or R;
$X_{19}$ is V, Q, or A;
$X_{20}$ is R, K, Q, or Aib;
$X_{21}$ is L, E, or D;
$X_{23}$ is I or V;
$X_{24}$ is E, A, Q, or Asparagine (N),
$X_{27}$ is K, V, K, M, or norleucine (Nle);
$X_{28}$ is D, R, K, A, or N;
$X_{29}$ is G, Y, Q, or G;
the peptide includes a C-terminal extension selected from the group consisting of KK(PEG$_2$PEG$_2$)-C$_5$N$_3$, KQ-Nle($\varepsilon N_3$), GPSSGAPPPS-Nle($\varepsilon N_3$) (SEQ ID NO:21), RG-Nle($\varepsilon N_3$), GPSSGAPPSKKKKKK-Nle($\varepsilon N_3$) (SEQ ID NO:22), GGGGGSGGGSGGGSA-Nle($\varepsilon N_3$) (SEQ ID NO:23), Nle($\varepsilon N_3$), KGLLNDWKHNITQ-Nle($\varepsilon N_3$) (SEQ ID NO:24), and KRNKNNIA-Nle($\varepsilon N_3$) (SEQ ID NO:25) linked to the amino acid at position 29; and the peptide optionally includes a protecting group that, if present, is joined to the C-terminal carboxy group of the peptide, and further the proviso that the peptide comprises only one Nle($\varepsilon N_3$).

In any one of the above embodiments of peptides, the C-terminal carboxyl group may be amidated.

Table 2 shows exemplary peptides comprising an azide group that may be conjugated to an insulin dimer molecule comprising an alkyne group under conditions suitable for the azide group and the alkyne group to form a 1,4-disubstituted 1, 2, 3-triazole.

TABLE 2

| Peptide | SEQ ID NO: | Sequence |
|---|---|---|
| PEP1 | 35 | HsQGTFTSD-K($\gamma$E$\gamma$EC$_{16}$)SKYLDERAAQ-Nle($\varepsilon N_3$)FVQWLLDT-NH$_2$ |
| PEP2 | 36 | HUQGTFTSD-K($\gamma$E$\gamma$EC$_{16}$)SKYLDERAAQDFV-Nle($\varepsilon N_3$)WLLDGRG-NH$_2$ |
| PEP3 | 37 | HUQGTFTSD-K($\gamma$E$\gamma$EC$_{16}$)SKYLDURAAQDFV-Nle($\varepsilon N_3$)WL2KGRG-NH$_2$ |
| PEP4 | 38 | HsQGTFTSD-K($\gamma$E$\gamma$EC$_{16}$)-SLYLDURAAQDFV-Nle($\varepsilon N_3$)WLLNT-K($\gamma$E)-NH$_2$ |
| PEP5 | 39 | HsQGTFTSD-K($\gamma$E$\gamma$EC$_{16}$)-SLYLDURAAQDFVQWLLNT-Nle($\varepsilon N_3$)-$\gamma$E-NH$_2$ |
| PEP6 | 40 | HUQGTFTSD-K($\gamma$E$\gamma$EC$_{16}$)SKYLDURRAQDFVQWLLDT-Nle($\varepsilon N_3$)$\gamma$E-NH$_2$ |
| PEP7 | 41 | HsQGTFTSD-K($\gamma$E$\gamma$EC$_{16}$)SKYLDURAAQDFV-Nle($\varepsilon N_3$)-WLLDT-NH$_2$ |
| PEP8 | 42 | HsQGTFTSD-K($\gamma$E$\gamma$EC$_{16}$)SSYLDURAAQDFVQWLLNT-Nle($\varepsilon N_3$)-$\gamma$E-NH$_2$ |
| PEP9 | 43 | HsQGTFTSD-K($\gamma$E$\gamma$EC$_{16}$)SSYLDURAAQDFV-Nle($\varepsilon N_3$)-WLLNTK$\gamma$E-NH$_2$ |
| PEP10 | 44 | HUQGTFTSD-K($\gamma$E$\gamma$EC$_{16}$)SKYLDURAAQDFV-Nle($\varepsilon N_3$)-WL2DT-NH$_2$ |

TABLE 2-continued

| Peptide | SEQ ID NO: | Sequence |
|---|---|---|
| PEP11 | 45 | HsQGTFTSD-K(γEγEC$_{16}$)SKYLDERAAQDFV-Nle(εN$_3$)-WLLγET-NH$_2$ |
| PEP12 | 46 | HsQGTFTSD-K(γEγEC$_{16}$)SKYLDNKRAQDFV-Nle(εN$_3$)-WLLQT-NH$_2$ |
| PEP13 | 47 | HsQGTFTSD-K(γEγEC$_{16}$)SKYLDSRRAHDFV-Nle(εN$_3$)-WLLNT-NH$_2$ |
| PEP14 | 48 | HsQGTFTSD-K(γEγEC$_{16}$)SKYLDERAAQDFV-K(PEG$_2$-C$_5$N$_3$)WLLDT-NH$_2$ |
| PEP15 | 49 | HsQGTFTSD-K(γEγEC$_{16}$)SKYLDERAAQDFV-K(PEG$_2$PEG$_2$-C$_5$N$_3$)-WLLDT-NH$_2$ |
| PEP16 | 50 | HsQGTFTSD-K(γEγEC$_{16}$)SKYLDERAA-K(PEG$_2$-C$_5$N$_3$)-DFVQWLLDT-NH$_2$ |
| PEP17 | 51 | HsQGTFTSD-K(γEγEC$_{16}$)SKYLDERAA-K(PEG$_2$PEG$_2$-C$_5$N$_3$)-DFVQWLLDT-NH$_2$ |
| PEP18 | 52 | HUQGTFTSDYSKYLDURAAQDFVQWLLDTK-Nle(εN$_3$)-NH$_2$ |
| PEP19 | 53 | HUQGTFTSD-K(γEγEC$_{16}$)SKYLDURAAQDFVQWLLDTK-Nle(εN$_3$)-NH$_2$ |
| PEP20 | 54 | HUQGTFTSD-K(γEγEC$_{16}$)SKYLDURAAQDFVQWLLDTK-K(PEG$_2$-C$_5$N$_3$)-NH$_2$ |
| PEP21 | 55 | HUQGTFTSD-K(γEγEC$_{16}$)SKYLDURAAQDFVQWLLDTK-K(PEG$_2$PEG$_2$-C$_5$N$_3$)-NH$_2$ |
| PEP22 | 56 | HUQGTFTSD-K(γEγEC$_{16}$)SKYLDURAAQDFV-Nle(εN$_3$)-WLLDTKγE-NH$_2$ |
| PEP23 | 57 | HsQGTFTSDK(γEγEC$_{16}$)SKYLDERAAQNle(εN$_3$)FVQWL2DT-NH$_2$ |
| PEP24 | 58 | HsQGTFTSDK(γEγEC$_{16}$)SKYLDERAAQNle(εN$_3$)FVQWL2αMDT-NH$_2$ |
| PEP25 | 59 | HsQGTFTSDYSKYLDERAAQDFV-K(PEG$_2$PEG$_2$γE-C$_{16}$N$_3$)-WLLDT-NH$_2$ |
| PEP26 | 60 | HsQGTFTSDYSKYLDERAA-K(PEG$_2$PEG$_2$γE-C$_{16}$N$_3$)-DFVQWLLDT-NH$_2$ |
| PEP27 | 61 | HsQGTFTSDYSKYLDERAAQ-K(PEG$_2$PEG$_2$γE-C$_{16}$N$_3$)-FVQWLLDT-NH$_2$ |
| PEP28 | 62 | HUQGTFTSDYSKYLDURAAQDFVQWLLDTK-K(PEG$_2$PEG$_2$γE-C$_{16}$N$_3$)-NH$_2$ |
| PEP29 | 63 | HsQGTFTSDK(PEG$_2$PEG$_2$γEC$_{18}$-OH)SKYLDERAAQDFVNle(εN$_3$)WLLDT-NH$_2$ |
| PEP30 | 64 | HUQGTFTSDYSKYLDARAAK(PEG$_2$PEG$_2$γEC18-OH)DFVNle(εN$_3$)WL2DT-NH$_2$ |
| PEP31 | 65 | HUQGTFTSDYSKYLDARAAK(PEG$_2$PEG$_2$γEC20-OH)DFVNle(εN$_3$)WL2DT-NH$_2$ |
| PEP32 | 66 | HsQGTFTSαMDK(γEγEC$_{16}$)SKYLeuDERAAQDFVNle(εN$_3$)WL2DT-NH$_2$ |
| PEP33 | 67 | HsQGTFTSDK(γEγEC$_{16}$)SKYαMLDERAAQDFVNle(εN$_3$)WL2DT-NH$_2$ |
| PEP34 | 68 | HsQGTFTSDK(γEγEC$_{16}$)SKYLDERAAQαMDFVNle(εN$_3$)WL2DT-NH$_2$ |
| PEP35 | 69 | HsQGTFTSDK(γEγEC$_{16}$)SKYLDERAAQDαMFVNle(εN$_3$)WL2DT-NH$_2$ |
| PEP36 | 70 | HsQGTFTSDK(γEγEC$_{16}$)SKYLDERAAQDFVNle(εN$_3$)αMWL2DT-NH$_2$ |
| PEP37 | 71 | HsQGTFTSDK(γEγEC$_{16}$)SKYLDERAAQDFVNle(εN$_3$)WαML2DT-NH$_2$ |
| PEP38 | 72 | HsQGTFTSDK(γEγEC$_{16}$)SKYLDERAAQDFVNle(εN$_3$)WL2αMDT-NH$_2$ |
| PEP39 | 73 | HαMSQGTFTSDK(γEγEC$_{16}$)SKYLDURAAQDFV-Nle(εN$_3$)-WLLATKγE-NH$_2$ |
| PEP40 | 74 | HαMsQGTFTSDK(γEγEC$_{16}$)SKYLDURAAQDFV-Nle(εN$_3$)-WLLATKγE-NH$_2$ |
| PEP41 | 75 | HαMSQGTFTSDK(γEγEC$_{16}$)SKYLDARAAQDFV-Nle(εN$_3$)-WLLDT-NH$_2$ |

TABLE 2-continued

| Peptide | SEQ ID NO: | Sequence |
|---|---|---|
| PEP42 | 76 | HαMsQGTFTSDK(γEγEC$_{16}$)SKYLDARAAQDFV-Nle(εN$_3$)-WLLDT-NH$_2$ |
| PEP43 | 77 | HαMsVGTFTSDK(γEγEC$_{16}$)SKYLDURAAQDFV-Nle(εN$_3$)-WL2DT-NH$_2$ |
| PEP44 | 78 | HUQGTFTSDK(γEγEC$_{16}$)SKYLDERAAQDFVNle(εN$_3$)WL2DGRG-NH$_2$ |
| PEP45 | 79 | HUQGTFTSDK(γEγEC$_{16}$)SKYLDERAAQDFVNle(εN$_3$)WL2αMDGRG-NH$_2$ |
| PEP46 | 80 | HUQGTFTSDK(γEγEC$_{16}$)SKYLDURAAQDFVQWLLDTNle(εN$_3$)γE-NH$_2$ |
| PEP47 | 81 | HUQGTFTSDK(γEγEC$_{16}$)SKYLDURAAQDFVQWL2DTNle(εN$_3$)γE-NH$_2$ |
| PEP48 | 82 | HUQGTFTSDK(γEγEC$_{16}$)SKYLDURAAQDFVQWL2αMDTNle(εN$_3$)γE-NH$_2$ |
| PEP49 | 83 | HUQGTFTSDK(γEγEC$_{16}$)SKYLDURAAQDFVNle(εN$_3$)WL2αMDT-NH$_2$ |
| PEP50 | 84 | HsEGTFTSDK(γEγEC$_{16}$)SKYLDERAAQDFVNle(εN$_3$)WLLDT-NH$_2$ |
| PEP51 | 85 | HsQGTFTSDK(γEγEC$_{16}$)SKYLDERAAQDFVK(PEG$_2$PEG$_2$-C$_5$N$_3$)WL2DT-NH$_2$ |
| PEP52 | 86 | HsQGTFTSDK(γEγEC$_{16}$)SKYLDERAAQDFVK(PEG$_2$PEG$_2$-C$_5$N$_3$)WL2αMDT-NH$_2$ |
| PEP53 | 87 | HsQGTFTSDK(γEγEC$_{16}$)SKYLDERAAQDFVK(PEG$_2$-C$_{10}$N$_3$)WLLDT-NH$_2$ |
| PEP54 | 88 | HsQGTFTSDK(γEγEC$_{16}$)SKYLDERAAQDFVK(PEG$_2$-C$_{16}$N$_3$)WLLDT-NH$_2$ |
| PEP55 | 89 | HUQGTFTSDK(γEγEC$_{16}$)SKYLDURAAQDFVK(PEG$_2$-C$_5$N$_3$)WL2DT-NH$_2$ |
| PEP56 | 90 | HUQGTFTSDK(γEγEC$_{16}$)SKYLDURAAQDFVK(PEG$_2$PEG$_2$-C$_5$N$_3$)WL2DT-NH$_2$ |
| PEP57 | 91 | HsQGTFTSDK(γEγEC$_{16}$)SKYLDERAAK(PEG$_2$PEG$_2$γE-C$_{10}$N$_3$)DFVQWLLDT-NH$_2$ |
| PEP58 | 92 | HsQGTFTSDK(γEγEC$_{16}$)SKYLDERAAK(PEG$_2$PEG$_2$γE-C$_{16}$N$_3$)DFVQWLLDT-NH$_2$ |
| PEP59 | 93 | HsQGTFTSDK(γEγEC$_{16}$)SKYLDURAAQDFVQWLLDTKNle(εN$_3$)-NH$_2$ |
| PEP60 | 94 | HsQGTFTSDK(γEγEC$_{16}$)SKYLDERAAQDFVQWLLDTKNle(εN$_3$)-NH$_2$ |
| PEP61 | 95 | HsQGTFTSDK(γEγEC$_{16}$)SKYLDURAAQDFVQWLLDTKK(PEG$_2$PEG$_2$-C$_5$N$_3$)NH$_2$ |
| PEP62 | 96 | HsQGTFTSDK(γEγEC$_{16}$)SKYLDERAAQDFVQWLLDTKK(PEG$_2$PEG$_2$-C$_5$N$_3$)NH$_2$ |
| PEP63 | 97 | HsQGTFTSDK(γEγEC$_{16}$)SKYLDURAAQDFVNle(εN$_3$)WLLDTKγE-NH$_2$ |
| PEP64 | 98 | HUQGTFTSDK(γEγEC$_{16}$)SKYLDURAAQDFVK(PEG$_2$-C$_5$N$_3$)WLLDTKγE-NH$_2$ |
| PEP65 | 99 | HUQGTFTSDK(γEγEC$_{16}$)SKYLDURAAQDFVK(PEG$_2$PEG$_2$-C$_5$N$_3$)WLLDTKγE-NH$_2$ |
| PEP66 | 100 | HsQGTFTSDK(γEγEC$_{16}$)SKYLDERAAQK(PEG$_2$PEG$_2$γEC$_{16}$N$_3$)FVQWLLDT-NH$_2$ |
| PEP67 | 101 | HsQGTFTSDK(γEγEC$_{16}$)SKYLDERAAQDFVK(PEG$_2$PEG$_2$γEC$_{16}$N$_3$)WLLDT-NH$_2$ |
| PEP68 | 102 | HUQGTFTSDKSKYLDURAAQDFVNle(εN$_3$)WLMNTKQ-COOH |
| PEP69 | 103 | HsQGTFTSDKSKYLDERAAQDFVNle(εN$_3$)WLLDT-NH$_2$ |
| PEP70 | 104 | HUQGTFTSDKSKYLDURAANle(εN$_3$)DFVQWLMNTKQ-COOH |
| PEP71 | 105 | HsQGTFTSDKSKYLDERAANle(εN$_3$)DFVQWLLDT-NH$_2$ |

TABLE 2-continued

| Peptide | SEQ ID NO: | Sequence |
|---|---|---|
| PEP72 | 106 | HUQGTFTSDKSKYLDURAAQDFVQWLMNTKQNle(εN$_3$)-NH$_2$ |
| PEP73 | 107 | HsQGTFTSDKSKYLDERAAQDFVQWLLDTNle(εN$_3$)-NH$_2$ |
| PEP74 | 108 | HsQGTFTSDK(γEγEC$_{16}$)SKYLDERAAQDFVNle(εN$_3$)WLLDT-NH$_2$ |
| PEP75 | 109 | HsEGTFTSDK(γEγEC$_{16}$)SKYLDERAAQDFVNle(εN$_3$)WLLDT-NH$_2$ |
| PEP76 | 110 | HGEGTFTSDLSKQMEEEAVRLFTEWLKNGGPSSGAPPPS-Nle(εN$_3$)-NH$_2$ |
| PEP77 | 111 | HAibEGTFTSDVSSYLEGQAAKEFIAWLVRGRG-Nle(εN$_3$)-OH |
| PEP78 | 112 | HAEGTFTSDVSSYLEGQAAKEFIAWLVRGRG-Nle(εN$_3$)-OH |
| PEP79 | 113 | HGEGTFTSKLSKQMEEEAVRLFTEWLKNGGPSSGAPPSKKKKKK-Nle(εN$_3$)-NH$_2$ |
| PEP80 | 114 | HGEGTFTSDVSSYLEEQAAKEFIAWLVKGGGGGSGGGSGGGSA-Nle(εN$_3$)-NH$_2$ |
| PEP81 | 115 | HSQGTFTSDYSKYLDSRRAQDFVQWLMNT-Nle(εN$_3$)-OH |
| PEP82 | 116 | YAEGTFISDYSIAMDKfflQQDFVNWLLAQKGKKNDWKHNITQ-Nle(εN$_3$)-OH |
| PEP83 | 117 | YAibEGTFTSDYSIYLDKQAAAibEFVNWLLAGGPSSGAPPPS-Nle(εN$_3$)-NH$_2$ |
| PEP84 | 118 | HAibQGTFTSDKSKYLDERAAQDFVQWLLDGGPSSGAPPPS-Nle(εN$_3$)-NH$_2$ |
| PEP85 | 119 | HSQGTFTSDYSKYLDSRRAQDFVQWLMNTKRNKNNIA-Nle(εN$_3$)-OH |
| PEP86 | 120 | HSQGTFTSDYSKYLDSRRAQDFVQWL-Nle(εN$_3$)-NTKRNKNNIA-OH |
| PEP87 | 121 | HsQGTFTSDK(γEγEC$_{16}$)SKYLDERAAQDFVNle(εN$_3$)WLLDT-NH$_2$ |
| PEP88 | 122 | HsQGTFTSDKSKYLDERAAQDFVNle(εN$_3$)WLLDT-NH$_2$ |
| PEP89 | 123 | HUQGTFTSDKSKYLDURAAQDFVQWLMNTKQNle(εN$_3$)-NH$_2$ |
| PEP90 | 124 | HsQGTFTSDYSKYLDERAAQDFVK(PEG$_2$PEG$_2$γE-C$_{16}$N$_3$)WLLDT-NH$_2$ |
| PEP91 | 125 | HUQGTFTSDK(γEγEC$_{16}$)SKYLDURAAQDFVQWLLDTKK(PEG$_2$PEG$_2$-C$_5$N$_3$)—CONH$_2$ |

Table legend:
U = aminoisobutyric acid;
γE = γ-glutamic acid;
2 = L-methionine sulphone;
αMD = alpha-Methyl-L-Aspartic acid;
αML = alpha-Methyl-L-leucine;
αMF = alpha-Methyl-L-phenylalanine;
αMW = alpha-Methyl-L-tryptophan;
s = D-serine;
αMS = alpha-Methyl-L-Serine;
αMs = alpha-Methyl-D-Serine;
Nle(εN$_3$) = ε-azidonorleucine;
PEG$_2$ = 8-amino-3,6-dioxaoctanoic acid;
C$_5$N$_3$ = 5-azido pentinoic acid;
C$_{10}$N$_3$ = 10-azido-decanoic acid;
C$_{16}$N$_3$ = 16-azido-hexadecanoic acid;
C$_{18}$-OH = —CO—(CH2)$_{16}$—COOH;;
C$_{20}$-OH = —CO—(CH2)$_{18}$—COOH;
NH$_2$ = C-terminal amide Linkers The linker conjugated to the insulin or the peptide may be any non-peptide linker comprising a terminal azide group or a terminal alkyne group with the proviso that when the incretin is conjugated to a linker comprising an azide group then the insulin is conjugated to a linker comprising an alkyne group and when the incretin is conjugated to a linker comprising an azide group then the insulin is conjugated to a linker comprising an alkyne group.

The non-peptide linker may comprise a $C_1$-$C_{50}$ hydrocarbon chain or substituted hydrocarbon chain, a $PEG_n$ wherein n is 1-50, a $(PEG_2)_n$ wherein n is 1-50, a $(PEG_2)_n$-$(γGlu)_p$-$C_n$ wherein each n is independently 1-50 and p is 1 or 2, a $(PEG_2)_n$-$C_n$ wherein each n is independently is 1-50, a $(PEG)_n(PEG)_n$ wherein each n is independently 1-50, a $(PEG)_n(PEG)_n(PEG)_n$ wherein each n is independently 1-50a $PEG_n$-$(Lys$-$(γGlu)_p$-$C_n)$-$C_n$ wherein each n is independently 1-50 and p is 1 or 2, and a $C_5$-Lys(γE-$C_n$)-$PEG_n$ wherein each n is independently 1-50.

In particular embodiments, the linker may be a propargyl-polyethylene glycol (PEG) linker having the general formula

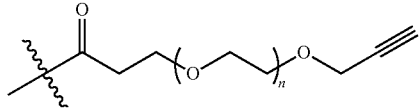

wherein n is 0-50 and the wavy line indicates the bond between the linker and an amino group on the insulin dimer molecule or analog or an amino group on the incretin peptide. In particular embodiments n is 1-25. In particular embodiments, the linker may be selected from the group In particular embodiments, the linker may be a propargyl-$C_5$-(polyethylene glycol 2)$_n$ (($PEG_2$)$_n$) linker having the general formula

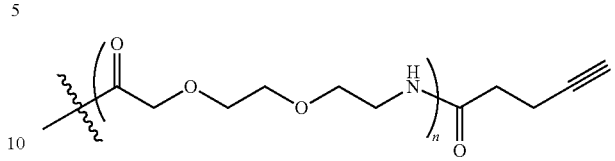

wherein n is 1-50 and the wavy line indicates the bond between the linker and an amino group on the insulin dimer molecule or analog or an amino group on the incretin peptide. In particular embodiments n is 1-5. In particular embodiments, the linker may be selected from the group

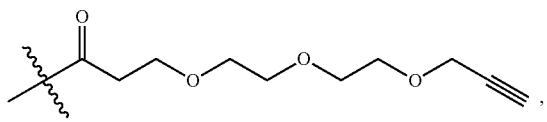

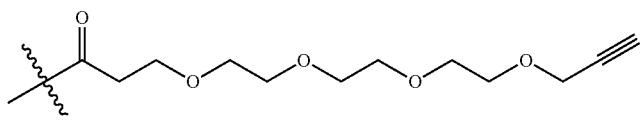

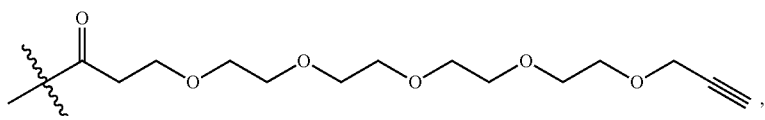

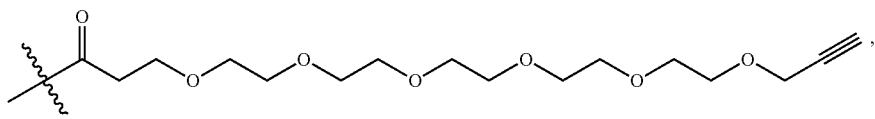

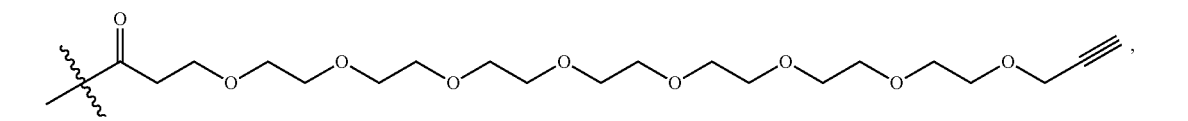

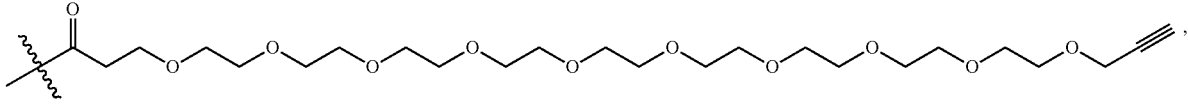

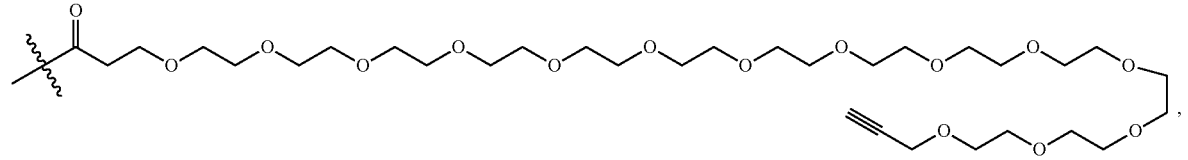

and

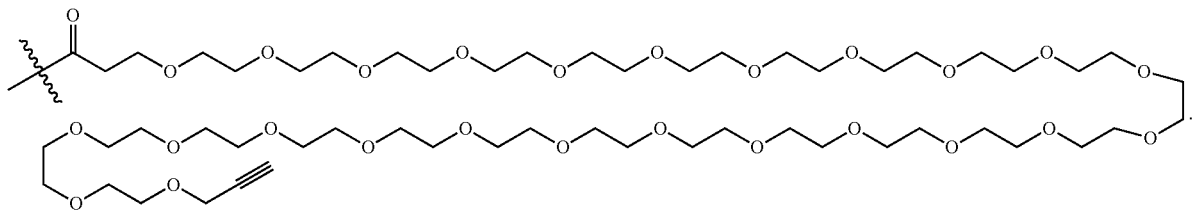

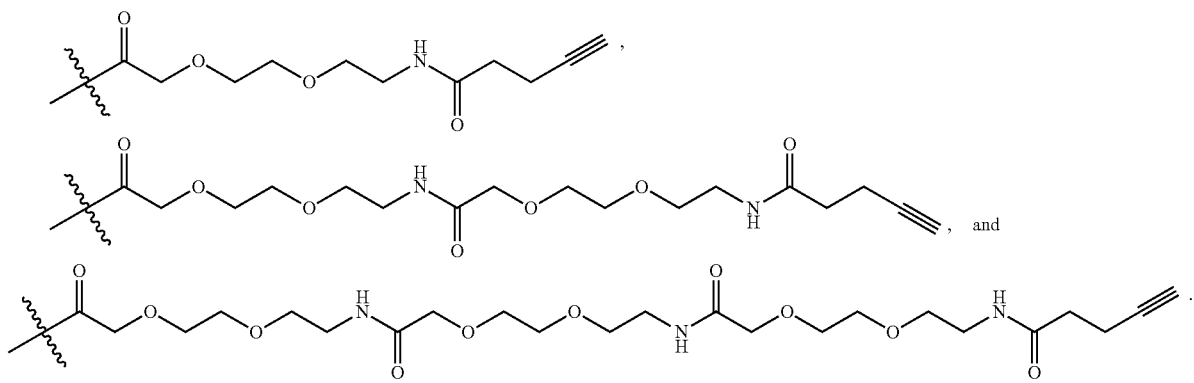

In particular embodiments, the linker may be a propargyl-$C_5$-Lys($\gamma$E-$C_n$)-$PEG_n$ linker having the general formula

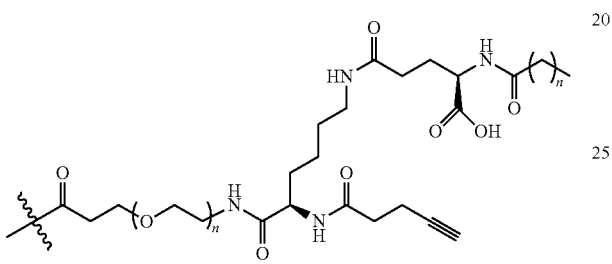

wherein each n is independently 1-50 and the wavy line indicates the bond between the linker and an amino group on the insulin dimer molecule or analog or an amino group on the incretin peptide. In particular embodiments, the linker has the formula

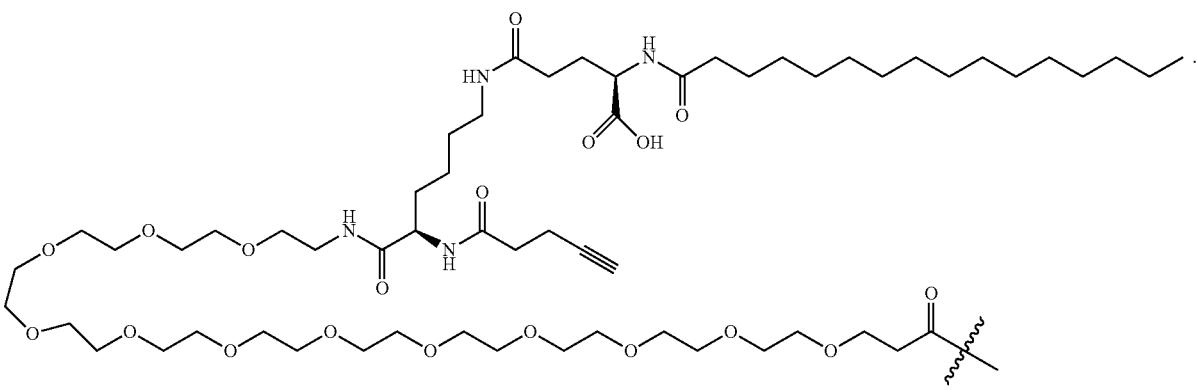 [SMILES: *C(=O)CCOCCOCCOCCOCCOCCOCCOCCOCCOCCOCCOCCOCCNC(=O)[C@@H](CCCCNC(=O)CC[C@@H](NC(=O)CCCCCCCCCCCCCCC)C(=O)O)NC(=O)CCC#C]

In particular embodiments, the linker may be a propargyl-$(PEG_n)(PEG_n)$ linker having the general formula

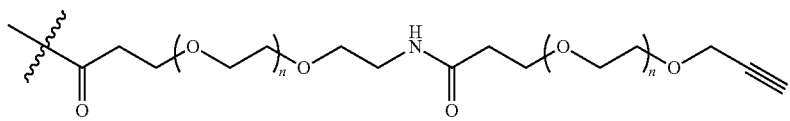

wherein each n is independently 0-50 and the wavy line indicates the bond between the linker and an amino group on the insulin dimer molecule or an amino group on the incretin peptide. In particular embodiments, the linker is selected from

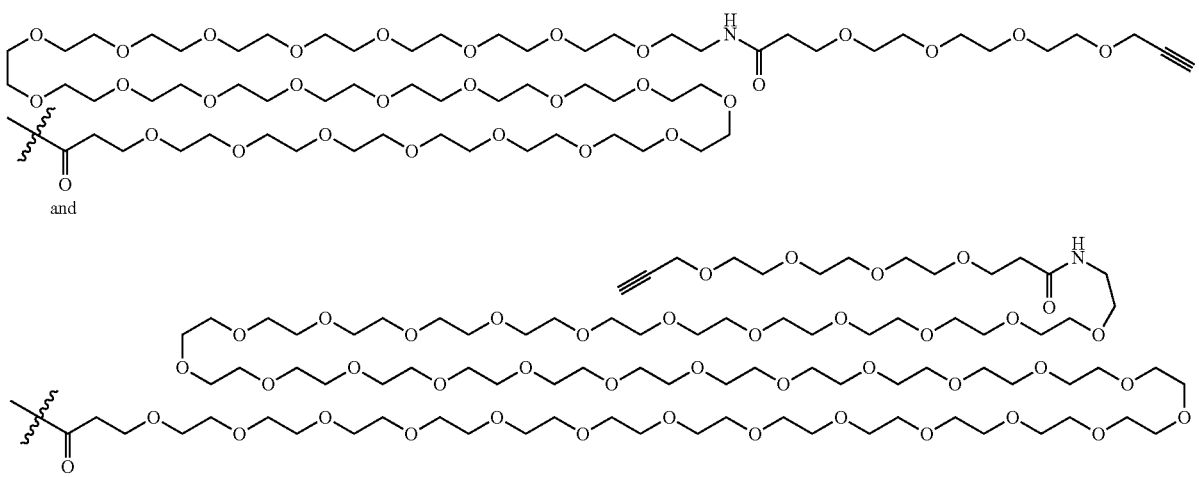

and

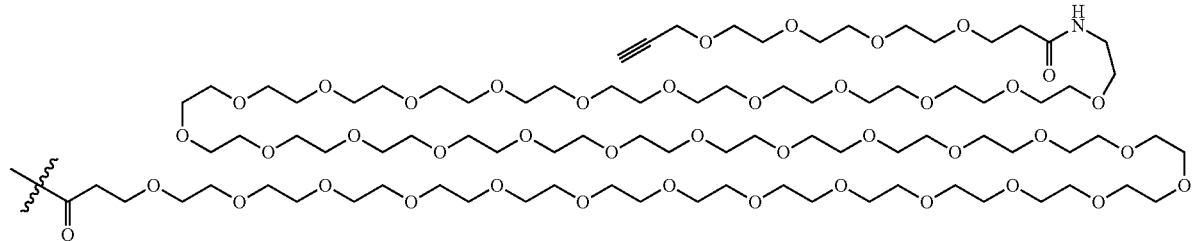

In particular embodiments, the linker may be an propargyl-(PEG$_n$)(PEG$_n$)(PEG$_n$) linker having the general formula

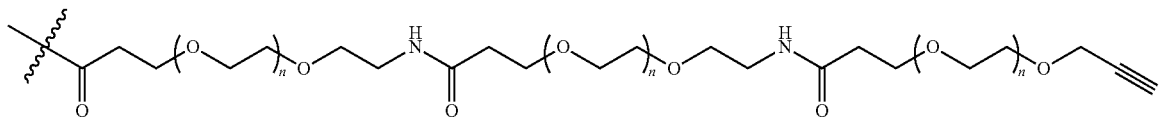

wherein each n is independently 0-50 and the wavy line indicates the bond between the linker and an amino group on the insulin dimer molecule or analog or an amino group on the incretin peptide. In particular embodiments, the linker may be

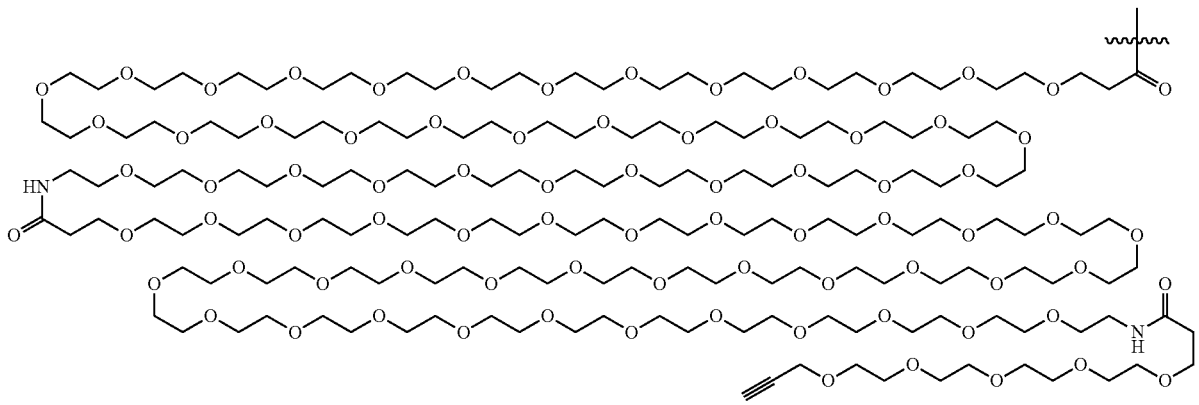 [SMILES: *C(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNC(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNC(=O)CCOCCOCCOCCOCCOCC#C]

In particular embodiments, the linker may be a propargyl-C$_n$ having the general formula

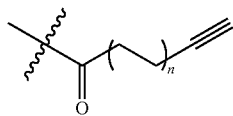

wherein n is 1-50 and the wavy line indicates the bond between the linker and an amino group on the insulin dimer molecule or analog or an amino group on the incretin peptide. In particular embodiments, the linker is

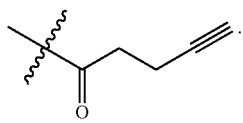 [SMILES: *C(=O)CCC#C]

In particular embodiments, the linker may be a BCN-PEG$_4$(endo) linker having the general formula

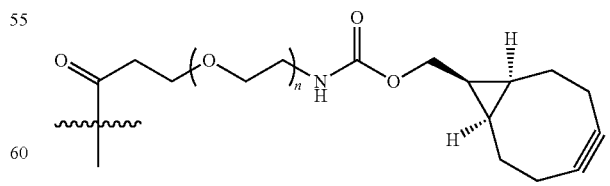

wherein n is 1-50 and the wavy line indicates the bond between the linker and an amino group on the insulin dimer molecule or an amino group on the incretin peptide. In particular embodiments, the linker is

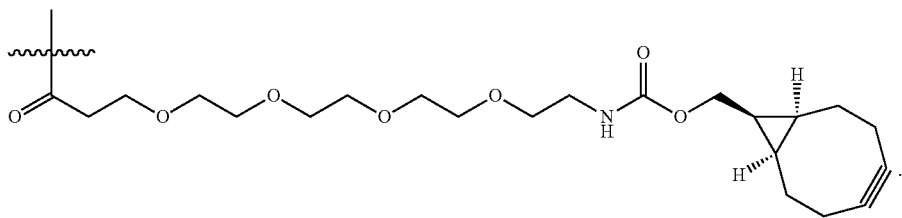 [SMILES: *C(=O)CCOCCOCCOCCOCCNC(=O)OC[C@@H]1[C@@H]2CCC#CCC[C@@H]21]

In particular embodiments, the linker may be a propargyl-phenylacetate linker having the general formula

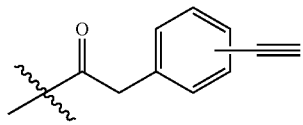

wherein the wavy line indicates the bond between the linker and an amino group on the insulin dimer molecule or analog or an amino group on the incretin peptide. In particular embodiments, the linker is selected from

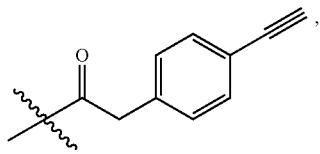

-continued

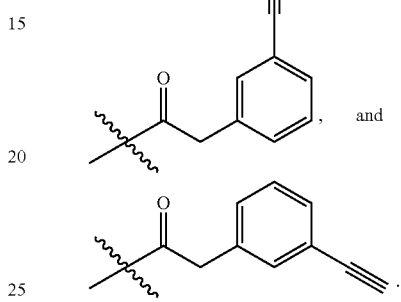

In particular embodiments, the linker may be an azido-polyethylene glycol (PEG) linker having the general formula

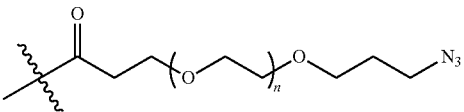

wherein n is 0-50 and the wavy line indicates the bond between the linker and an amino group on the insulin dimer molecule or analog or an amino group on the incretin peptide. In particular embodiments n is 1-25. In particular embodiments, the linker may be selected from the group

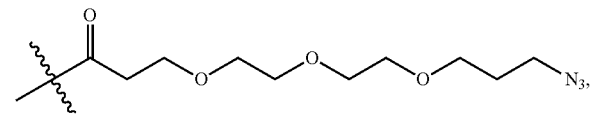

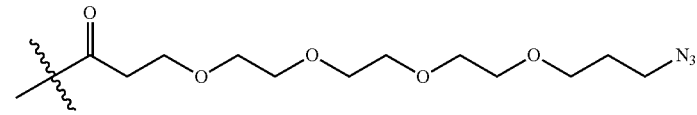

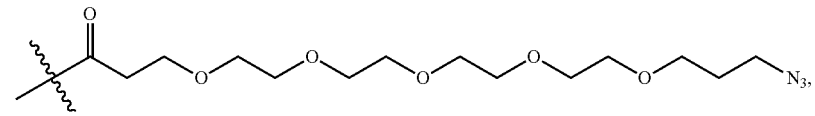

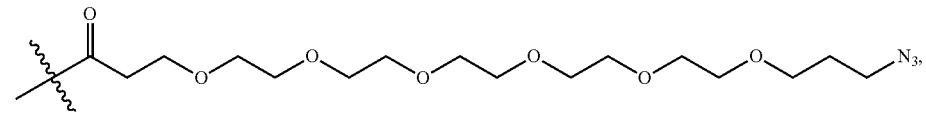

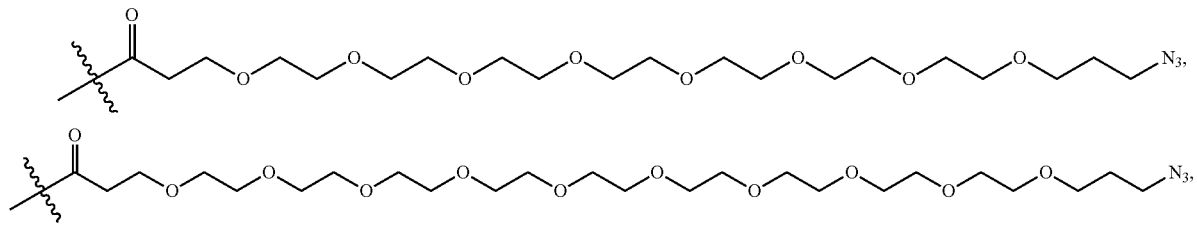

-continued

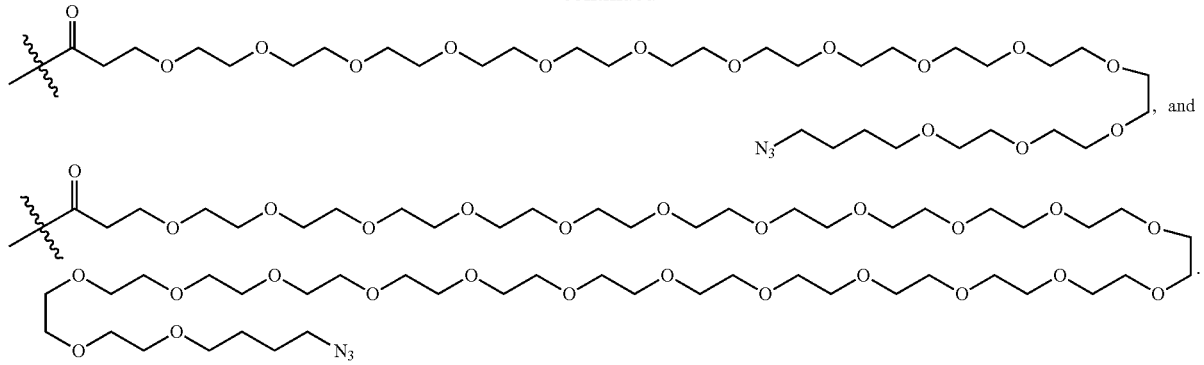

, and

In particular embodiments, the linker may be an azido-$C_5$-Lys($\gamma$E-$C_n$)-PEG$_n$ linker having the general formula

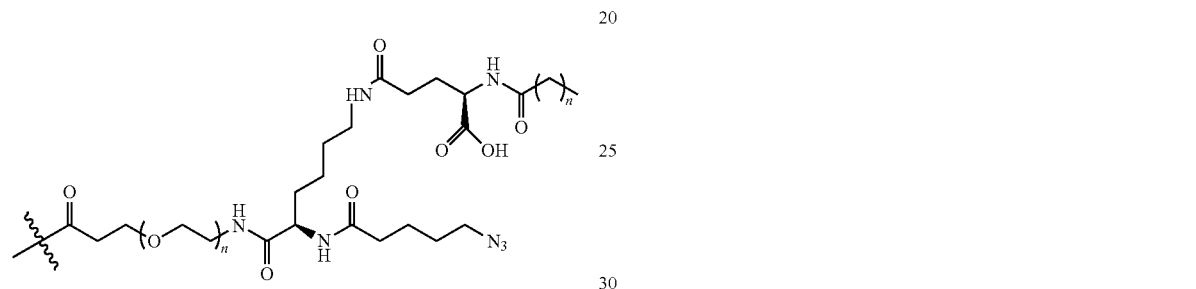

wherein each n is independently 1-50 and the wavy line indicates the bond between the linker and an amino group on the insulin dimer molecule or analog or an amino group on the incretin peptide. In particular embodiments, the linker has the formula

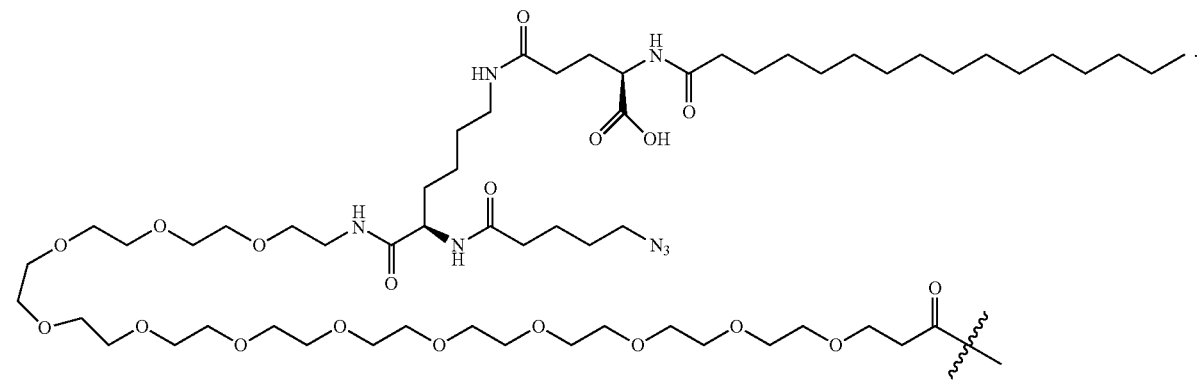 [SMILES: *C(=O)CCOCCOCCOCCOCCOCCOCCOCCOCCOCCOCCOCCOCCNC(=O)[C@@H](CCCCNC(=O)CC[C@@H](NC(=O)CCCCCCCCCCCCCCC)C(=O)O)NC(=O)CCCCN=[N+]=[N-]]

In particular embodiments, the linker may be an azido-(PEG$_n$)(PEG$_n$) linker having the general formula

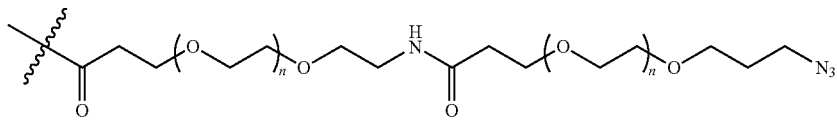

wherein each n is independently 0-50 and the wavy line indicates the bond between the linker and an amino group on the insulin dimer molecule or an amino group on the incretin peptide. In particular embodiments, the linker is selected from

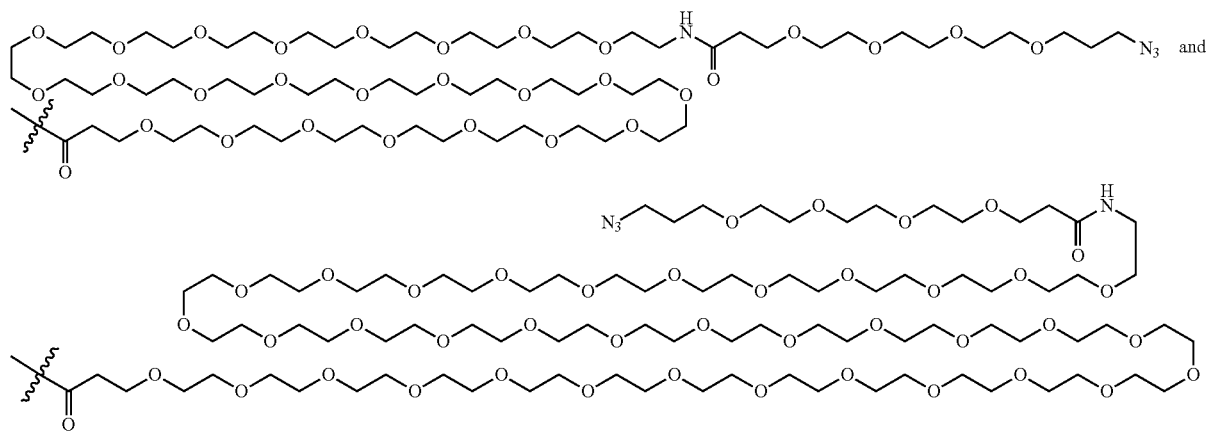

In particular embodiments, the linker may be an azido-(PEG$_n$)(PEG$_n$)(PEGn) linker having the general formula

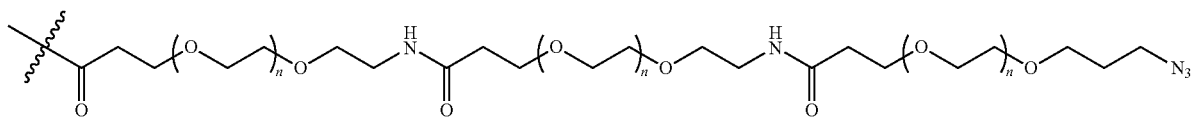

wherein each n is independently 0-50 and the wavy line indicates the bond between the linker and an amino group on the insulin dimer molecule or analog or an amino group on the incretin peptide. In particular embodiments, the linker may be

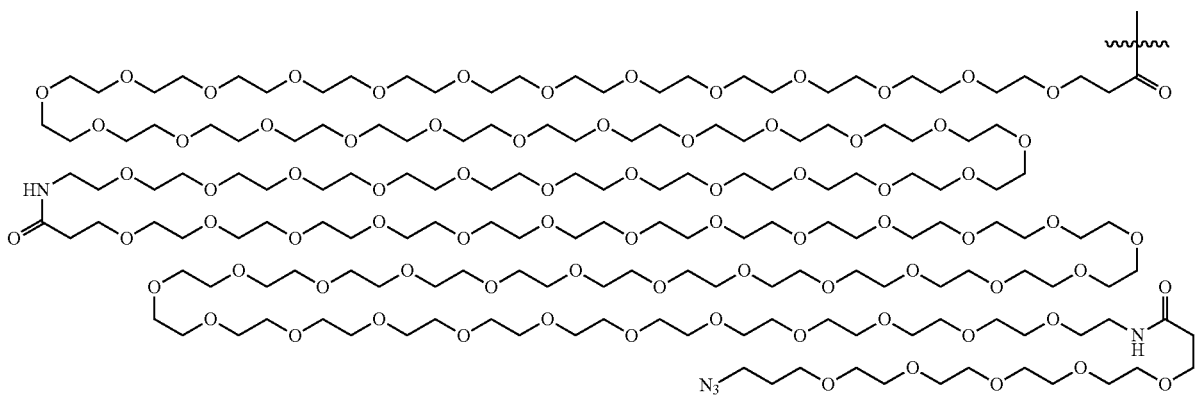 [SMILES: *C(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNC(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNC(=O)CCOCCOCCOCCOCCOCCCN=[N+]=[N-]]

In particular embodiments, the linker may be an azido-C$_n$ having the general formula

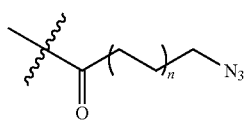

wherein n is 1-50 and the wavy line indicates the bond between the linker and an amino group on the insulin dimer molecule or analog or an amino group on the incretin peptide. In particular embodiments, the linker is

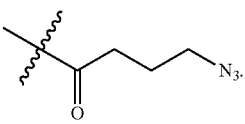 [SMILES: *C(=O)CCCN=[N+]=[N-]]

In particular embodiments, the linker may be an azido-phenylacetate linker having the general formula

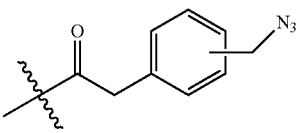

wherein the wavy line indicates the bond between the linker and an amino group on the insulin dimer molecule or analog or an amino group on the incretin peptide. In particular embodiments, the linker is selected from

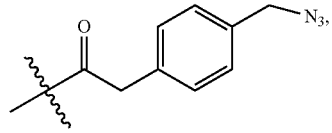

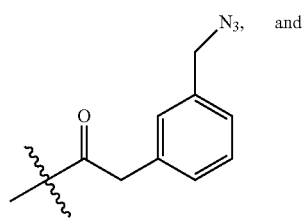 and

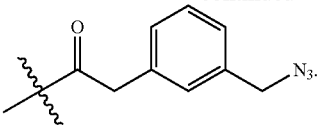

In particular embodiments, the linker may be an azido-$C_n$-$(PEG_2)_n$ linker having the general formula

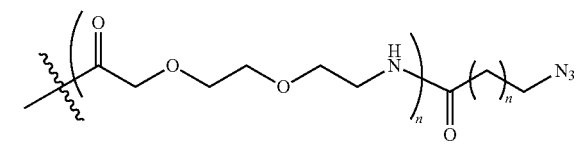

wherein each n is independently 1-10 and the wavy line indicates the bond between the linker and an amino group on the insulin dimer molecule or analog or an amino group on the incretin peptide.

In particular embodiments, $C_n$ is $C_5$ and the linker may be selected from the group

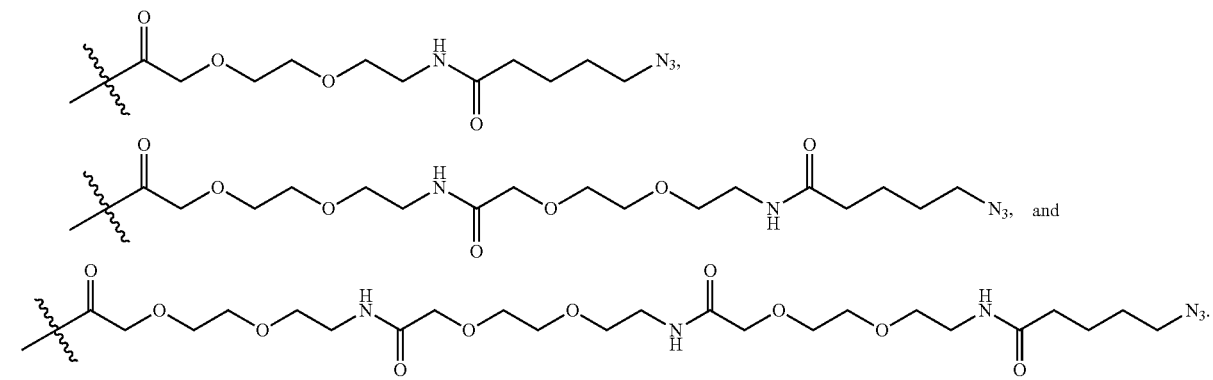

In particular embodiments, $C_n$ is $C_{10}$ and the linker may be selected from the group

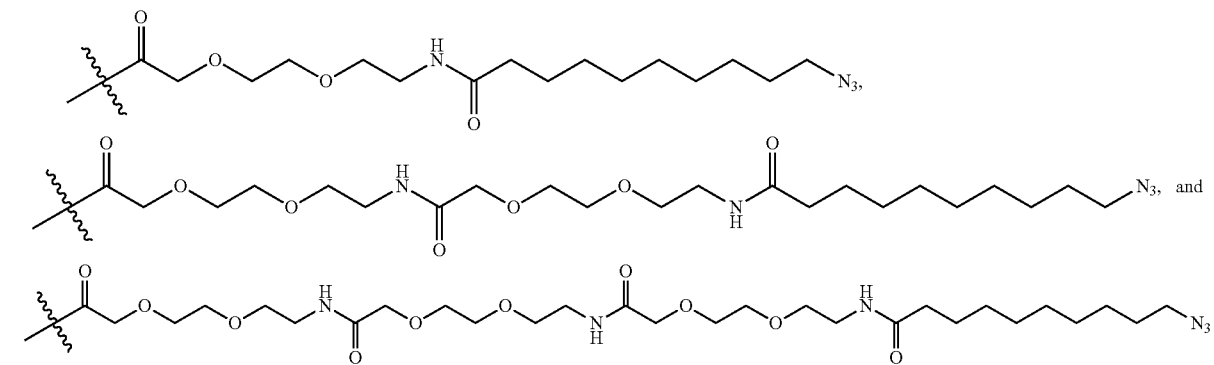

In particular embodiments, $C_n$ is $C_{16}$ and the linker may be selected from the group

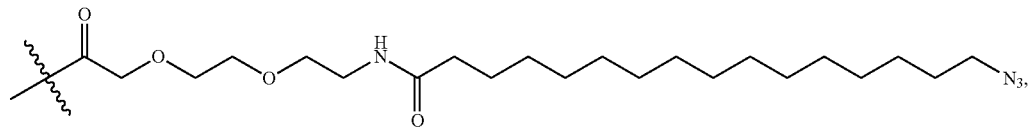

-continued

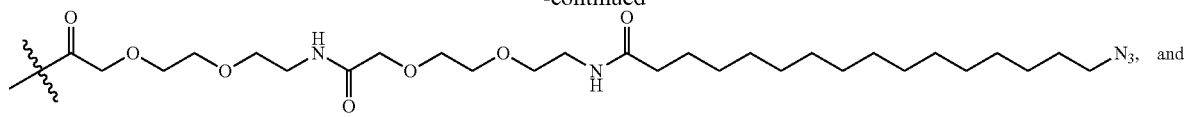

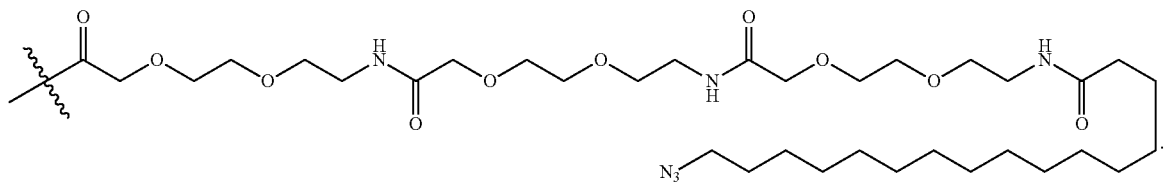

In particular embodiments, the linker may be an azido-$C_n$-γE-(PEG$_2$)$_n$-linker having the general formula

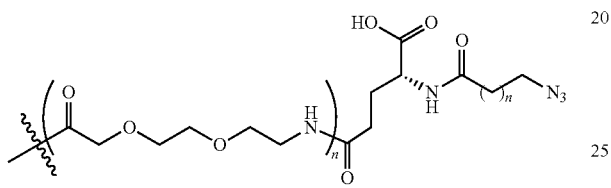

wherein each n is independently 1-10 and the wavy line indicates the bond between the linker and an amino group on the insulin dimer molecule or analog or an amino group on the incretin peptide.

In particular embodiments, $C_n$ is $C_{16}$ and the linker may be selected from the group

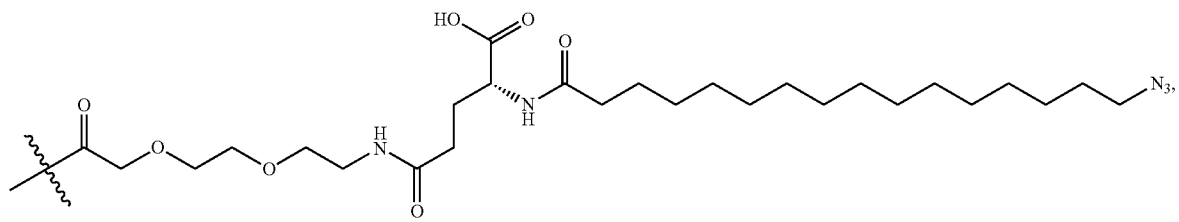

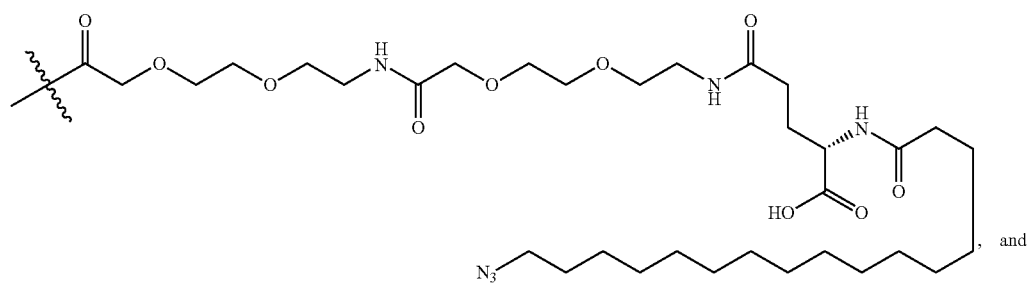

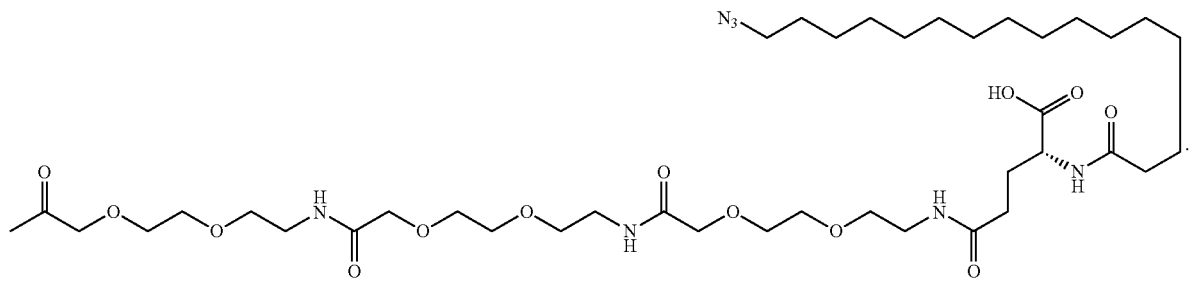

In particular embodiments, $C_n$ is $C_{10}$ and the linker may be selected from the group

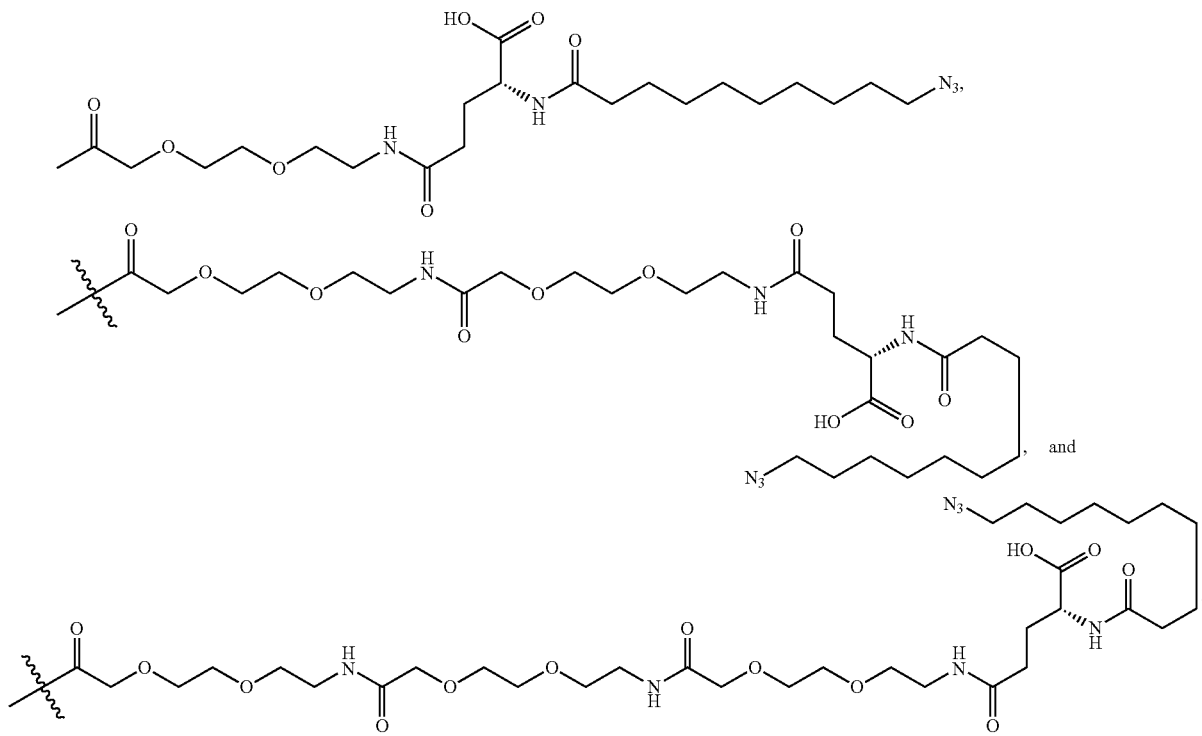

In particular embodiments, the linker may be azido-norleucine having the structure

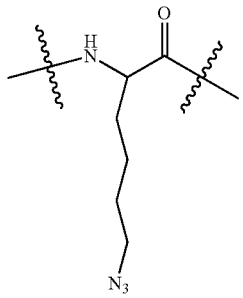 [SMILES: *NC(CCCCN=[N+]=[N-])C(*)=O]

wherein the wavy lines indicate the bonds between the azido-norleucine and adjacent amino acids in either the insulin dimer molecule or the incretin peptide.

In particular embodiments, the second linking moiety conjugating the insulin molecule to the incretin peptide comprises the formula

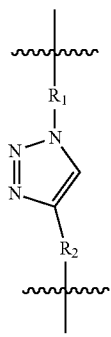

wherein $R_1$ and $R_2$ independently comprise a $C_1$-$C_{50}$ hydrocarbon chain or substituted hydrocarbon chain, a $PEG_n$ wherein n is 1-50, a $(PEG_2)_n$ wherein n is 1-50, a $(PEG_2)_n$-$(\gamma Glu)_p$-$C_n$ wherein each n is independently 1-50 and p is 1 or 2, a $(PEG_2)_n$-$C_n$ wherein each n is independently is 1-50, a $(PEG)_n(PEG)_n$ wherein each n is independently 1-50, a $PEG_n$-$(Lys$-$(\gamma Glu)_p$-$C_n)$-$C_n$ wherein each n is independently 1-50 and p is 1 or 2, and a $C_5$-$Lys(\gamma E$-$C_n)$-$PEG_n$ wherein each n is independently 1-50, and wherein the bond between the linking moiety and the insulin dimer molecule and the incretin peptide are indicated by the wavy lines with the proviso that if the bond adjacent to $R_1$ is to insulin then the bond adjacent to $R_2$ is to the incretin peptide or that if the bond adjacent to $R_1$ is to the incretin peptide then the bond adjacent to $R_2$ is to insulin.

Exemplary second linking moieties are shown in Table 3. For the structures shown, the wavy line on the left indicates the bond between alpha and beta carbons of Norleucine (Nle) or Lysine (Lys or K) and the wavy line on the right indicates the bond between the CO of the moiety and the amino group of an amino acid of the insulin dimer, e.g., the A1 or B1 amino acid.

TABLE 3

| # | Name | Structure |
|---|------|-----------|
| 1 | Nle(εN₃) × C₅ | 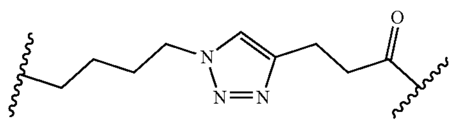 [SMILES: *CCCCn1cc(CCC(*)=O)nn1] |
| 2 | Nle(εN₃ × PEG₃ | 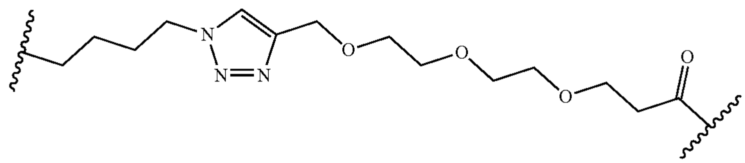 [SMILES: *CCCCn1cc(COCCOCCOCCC(*)=O)nn1] |
| 3 | Nle(εN₃) × PEG₄ | 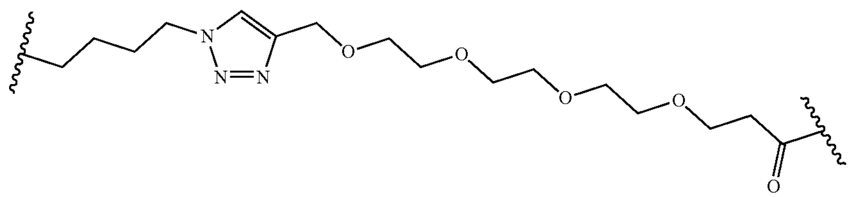 [SMILES: *CCCCn1cc(COCCOCCOCCOCCC(*)=O)nn1] |
| 4 | Nle(εN₃) × PEG₅ | 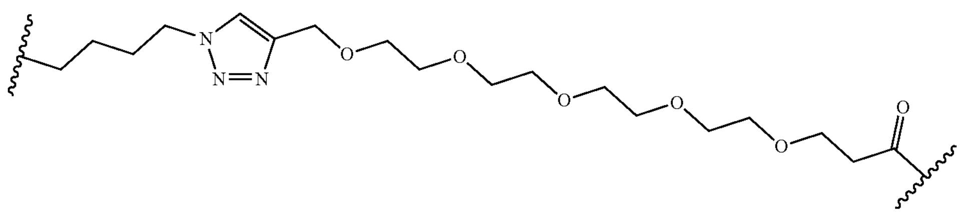 [SMILES: *CCCCn1cc(COCCOCCOCCOCCOCCC(*)=O)nn1] |
| 5 | Nle(εN₃) × PEG₆ | 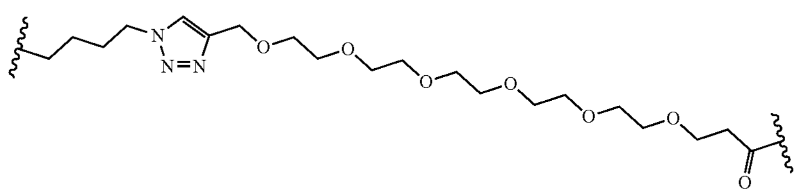 [SMILES: *CCCCn1cc(COCCOCCOCCOCCOCCOCCC(*)=O)nn1] |
| 6 | Nle(εN₃) × PEG₈ | 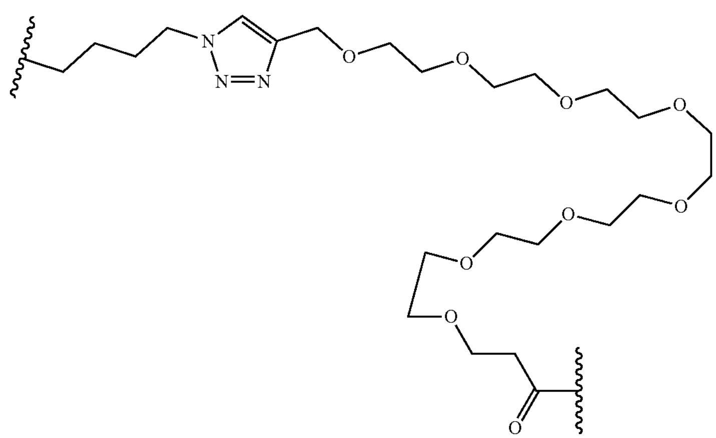 [SMILES: *CCCCn1cc(COCCOCCOCCOCCOCCOCCOCCOCCC(*)=O)nn1] |

TABLE 3-continued

| | Linking Moieties | |
|---|---|---|
| # | Name | Structure |
| 7 | Nle(εN$_3$) × PEG$_{10}$ | (structure) |
| 8 | Nle(εN$_3$) × PEG$_{13}$ | (structure) |
| 9 | Nle(εN$_3$) × PEG$_{14}$ | (structure) |

TABLE 3-continued

| Linking Moieties | | |
|---|---|---|
| # | Name | Structure |
| 10 | Nle(εN₃) × PEG₂₅ | |
| 11 | Nle(εN₃) × (PEG₂)C₅ | |
| 12 | Nl(εN₃) × (PEG₂)₃C₅ | |
| 13 | Nle(εN₃) × (PEG₂₄)(PEG₄) | |
| 14 | Nle(εN₃) × (PEG₃₆)(PEG₄) | |

TABLE 3-continued

Linking Moieties

| # | Name | Structure |
|---|------|-----------|
| 15 | Nle(εN₃) × PEG₁₂(LysγE-C₁₆)C₅ | 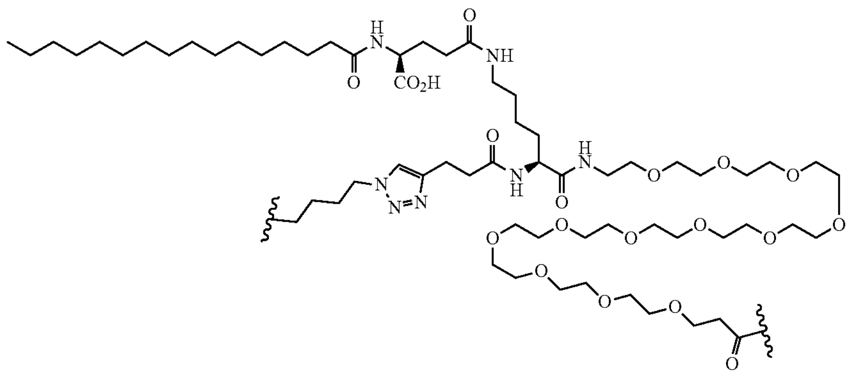 [SMILES: *CCCCn1cc(CCC(=O)N[C@@H](CCCCNC(=O)CC[C@H](NC(=O)CCCCCCCCCCCCCCC)C(=O)O)C(=O)NCCOCCOCCOCCOCCOCCOCCOCCOCCOCCOCCOCCOCCC(*)=O)nn1] |
| 16 | Nle(εN₃) × BCN | 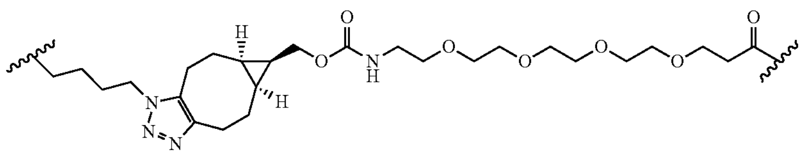 [SMILES: *CCCCn1nnc2c1CC[C@@H]1[C@H](CC2)[C@@H]1COC(=O)NCCOCCOCCOCCOCCC(*)=O] |
| 17 | Lys(PEG₂)C₅N₃ × C₅) | 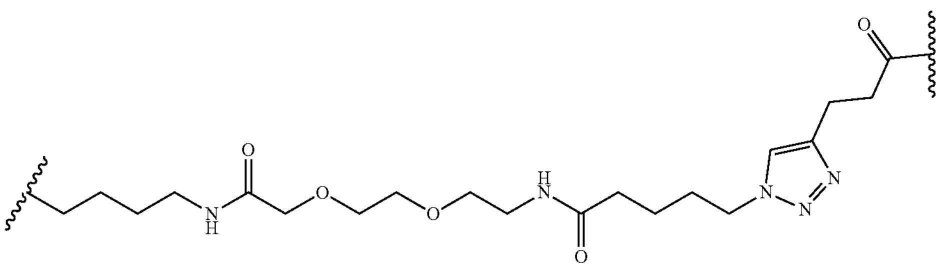 [SMILES: *CCCCNC(=O)COCCOCCNC(=O)CCCCn1cc(CCC(*)=O)nn1] |
| 18 | Lys(PEG₂)(PEG₂)C₅N₃ × C₅) | 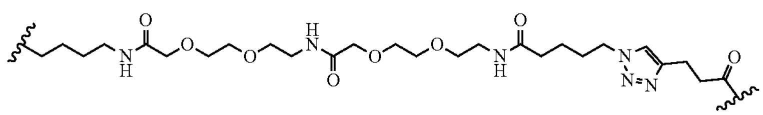 [SMILES: *CCCCNC(=O)COCCOCCNC(=O)COCCOCCNC(=O)CCCCn1cc(CCC(*)=O)nn1] |
| 19 | Lys(PEG₂)₂γEC₁₆N₃ × C₅) | 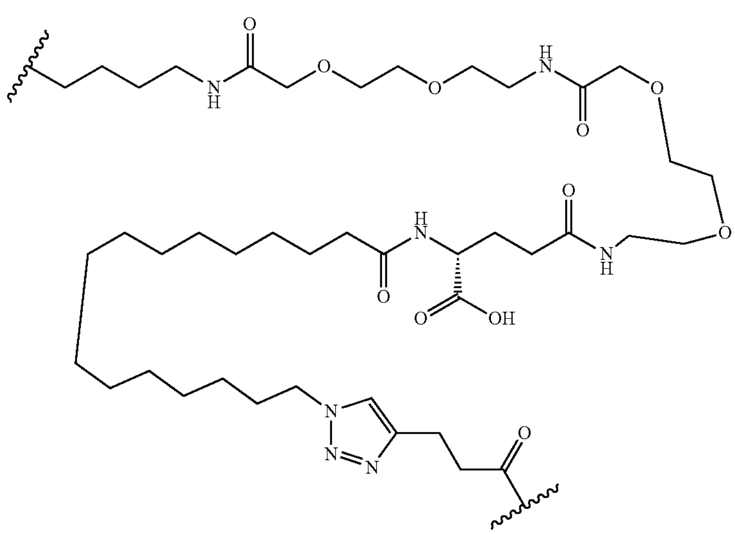 [SMILES: *CCCCNC(=O)COCCOCCNC(=O)COCCOCCNC(=O)CC[C@@H](NC(=O)CCCCCCCCCCCCCCCn1cc(CCC(*)=O)nn1)C(=O)O] |

TABLE 3-continued

Linking Moieties

| # | Name | Structure |
|---|------|-----------|
| 20 | Nle(εN₃) × (PEG₃₆)₂(PEG₅) | 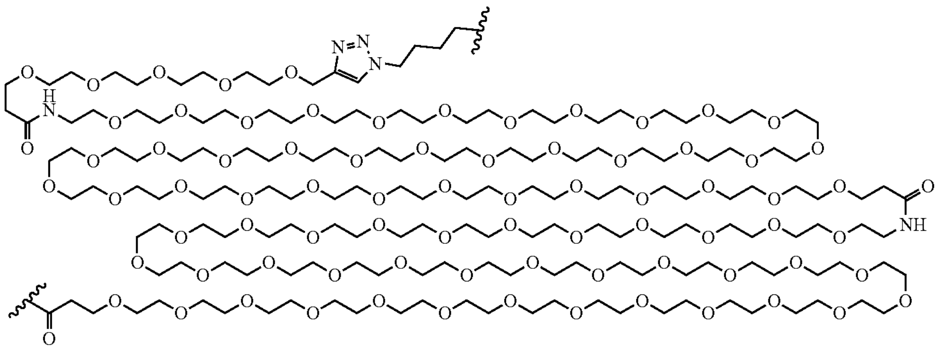 [SMILES: *CCCCn1cc(COCCOCCOCCOCCOCCC(=O)NCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCC(=O)NCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCC(*)=O)nn1] |

Pharmaceutical Compositions

In accordance with one embodiment a pharmaceutical composition is provided comprising any of the compounds disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an insulin dimer as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed compounds are believed to be suitable for any use that has previously been described for insulin peptides. Accordingly, the compounds disclosed herein can be used to treat hyperglycemia, or treat other metabolic diseases that result from high blood glucose levels. Accordingly, the present invention encompasses pharmaceutical compositions comprising a compound as disclosed herein and a pharmaceutically acceptable carrier for use in treating a patient suffering from high blood glucose levels. In accordance with one embodiment the patient to be treated using a compound disclosed herein is a domesticated animal, and in another embodiment the patient to be treated is a human.

One method of treating hyperglycemia in accordance with the present disclosure comprises the steps of administering the disclosed compounds to a patient using any standard route of administration, including parenterally, such as intravenously, intraperitoneally, subcutaneously or intramuscularly, intrathecally, transdermally, rectally, orally, nasally or by inhalation. In one embodiment a composition comprising the disclosed compounds is administered subcutaneously or intramuscularly. In one embodiment, the composition is administered parenterally and the insulin polypeptide, or prodrug derivative thereof, is prepackaged in a syringe.

The compounds disclosed herein may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the compounds disclosed herein can be formulated and administered to patients using standard pharmaceutically acceptable carriers and routes of administration known to those skilled in the art. Accordingly, the present disclosure also encompasses pharmaceutical compositions comprising one or more of the compounds disclosed herein, or a pharmaceutically acceptable salt thereof, in combination with a pharmaceutically acceptable carrier. For example, the pharmaceutical compositions comprising a compound disclosed herein may optionally contain zinc ions, preservatives (e.g., phenol, cresol, parabens), isotonicizing agents (e.g., mannitol, sorbitol, lactose, dextrose, trehalose, sodium chloride, glycerol), buffer substances, salts, acids and alkalis and also further excipients. These substances can in each case be present individually or alternatively as mixtures. Glycerol, dextrose, lactose, sorbitol and mannitol are customarily present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, commonly from about 10-100 mM. Further excipients can be, inter alia, salts or arginine.

In one embodiment the pharmaceutical composition comprises a 1 mg/mL concentration of the compound at a pH of about 4.0 to about 7.0 in a phosphate buffer system.

The pharmaceutical compositions may comprise the compound as the sole pharmaceutically active component, or the compound can be combined with one or more additional active agents.

All therapeutic methods, pharmaceutical compositions, kits and other similar embodiments described herein contemplate that compounds include all pharmaceutically acceptable salts or carriers thereof.

In one embodiment the kit is provided with a device for administering compositions comprising one or more of the disclosed compounds to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the composition comprising the one or more compounds disclosed herein is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

The following examples are intended to promote a further understanding of the present invention.

EXAMPLES

General Procedures

All chemicals were purchased from commercial sources, unless otherwise noted. Reactions were usually carried out at ambient temperature or at room temperature unless otherwise noted. Reactions sensitive to moisture or air were performed under nitrogen or argon using anhydrous solvents and reagents. The progress of reactions was monitored by analytical thin layer chromatography (TLC), and ultra performance liquid chromatography-mass spectrometry (UPLC-MS). TLC was performed on E. Merck TLC plates precoated with silica gel 60F-254, layer thickness 0.25 mm. The plates were visualized using 254 nm UV and/or by exposure to cerium ammonium molybdate (CAM) or p-anisaldehyde staining solutions followed by charring. Ultra performance liquid chromatography (UPLC) was performed on a Waters Acquity™ UPLC® system.

UPLC-MS Method A: Waters Acquity™ UPLC® BEH C18 1.7 μm 1.0×50 mm column with gradient 10:90-95:5 v/v $CH_3CN/H_2O$+v 0.05% TFA over 2.0 min; flow rate 0.3 mL/min, UV wavelength 215 nm; UPLC-MS;

Method B: Waters Acquity™ UPLC® BEH C18 1.7 μm 2.1×100 mm column with gradient 60:40-100:0 v/v $CH_3CN/H_2O$+v 0.05% TFA over 4.0 min and 100:0-95:5 v/v $CH_3CN/H_2O$+v 0.05% TFA over 40 sec; flow rate 0.3 mL/min, UV wavelength 200-300 nm; UPLC-MS;

Method C: Waters Acquity™ UPLC® BEH C18 1.7 μm 2.1×100 mm column with gradient 20:80-90:10 v/v $CH_3CN/H_2O$+v 0.05% TFA over 4.0 min and 90:10-95:5 v/v $CH_3CN/H_2O$+v 0.05% TFA over 0.5 min; flow rate 0.3 mL/min, UV wavelength 200-300 nm; UPLC-MS;

Method D: Waters Acquity™ UPLC® BEH C8 1.7 μm 2.1×100 mm column with gradient 10:90-55:45 v/v $CH_3CN/H_2O$+v 0.05% TFA over 4.0 min and 55:45-95:5 v/v $CH_3CN/H_2O$+v 0.05% TFA over 40 sec; flow rate 0.3 mL/min, UV wavelength 200-300 nm; UPLC-MS;

Method E: Waters Acquity™ UPLC® BEH300 C4 1.7 μm 2.1×100 mm column with gradient 10:90-50:50 v/v $CH_3CN/H_2O$+v 0.05% TFA over 4.3 min and 50:50-70:30 v/v $CH_3CN/H_2O$+v 0.05% TFA over 0.5 min; flow rate 0.3 mL/min, UV wavelength 200-300 nm; UPLC-MS;

Method F: Waters Acquity™ UPLC® BEH C8 1.7 μm 2.1×100 mm column with gradient 20:80-72.5:27.5 v/v $CH_3CN/H_2O$+v 0.05% TFA over 4.3 min and 72.5:27.5-95:5 v/v $CH_3CN/H_2O$+v 0.05% TFA over 0.5 min; flow rate 0.3 mL/min, UV wavelength 200-300 nm, and UPLC-MS;

Method G: Waters Acquity™ UPLC® BEH C8 1.7 μm 2.1×100 mm column with gradient 20:80-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.

Mass analysis was performed on a Waters SQ Detector with electrospray ionization in positive ion detection mode and the scan range of the mass-to-charge ratio was 170-900 or a Waters Micromass® LCT Premier™ XE with electrospray ionization in positive ion detection mode and the scan range of the mass-to-charge ratio was 300-2000. The identification of the produced insulin conjugates or IRPA was confirmed by comparing the theoretical molecular weight to the experimental value that was measured using UPLC-MS. For the determination of the linkage positions, specifically, insulin dimers were subjected to DTT treatment (for a/b chain) or Glu-C digestion (with or without reduction and alkylation), and then the resulting peptides were analyzed by LC-MS. Based on the measured masses, the linkage positions were deduced.

Flash chromatography was performed using either a Biotage Flash Chromatography apparatus (Dyax Corp.) or a CombiFlash® Rf instrument (Teledyne Isco). Normal-phase chromatography was carried out on silica gel (20-70 μm, 60 Å pore size) in pre-packed cartridges of the size noted. Ion exchange chromatography was carried out on a silica-based material with a bonded coating of a hydrophilic, anionic poly(2-sulfoethyl aspartamide) (PolySULFOETHYL A column, PolyLC Inc., 250X$^{21}$ mm, 5 μm, 1000 Å pore size). Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters DELTA PAK C4 15 μm, 300 Å, 50×250 mm column or KROMASIL® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

Abbreviations: acetonitrile (AcCN), aqueous (aq), N,N-diisopropylethylamine or Hunig's base (DIPEA), N,N-dimethylformamide (DMF), dimethyl sulfoxide (DMSO), ethyl acetate (EtOAc), N-(3-dimethylaminopropyl)-N'-ethylcarbodiimide hydrochloride (EDC), gram(s) (g), 1-hydroxybenzotriazole hydrate (HOBt), hour(s) (h or hr), mass spectrum (ms or MS), microgram(s) (m), microliter(s) (μL), micromole (μmol), milligram(s) (mg), milliliter(s) (mL), millimole (mmol), minute(s) (min), retention time ($R_t$), room temperature (rt), saturated (sat. or sat'd), saturated aq sodium chloride solution (brine), triethylamine (TEA), trifluoroacetic acid (TFA), and N,N,N',N'-tetramethyl-O—(N-succinimidyl)uronium tetrafluoroborate (TSTU).

The term "RHI" refers to recombinant human insulin and is used to indicate that the insulin has the amino acid sequence characteristic of native, wild-type human insulin. As used herein in the tables, the term indicates that the amino acid sequence of the insulin comprising the dimer is that of native, wild-type human insulin.

Synthesizing Peptides

A general procedure for synthesizing the peptides disclosed herein may be performed as follows.

The peptides may be synthesized by solid phase synthesis using Fmoc/t-Bu chemistry on a peptide multisynthesizer Symphony (Protein Technologies Inc.) on a 150 μmol scale, using either a Rink-amide PEG-PS resin (Champion, Biosearch Technologies, loading 0.28 mmol/g) or a Rink-amide PS resin (ChemImpex loading 0.47 mmol/g).

All the amino acids are dissolved at a 0.3 M concentration in DMF. The amino acids are activated with equimolar amounts of HATU (O-(7-azabenzotriazol-1-yl)-N,N,N',N'-tetramethyluronium hexafluorophosphate) solution 0.3 M in DMF, and a 2-fold molar excess of DIEA (N,N-diisopropylethylamine), solution 2M in NMP. The acylation reactions are performed in general for 1 hour with a 5-fold excess of activated amino acid over the resin free amino groups with double 45 minutes acylation reactions performed from His' to Thr$^7$, from D$^{15}$ to U$^{16}$ and from F$^{22}$ to V$^{23}$.

The side chain protecting groups may be: tert-butyl for Glu, Ser, D-Ser, Thr and Tyr; trityl for Asn, Gln and His; tert-butoxy-carbonyl for Lys, Trp; and, 2,2,4,6,7-pentamethyldihydrobenzofuran-5-sulfonyl for Arg; His may be introduced as Boc-His(Trt)-OH at the end of the sequence assembly. Amino acid 2 (L-methionine-sulphone) may be introduced by acylation of Fmoc-L-methionine-sulphone-COOH; Nle(εN$_3$) (ε-azidonorleucine) was introduced by acylation of Fmoc-ε-azidonorleucine-COOH.

The lysine that may be used for linker-lipid derivatization, may be incorporated with a Dde [1-(4,4-dimethyl-2,6-dioxocyclohex-1-ylidene)ethyl] protecting group or Alloc (allyloxycarbonyl) protecting group on the side chain amino group. For those sequences comprising an alpha methyl amino acid and the corresponding following residue, the incorporation may be performed by manual coupling with HOAt (Hydroxybenzoazatriazole) and DIC (N,N'-diisopropylcarbodiimide).

At the end of the assembly, the Dde protecting group of Lys(Dde) is removed by treatment with 2% hydrazine in DMF and the Alloc protecting group of Lys(Alloc) is removed by treatment with Pd(PPh$_3$)$_4$ and PhSiH$_3$. The side chains of Lys are derivatized with different linkers and fatty acids by incorporation of Fmoc-Glu-OtBu (γ-glutamic acid), Fmoc-PEG$_2$ [8-(9-Fluorenylmethyloxycarbonyl-amino)-3,6-dioxaoctanoic acid], the lipid diacids (Octadecanedioic acid; Eicosanedioic acid) and Azido acids (C$_5$N$_3$=5-azido pentinoic acid; C$_{10}$N$_3$=10-azido-decanoic acid; C$_{16}$N$_3$=16-azido-hexadecanoic acid) using HOAt and DIC as activators.

At the end of the synthesis, the dry peptide-resins are individually treated with 25 mL of the cleavage mixture, 88% TFA, 5% phenol, 2% triisopropylsilane and 5% water for 1.5 hours at room temperature. Each resin is then filtered and then added to cold methyl-t-butyl ether in order to precipitate the peptide. After centrifugation, the peptide pellets are washed with fresh cold methyl-t-butyl ether to remove the organic scavengers. The process may be repeated twice. Final pellets are dried, resuspended in H$_2$O, 20% acetonitrile, and lyophilized. The crude peptides (140 mg in 3 mL of DMSO) are purified by reverse-phase HPLC using preparative Waters Deltapak C4 (40×200 mm, 15 μm, 300 Å) and using as eluents (A) 0.1% TFA in water and (B) 0.1% TFA in acetonitrile.

Analytical HPLC may be performed on an Acquity UPLC Waters Chromatograph with a BEH300 C4 Acquity Waters column 2.1×100 mm, 1.7 μm, at 45° C., using H$_2$O, 0.1% TFA (A) and CH$_3$CN, 0.1% TFA (B) as solvents. The peptides may be characterized by electrospray mass spectrometry on an Acquity SQ Detector.

Example 1

Synthesis of 2,5-dioxopyrrolidin-1-yl 20-(3-((2,5-dioxopyrrolidin-1-yl)oxy)-3-oxopropyl)-19-oxo-4,7,10,13,16-pentaoxa-20-azatricos-1-yn-23-oate (Linker 51) is described

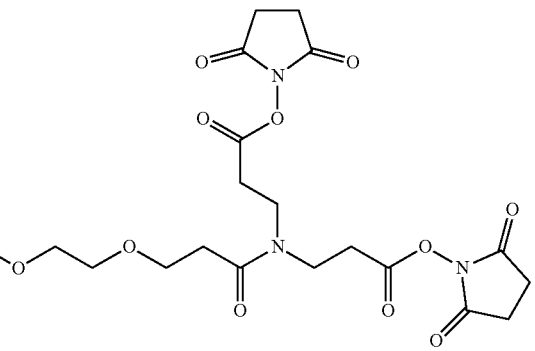

Step 1 20-(2-carboxyethyl)-19-oxo-4,7,10,13,16-pentaoxa-20-azatricos-1-yn-23-oic Acid To a solution of 4,7,10,13,16-pentaoxanonadec-18-yn-1-oic acid (533 mg, 1.75 mmol) in anhydrous DMF (20 ml) at rt was added TSTU (527 mg, 1.75 mmol) and Et$_3$N (0.244 ml, 1.75 mmol). The mixture was allowed to stir at 0° C. for 1 hour and then gradually warmed up to rt and stirred for 30 minutes. The crude NHS ester solution was used without further purification.

To a solution of 3,3'-azanediyldipropanoic acid (310 mg, 1.93 mmol) and Et$_3$N (3 eq) in DMF (10 mL) at rt was added the crude NHS ester solution. The resulting mixture was stirred at rt overnight. After overnight, the mixture was concentrated and the resulting residue was purified on 120 g C18 with gradient 0-40% AcCN in water to give the desired product. UPLC-MS Method A: Rt=3.71 min, m/z=448 [M+1].

Step 2,5-dioxopyrrolidin-1-yl 20-(3-((2,5-dioxopyrrolidin-1-yl)oxy)-3-oxopropyl)-19-oxo-4,7,10,13,16-pentaoxa-20-azatricos-1-yn-23-oate To a solution of of the product of Step 1 (320 mg, 0.72 mmol) in DMF (2 mL) at 0° C. was added TSTU (538 mg, 1.79 mmol) and Et$_3$N (0.199 mL, 1.43 mmol). The mixture was allowed to stir at 0° C. for 30 min and then at rt for 1 hr. The mixture was then concentrated and the residue was purified on 120 g C18 with gradient 0-50% AcCN in water to give the desired product after lyophilization. UPLC-MS Method A: Rt=3.17 min, m/z=642 [M+1].

Example 2

Synthesis of (R)-16-((4-(bis(3-((2,5-dioxopyrrolidin-1-yl)oxy)-3-oxopropyl)amino)-1-carboxy-4-oxobutyl)amino)-16-oxohexadecanoic acid (Linker 52) is described gradient 30% to 100% EtOAc in Hex over 30 min) gave the product. UPLC-MS Method D: Rt=1.70 min, m/z=933 [M+1].

Step 2: (R)-16-((4-(bis(3-((2,5-dioxopyrrolidin-1-yl)oxy)-3-oxopropyl)amino)-1-carboxy-4-oxobutyl)amino)-16-oxohexadecanoic Acid To a solution of the product of Step 1 (256 mg, 0.27 mmol) in acetone (5 mL) was added 10% Pd/C (29.2 mg, 0.027 mmol) and the flask was evacuated carefully to remove ambient air by vacuum, replaced by hydrogen balloon for three times. The mixture was stirred for 2 hrs and filtered through syringe filter. The filtrate was concentrated under vacuum and used without further purification.

The following linkers, i.e., Linker 53, 54, 55, 30, and 13, shown in Table 4 were prepared using procedure analogous to those described for EXAMPLE 1 substituting appropriate acids or activated ester directly and appropriate amines, respectively, in Step 1. The analogs were characterized using UPLC-MS Method A, except Linker 5 that was characterized using UPLC-MS Method D.

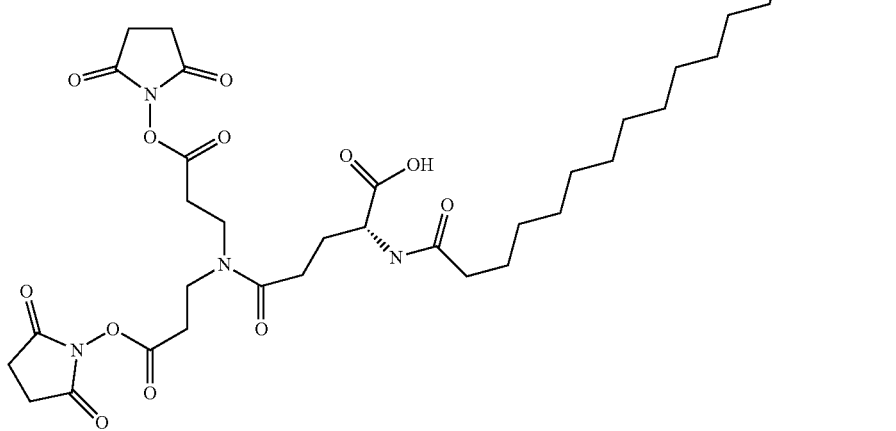

Step 1: Bs(2,5-dioxopyrrolidin-1-yl) 3,3'-((5-(benzyloxy)-4-(16-(benzyloxy)-16-oxohexadecanamido)-5-oxopentanoyl)azanediyl)(R)-dipropionate To a solution of (R)-3,3'-((5-(benzyloxy)-4-(16-(benzyloxy)-16-oxohexadecanamido)-5-oxopentanoyl)azanediyl) dipropionic acid (1.136 g, 1.54 mmol)) in DMF (11 mL) was added TSTU (0.949 g, 3.15 mmol) followed by DIPEA (0.403 mL, 2.31 mmol). Additional 50 mg of TSTU and stirring continued for 10 minutes. TFA (0.474 mL, 6.15 mmol) was added to quench the reaction. The reaction was worked up by pouring into 25 mL of MTBE in 125 mL separatory funnel and diluted with 12 mL of H$_2$O. The aqueous layer was extracted w/MTBE (20 mL×2) and the combined organic layers were washed with H$_2$O (10 mL×2) and brine (10 mL) and dried over Na$_2$SO$_4$, filtered and conc. in vacuum. Purification by ISCO (silica gel, 40 g gold,

TABLE 4

| Linker No. | Structure | Rt (min) | M + 1 |
|---|---|---|---|
| 53 | (structure) | 2.51 | 404 |
| 54 | (structure) | 3.47 | 1034 |
| 55 | (structure) Exact Mass: 2297.22 | 3.63 | 767 ((M + 4)/4) |

TABLE 4-continued
| Linker No. | Structure | Rt (min) | M + 1 |
|---|---|---|---|
| 30 | 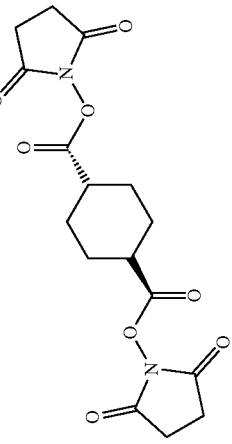 | 0.75 (2 min method) | 367 |
| 13 | suberic (commercial) | | |

141

Example 3

General Method A: Synthesis of $N^{6,29B},N^{6,29B'}$-Insulin Dimers Using Organic Base Condition In an appropriate sized container, insulin or insulin analog is suspended at rt in an organic solvent or mixed aqueous (aq)/organic solvents, e.g., DMSO, in the presence of a base, e.g., TEA. The mixture is allowed to stir gently until insulin is completely dissolved. To the resulting solution is added an activated ester intermediate (linker) in solution of organic solvents, such as DMSO or DMF. After UPLC chromatogram shows that a substantial portion of the reaction mixture has converted into $N^{6,29B}, N^{6,B29B'}$-insulin dimer (or $N^{6,28B}, N^{6,28B'}$-insulin lispro dimer). The reaction mixture may be subjected directly to reverse phase HPLC purification (Waters C4 250×50 mm column, 10 µm, 1000 Å column or KROMASIL C8 250×50 mm, 10 µm, 100 Å column; Buffer A: 0.05-0.1% TFA in deionized water; Buffer B: 0.05-0.1% TFA in AcCN), or the reaction may be quenched by careful dilution with cold acidic $H_2O$ (20×, pH about 3.0) at 0° C. and its pH is adjusted to a final pH of 2.5 using 1 N HCl (and 0.1 N NaOH if needed). The solution may first be concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250X$^{21}$ mm, 5 µm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing B29-conjugate with desired purity are combined and concentrated using TFF system or Amicon Ultra-15. The concentrated solution is then subjected to reverse phase HPLC purification (Waters C4 250×50 mm column, 10 µm, 1000 Å column or KROMASIL C8 250×50 mm, 10 µm, 100 Å column; Buffer A: 0.05-0.1% TFA in deionized water; Buffer B: 0.05-0.1% TFA in AcCN). Fractions containing the desired insulin dimer are combined and freeze-dried or buffer exchanged using TFF system and/or Amicon Ultra-15 to give the $N^{6,29B},N^{6,29B'}$-insulin dimers.

Example 4

General Method B: Synthesis of $N^{6,29B},N^{6,29B'}$-Insulin Dimers Using Aqueous Base Conditions In an appropriate sized container, insulin or insulin analog is dissolved, with gentle stirring, at rt in a mixed solvent: 2:3 v/v 0.1 M $Na_2CO_3$:AcCN. After the mixture cleared, the pH is adjusted to the value of 10.5-10.8 using alkaline solution, e.g., 0.1 N NaOH. In a separate vial, an activated ester intermediate (linker) is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into $N^{6,B29},N^{6,B29'}$-insulin dimer (or $N^{6,28B},N^{6,28B}$-insulin lispro dimer). The reaction is quenched by the addition of an amine nucleophile, e.g., 2-aminoethanol. The reaction solution is stirred at rt for 30 minutes. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250X$^{21}$ mm, 5 µm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing B29-conjugate with desired purity are combined and concentrated using TFF system or Amicon Ultra-15. The resulting solution is then further purified by reverse phase HPLC (Waters C4 250×50 mm column, 10 µm, 1000 Å column or KROMASIL C8 250×50 mm, 10 µm, 100 Å column; Buffer A: 0.05-0.1% TFA in water; Buffer B: 0.05-0.1% TFA in AcCN). Fractions containing the title insulin dimer are combined and freeze-dried or buffer exchanged using TFF system and/or Amicon Ultra-15 to give the $N^{6,29B},N^{6,29B'}$-insulin dimers.

Example 5

This example illustrates the synthesis of $N^{6,B29},N^{6,B29'}$-(3,3'-((4,7,10,13,16-pentaoxanonadec-18-ynoyl)azanediyl)dipropionyl)bis[insulin human] (Dimer 1).

Dissolved RHI (208 mg, 0.036 mmol) in 10 mL of sodium carbonate water/acetonitrile (3:2) was added 2,5-dioxopyrrolidin-1-yl 20-(3-((2,5-dioxopyrrolidin-1-yl)oxy)-3-oxopropyl)-19-oxo-4,7,10,13,16-pentaoxa-20-azatricos-1-yn-23-oate (Linker 51) (11.5 mg, 0.018 mmol) in AcCN (500 µL) in four portions over a period of 2 hr. The reaction progress was monitored by analysis of an aliquot of reaction mixture on UPLC-MS. After 2 hr, poured the reaction mixture into 60 mL of 20% AcCN/0.1% TFA/water, adjusted pH to 2.5, and diafiltrated using Amicon Ultra-15 with 10K MWCO membrane to concentrate until the resulting volume was about 10 mL. The resulting solution was subjected to ion-exchange chromatography (PolySULFOETHYL A column, 250X$^{21}$ mm, 5 µm, 1000 Å, gradient 20-80% of Buffer B in Buffer A over 30 min; Buffer A: 0.1% (v/v)$H_3PO_4$/25% AcCN; Buffer B: 0.1% (v/v)$H_3PO_4$/25% AcCN/0.5M NaCl). Fractions containing the title compound was combined and concentrated. The resulting solution was then subjected to reverse phase chromatography (KROMASIL C8 250×50 mm, 10 µm, 100 Å column; gradient 20-40% of AcCN with 0.05% TFA in water with 0.05% TFA). Fractions containing the desired product were combined and lyophilized. UPLC-MS Method E: Rt=3.45 min, m/z=1504 (z=8), 1718 (z=7).

Example 6

This example illustrates the synthesis of $N^{2,B1}$-C5-alkyne $N^{6,B29}, N^{6,B29'}$-suberic-bis[insulin human] and $N^{2,B1}, N^{2,B1'}$-bis-C5-alkyne $N^{6,B29}, N^{6,B29'}$-suberic-bis[insulin human] (Dimer 2 and 3).

Step 1. $N^{6B29},N^{6B29'}$-Suberic-Bis[Insulin Human]

To a solution of RHI (331 mg, 0.057 mmol) in DMSO (6 mL) was added 1,1,3,3-tetramethylguanidine (107 µl, 0.855 mmol), followed by dropwise addition of a solution of bis(2,5-dioxopyrrolidin-1-yl) octanedioate (10.5 mg, 0.029 mmol) in 0.16 mL DMSO (from a stock solution of 12.5 mg in 1 mL of DMSO) over 30 min. After stirred at rt for 0.5 h, the reaction solution was added dropwise into 20 mL of mixture of IPAc/MTBE (4:1) containing 0.5 mL HOAc. The precipitates were filtered and dried under $N_2$ and vacuum overnight. Purification by reverse phase prep HPLC (C8 column, 50X$^{250}$ cm, 85 ml/min, gradient from 29% to 38% of AcCN with 0.05% TFA in water with 0.05% TFA in 25 min). The selected fractions were lyophilyzed to isolate desired product.

Step 2: $N^{2,B1}$-C5-Alkyne $N^{6,B29}$, $N^{6,B29'}$-Suberic-Bis[Insulin Human] and $N^{2,B1}$, $N^{2,B1'}$-Bis-C5-Alkyne $N^{6,B29}$, $N^{6,B29'}$-Suberic-Bis[Insulin Human]

$N^{6,B29}$,$N^{6,B29'}$-suberic-bis[insulin human] (103.2 mg, 8.78 μmol) was dissolved in DMSO (2 ml). 2,2,6,6-tetramethylpiperidine (29.6 μl, 0.176 mmol) was added followed by dropwise addition of tert-butyl (2,5-dioxopyrrolidin-1-yl) carbonate (3.78 mg, 0.018 mmol) in 0.17 mL DMSO (from a stock solution of 11 mg in 0.5 mL DMSO) over 30 min via syringe pump. The reaction mixture was stirred at rt for 1 hr and 10 more eq of 2,2,6,6-tetramethylpiperidine was added. After 45 min, UPLC-MS showed bis-Boc and tri-Boc intermediates as major peaks. 2,5-Dioxopyrrolidin-1-yl pent-4-ynoate (1.714 mg, 8.78 μmol) was added in 0.20 ml of DMSO (from a stock solution of 8.7 mg in 1 mL) and the reaction mixture was stirred for overnight.

The products were precipitated out as a white solid by dropwise adding into 12 mL 4:1 mixture of IPAc/MTBE containing HOAc (200 uL). The solid was filtered and dried under $N_2$ and vacuum. The crude solid was dissolved in 1 mL TFA and immediately precipitated into MTBE (5 mL). The resulting solid was filtered and dried under vacuum and $N_2$. Purification by reverse phase prep HPLC (C-8 column, 50X$^{250}$ cm, 85 ml/min, gradient from 29% to 38% of AcCN with 0.05% TFA in water with 0.05% TFA in 25 min). The selected fractions were lyophilyzed to isolate both B1 mono-alkyne (UPLC-MS Method D: Rt=2.19 min, m/z=1480 (z=8), 1691 (z=7)) and B1,B1'bis-alkyne products (UPLC-MS Method D: Rt=2.25 min, m/z=1490 (z=8), 1702 (z=7)) as a white powder, respectively.

Example 7

This example illustrates the synthesis of $N^{2,A1}$-PEG14-alkyne $N^{6,B29}$,$N^{6,B29'}$-linker 52-bis[insulin human] (Dimer 4).

Step 1: $N^{6,B29}$, $N^{6,B29'}$-Linker 52-Bis[Insulin Human]

To a solution of RHI (2928 mg, 0.504 mmol) in DMSO (30 mL) was a added 1,1,3,3-tetramethylguanidine (380 μl, 3.03 mmol), followed by dropwise addition of Linker 52 (207.4 mg, 0.252 mmol) in DMSO (2 mL) via syringe pump over 30 min. After stirred at rt for 30 min, the products were precipitated by dropping reaction mixture into a 150 mL mixture of 4:1 IPAc/MTBE. The solid was filtered and dried under $N_2$ and vacuum overnight. Purification on reverse phase prep HPLC (C-8 column, 50×250 cm, 85 ml/min, gradient 28.5-39% of AcCN with 0.05% TFA in $H_2O$ with 0.05% TFA) followed by lyophilization gave the desired product (UPLC-MS Method D: Rt=2.29 min, m/z=1517 (z=8), 1735 (z=7)).

Step 2: $N^{2,A1}$-PEG14-Alkyne $N^{6,B29}$, $N^{6,B29'}$-Linker 52-Bis[Insulin Human]

To a solution of the product of Step 1 (87 mg, 7.17 μmol) in DMSO (2 ml) was added 2,2,6,6-tetramethylpiperidine (0.036 ml, 0.215 mmol) followed by dropwise addition of alkyne-PEG14-NHS ester (8.18 mg, 10.25 μmol, freshly made by reacting acid with 1.2 eq TSTU and 3.5 eq TEA in 0.2 mL DMF for 1 h at rt and used directly) in 0.20 mL DMF dropwise via syringe pump. After stirred at rt for 30 min, the products were precipitated by dropping reaction mixture into a 12 mL mixture of 4:1 IPAc/MTBE. The solid was filtered and dried under $N_2$ and vacuum for 15 min. Purification by reverse phase prep HPLC (C-8 column, 50X$^{250}$ cm, 85 ml/min, gradient from 29% to 42% of AcCN with 0.05% TFA in $H_2O$ with 0.05% TFA in 30 min) followed by lyophilization gave product (UPLC-Method D: Rt=3.47 min, m/z=1604 (z=8), 1832 (z=7)).

Example 8

Table 5 shows dimers that were prepared using appropriate Linker following either General Method A or General Method B as noted using RHI. The dimers were characterized using UPLC-MS Method D or UPLC-MS Method E, exhibiting either six charged, i.e. [(M+6)/6], (or seven charged, i.e. [(M+7)/7]) species of parent compound at certain retention time (Rt).

TABLE 5

| Dimer No. | Linker Used | Prep. Method | Rt (min) | (M + 6)/6 or (M + 7)/7 |
|---|---|---|---|---|
| 5 | 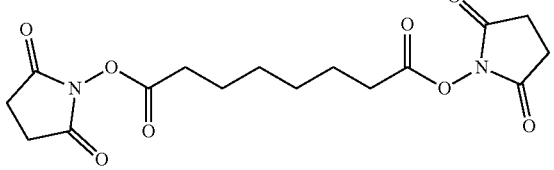 | Example 6 | 2.87 | 1761 |

TABLE 5-continued

| Dimer No. | Linker Used | Prep. Method | Rt (min) | (M + 6)/6 or (M + 7)/7 |
|---|---|---|---|---|
| 6 | | Example 6 | | |
| 7 | | Example 6 | | |
| 8 | | Example 6 | 2.42 | 1746 |
| 9 | | Example 6, step 1 | 2.07 | 1712 |
| 10 | | Example 6 | 2.44 | 1713 |

TABLE 5-continued

| Dimer No. | Linker Used | Prep. Method | Rt (min) | (M + 6)/6 or (M + 7)/7 |
|---|---|---|---|---|
| 11 | | Example 6 | 3.73 | 1775 |
| 12 | | Example 6 | | |

Example 9

General Method C: Conjugation of Acetylene Containing Insulin Dimers with Azido Containing Peptides Using $Cu^{2+}$-Catalyzed Click Chemistry in the Presence of a Ligand In an appropriate sized container, appropriate acetylene containing insulin dimers (Dimer) was dissolved, with gentle stirring, at rt in a mixed solvent of DMSO and aq. triethylammonium acetate buffer (pH 7.0, final concentration 0.2 mM). In another appropriate sized container, appropriate azido containing peptide was dissolved, with gentle stirring, at rt in a mixed solvent of DMSO and water. Both solutions were combined, thoroughly mixed, degassed by gently bubbling $N_2$ through. To the resulting solution was added freshly prepared sodium ascorbate or ascorbic acid solution (final concentration is 0.5 mM) and, after thoroughly mixed, a solution of 10 mM $CuSO_4$ and a ligand, e.g., tris[(1-benzyl-1H-1,2,3-triazol-4-yl)methyl]amine or TBTA ligand, in 55% DMSO. After degassed by gently bubbling $N_2$ through and mixed thoroughly, the mixture was stored at rt, with occasional mixing, overnight. The reaction mixture was carefully diluted with a mix solvent (v/v 7:3 AcCN/water with 0.05% TFA) at 0° C. and pH was adjusted to 2.50 using 0.1, 1.0 N HCl (and 0.1 N NaOH if needed). The solution was first concentrated by ultrafiltration, either through a tangential flow filtration (TFF) system or using Amicon Ultra-15 Centrifugal Units, with 1K, 3K, or 10K MWCO membrane. The concentrated solution was usually first subjected to ion exchange chromatography (PolySUL-FOETHYL A column, PolyLC Inc., 250X$^{21}$ mm, 5 µm, 1000 Å; Buffer A: 0.1% (v/v)$H_3PO_4$/25% AcCN; Buffer B: 0.1% (v/v)$H_3PO_4$/25% AcCN/0.5 M NaCl). Fractions containing desired product with desired purity were combined and concentrated using TFF system or Amicon Ultra-15. The resulting solution was then further purified by reverse phase HPLC (Waters C4 250×50 mm column, 10 µm, 1000 Å column or KROMASIL C8 250×50 mm, 10 µm, 100 Å column; Buffer A: 0.05-0.1% TFA in water; Buffer B: 0.05-0.1% TFA in AcCN). Fractions containing the desired product with desired purity were combined and freeze-dried or buffer exchanged using TFF system and/or Amicon Ultra-15 to give the insulin dimers.

Example 10

This example illustrates the conjugation of $N^{6,B29}$, $N^{6,B29'}$-(3,3'-((4,7,10,13,16-pentaoxanonadec-18-ynoyl) azanediyl)dipropionyl)bis[insulin human] (Dimer 1) and PEP76 using General Method D to product CONJ1.

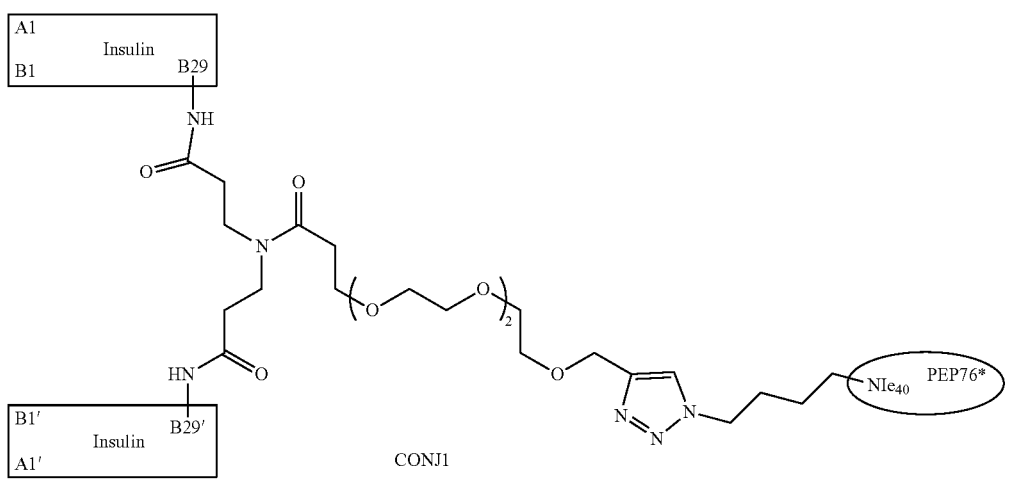

CONJ1

To a solution of Dimer 1 (23 mg, 1.912 μmol) and PEP76 (8.30 mg, 1.912 μmol) in a mixture of DMSO (9.0 mL) and water (8.0 mL) was added 2M triethylammonium acetate pH 7.0 buffer (2.0 mL) and 5 mM sodium ascorbate (2.0 mL). The resulting mixture was bubbled through with $N_2$ for 1 min and then 10 mM $CuSO_4$-TBTA complex (1.0 mL, 55 v % DMSO). The resulting mixture was bubbled through $N_2$ for 30 s. The mixture was shaken occasionally and let it stand at rt overnight.

After overnight, the mixture was acidified carefully to pH~3 using 1 N HCl. The resulting mixture was purified on Gilson (C8, 50×250 mm, gradient 28-40% AcCN in water with 0.05% TFA over 25 min, flow rate 85 mL/min). Fractions containing the desired product were combined and lyophilized to give the desired product as a white powder. UPLC-MS Method D: Rt=3.64 min, m/z=1637 (z=10), 1819 (z=9).

Example 11

The following insulin dimer and peptide conjugates were prepared following General Method C, using procedure analogous to those described for EXAMPLE 18 substituting appropriate acetylene containing insulin dimers and appropriate azido containing peptides, respectively. The products were characterized using UPLC-MS Method E, except CONJ 19-24 using UPLC-Method G. FIGS. 2A-2G show the structure of the conjugates in Table 6.

TABLE 6

| CONJ No. | Dimer No. | Peptide No. | Rt (min) | (M + 10)/10 |
|---|---|---|---|---|
| 2 | Dimer 3 | PEP87 | 3.22 | 1795 |
| 3 | Dimer 5 | PEP87 | 3.25 | 2015 |
| 4 | Dimer 2 | PEP87 | 2.61 | 1575 |
| 5 | Dimer 6 | PEP87 | 2.93 | 1574 |
| 6 | Dimer 7 | PEP87 | 2.95 | 1631 |
| 7 | Dimer 7 | PEP88 | 4.59 | 1581 |
| 8 | Dimer 8 | PEP88 | 2.40 | 1564 |
| 9 | Dimer 9 | PEP87 | 3.00 | 1590 |
| 10 | Dimer 1 | PEP88 | 2.80 | 1545 |
| 11 | Dimer 1 | PEP89 | 3.24 | 1581 |
| 12 | Dimer 1 | PEP90 | 2.54 | 1616 |
| 13 | Dimer 1 | PEP91 | | 1650? |
| 14 | Dimer 4 | PEP88 | 3.03 | 1624 |
| 15 | Dimer 1 | PEP87 | 2.64 | 1595 |

TABLE 6-continued

| CONJ No. | Dimer No. | Peptide No. | Rt (min) | (M + 10)/10 |
|---|---|---|---|---|
| 16 | Dimer 10 | PEP89 | 2.42 | 1712 |
| 17 | Dimer 1 | PEP81 | 2.20 | 1567 |
| 18 | Dimer 1 | PEP78 | 2.26 | 1557 |
| 19 | Dimer 11 | PEP76 | 0.88 | 1677 |
| 20 | Dimer 1 | PEP82 | 0.83 | 1718 |
| 21 | Dimer 1 | PEP83 | 0.90 | 1630 |
| 22 | Dimer 1 | PEP84 | 0.86 | 1636 |
| 23 | Dimer 11 | PEP85 | 0.82 | 1701 |
| 24 | Dimer 11 | PEP86 | 0.88 | 1677 |
| 25 | Dimer 1 | PEP80 | 2.25 | 1661 |
| 26 | Dimer 1 | PEP77 | 2.27 | 1559 |
| 27 | Dimer 10 | PEP76 | | 1805 |

Example 12

Activity of the peptides and the conjugates at the Glucagon receptor (GCGR) and GLP-1 receptor (GLP1R) may be measured in a cAMP activity assay as follows.

Peptides are dissolved in 100% DMSO and serially diluted to generate 10 point titrations. The peptide solutions are then transferred into 384-well assay plates (150 nL/well). Assay ready frozen cells expressing human GIPR, GLP1R or human GCGR are suspended in growth media consisting of DMEM medium (GIBCO), 10% FBS (GIBCO), 1×NEAA(GIBCO), 1×P/S (GIBCO), 10 μg/mL Blasticidin (GIBCO) and 200 μg/mL Hygromycin (GIBCO). Cells are then diluted in assay buffer consisting of PBS (GIBCO), 7.5% BSA (Perkin Elmer), 100 RO 20-1724 (Sigma), with or without 20% human serum (MP Biomedical). The cell suspensions (15 μL) are then added to the assay plates containing the peptide solutions (30,000 cells/well for human GCGR; 10,000 cells/well for human GLP1R and 15,000 cells/well for human GIPR). The cells are incubated for one hour at room temperature in the dark.

Production of cAMP may be determined using HitHunter™ cAMPXS kits (DiscoverX) following the manufacturer's protocol. The plates are incubated for overnight at room temperature in the dark. Luminescence may be measured using an EnVision Multilabel plate reader (Perkin Elmer). Native GIP, GLP-1 and Glucagon (Bachem) may be used as control peptides. $EC_{50}$ values may be calculated using uses a 4 parameter logistic fit based on the Levenberg-Marquardt algorithm. The results for several of the peptides are shown in Table 7.

TABLE 7

| Peptide Name | hGIP_EC$_{50}$ (nM) | hGCGR_EC$_{50}$ (nM) | hGLP1R EC$_{50}$ (nM) | GCGR/GLP1R ratio |
|---|---|---|---|---|
| PEP87 | | 0.019 | 0.049 | 0.39 |
| PEP88 | | 0.093 | 0.090 | 0.97 |
| PEP89 | | 3.9 | 0.044 | 88.63 |
| PEP90 | | 0.041 | 0.062 | 0.66 |
| PEP91 | | 0.10 | 0.073 | 1.37 |

Example 13

The conjugate binding or affinity to the insulin receptor may be performed using the following Insulin Receptor Binding Assays.

Two competition binding assays may be utilized to determine affinity for the human insulin receptor type B (IR(B)) against the endogenous ligand, insulin, labeled with $^{125}$[I].

Method 1 IR binding assay is a whole cell binding method using CHO cells overexpressing human IR(B). The cells are grown in F12 media containing 10% FBS and antibiotics (G418, Penicillin/Strepavidin), plated at 40,000 cells/well in a 96-well tissue culture plate for at least eight hours. The cells are then serum starved by switching to DMEM media containing 1% BSA (insulin-free) overnight. The cells are washed twice with chilled DMEM media containing 1% BSA (insulin-free) followed by the addition of conjugate at appropriate concentration in 90 μL of the same media. The cells are incubated on ice for 60 minutes. The $^{125}$[I]-insulin (10 μL) is added at 0.015 nM final concentration and incubated on ice for four hours. The cells are then gently washed three times with chilled media and lysed with 30 μL of Cell Signaling lysis buffer (cat #9803) with shaking for 10 minutes at room temperature. The lysate is added to scintillation liquid and counted to determine $^{125}$[I]-insulin binding to IR and the titration effects of the conjugate on this interaction.

Method 2 IR binding assay is run in a scintillation proximity assay (SPA) in 384-well format using cell membranes prepared from CHO cells overexpressing human IR(B) grown in F12 media containing 10% FBS and antibiotics (G418, Penicillin/Strepavidin). Cell membranes are prepared in 50 mM Tris buffer, pH 7.8 containing 5 mM MgCl$_2$. The assay buffer contains 50 mM Tris buffer, pH 7.5, 150 mM NaCl, 1 mM CaCl$_2$, 5 mM MgCl$_2$, 0.1% BSA and protease inhibitors (Complete-Mini-Roche). Cell membranes are added to WGA PVT PEI SPA beads (5 mg/mL final concentration) followed by addition of conjugate at appropriate concentrations. After 5-15 min incubation at room temperature, $^{125}$[I]-insulin is added at 0.015 nM final concentration for a final total volume of 50 μL. The mixture is then incubated with shaking at room temperature for 1 to 12 hours followed by scintillation counting to determine $^{125}$[I]-insulin binding to IR and the titration effects of conjugate on this interaction.

Example 14

Conjugate agonist activity at the insulin receptor may be performed using the following Insulin Receptor Phosphorylation Assays.

Insulin receptor activation can be assessed by measuring phosphorylation of the Akt protein, a key step in the insulin receptor signaling cascade. CHO cell lines overexpressing either human, minipig or dog IR are utilized in an HTRF sandwich ELISA assay kit (Cisbio "Phospho-AKT(Ser473) and Phospho-AKT(Thr308) Cellular Assay Kits"). Cells are grown in F12 media supplemented with 10% FBS, 400 ug/ml G418 and 10 mM HEPES. Prior to assay, the cells are incubated in serum free media for 2 to 4 hours. Alternatively, the cells may be frozen and aliquoted ahead of time in media containing 20% DMSO and used in the assay upon thawing, spin down and re-suspension.

Cells are plated at 10,000 cells per well in 20 uL of the serum free F12 media in 384-well plates. Humulin and glargine controls were run on each plate of test compounds. The titrated compounds are added to the cells (2 μL per well, final concentrations=1000 nM titrated down to 0.512 pM in 1:5 fold dilutions) and incubated at 37° C. for 30 minutes. The cells are lysed with 8 μL of the prepared lysis buffer provided in the CisBio kit and incubated at 25° C. for one hour. The diluted antibody reagents (anti-AKT-d2 and anti-pAKT-Eu3/cryptate) are prepared according to the kit instructions and then 10 μL is added to each well of cell lysate followed by incubation at 25° C. for 3.5 to 5 hours. The plate may be read by in an Envision plate reader (Excitation=320 nm; Emission=665 nm) to determine the IR pAkt agonist activity with regard to both potency and maximum response for each compound. Alternatively, the compounds may be tested in the same manner in the presence of 1.6 nM of Humulin to determine how each compound was able to compete against the full agonist activity of insulin.

Example 15

Table 8 shows the incretin and insulin agonist activity of the various insulin incretin conjugates disclosed herein. Control molecule PEP92 has the amino acid sequence HsQGTFTSDK(γEγEC$_{16}$)SKYLDERAAQDFVQWLLDT-NH$_2$ (SEQ ID NO:141) and corresponds to the amino acid sequence of PEP74 except that PEP92 has the amino acid Gln (Q) at position 24 instead of Nle(εN$_3$) as in PEP74.

TABLE 8

| CONJ No. | Incretin Receptor Assay (cAMP) EC$_{50}$ (nM) | | | Insulin Receptor Binding | |
|---|---|---|---|---|---|
| | GCGR | GLP1R | GIP | pAK Assay EC$_{50}$ (nM) | pAK Assay (% Max) |
| CON1 | >20 | 0.37 | | 0.64 | 64.17 |
| CON2 | 4.461 | 8.008 | | 337.6 | 96.73 |
| CON3 | 1.107 | 2.518 | | 4355 | 111.8 |
| CON4 | 3.276 | 3.77 | | 30.68 | 89.15 |
| CON5 | 1.292 | 1.391 | | 67.61 | 80.63 |
| CON6 | 3.213 | 1.819 | | 25.89 | 90.2 |
| CON7 | 11.24 | 11.01 | | 0.2255 | 30.93 |

TABLE 8-continued

| CONJ No. | Incretin Receptor Assay (cAMP) EC$_{50}$ (nM) | | | Insulin Receptor Binding | |
|---|---|---|---|---|---|
| | GCGR | GLP1R | GIP | pAK Assay EC$_{50}$ (nM) | pAK Assay (% Max) |
| CON8 | 19.8 | 19.8 | | 41.22 | 71.95 |
| CON9 | 0.602 | 1.653 | | 7.643 | 92.05 |
| CON10 | 6.005 | 19.8 | | 0.07676 | 18.76 |
| CON11 | 19.8 | 1.341 | | 0.6245 | 34.03 |
| CON12 | 1.76 | 3.84 | | 0.17 | 57.83 |
| CON13 | 2.92 | 0.66 | | 15.94 | 73.56 |
| CON14 | 19.8 | 19.8 | | 8.014 | 31.3 |
| CON15 | 0.78 | 2.79 | | 41.88 | 95.27 |
| CON16 | 2.2 | 3.1 | | 0.44 | 70.49 |
| CON17 | 0.73 | >5 | | 1.143 | 37.84 |
| CON18 | >19.8 | 0.1 | | 0.3522 | 50.17 |
| CON19 | >19.8 | 0.17 | | 0.4231 | 51.21 |
| CON20 | >19.8 | >19.8 | | 0.4691 | 36.83 |
| CON21 | >19.8 | 2.3 | | 0.1488 | 28.46 |
| CON22 | >5 | 0.11 | | 0.1092 | 43.53 |
| CON23 | 4.60 | >4.95 | | 5.259 | 67.19 |
| CON24 | >4.95 | >4.95 | | 0.7679 | 52.83 |
| CON25 | >19.8 | 0.07 | | 0.1614 | 53.69 |
| CON26 | >19.8 | 0.16 | | 0.1792 | 35.35 |
| CON27 | >19.8 | 0.06 | | 0.2053 | 66.14 |

Example 16

Synthesis of Linker 16-Azido esadecanoic acid may be performed as follows.

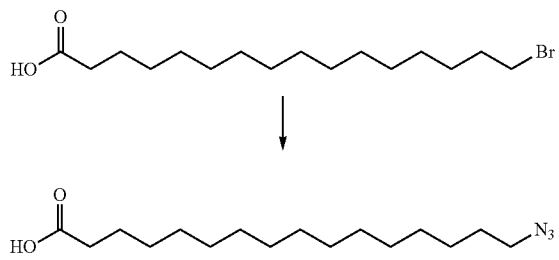

To a solution of 16-bromo hexadecanoic acid in DMF, sodium azide (2 eq) is added. After 12 hours at 85 C°, the reaction mixture is cooled to room temperature. DCM is added and the organic phase is washed with HCl 0.1N, brine and dried over Na$_2$SO$_4$. The solvents are removed under reduced pressure and 16-azido hexadecanoic acid is obtained. $^1$H NMR (400 MHz, CDCl$_3$-d$_6$, 300K) δ 12.35 (s, 1H), 3.30-3.22 (m, 2H), 2.40-2.32 (m, 2H), 1.69-1.56 (m, 4H), 1.4-1.2 (m, 20H).

Example 17

Synthesis of Linker Propargyl-PEG$_{25}$-acid may be as follows.

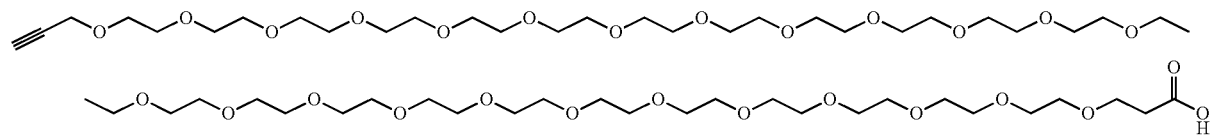

Step 1:

To a suspension of sodium hydride, 60% dispersion in mineral oil (18 mg, 0.450 mmol) in THF (1 mL) cooled in an ice bath is added a solution of hydroxy-PEG$_{24}$-t-butyl ester (250 mg, 0.208 mmol) in Tetrahydrofuran (THF) (1.5 mL). The reaction mixture is stirred for 15 minutes and propargyl bromide, 80% in toluene (26.9 µl, 0.249 mmol) is added. The ice bath is removed and the reaction is allowed to warm to room temperature (RT) and stirred overnight. The reaction is quenched with water (50 µL), diluted with EtOAc, dried over sodium sulfate, filtered and concentrated to give the crude product propargyl-PEG25-t-butyl ester.

Step 2:

TFA (1 mL, 12.98 mmol) is added to the crude propargyl-PEG$_{25}$-t-butyl ester and the reaction is stirred at RT for one hour. The volatiles are evaporated and the residue is purified by mass-directed RP-HPLC (ACN/water with 0.1% ammonium hydroxide as modifier) to give propargyl-PEG$_{25}$-acid. MS: 1186 (M+1).

Example 18

Synthesis of Linker 2-(2-(2-(Pent-4-ynamido)ethoxy)ethoxy)acetic acid (Propargyl-C$_5$-PEG$_2$-acid) may be as follows.

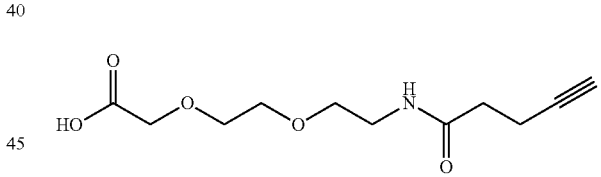

To a solution of 2-(2-(2-aminoethoxy)ethoxy)acetic acid (1.0 g, 6.13 mmol) and 2,5-dioxopyrrolidin-1-yl pent-4-ynoate (1.2 g, 6.13 mmol) in dimethylformamide (DMF) (10 mL) is added N,N-diisopropylethylamine (DIPEA) (1.28 ml, 7.35 mmol) at RT. The mixture is stirred at RT overnight. The reaction is quenched with water and lyophilized to dryness. The residue is purified by mass-directed RP-HPLC (ACN/water with 0.1% TFA as modifier) to give 2-(2-(2-(pent-4-ynamido)ethoxy)ethoxy)acetic acid. MS: 266 (M+23).

Example 19

Synthesis of Linker 10,19,28-Trioxo-3,6,12,15,21,24-hexaoxa-9,18,27-triazadotriacont-31-ynoic acid (Propargyl-C₅-(PEG₂)₃-acid)

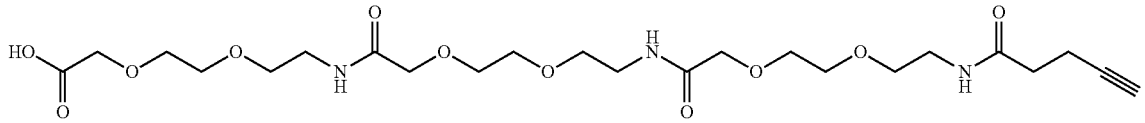 [SMILES: C#CCCC(=O)NCCOCCOCC(=O)NCCOCCOCC(=O)NCCOCCOCC(=O)O]

Step 1:

In a 20 mL vial is added 2-(2-(2-(pent-4-ynamido)ethoxy)ethoxy)acetic acid (500 mg, 2.055 mmol) and DMSO (2 mL). TSTU (dimethylamino-(2,5-dioxopyrrolidin-1-yl)oxymethylidene]-dimethylazanium; tetrafluoroborate; 681 mg, 2.261 mmol) and triethylamine (573 µl, 4.11 mmol) are added. The mixture is stirred at RT for two hours. The freshly prepared N-Hydroxysuccinimide (NETS) ester is then added to a solution of 2-(2-aminoethoxy)ethoxy)acetic acid (419 mg, 2.57 mmol) and triethylamine (2.86 ml, 20.55 mmol) in DMSO (1 mL). The reaction is stirred at RT for 48 hours and triethylamine is removed under reduced pressure. Two drops of trifluoroacetate (TFA) are added to neutralize the reaction. The mixture is filtered through a syringe filter. The residue is purified by mass-directed RP-HPLC (ACN/water with 0.1% TFA as modifier) to give 10,19-dioxo-3,6,12,15-tetraoxa-9,18-diazatricos-22-ynoic acid.

Step 2:

In a 20 ml vial is added 10,19-dioxo-3,6,12,15-tetraoxa-9,18-diazatricos-22-ynoic acid (132 mg, 0.340 mmol) and DMSO (1 mL). TSTU (113 mg, 0.374 mmol) and triethylamine (95 µl, 0.680 mmol) are added. The mixture is stirred at RT for two hours. The freshly prepared NETS ester is then added to a solution of 2-(2-(2-aminoethoxy)ethoxy)acetic acid (111 mg, 0.680 mmol) and triethylamine (474 µl, 3.40 mmol) in DMSO (1 mL). The reaction is quenched with TFA aqueous solution to slightly acidic. Water is added and the mixture is lyophilized to dryness. The residue purified by mass-directed RP-HPLC (ACN/water with 0.1% TFA as modifier) to give 10,19,28-trioxo-3,6,12,15,21,24-hexaoxa-9,18,27-triazadotriacont-31-ynoic acid. MS: 534 (M+1).

Example 20

Synthesis of Linker Propargyl-C₅-Lys(γE-$^t$BuC₁₆)-PEG₁₂-Acid

Step 1:

To a mixture of L-Glu-O$^t$Bu (580 mg, 2.85 mmol) and NaHCO₃ (527 mg, 6.28 mmol) in water (10 mL) and THF (5 ml) at RT is added a solution of 2,5-dioxopyrrolidin-1-yl palmitate (1.01 g, 2.85 mmol) in THF (10 ml). The reaction mixture is stirred at RT overnight. THF is evaporated under reduced pressure. The reaction mixture is neutralized with 1N HCl (7 mL), diluted with water, extracted with EtOAc, washed with brine, dried over sodium sulfate, filtered and concentrated to give the crude product (S)-5-(tert-butoxy)-5-oxo-4-palmitamidopentanoic acid.

Step 2:

To a mixture of H-Lys(Boc)-OH (600 mg, 2.436 mmol) and NaHCO₃ (450 mg, 5.36 mmol) in water (10 mL) and THF (5 mL) at RT is added a solution of 2,5-dioxopyrrolidin-1-yl pent-4-ynoate (475 mg, 2.436 mmol) in THF (10 mL). The reaction mixture is stirred at RT overnight. THF is evaporated under reduced pressure. The reaction mixture is neutralized with 1N HCl (7 mL), diluted with water, extracted with EtOAc, washed with brine, dried over sodium sulfate, filtered and concentrated to give the product (S)-6-((tert-butoxycarbonyl)amino)-2-(pent-4-ynamido)hexanoic acid as light yellow oil. TFA (3 mL, 38.9 mmol) is added to the crude (S)-6-((tert-butoxycarbonyl)amino)-2-(pent-4-ynamido)hexanoic acid (0.795 g, 2.436 mmol) at room temperature and the reaction mixture is stirred for one hour. TFA is evaporated under reduced pressure and the residue is quenched with water and lyophilized to give the product (S)-6-amino-2-(pent-4-ynamido)hexanoic acid, 2TFA.

Step 3:

In a 20 mL vial is added (S)-5-(tert-butoxy)-5-oxo-4-palmitamidopentanoic acid (500 mg, 1.13 mmol) and DMSO (1 mL). TSTU (375 mg, 1.245 mmol) and triethylamine (316 µl, 2.264 mmol) are added. The mixture is stirred at RT for two hours. The freshly prepared NHS ester is then added to a solution of (S)-6-amino-2-(pent-4-ynamido)hexanoic acid, 2TFA (643 mg, 1.415 mmol) and triethylamine (1.58 mL, 11.32 mmol) in DMSO (1 mL). The reaction mixture is stirred at RT overnight. The reaction is diluted with water, acidified with 1N HCl, extracted with EtOAc, washed with water and brine, dried over sodium sulfate, filtered and concentrated. The residue is purified by mass-directed RP-HPLC (ACN/water with 0.1% TFA as modifier) to give N⁶—((S)-5-(tert-butoxy)-5-oxo-4-palmitamidopentanoyl)-N²-(pent-4-ynoyl)-L-lysine.

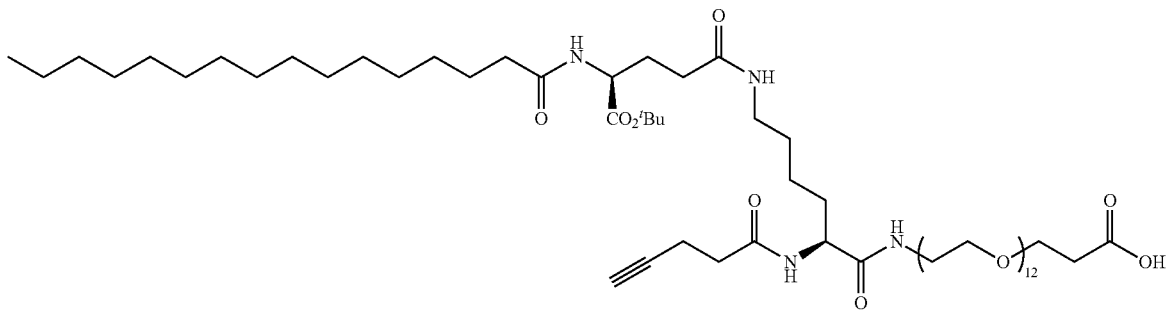

Step 4:

In a 20 mL vial is added N⁶—((S)-5-(tert-butoxy)-5-oxo-4-palmitamidopentanoyl)-N²-(pent-4-ynoyl)-L-lysine (100 mg, 0.154 mmol) and DMSO (0.8 mL). TSTU (51 mg, 0.169 mmol) and triethylamine (43 μl, 0.308 mmol) is added. The mixture is stirred at RT for two hours. The freshly prepared NHS ester is then added to a solution of amino-PEG$_{12}$-acid (124 mg, 0.192 mmol) and triethylamine (214 μl, 1.539 mmol) in DMSO (0.5 mL). The reaction is stirred at RT overnight. The reaction is diluted with water and lyophilized to dryness. The residue is purified by mass-directed RP-HPLC (ACN/water with 0.1% TFA as modifier) to give propargyl-C$_5$-Lys(γE-$^t$Bu$_{16}$)-PEG$_{12}$-acid. MS: 1250 (M+1).

Example 21

Synthesis of Propargyl-(PEG$_4$)(PEG$_{24}$)-acid

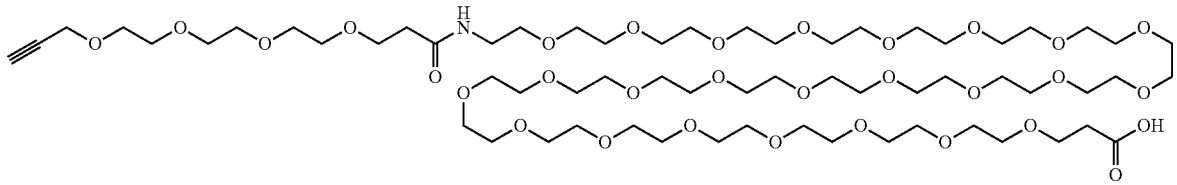 [SMILES: C#CCOCCOCCOCCOCCC(=O)NCCOCCOCCOCCOCCOCCOCCOCCOCCOCCOCCOCCOCCOCCOCCOCCOCCOCCOCCOCCOCCOCCOCCOCCOCCC(=O)O]

Amino-PEG$_{24}$-acid (100 mg, 0.087 mmol) and NaHCO$_3$ (16.12 mg, 0.192 mmol) are suspended in water (2 mL) and THF (1 ml) at room temperature. To the mixture is added a solution of propargyl-PEG$_4$-NHS (32.7 mg, 0.092 mmol) in THF (2 mL). The reaction is stirred at RT overnight. The reaction is neutralized by 0.1 M HCl (2 mL) and lyophilized to dryness. The residue is purified by mass-directed RP-HPLC (ACN/water with 0.1% TFA as modifier) to give propargyl-(PEG$_4$)(PEG$_{24}$)-acid. MS: 695 (M+2)/2.

Example 22

Synthesis of Propargyl-(PEG$_4$)(PEG$_{36}$)-acid

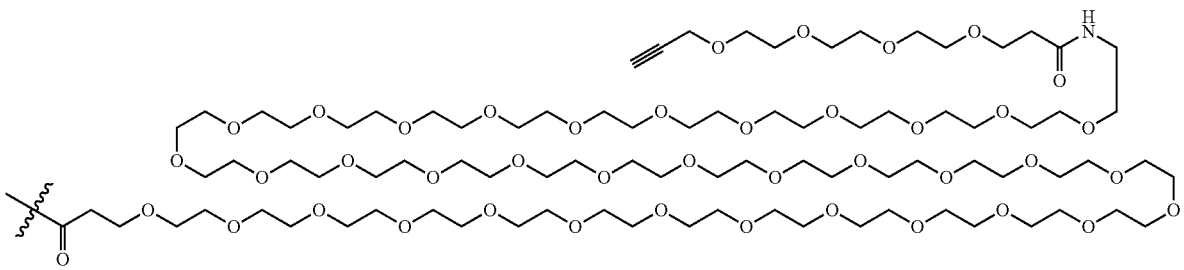 [SMILES: *C(=O)CCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCNC(=O)CCOCCOCCOCCOCC#C]

Amino-PEG$_{36}$-acid (100 mg, 0.060 mmol) and NaHCO$_3$ (11.03 mg, 0.131 mmol) are suspended in water (2 mL) and THF (1 mL) at room temperature. To the mixture is added a solution of propargyl-PEG$_4$-NHS (22.4 mg, 0.063 mmol) in THF (2 mL). The reaction is stirred at RT overnight. The reaction is neutralized by 0.1 M HCl (2 mL) and lyophilized to dryness. The residue is purified by mass-directed RP-HPLC (ACN/water with 0.1% TFA as modifier) to give propargyl-(PEG$_4$)(PEG$_{36}$)-acid. MS: 640 (M+3)/3.

Example 23

Synthesis of Propargyl-(PEG$_5$(PEG$_{36}$)$_2$-Acid

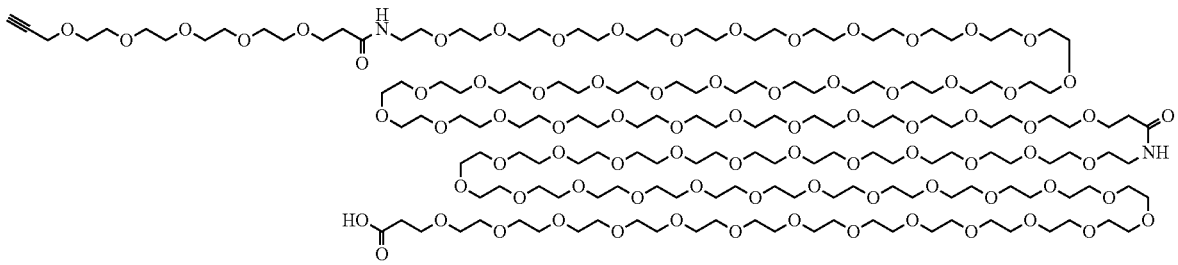 [SMILES: C#CCOCCOCCOCCOCCOCCC(=O)NCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCC(=O)NCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCOCCC(=O)O]

Step 1:

Amino-PEG$_{36}$-acid (1.04 g, 0.623 mmol) and NaHCO$_3$ (115 mg, 1.37 mmol) are suspended in water (20 mL) and THF (10 mL) at room temperature. To the mixture is added a solution of propargyl-PEG$_5$-NHS (262 mg, 0.65 mmol) in THF (20 mL). The reaction is stirred at RT overnight. The reaction is neutralized by 0.1 M HCl (20 mL) and lyophilized to dryness. The residue is purified by mass-directed RP-HPLC (ACN/water with 0.1% TFA as modifier) to give propargyl-(PEG$_5$)(PEG$_{36}$)-acid.

Step 2:

In a 20 ml vial was added propargyl-(PEG$_5$)(PEG$_{36}$)-acid (100 mg, 0.051 mmol) and DMSO (0.8 mL). TSTU (16.88 mg, 0.056 mmol) and triethylamine (14.21 μl, 0.102 mmol) was added. The mixture was stirred at RT for two hours. The freshly prepared NHS ester is then added to a solution of amino-PEG$_{36}$-acid (107 mg, 0.064 mmol) and triethylamine (71.1 μl, 0.510 mmol) in DMSO (0.5 mL). The reaction is stirred at RT overnight. The reaction is diluted with water and lyophilized to dryness. The residue is purified by mass-directed RP-HPLC (ACN/water with 0.1% TFA as modifier) to give proparyl-(PEG$_5$)(PEG$_{36}$)$_2$-acid. MS: 517.85 (M+7)/7.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

---

What is claimed:

1. A compound comprising:
an insulin dimer conjugated to a peptide having at least one incretin activity selected from the group consisting of glucagon-like 1 (GLP-1) activity, glucagon (GCG) activity, and gastric inhibitory protein (GIP) activity; wherein the insulin dimer comprises a first insulin or insulin analog heterodimer and a second insulin or insulin analog heterodimer, each heterodimer including an A-chain polypeptide and a B-chain polypeptide, wherein the A-chain polypeptide and the B-chain polypeptide are linked together through interchain disulfide bonds; wherein the first and second insulin or insulin analog heterodimers are covalently linked together through a first linking moiety joining the side chain of an amino acid at or near the carboxy terminus of the first insulin or insulin analog heterodimer B-chain polypeptide to the side chain of an amino acid at or near the carboxy terminus of the second insulin or insulin analog heterodimer B-chain polypeptide, wherein the first linking moiety is a bivalent, straight or branched, saturated or unsaturated, optionally substituted C1-C20 hydrocarbon chain wherein one or more methylene units are optionally and independently replaced by —S—, —N(R)—, —C(O)—, C(O)O—, OC(O)—, —N(R)C(O)—, —C(O)N(R)—, —S(O)$_2$—, —N(R)SO$_2$—, SO$_2$N(R)—, a heterocyclic group, an aryl group, or a heteroaryl group, wherein each occurrence of R is hydrogen, an acyl moiety, an arylalkyl moiety, an aliphatic moiety, an aryl moiety, a heteroaryl moiety, a heteroaliphatic moiety; an alkyldioyl; or —C(O)(CH$_2$)$_n$C(O)—, wherein n=0-4; or an acyl moiety; or —C(O)RC(O)—, wherein R is an alkyl chain, an amide-containing chain, a triazole(s)-containing chain, a cyclooctyne-containing moiety, or a substituted acyl chain; or a cyclic or acyclic bisamide; or a heterocycle; or a substituted heterocycle.

2. The compound of claim 1, wherein the first and second insulin or insulin analog heterodimers are the same or wherein the first and second insulin or insulin analog heterodimers are different.

3. The compound of claim 1, wherein the first linking moiety covalently links the epsilon amino group of a lysine residue at or near the carboxy terminus of the B-chain polypeptide of the first insulin or insulin analog heterodimer to the epsilon amino group of a lysine residue at or near the carboxy terminus of the B-chain polypeptide of the second insulin or insulin analog heterodimer.

4. The compound of claim 1, wherein the first and second insulin or insulin analog, are each independently selected from the group consisting of native human insulin, insulin lispro, insulin aspart, desB30 insulin, and insulin glargine.

5. The compound of claim 1, wherein each A-chain polypeptide independently comprises the amino acid sequence GX$_2$X$_3$EQCCX$_8$SICSLYQLX$_{17}$NX$_{19}$CX$_{23}$ (SEQ ID NO:133) and each B-chain polypeptide independently comprises the amino acid sequence X$_{25}$LCGX$_{29}$X$_{30}$LVEALYLVCGERGF X$_{27}$YTX$_{31}$X$_{32}$ (SEQ ID NO:134) or X$_{22}$VNQX$_{25}$X$_{26}$CGX$_{29}$X$_{30}$LVEALYLVCGERGFX$_{27}$YTX$_{31}$X$_{32}$X$_{33}$X$_{34}$X$_{35}$ (SEQ ID NO:135) wherein X$_2$ is isoleucine or threonine; X$_3$ is valine, glycine, or leucine; X$_8$ is or histidine; X$_{17}$ is glutamic acid or glutamine; X$_{19}$ is tyrosine, 4-methoxy-phenylalanine, alanine, or 4-amino phenylalanine; X$_{23}$ is asparagine or glycine; X$_{22}$ is or phenylalanine and desamino-phenylalanine; X$_{25}$ is histidine or threonine; X$_{26}$ is leucine or glycine; X$_{27}$ is phenylalanine or aspartic acid; X$_{29}$ is alanine, glycine, or serine; X$_{30}$ is histidine, aspartic acid, glutamic acid, homocysteic acid, or cysteic acid; X$_{31}$ is aspartic acid, proline, or lysine; X$_{32}$ is lysine or proline; X$_{33}$ is threonine, alanine or absent; X$_{34}$ is arginine or absent; and X$_{35}$ is arginine or absent; with the proviso at least one of X$_{31}$ or X$_{32}$ is lysine.

6. The compound of claim 1, wherein the peptide comprises the amino acid sequence (SEQ ID NO: 20)
X$_1$X$_2$X$_3$GTFX$_7$SX$_9$X$_{10}$X11X$_{12}$X$_{13}$X$_{14}$X$_{15}$X$_{16}$X17X$_{18}$X$_{19}$X$_{20}$

X$_{21}$FX$_{23}$X$_{24}$WLX$_{27}$X$_{28}$X$_{29}$ wherein

X$_1$ is histidine, phenylalanine, or tyrosine;
X$_2$ is serine, D-serine, glycine, alanine, or α-aminoisobutyric acid;
X$_3$ is glutamic acid or glutamine;
X$_7$ is tyrosine;
X$_9$ is aspartic acid or lysine;
X$_{10}$ is lysine, valine, leucine, or tyrosine;
X$_{11}$ is serine or valine;
X$_{12}$ is lysine, isoleucine or serine;
X$_{13}$ is glutamine, alanine or tyrosine;
X$_{14}$ is methionine, methionine sulphone, or leucine;
X$_{15}$ is glutamic acid, or aspartic acid;
X$_{16}$ is lysine, α-aminoisobutyric acid, glutamic acid, glycine or serine;
X$_{17}$ is glutamic acid, isoleucine, glutamine, or arginine;
X$_{18}$ is alanine, histidine or arginine;
X$_{19}$ is valine, glutamine or alanine;
X$_{20}$ is arginine, lysine, glutamine or α-aminoisobutyric acid;
X$_{21}$ is leucine, glutamic acid or aspartic acid;
X$_{23}$ is isoleucine or valine;
X$_{24}$ is glutamic acid, alanine, glutamine or asparagine;
X$_{27}$ is lysine, valine, methionine or norleucine;

$X_{28}$ is aspartic acid, arginine, lysine, alanine or asparagine; and $X_{29}$ is glycine, tyrosine or glutamine; and the peptide optionally includes a protecting group that, if present, is joined to the C-terminal carboxy group of the peptide.

7. The compound of claim 6, wherein the amino acid at position 10 is conjugated to a palmitoyl group by either a gamma-glutamic acid (γE) spacer or a gamma-glutamic acid-gamma-glutamic acid dipeptide (γEγE) spacer.

8. The compound of claim 6, wherein the peptide further includes a C-terminal extension selected from the group consisting of KK, KQ, RG, KRNKNNIA (SEQ ID NO:26), GPSSGAPPPS (SEQ ID NO:27), GPSSGAPPSKKKKKK (SEQ ID NO:28), GGGGGSGGGSGGGSA (SEQ ID NO:29), and KGLLNDWKHNITQ (SEQ ID NO:30) is linked to the amino acid at position 29.

9. The compound of claim 1, wherein the peptide comprises the amino acid sequence (SEQ ID NO: 1)
HSQGTFTSDYSKYLDERAAQDFVQWLLDT which further includes at least the following modifications: (i) a substitution of the amino acid at position 2 with an amino acid that makes the peptide resistant to cleavage and inactivation by dipeptidyl peptidase IV; (ii) a lipid moiety covalently linked to the peptide at a lysine residue substituted for the tyrosine residue at position 10 or the glutamine at position 20 of the peptide; (iii) an azide group or an alkyne group conjugated to an amino acid at position 20, 21, 24, 30, or 31; and (iv) 0, 1, or 2 additional amino acid substitutions or additions in addition to the substitution at position 2; and optionally, a protecting group that is joined to the C-terminal carboxy group and/or the N-terminal amino group.

10. The compound of claim 9, wherein the peptide comprises a substitution of the histidine at position 1 with tyrosine, phenylalanine, tryptophan, or other amino acid with an aromatic group.

11. The compound of claim 9, wherein the peptide comprises a substitution of the serine at position 2 with valine, isoleucine, aspartic acid, glutamic acid, methionine, tryptophan, asparagine, D-Alanine, D-Serine, α-methyl-Serine, α-methyl-D-Serine or α-aminoisobutyric acid.

12. The compound of claim 9, wherein the peptide comprises a substitution of the glutamine at position 16 with α-aminoisobutyric acid, asparagine, serine, or alanine.

13. The compound of claim 1, wherein the insulin dimer comprises (a) a first linking moiety having a proximal end linked to an amino acid of the peptide and a distal end linked to an azido group and the insulin dimer comprises a second linking moiety having a proximal end linked to an amino acid of the insulin dimer and a distal end linked to an alkynyl group, wherein the azido group and the alkynyl group form a 1,4-disubstituted 1,2,3-triazole; or (b) a first linking moiety having a proximal end linked to an amino acid of the peptide and a distal end linked to an alkynyl group and the insulin dimer comprises a second linking moiety having a proximal end linked to an amino acid of the insulin dimer and a distal end linked to an azido group, wherein the azido group and the alkynyl group form a 1,4-disubstituted 1,2,3-triazole.

14. The compound of claim 13, wherein the second linking moiety is linked to the amino acid at the N-terminus of one or both A-chain polypeptides of the insulin dimer or the amino acid at the N-terminus of one or both B-chain polypeptides of the insulin dimer.

15. The compound of claim 1, wherein the peptide comprises within its amino acid sequence (a) an azido-norleucine and the insulin dimer comprises a linking moiety having a proximal end linked to the amino group of an amino acid of the insulin dimer and a distal end linked to an alkynyl group, wherein the azido group and the alkynyl group form the 1,4-disubstituted 1,2,3-triazole; or (b) an alkynyl-norleucine and the insulin dimer comprises a linking moiety having a proximal end linked to the amino group of an amino acid of the insulin dimer and a distal end linked to an azido group, wherein the azido group and the alkynyl group form the 1,4-disubstituted 1,2,3-triazole; or (c) a propargyl-Glycine and the insulin dimer comprises a linking moiety having a proximal end linked to the amino group of an amino acid of the insulin dimer and a distal end linked to an azido group, wherein the azido group and the alkynyl group form the 1,4-disubstituted 1,2,3-triazole.

16. The compound of claim 1, wherein the insulin dimer comprises within its amino acid sequence (a) an azido-norleucine and the peptide comprises a linking moiety having a proximal end linked to the amino group of an amino acid of the peptide and a distal end linked to an alkynyl group, wherein the azido group and the alkynyl group form the 1,4-disubstituted 1,2,3-triazole; or (b) an alkynyl-norleucine and the peptide comprises a linking moiety having a proximal end linked to the amino group of an amino acid of the peptide and a distal end linked to an azido group, wherein the azido group and the alkynyl group form the 1,4-disubstituted 1,2,3-triazole; or (c) a propargyl-Glycine and the insulin dimer comprises a linking moiety having a proximal end linked to the amino group of an amino acid of the insulin dimer and a distal end linked to an azido group, wherein the azido group and the alkynyl group form the 1,4-disubstituted 1,2,3-triazole.

17. The compound of claim 1, wherein the peptide has glucagon-like 1 (GLP-1) activity and glucagon (GCG) activity or GLP-1 activity and gastric inhibitory protein (GIP) activity.

18. A composition comprising the compound of claim 1 and a pharmaceutically acceptable carrier.

19. The composition of claim 18 for the treatment of diabetes.

20. The composition of claim 19, wherein the diabetes is Type 1 diabetes, Type 2 diabetes, or gestational diabetes.

21. A method for treating diabetes comprising administering to an individual with diabetes a therapeutically effective amount of the composition of claim 18.

22. The method of claim 21, wherein the diabetes is Type 1 diabetes, Type 2 diabetes, or gestational diabetes.

* * * * *